United States Patent
Kozono et al.

(10) Patent No.: US 10,597,727 B2
(45) Date of Patent: Mar. 24, 2020

(54) STOMACH CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Satoko Kozono, Kamakura (JP); Hitoshi Nobumasa, Kamakura (JP); Satoshi Kondou, Kamakura (JP); Hiroko Sudo, Kamakura (JP); Junpei Kawauchi, Kamakura (JP); Atsushi Ochiai, Kashiwa (JP); Motohiro Kojima, Kashiwa (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 298 days.

(21) Appl. No.: 15/319,203

(22) PCT Filed: Jun. 16, 2015

(86) PCT No.: PCT/JP2015/067267
§ 371 (c)(1),
(2) Date: Dec. 15, 2016

(87) PCT Pub. No.: WO2015/194535
PCT Pub. Date: Dec. 23, 2015

(65) Prior Publication Data
US 2017/0130276 A1     May 11, 2017

(30) Foreign Application Priority Data

Jun. 16, 2014 (JP) .................................. 2014-123224
Mar. 31, 2015 (JP) .................................. 2015-071485

(51) Int. Cl.
| C12Q 1/68 | (2018.01) |
| C12P 19/34 | (2006.01) |
| C12Q 1/6886 | (2018.01) |
| G01N 33/53 | (2006.01) |
| G01N 37/00 | (2006.01) |

(52) U.S. Cl.
CPC .............. *C12Q 1/6886* (2013.01); *C12Q 1/68* (2013.01); *G01N 33/53* (2013.01); *G01N 37/00* (2013.01); *C12Q 2600/158* (2013.01); *C12Q 2600/178* (2013.01)

(58) Field of Classification Search
CPC .. C12Q 1/68; C12Q 1/6886; C12Q 2600/158; C12Q 2600/178
See application file for complete search history.

(56) References Cited

U.S. PATENT DOCUMENTS

2001/0053519 A1* 12/2001 Fodor .................. B01J 19/0046
                                                                     435/6.11
2013/0142728 A1* 6/2013 Beaudenon-Huibregtse ...............
                                                         C12Q 1/6886
                                                         424/1.11

FOREIGN PATENT DOCUMENTS

| CN | 103476947 A | 12/2013 |
| JP | 2012-507300 A | 3/2012 |
| JP | 2013-85542 A | 5/2013 |
| JP | 2014-60993 A | 4/2014 |
| WO | WO 2007/081740 A2 | 7/2007 |
| WO | WO 2009/108853 A1 | 9/2009 |
| WO | WO 2010/062706 A2 | 6/2010 |
| WO | 2012/119051 A2 | 9/2012 |

OTHER PUBLICATIONS

Schrauder MG et al. (2012) Circulating Micro-RNAs as Potential Blood-Based Markers for Early Stage Breast Cancer Detection. PLoS ONE 7(1): e29770. doi:10.1371/journal.pone.0029770 (Year: 2012).*
Cheung, V.G. et al. Nature Genetics, p. 422-425, vol. 33, Mar. (Year: 2003).*
Cobb, J. P. et al., Crit Care Med, pp. 2711-2721, vol. 30, No. 12 (Year: 2002).*
Hoshikawa, Y. et al, Physiol Genomics 12: 209-219 (Year: 2003).*
Phua, L.C. et al. "Global fecal microRNA profiling in the identification of biomarkers for colorectal cancer screening among Asians" Oncology Reports 32: 97-104, Published online on: May 16, 2014. (Year: 2014).*
Lu, J. et al. "Predictive value of miR-9 as a potential biomarker for nasopharyngeal carcinoma metastasis" British Journal of Cancer vol. 110, pp. 392-398 (Jan. 21, 2014) (Year: 2014).*
American Cancer Society, "Stomach Cancer", 2013, p. 3, 6, and 18-20.
Eto et al., "Prospect of microRNA toward laboratory medicine Gastrointestinal Cancer and microRNA", Clinical Chemistry, vol. 43, No. 2, 2014, p. 99-105.
International Search Report, issued in PCT/JP2015/067267, PCT/ISA/210, dated Sep. 15, 2015.

(Continued)

*Primary Examiner* — Stephen T Kapushoc
(74) *Attorney, Agent, or Firm* — Birch, Stewart, Kolasch & Birch, LLP

(57) ABSTRACT

This invention relates to a kit or a device for the detection of stomach cancer and a method for detecting stomach cancer, and provides a kit or a device for the detection of stomach cancer, comprising a nucleic acid(s) capable of specifically binding to a miRNA(s) in a sample from a subject, and a method for detecting stomach cancer, comprising measuring the miRNA(s) in vitro.

6 Claims, 4 Drawing Sheets

Specification includes a Sequence Listing.

(56) References Cited

OTHER PUBLICATIONS

Kim et al., "Chemotherapy-induced transient CEA and CA19-9 surges in patients with metastatic or recurrent gastric cancer", Acta Oncologica., 2009, vol. 48, p. 385-390.
Sobin et al., "TNM Classification of Malignant Tumours, the 7th edition, Japanese version", 2010, p. 69-73.
Takizawa et al., "miRNA Profiling in Serum Samples Using DNA Chip 3D-Gene®", BIO Clinica, Jun. 10, 2014, vol. 29, No. 6, pp. 588-589.
Takizawa et al., "Simultaneous Profiling of Multiple miRNAs in FFPE or Serum Samples Using DNA Chip 3D-Gene®", BIO Clinica, 2013, vol. 28, No. 9, pp. 872-873.
Written Opinion of the International Searching Authority, issued in PCT/JP2015/067267, PCT/ISA/237, dated Sep. 15, 2015.
Berillo et al., "Binding of intronic miRNAs to the mRNAs of host genes encoding intronic miRNAs and proteins that participate in tumourigenesis," Computers in Biology and Medicine (2013), vol. 43, pp. 1374-1381.
Communication Pursuant to Rule 164(1) EPC dated Dec. 15, 2017, in European Patent Application No. 15809520.8.
Genechip: "Data Sheet GeneChip TM miRNA 3.0 Array," Mar. 29, 2012, XP055222758, Retrieved from the Internet: URL:http://www.carreraresearch.org/genech ip-mirna-3-0-array-38713.pdf.
Li et al., "Plasma microRNAs, miR-223, miR-21 and miR-218, as Novel Potential Biomarkers for Gastric Cancer Detection," PLoS ONE (Jul. 2012), vol. 7, No. 7, e41629, pp. 1-8.
Liu et al,. "A five-microRNA signature identified from genome-wide serum microRNA expression profiling serves as a fingerprint for gastric cancer diagnosis," European Journal of Cancer (2011), vol. 47, pp. 784-791.
Liu et al., "MicroRNA expression profile of gastric cancer stem cells in the MKN-45 cancer cell line," Acta Biochim. Biophys. Sin. (2014), vol. 46, pp. 92-99.
Tsujiura et al., "Circulating microRNAs in plasma of patients with gastric cancers," British Journal of Cancer (2010), vol. 102, pp. 1174-1179.
He, M. and Z.-W. Wang, "Current status and development of miRNA and siRNA research on gastric cancer," Hereditas (Beijing) (2011), vol. 33, No. 9, pp. 925-930. (with English abstract).
Office Action dated Feb. 26, 2019, in Chinese Patent Application No. 201580031876.5.

\* cited by examiner

Fig. 1

```
                                                                cgcccuggggcu
                              gg      -ag aca                   ||||||||||| c
    uggg  cggc cag ggg  gg . ag   gg                            gugggaccccgu
ig      ua    c    u        ||   ||    ||
    |||| |||| ||| |||  ||   uc   cc                            hsa-mir-1225
    accc gccg guc ccc  uc                                       (SEQ ID NO: 206)
lg     cc    u     .gag.i ag   agg   gac
                              ↑
hsa-miR-1225-5p                hsa-miR-1225-3p
(SEQ ID NO: 52)                (SEQ ID NO: 7)
```

STOMACH CANCER DETECTION KIT OR DEVICE, AND DETECTION METHOD

TECHNICAL FIELD

The present invention relates to a kit or a device for the detection of stomach cancer, comprising a nucleic acid(s) capable of specifically binding to a particular miRNA(s), which is used for examining the presence or absence of stomach cancer in a subject, and a method for detecting stomach cancer, comprising measuring an expression level(s) of the miRNA(s) using the nucleic acid.

BACKGROUND ART

The stomach is a sac-like digestive organ connected to the esophagus. The stomach temporarily stores food from the esophagus and plays a role in the first step of digestion by secreting gastric juice. The stomach is divided into the cardial end located around the inlet leading to the esophagus, the pyloric end located around the outlet leading to the duodenum, and the other site called the gastric corpus (Non-Patent Literature 1). According to the statistics of the number of cancer type-specific incidences and deaths in Japan disclosed by the Center for Cancer Control and Information Services, National Cancer Center, estimated 125,730 individuals in total involving 86,728 males and 39,002 females were affected by stomach cancer in 2010. The number of stomach cancer deaths was a total of 49,129 people involving 32,206 males and 16,923 females in 2012. Thus, stomach cancer was the second leading cause of cancer death in Japan. Also, 22,220 Americans were affected by stomach cancer in 2014, among which 10,990 people would die of stomach cancer (Non-Patent Literature 1).

The stages of stomach cancer progression are defined in Non-Patent Literature 2 and classified into stages 0, IA, IB, IIA, IIB, IIIA, IIIB, IIIC, and IV according to tumor size, infiltration, lymph node metastasis, distant metastasis, etc. The 5-year relative survival rate of stomach cancer largely depends on the stages of cancer progression and is reportedly 57 to 71% for stage I, 33 to 46% for stage II, 9 to 20% for stage III, and 4% for stage IV (Non-Patent Literature 1). Thus, the early detection of stomach cancer leads to improvement in the survival rate. Therefore, an approach that enables early detection is strongly desired.

The treatment of stomach cancer is performed by the combined use of surgical therapy, drug therapy, and radiotherapy. Particularly, in very early stomach cancer under no suspicion of lymph node metastasis, endoscopic mucosal resection (EMR) or endoscopic submucosal dissection (ESD) is often applicable and the cancer can thus be treated without any burden on patients.

With the aim of detecting stomach cancer early, Japanese men and women aged 40 or older are recommended to take stomach cancer screening once a year. The efficacy of "gastric X-ray examination" as a method for stomach cancer screening has been shown. When detailed examination is required as a result of X-ray examination, gastroscopy is carried out. Alternatively, diagnostic imaging such as CT, PET, or MRI is also utilized for detecting stomach cancer (Non-Patent Literature 1).

On the other hand, no blood marker has been established for the screening of stomach cancer. Although the association of protein tumor markers such as CEA and CA19-9 in serum with stomach cancer has been suggested (Non-Patent Literature 3), there is no enough evidence to recommend using these markers for the purpose of screening. Meanwhile, as shown in Patent Literatures 1 to 3, there are reports, albeit at a research stage, on the detection of stomach cancer using the expression levels of microRNAs (miRNAs) or combinations of the expression levels of miRNAs and the expression levels of additional protein markers in biological samples including blood.

Patent Literature 1 discloses a method for detecting cancers including stomach cancer using hsa-miR-125a-3p in blood.

Patent Literature 2 discloses a method for detecting stomach cancer using hsa-miR-23a-3p, miR-92-1, and miR-92-2 (miR-92a-1-3p and miR-92a-2-3p) and also using miR-128b (miR-128-2-3p), miR-30c (miR-30c-5p), miR-135-1, miR-135-2 (miR-135a-5p), and miR-149 (miR-149-5p), and other miRNAs in blood or tissues.

Patent Literature 3 discloses a method for detecting stomach cancer using hsa-miR-451 and 468 (hsa-miR-468-5p) in blood.

CITATION LIST

Patent Literature

Patent Literature 1: International Publication No. WO 2010/062706
Patent Literature 2: JP Patent Publication (Kokai) No. 2014-060993 A (2014)
Patent Literature 3: JP Patent Publication (Kokai) No. 2013-085542 A (2013)

Non-Patent Literature

Non-Patent Literature 1: American Cancer Society, "Stomach Cancer", 2013, p. 3, 6, and 18 to 20, http://www.cancer.orgiacs/groups/cid/documents/webcontent003141-pdf.pdf
Non-Patent Literature 2: Sobin, L. et al, "TNM Classification of Malignant Tumours, the 7th edition. Japanese version", 2010, p. 69 to 73
Non-Patent Literature 3: Kim, H. J. et al., Acta Oncologica, 2009, Vol. 48, p. 385 to 390

SUMMARY OF INVENTION

Technical Problem

An object of the present invention is to find a novel tumor marker(s) for stomach cancer and to provide a method that can effectively detect stomach cancer using a nucleic acid(s) capable of specifically binding to the marker(s). Primary tests of stomach cancer include imaging tests such as gastric X-ray examination, which is routinely used in Japan, as well as CT, PET, and MRI (Non-Patent Literature 1). In Japan, however, stomach cancer is still the second leading cause of cancer death. Thus, the imaging tests cannot always work as a deterrent against stomach cancer death.

For example, CEA and CA19-9 are known as tumor markers for the detection of stomach cancer. In general, as shown in Non-Patent Literature 3, 5 ng/mL for CEA and 37 U/mL for CA19-9 are used as reference values. Although these tumor markers may be helpful in confirming the recurrence of or therapeutic effects on stomach cancer, their expression very rarely elevates in early stomach cancer. Therefore, these markers may not be useful for the purpose of stomach cancer screening. The tumor markers such as CEA and CA19-9 may also elevate for reasons other than those due to stomach cancer. Therefore, these markers alone allegedly fail to determine the presence or absence of stomach cancer. The false diagnosis of other cancers as stomach cancer wastes appropriate therapeutic opportunity or places unnecessary economical and physical burdens on patients due to the application of wrong medicine.

As described below, there are reports, albeit at a research stage, on the determination of stomach cancer using the expression levels of microRNAs (miRNAs) in biological samples including blood, none of which, however, have yet been brought into practical use.

Patent Literature 1 discloses a method for detecting cancers including stomach cancer using hsa-miR-125a-3p and other miRNAs in blood. This detection method, however, does not describe specific detection performance such as accuracy, sensitivity, or specificity for determining stomach cancer and is thus industrially less practical.

Patent Literature 2 discloses a method for detecting stomach cancer using hsa-miR-23a-3p, miR-92-1, and miR-92-2 (miR-92a-1-3p and miR-92a-2-3p) and further using miR-128 (miR-128-2-5p), miR-30c (miR-30c-5p), miR-135-1, miR-135-2 (miR-135a-5p), miR-149 (miR-149-5p), and other miRNAs in blood or tissues.

Among them, hsa-miR-23a-3p, miR-92-1, and miR-92-2 (miR-92a-1-3p and miR-92a-2-3p) are particularly described as miRNAs for detecting stomach cancer. According to the description therein, these markers in blood, however, were not validated, and specific detection examples were given for miRNAs in tissues. This is not an easy screening test. Therefore, this detection method is industrially less practical.

As mentioned above, the existing tumor markers exhibit low performance in the detection of stomach cancer, or neither detection methods nor performance is specifically shown as to the markers at a research stage. Therefore, use of these markers might lead to carrying out needless extra examination due to the false detection of healthy subjects as being stomach cancer patients, or might waste therapeutic opportunity because of overlooking stomach cancer patients. In addition, the measurement of dozens to several hundreds of miRNAs increases examination cost and is therefore difficult to use in large-scale screening for medical checkup, etc. Furthermore, the collection of gastric tissues for measuring the tumor markers is highly invasive to patients and is not favorable. Hence, there is a demand for a highly accurate stomach cancer marker that is detectable from blood, which can be collected with limited invasiveness, and is capable of correctly discriminating a stomach cancer patient from a healthy subject. Particularly, screening based on an imaging test, such as gastric X-ray examination, which is currently carried out for the early detection of stomach cancer, presents problems associated with radiation exposure, high cost, etc. Therefore, the provision of a more convenient primary screening test of stomach cancer probably leads to benefits to subjects and the health service.

Solution to Problem

The present inventors have conducted diligent studies to attain the object and consequently completed the present invention by finding multiple genes usable as markers for the detection of stomach cancer from blood, which can be collected with limited invasiveness, and finding that stomach cancer can be significantly detected by using a nucleic acid(s) capable of specifically binding to any of these markers.

SUMMARY OF INVENTION

Specifically, the present invention has the following features:

(1) A kit for the detection of stomach cancer, comprising a nucleic acid(s) capable of specifically binding to at least one or more polynucleotides selected from the group consisting of the following stomach cancer markers: miR-4257, miR-6726-5p, miR-1343-3p, miR-1247-3p, miR-6787-5p, miR-6875-5p, miR-1225-3p, miR-8063, miR-6781-5p, miR-4746-3p, miR-1908-5p, miR-6756-5p, miR-204-3p, miR-4651, miR-6757-5p, miR-6825-5p, miR-7108-5p, miR-4792, miR-7641, miR-3188, miR-3131, miR-6780b-5p, miR-8069, miR-6840-3p, miR-8072, miR-1233-5p, miR-6887-5p, miR-1231, miR-5572, miR-6738-5p, miR-6784-5p, miR-6791-5p, miR-6749-5p, miR-6741-5p, miR-128-1-5p, miR-4419b, miR-6746-5p, miR-3184-5p, miR-3679-5p, miR-7110-5p, miR-4516, miR-6717-5p, miR-6826-5p, miR-4433b-3p, miR-3679-3p, miR-3135b, miR-3622a-5p, miR-711, miR-4467, miR-6857-5p, miR-6515-3p, miR-1225-5p, miR-187-5p, miR-3185, miR-642b-3p, miR-1249, miR-744-5p, miR-4442, miR-1228-3p, miR-939-5p, miR-6845-5p, miR-887-3p, miR-7845-5p, miR-6729-5p, miR-4632-5p, miR-615-5p, miR-6724-5p, miR-4728-5p, miR-6732-5p, miR-6816-5p, miR-4695-5p, miR-6088, miR-7975, miR-3197, miR-6125, miR-4433-3p, miR-6727-5p, miR-4706, miR-7847-3p, miR-6805-3p, miR-6766-3p, miR-1913, miR-4649-5p, miR-602, miR-3663-3p, miR-6893-5p, miR-6861-5p, miR-4449, miR-6842-5p, miR-4454, miR-5195-3p, miR-663b, miR-6765-5p, miR-4513, miR-614, miR-6785-5p, miR-6777-5p, miR-940, miR-4741, miR-6870-5p, miR-6131, miR-150-3p, miR-4707-5p, miR-1915-3p, miR-3937, miR-937-5p, miR-4443, miR-1914-3p, miR-3620-5p, miR-1268b, miR-1227-5p, miR-6880-5p, miR-4417, miR-6802-5p, miR-6769a-5p, miR-663a, miR-6721-5p, miR-4532, miR-7977, miR-92b-5p, miR-371a-5p, miR-6126, miR-4734, miR-4665-3p, miR-423-5p, miR-1469, miR-4675, miR-1915-5p, miR-6716-5p, miR-718, miR-4281, miR-6820-5p, miR-6795-5p, miR-6779-5p, miR-7109-5p, miR-6798-5p, miR-4648, miR-8059, miR-6765-3p, miR-6132, miR-4492, miR-7107-5p, miR-3195, miR-3180, miR-296-3p, miR-564, miR-1268a, miR-68.48-5p, miR-762, miR-2861, miR-1203, miR-1260b, miR-4476, miR-6885-5p, miR-6769b-5p, miR-23b-3p, miR-1343-5p, miR-3621, miR-4688, miR-4286, miR-4640-5p, miR-4739, miR-1260a, miR-4276, miR-7106-5p, miR-6794-5p, miR-6774-5p, miR-4707-3p, miR-4534, miR-4294, miR-6850-5p, miR-6089 and miR-671-5p.

(2) The kit according to (1), wherein miR-4257 is hsa-miR-4257, miR-6726-5p is hsa-miR-6726-5p, miR-1343-3p is hsa-miR-1343-3p, miR-1247-3p is hsa-miR-1247-3p, miR-6787-5p is hsa-miR-6787-5p, miR-6875-5p is hsa-miR-6875-5p, miR-1225-3p is hsa-miR-1225-3p, miR-8063 is hsa-miR-8063, miR-6781-5p is hsa-miR-6781-5p, miR-4746-3p is hsa-miR-4746-3p, miR-1908-5p is hsa-miR-1908-5p, miR-6756-5p is hsa-miR-6756-5p, miR-204-3p is hsa-miR-204-3p, miR-4651 is hsa-miR-4651, miR-6757-5p is hsa-miR-6757-5p, miR-6825-5p is hsa-miR-6825-5p, miR-7108-5p is hsa-miR-7108-5p, miR-4792 is hsa-miR-4792, miR-7641 is hsa-miR-7641, miR-3188 is hsa-miR-3188, miR-3131 is hsa-miR-3131, miR-6780b-5p is hsa-miR-6780b-5p, miR-8069 is hsa-miR-8069, miR-6840-3p is hsa-miR-6840-3p, miR-8072 is hsa-miR-8072, miR-1233-5p is hsa-miR-1233-5p, miR-6887-5p is hsa-miR-6887-5p, miR-1231 is hsa-miR-1231, miR-5572 is hsa-miR-5572, miR-6738-5p is hsa-miR-6738-5p, miR-6784-5p is hsa-miR-6784-5p, miR-6791-5p is hsa-miR-6791-5p, miR- 6749-5p is hsa-miR-6749-5p, miR-6741-5p is hsa-miR-6741-5p, miR-128-1-5p is hsa-miR-128-1-5p, miR-4419b is hsa-miR-4419b, miR-6746-5p is hsa-miR-6746-5p, miR-3184-5p is hsa-miR-3184-5p, miR-3679-5p is hsa-miR-3679-5p, miR-7110-5p is hsa-miR-7110-5p, miR-4516 is hsa-miR-4516, miR-6717-5p is hsa-miR-6717-5p, miR-6826-5p is hsa-miR-6826-5p, miR-4433b-3p is hsa-miR-4433b-3p, miR-3679-3p is hsa-miR-3679-3p, miR-3135b is hsa-miR-3135b, miR-3622a-5p is hsa-miR-3622a-5p, miR-711 is hsa-miR-711, miR-4467 is hsa-miR-4467, miR-6857-5p is hsa-miR-6857-5p, miR-6515-3p is hsa-miR-6515-3p, miR-1225-5p is hsa-miR-1225-5p, miR-187-5p is hsa-miR-187-5p, miR-3185 is hsa-miR-3185, miR-642b-3p is hsa-miR-642b-3p, miR-1249 is hsa-miR-1249, miR-744-5p is hsa-miR-744-5p, miR-4442 is hsa-miR-4442, miR-1228-3p is hsa-miR-1228-3p, miR-939-5p is hsa-miR-939-5p, miR-6845-5p is hsa-miR-6845-5p, miR-887-3p is hsa-miR-887-3p, miR-7845-5p is hsa-miR-7845-5p, miR-6729-5p is hsa-miR-6729-5p, miR-4632-5p is hsa-miR-4632-5p, miR-615-5p is hsa-miR-615-5p, miR-6724-5p is hsa-miR-6724-5p, miR-4728-5p is hsa-miR-4728-5p, miR-6732-5p is hsa-miR-6732-5p, miR-6816-5p is hsa-miR-6816-5p, miR-4695-5p is hsa-miR-4695-5p, miR-6088 is hsa-miR-6088, miR-7975 is hsa-miR-7975, miR-3197 is hsa-miR-3197, miR-6125 is hsa-miR-6125, miR-4433-3p is hsa-miR-4433-3p, miR-6727-5p is hsa-miR-6727-5p, miR-4706 is hsa-miR-4706, miR-7847-3p is hsa-miR-7847-3p, miR-6805-3p is hsa-miR-6805-3p, miR-6766-3p is hsa-miR-6766-3p, miR-1913 is hsa-miR-1913, miR-4649-5p is hsa-miR-4649-5p, miR-602 is hsa-miR-602, miR-3663-3p is hsa-miR-3663-3p, miR-6893-5p is hsa-miR-6893-5p, miR-6861-5p is hsa-miR-6861-5p, miR-4449 is hsa-miR-4449, miR-6842-5p is hsa-miR-6842-5p, miR-4454 is hsa-miR-4454, miR-5195-3p is hsa-miR-5195-3p, miR-663b is hsa-miR-663b, miR-6765-5p is hsa-miR-6765-5p, miR-4513 is hsa-miR-4513, miR-614 is hsa-miR-614, miR-6785-5p is hsa-miR-6785-5p, miR-6777-5p is hsa-miR-6777-5p, miR-940 is hsa-miR-940, miR-4741 is hsa-miR-4741, miR-6870-5p is hsa-miR-6870-5p, miR-6131 is hsa-miR-6131, miR-150-3p is hsa-miR-150-3p, miR-4707-5p is hsa-miR-4707-5p, miR-1915-3p is hsa-miR-1915-3p, miR-3937 is hsa-miR-3937, miR-937-5p is hsa-miR-937-5p, miR-4443 is hsa-miR-4443, miR-1914-3p is hsa-miR-1914-3p, miR-3620-5p is hsa-miR-3620-5p, miR-1268b is hsa-miR-1268b, miR-1227-5p is hsa-miR-1227-5p, miR-6880-5p is hsa-miR-6880-5p, miR-4417 is hsa-miR-4417, miR-6802-5p is hsa-miR-6802-5p, miR-6769a-5p is hsa-miR-6769a-5p, miR-663a is hsa-miR-663a, miR-6721-5p is hsa-miR-6721-5p, miR-4532 is hsa-miR-4532, miR-7977 is hsa-miR-7977, miR-92b-5p is hsa-miR-92b-5p, miR-371a-5p is hsa-miR-371a-5p, miR-6126 is hsa-miR-6126, miR-4734 is hsa-miR-4734, miR-4665-3p is hsa-miR-4665-3p, miR-423-5p is hsa-miR-423-5p, miR-1469 is hsa-miR-1469, miR-4675 is hsa-miR-4675, miR-1915-5p is hsa-miR-1915-5p, miR-6716-5p is hsa-miR-6716-5p, miR-718 is hsa-miR-718, miR-4281 is hsa-miR-4281, miR-6820-5p is hsa-miR-6820-5p, miR-6795-5p is hsa-miR-6795-5p, miR-6779-5p is hsa-miR-6779-5p, miR-7109-5p is hsa-miR-7109-5p, miR-6798-5p is hsa-miR-6798-5p, miR-4648 is hsa-miR-4648, miR-8059 is hsa-miR-8059, miR-6765-3p is hsa-miR-6765-3p, miR-6132 is hsa-miR-6132, miR-4492 is hsa-miR-4492, miR-7107-5p is hsa-miR-7107-5p, miR-3195 is hsa-miR-3195, miR-3180 is hsa-miR-3180, miR-296-3p is hsa-miR-296-3p, miR-564 is hsa-miR-564, miR-1268a is hsa-miR-1268a, miR-6848-5p is hsa-miR-6848-5p, miR-762 is hsa-miR-762, miR-2861 is hsa-miR-2861, miR-1203 is hsa-miR-1203, miR-1260b is hsa-miR-1260b, miR-4476 is hsa-miR-4476, miR-6885-5p is hsa-miR-6885-5p, miR-6769b-5p is hsa-miR-6769b-5p, miR-23b-3p is hsa-miR-23b-3p, miR-1343-5p is hsa-miR-1343-5p, miR-3621 is hsa-miR-3621, miR-4688 is hsa-miR-4688, miR-4286 is hsa-miR-4286, miR-4640-5p is hsa-miR-4640-5p, miR-4739 is hsa-miR-4739, miR-1260a is hsa-miR-1260a, miR-4276 is hsa-miR-4276, miR-7106-5p is hsa-miR-7106-5p, miR-6794-5p is hsa-miR-6794-5p, miR-6774-5p is hsa-miR-6774-5p, miR-4707-3p is hsa-miR-4707-3p, miR-4534 is hsa-miR-4534, miR-4294 is hsa-miR-4294, miR-6850-5p is hsa-miR-6850-5p, miR-6089 is hsa-miR-6089, and miR-671-5p is hsa-miR-671-5p.

(3) The kit according to (1) or (2), wherein the nucleic acid is a polynucleotide selected from the group consisting of the following polynucleotides (a) to (e):

(a) a polynucleotide consisting of a nucleotide sequence represented by any of SEQ ID NOs: 1 to 165 and 635 to 642 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 165 and 635 to 642, (c) a polynucleotide consisting of a nucleotide sequence complementary to a nucleotide sequence represented by any of SEQ ID NOs: 1 to 165 and 635 to 642 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 165 and 635 to 642 or a nucleotide sequence derived from the nucleotide sequence by the replacement of u with t, and (e) a polynucleotide hybridizing under stringent conditions to any of the polynucleotides (a) to (d).

(4) The kit according to any of (1) to (3), wherein the kit further comprises a nucleic acid(s) capable of specifically binding to at least one or more polynucleotides selected from the group consisting of the following other stomach cancer markers: miR-128-2-5p, miR-125a-3p, miR-92a-2-5p, and miR-486-3p.

(5) The kit according to (4), wherein miR-128-2-5p is hsa-miR-128-2-5p, miR-125a-3p is hsa-miR-125a-3p, miR-92a-2-5p is hsa-miR-92a-2-5p, and miR-486-3p is hsa-miR-486-3p.

(6) The kit according to (4) or (5), wherein the nucleic acid is a polynucleotide selected from the group consisting of the following polynucleotides (f) to (j):

(f) a polynucleotide consisting of a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 166 to 169, (h) a polynucleotide consisting of a nucleotide sequence complementary to a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 166 to 169 or a nucleotide sequence derived from the nucleotide sequence by the replacement of u with t, and (j) a polynucleotide hybridizing under stringent conditions to any of the polynucleotides (f) to (i).

(7) The kit according to any of (1) to (6), wherein the kit further comprises a nucleic acid(s) capable of specifically binding to at least one or more polynucleotides selected from the group consisting of the following other stomach cancer markers: miR-3196, miR-211-3p, miR-4271, miR-6851-5p, miR-149-3p, miR-4667-5p, miR-135a-3p, miR-4486, miR-4697-5p, miR-4725-3p, miR-6510-5p, miR-5001-5p, miR-4673, miR-4466, miR-23a-3p, miR-3656, miR-6782-5p, miR-4689, miR-451a, miR-4446-3p, miR-3180-3p, miR-642a-3p, miR-6889-5p, miR-3178, miR-4665-5p, miR-6722-3p, miR-30c-1-3p, miR-4507, miR-3141 and miR-1199-5p.

(8) The kit according to (7), wherein miR-3196 is hsa-miR-3196, miR-211-3p is hsa-miR-211-3p, miR-4271 is hsa-miR-4271, miR-6851-5p is hsa-miR-6851-5p, miR-149-3p is hsa-miR-149-3p, miR-4667-5p is hsa-miR-4667-5p, miR-135a-3p is hsa-miR-135a-3p, miR-4486 is hsa-miR-4486, miR-4697-5p is hsa-miR-4697-5p, miR-4725-3p is hsa-miR-4725-3p, miR-6510-5p is hsa-miR-6510-5p, miR-5001-5p is hsa-miR-5001-5p, miR-4673 is hsa-miR-4673, miR-4466 is hsa-miR-4466, miR-23a-3p is hsa-miR-23a-3p, miR-3656 is hsa-miR-3656, miR-6782-5p is hsa-miR-6782-5p, miR-4689 is hsa-miR-4689, miR-451a is hsa-miR-451a, miR-4446-3p is hsa-miR-4446-3p, miR-3180-3p is hsa-miR-3180-3p, miR-642a-3p is hsa-miR-642a-3p, miR-6889-5p is hsa-miR-6889-5p, miR-3178 is hsa-miR-3178, miR-4665-5p is hsa-miR-4665-5p, miR-6722-3p is hsa-miR-6722-3p, miR-30c-1-3p is hsa-miR-30c-1-3p, miR-4507 is hsa-miR-4507, miR-3141 is hsa-miR-3141, and miR-1199-5p is hsa-miR-1199-5p.

(9) The kit according to (7) or (8), wherein the nucleic acid is a polynucleotide selected from the group consisting of the following polynucleotides (k) to (o):
(k) a polynucleotide consisting of a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides,
(l) a polynucleotide comprising a nucleotide sequence represented by any of SEQ ID NOs: 170 to 199,
(m) a polynucleotide consisting of a nucleotide sequence complementary to a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides,
(n) a polynucleotide comprising a nucleotide sequence complementary to a nucleotide sequence represented by any of SEQ ID NOs: 170 to 199 or a nucleotide sequence derived from the nucleotide sequence by the replacement of u with t, and
(o) a polynucleotide hybridizing under stringent conditions to any of the polynucleotides (k) to (n).

(10) The kit according to any one of (1) to (9), wherein the kit comprises at least two or more nucleic acids capable of specifically binding to at least two or more polynucleotides, respectively, selected from all of the stomach cancer markers according to (1) or (2).

(11) A device for the detection of stomach cancer, comprising a nucleic acid(s) capable of specifically binding to at least one or more polynucleotides selected from the group consisting of the following stomach cancer markers: miR-4257, miR-6726-5p, miR-1343-3p, miR-1247-3p, miR-6787-5p, miR-6875-5p, miR-1225-3p, miR-8063, miR-6781-5p, miR-4746-3p, miR-1908-5p, miR-6756-5p, miR-204-3p, miR-4651, miR-6757-5p, miR-6825-5p, miR-7108-5p, miR-4792, miR-7641, miR-3188, miR-3131, miR-6780b-5p, miR-8069, miR-6840-3p, miR-8072, miR-1233-5p, miR-6887-5p, miR-1231, miR-5572, miR-6738-5p, miR-6784-5p, miR-6791-5p, miR-6749-5p, miR-6741-5p, miR-128-1-5p, miR-4419b, miR-6746-5p, miR-3184-5p, miR-3679-5p, miR-7110-5p, miR-4516, miR-6717-5p, miR-6826-5p, miR-4433b-3p, miR-3679-3p, miR-3135b, miR-3622a-5p, miR-711, miR-4467, miR-6857-5p, miR-6515-3p, miR-1225-5p, miR-187-5p, miR-3185, miR-642b-3p, miR-1249, miR-744-5p, miR-4442, miR-1228-3p, miR-939-5p, miR-6845-5p, miR-887-3p, miR-7845-5p, miR-6729-5p, miR-4632-5p, miR-615-5p, miR-6724-5p, miR-4728-5p, miR-6732-5p, miR-6816-5p, miR-4695-5p, miR-6088, miR-7975, miR-3197, miR-6125, miR-4433-3p, miR-6727-5p, miR-4706, miR-7847-3p, miR-6805-3p, miR-6766-3p, miR-1913, miR-4649-5p, miR-602, miR-3663-3p, miR-6893-5p, miR-6861-5p, miR-4449, miR-6842-5p, miR-4454, miR-5195-3p, miR-663b, miR-6765-5p, miR-4513, miR-614, miR-6785-5p, miR-6777-5p, miR-940, miR-4741, miR-6870-5p, miR-6131, miR-150-3p, miR-4707-5p, miR-1915-3p, miR-3937, miR-937-5p, miR-4443, miR-1914-3p, miR-3620-5p, miR-1268b, miR-1227-5p, miR-6880-5p, miR-4417, miR-6802-5p, miR-6769a-5p, miR-663a, miR-6721-5p, miR-4532, miR-7977, miR-92b-5p, miR-371a-5p, miR-6126, miR-4734, miR-4665-3p, miR-423-5p, miR-1469, miR-4675, miR-1915-5p, miR-6716-5p, miR-718, miR-4281, miR-6820-5p, miR-6795-5p, miR-6779-5p, miR-7109-5p, miR-6798-5p, miR-4648, miR-8059, miR-6765-3p, miR-6132, miR-4492, miR-7107-5p, miR-3195, miR-3180, miR-296-3p, miR-564, miR-1268a, miR-6848-5p, miR-762, miR-2861, miR-1203, miR-1260b, miR-4476, miR-6885-5p, miR-6769b-5p, miR-23b-3p, miR-1343-5p, miR-3621, miR-4688, miR-4286, miR-4640-5p, miR-4739, miR-1260a, miR-4276, miR-7106-5p, miR-6794-5p, miR-6774-5p, miR-4707-3p, miR-4534, miR-4294, miR-6850-5p, miR-6089 and miR-671-5p.

(12) The device according to (11), wherein miR-4257 is hsa-miR-4257, miR-6726-5p is hsa-miR-6726-5p, miR-1343-3p is hsa-miR-1343-3p, miR-1247-3p is hsa-miR-1247-3p, miR-6787-5p is hsa-miR-6787-5p, miR-6875-5p is hsa-miR-6875-5p, miR-1225-3p is hsa-miR-1225-3p, miR-8063 is hsa-miR-8063, miR-6781-5p is hsa-miR-6781-5p, miR-4746-3p is hsa-miR-4746-3p, miR-1908-5p is hsa-miR-1908-5p, miR-6756-5p is hsa-miR-6756-5p, miR-204-3p is hsa-miR-204-3p, miR-4651 is hsa-miR-4651, miR-6757-5p is hsa-miR-6757-5p, miR-6825-5p is hsa-miR-6825-5p, miR-7108-5p is hsa-miR-7108-5p, miR-4792 is hsa-miR-4792, miR-7641 is hsa-miR-7641, miR-3188 is hsa-miR-3188, miR-3131 is hsa-miR-3131, miR-6780b-5p is hsa-miR-6780b-5p, miR-8069 is hsa-miR-8069, miR-6840-3p is hsa-miR-6840-3p, miR-8072 is hsa-miR-8072, miR-1233-5p is hsa-miR-1233-5p, miR-6887-5p is hsa-miR-6887-5p, miR-1231 is hsa-miR-1231, miR-5572 is hsa-miR-5572, miR-6738-5p is hsa-miR-6738-5p, miR-6784-5p is hsa-miR-6784-5p, miR-6791-5p is hsa-miR-6791-5p, miR-6749-5p is hsa-miR-6749-5p, miR-6741-5p is hsa-miR-6741-5p, miR-128-1-5p is hsa-miR-128-1-5p, miR-4419b is hsa-miR-4419b, miR-6746-5p is hsa-miR-6746-5p, miR-3184-5p is hsa-miR-3184-5p, miR-3679-5p is hsa-miR-3679-5p, miR-7110-5p is hsa-miR-7110-5p, miR-4516 is hsa-miR-4516, miR-6717-5p is hsa-miR-6717-5p, miR-6826-5p is hsa-miR-6826-5p, miR-4433b-3p is hsamiR-4433b-3p, miR-3679-3p is hsa-miR-3679-3p, miR-3135b is hsa-miR-3135b, miR-3622a-5p is hsa-miR-3622a-5p, miR-711 is hsa-miR-711, miR-4467 is hsa-miR-4467, miR-6857-5p is hsa-miR-6857-5p, miR-6515-3p is hsa-miR-6515-3p, miR-1225-5p is hsa-miR-1225-5p, miR-187-5p is hsa-miR-187-5p, miR-3185 is hsa-miR-3185, miR-642b-3p is hsa-miR-642b-3p, miR-1249 is hsa-miR-1249, miR-744-5p is hsa-miR-744-5p, miR-4442 is hsa-miR-4442, miR-1228-3p is hsa-miR-1228-3p, miR-939-5p is hsa-miR-939-5p, miR-6845-5p is hsa-miR-6845-5p, miR-887-3p is hsa-miR-887-3p, miR-7845-5p is hsa-miR-7845-5p, miR-6729-5p is hsa-miR-6729-5p, miR-4632-5p is hsa-miR-4632-5p, miR-615-5p is hsa-miR-615-5p, miR-6724-5p is hsa-miR-6724-5p, miR-4728-5p is hsa-miR-4728-5p, miR-6732-5p is hsa-miR-6732-5p, miR-6816-5p is hsa-miR-6816-5p, miR-4695-5p is hsa-miR-4695-5p, miR-6088 is hsa-miR-6088, miR-7975 is hsa-miR-7975, miR-3197 is hsa-miR-3197, miR-6125 is hsa-miR-6125, miR-4433-3p is hsa-miR-4433-3p, miR-6727-5p is hsa-miR-6727-5p, miR-4706 is hsa-miR-4706, miR-7847-3p is hsa-miR-7847-3p, miR-6805-3p is hsa-miR-6805-3p, miR-6766-3p is hsa-miR-6766-3p, miR-1913 is hsa-miR-1913, miR-4649-5p is hsa-miR-4649-5p, miR-602 is hsa-miR-602, miR-3663-3p is hsa-miR-3663-3p, miR-6893-5p is hsa-miR-6893-5p, miR-6861-5p is hsa-miR-6861-5p, miR-4449 is hsa-miR-4449, miR-6842-5p is hsa-miR-6842-5p, miR-4454 is hsa-miR-4454, miR-5195-3p is hsa-miR-5195-3p, miR-663b is hsa-miR-663b, miR-6765-5p is hsa-miR-6765-5p, miR-4513 is hsa-miR-4513, miR-614 is hsa-miR-614, miR-6785-5p is hsa-miR-6785-5p, miR-6777-5p is hsa-miR-6777-5p, miR-940 is hsa-miR-940, miR-4741 is hsa-miR-4741, miR-6870-5p is hsa-miR-6870-5p, miR-6131 is hsa-miR-6131, miR-150-3p is hsa-miR-150-3p, miR-4707-5p is hsa-miR-4707-5p, miR-1915-3p is hsa-miR-1915-3p, miR-3937 is hsa-miR-3937, miR-937-5p is hsa-miR-937-5p, miR-4443 is hsa-miR-4443, miR-1914-3p is hsa-miR-1914-3p, miR-3620-5p is hsa-miR-3620-5p, miR-1268b is hsa-miR-1268b, miR-1227-5p is hsa-miR-1227-5p, miR-6880-5p is hsa-miR-6880-5p, miR-4417 is hsa-miR-4417, miR-6802-5p is hsa-miR-6802-5p, miR-6769a-5p is hsa-miR-6769a-5p, miR-663a is hsa-miR-663a, miR-6721-5p is hsa-miR-6721-5p, miR-4532 is hsa-miR-4532, miR-7977 is hsa-miR-7977, miR-92b-5p is hsa-miR-92b-5p, miR-371a-5p is hsa-miR-371a-5p, miR-6126 is hsa-miR-6126, miR-4734 is hsa-miR-4734, miR-4665-3p is hsa-miR-4665-3p, miR-423-5p is hsa-miR-423-5p, miR-1469 is hsa-miR-1469, miR-4675 is hsa-miR-4675, miR-1915-5p is hsa-miR-1915-5p, miR-6716-5p is hsa-miR-6716-5p, miR-718 is hsa-miR-718, miR-4281 is hsa-miR-4281, miR-6820-5p is hsa-miR-6820-5p, miR-6795-5p is hsa-miR-6795-5p, miR-6779-5p is hsa-miR-6779-5p, miR-7109-5p is hsa-miR-7109-5p, miR-6798-5p is hsa-miR-6798-5p, miR-4648 is hsa-miR-4648, miR-8059 is hsa-miR-8059, miR-6765-3p is hsa-miR-6765-3p, miR-6132 is hsa-miR-6132, miR-4492 is hsa-miR-4492, miR-7107-5p is hsa-miR-7107-5p, miR-3195 is hsa-miR-3195, miR-3180 is hsa-miR-3180, miR-296-3p is hsa-miR-296-3p, miR-564 is hsa-miR-564, miR-1268a is hsa-miR-1268a, miR-6848-5p is hsa-miR-6848-5p, miR-762 is hsa-miR-762, miR-2861 is hsa-miR-2861, miR-1203 is hsa-miR-1203, miR-1260b is hsa-miR-1260b, miR-4476 is hsa-miR-4476, miR-6885-5p is hsa-miR-6885-5p, miR-6769b-5p is hsa-miR-6769b-5p, miR-23b-3p is hsa-miR-23b-3p, miR-1343-5p is hsa-miR-1343-5p, miR-3621 is hsa-miR-3621, miR-4688 is hsa-miR-4688, miR-4286 is hsa-miR-4286, miR-4640-5p is hsa-miR-4640-5p, miR-4739 is hsa-miR-4739, miR-1260a is hsa-miR-1260a, miR-4276 is hsa-miR-4276, miR-7106-5p is hsa-miR-7106-5p, miR-6794-5p is hsa-miR-6794-5p, miR-6774-5p is hsa-miR-6774-5p, miR-4707-3p is hsa-miR-4707-3p, miR-4534 is hsa-miR-4534, miR-4294 is hsa-miR-4294, miR-6850-5p is hsa-miR-6850-5p, miR-6089 is hsa-miR-6089, and miR-671-5p is hsa-miR-671-5p.

(13) The device according to (11) or (12), wherein the nucleic acid is a polynucleotide selected from the group consisting of the following polynucleotides (a) to (e):
(a) a polynucleotide consisting of a nucleotide sequence represented by any of SEQ ID NOs: 1 to 165 and 635 to 642 or a nucleotide sequence derived from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 165 and 635 to 642,
(c) a polynucleotide consisting of a nucleotide sequence complementary to a nucleotide sequence represented by any of SEQ ID NOs: 1 to 165 and 635 to 642 or a nucleotide sequence derived from the nucleotide sequence by the replacement of u with t, a variant thereof, a derivative thereof, or a fragment thereof comprising 15 or more consecutive nucleotides,
(d) a polynucleotide comprising a nucleotide sequence complementary to a nucleotide sequence represented by any of SEQ ID NOs: 1 to 165 and 635 to 642 or a nucleotide sequence derived from the nucleotide sequence by the replacement of u with t, and
(e) a polynucleotide hybridizing under stringent conditions to any of the polynucleotides (a) to (d).

(14) The device according to any of (11) to (13), wherein the device further comprises a nucleic acid(s) capable of specifically binding to at least one or more polynucleotides selected from the group consisting of the following other stomach cancer markers: miR-128-2-5p, miR-125a-3p, miR-92a-2-5p, and miR-486-3p.

(15) The device according to (14), wherein miR-128-2-5p is hsa-miR-128-2-5p, miR-125a-3p is hsa-miR-125a-3p, miR-92a-2-5p is hsa-miR-92a-2-5p, and miR-486-3p is hsa-miR-486-3p.

(16) The device according to (14) or (15), wherein the nucleic acid is a polynucleotide selected from the group consisting of the following polynucleotides (f) to (j):
(f) a polynucleotide consisting of a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides,
(g) a polynucleotide comprising a nucleotide sequence represented by any of SEQ ID NOs: 166 to 169,
(h) a polynucleotide consisting of a nucleotide sequence complementary to a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides,
(i) a polynucleotide comprising a nucleotide sequence complementary to a nucleotide sequence represented by any of SEQ ID NOs: 166 to 169 or a nucleotide sequence derived from the nucleotide sequence by the replacement of u with t, and
(j) a polynucleotide hybridizing under stringent conditions to any of the polynucleotides (f) to (i).

(17) The device according to any of (11) to (16), wherein the device further comprises a nucleic acid(s) capable of specifically binding to at least one or more polynucleotides selected from the group consisting of the following other stomach cancer markers: miR-3196, miR-211-3p, miR-4271, miR-6851-5p, miR-149-3p, miR-4667-5p, miR-135a-3p, miR-4486, miR-4697-5p, miR-4725-3p, miR-6510-5p, miR-5001-5p, miR-4673, miR-4466, miR-23a-3p, miR-3656, miR-6782-5p, miR-4689, miR-451a, miR-4446-3p, miR-3180-3p, miR-642a-3p, miR-6889-5p, miR-3178, miR-4665-5p, miR-6722-3p, miR-30c-1-3p, miR-4507, miR-3141 and miR-1199-5p.

(18) The device according to (17), wherein miR-3196 is hsa-miR-3196, miR-211-3p is hsa-miR-211-3p, miR-4271 is hsa-miR-4271, miR-6851-5p is hsa-miR-6851-5p, miR-149-3p is hsa-miR-149-3p, miR-4667-5p is hsa-miR-4667-5p, miR-135a-3p is hsa-miR-135a-3p, miR-4486 is hsa-miR-4486, miR-4697-5p is hsa-miR-4697-5p, miR-4725-3p is hsa-miR-4725-3p, miR-6510-5p is hsa-miR-6510-5p, miR-5001-5p is hsa-miR-5001-5p, miR-4673 is hsa-miR-4673, miR-4466 is hsa-miR-4466, miR-23a-3p is hsa-miR-23a-3p, miR-3656 is hsa-miR-3656, miR-6782-5p is hsa-miR-6782-5p, miR-4689 is hsa-miR-4689, miR-451a is hsa-miR-451a, miR-4446-3p is hsa-miR-4446-3p, miR-3180-3p is hsa-miR-3180-3p, miR-642a-3p is hsa-miR-642a-3p, miR-6889-5p is hsa-miR-6889-5p, miR-3178 is hsa-miR-3178, miR-4665-5p is hsa-miR-4665-5p, miR-6722-3p is hsa-miR-6722-3p, miR-30c-1-3p is hsa-miR-30c-1-3p, miR-4507 is hsa-miR-4507, miR-3141 is hsa-miR-3141, and miR-1199-5p is hsa-miR-1199-5p.

(19) The device according to (17) or (18), wherein the nucleic acid is a polynucleotide selected from the group consisting of the following polynucleotides (k) to (o):
(k) a polynucleotide consisting of a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides,
(l) a polynucleotide comprising a nucleotide sequence represented by any of SEQ ID NOs: 170 to 199,
(m) a polynucleotide consisting of a nucleotide sequence complementary to a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides,
(n) a polynucleotide comprising a nucleotide sequence complementary to a nucleotide sequence represented by any of SEQ ID NOs: 170 to 199 or a nucleotide sequence derived from the nucleotide sequence by the replacement of u with t, and
(o) a polynucleotide hybridizing under stringent conditions to any of the polynucleotides (k) to (n).

(20) The device according to any one of (11) to (19), wherein the device is for measurement based on a hybridization technique.

(21) The device according to (20), wherein the hybridization technique is a nucleic acid array technique.

(22) The device according to any one of (11) to (21), wherein the device comprises at least two or more nucleic acids capable of specifically binding to at least two or more polynucleotides, respectively, selected from all of the stomach cancer markers according to (11) or (12).

(23) A method for detecting stomach cancer, comprising measuring an expression level(s) of a target nucleic acid(s) in a sample from a subject using the kit according to any one of (1) to (10) or the device according to any one of (11) to (22), and evaluating in vitro whether or not the subject has stomach cancer using both of the measured expression level(s) and a control expression level(s) in a sample from a healthy subject measured in the same way.

(24) The method according to (23), wherein the subject is a human.

(25) The method according to (23) or (24), wherein the sample is blood, serum, or plasma.

Definition of Terms

The terms used herein are defined as follows.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein refers to a nucleic acid including all of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA and synthetic RNA. Herein, the "synthetic DNA" and the "synthetic RNA" refer to DNA and RNA artificially prepared using, for example, an automatic nucleic acid synthesizer, on the basis of predetermined nucleotide sequences (which may be any of natural and non-natural sequences). The "non-natural sequence" is intended to be used in a broad sense and includes, for example, a sequence containing substitution, deletion, insertion, and/or addition of one or more nucleotides (i.e., a variant sequence) and a sequence containing one or more modified nucleotides (i.e., a modified sequence), which are different from the natural sequence. Herein, the polynucleotide is used interchangeably with a nucleic acid.

The term "fragment" used herein is a polynucleotide having a nucleotide sequence having a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus strand (or a sense strand) or a complementary strand (or an antisense strand) that constitutes a duplex. The gene is not particularly limited by its length.

Thus, herein, the "gene" includes any of double-stranded DNA including human genomic DNA, single-stranded DNA (plus strand), single-stranded DNA having a sequence complementary to the plus strand (complementary strand) including cDNA, microRNA (miRNA), and their fragments, and their transcripts, unless otherwise specified. The "gene" includes not only a "gene" represented by a particular nucleotide sequence (or SEQ ID NO) but "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 657 or a nucleotide sequence derived from the nucleotide sequence by the replacement of u with t. The "gene" is not particularly limited by its functional region and can contain, for example, an expression regulatory region(s), a coding region(s), an exon(s), or an intron(s). The "gene" may be contained in a cell or may exist alone after being released from a cell. Alternatively, the "gene" may be enclosed in a vesicle called exosome.

The term "exosome" used herein is a vesicle that is delimited by a lipid bilayer and secreted from a cell. The exosome is derived from a multivesicular endosome and may incorporate biomaterials such as a "gene" (e.g., RNA or DNA) or a protein when released into an extracellular environment. The exosome is known to be contained in a body fluid such as blood, serum, plasma, or lymph.

The term "transcript" used herein refers to an RNA synthesized from the DNA sequence of a gene as a template. RNA polymerase binds to a site called a promoter located upstream of the gene and adds ribonucleotides complementary to the nucleotide sequence of the DNA to the 3' end to synthesize RNA. This RNA contains not only the gene itself but also the whole sequence from a transcription initiation site to the end of a polyA sequence, including an expression regulatory region, a coding region, an exon, or an intron.

Unless otherwise specified, the term "microRNA (miRNA)" used herein is intended to mean a 15- to 25-nucleotide non-coding RNA that is involved in the suppression of translation of mRNA, and that transcribed as an RNA precursor having a hairpin-like structure, cleaved by a dsRNA-cleaving enzyme which has RNase III cleavage activity, and integrated into a protein complex called RISC. The term "miRNA" used herein includes not only a "miRNA" represented by a particular nucleotide sequence (or SEQ ID NO) but a precursor of the "miRNA" (pre-miRNA or pri-miRNA), and miRNAs having biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 657. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting RNA resulting from the expression of a gene or a polynucleotide derived from the RNA, and/or a polynucleotide complementary thereto.

The term "primer" used herein includes a polynucleotide that specifically recognizes and amplifies RNA resulting from the expression of a gene or a polynucleotide derived from the RNA, and/or a polynucleotide complementary thereto.

In this context, the complementary polynucleotide (complementary strand or reverse strand) means a polynucleotide in a complementary relationship of A:T (U) and G:C base pairs with the full-length sequence of a polynucleotide consisting of a nucleotide sequence defined by any of SEQ ID NOs: 1 to 657 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence that is 100% complementary to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1 or 2 or more nucleotides in a nucleotide sequence represented by any of SEQ ID NOs: 1 to 657 or a nucleotide sequence derived from the nucleotide sequence by the replacement of u with t, or a partial sequence thereof: a variant that exhibits percent (%) identity of approximately 90% or higher, approximately 95% or higher, approximately 97% or higher, approximately 98% or higher, approximately 99% or higher to each of these nucleotide sequences or the partial sequences thereof; or a nucleic acid hybridizing under the stringent conditions defined above to a polynucleotide or an oligonucleotide comprising each of these nucleotide sequences or the partial sequences thereof.

The term "several" used herein means an integer of approximately 10, 9, 8, 7, 6, 5, 4, 3, or 2.

The variant used herein can be prepared by use of a well-known technique such as site-directed mutagenesis or PCR-based mutagenesis.

The term "percent (%) identity" used herein can be determined with or without an introduced gap, using a protein or gene search system based on BLAST or FASTA described above (Zheng Zhang et al., 2000, J. Comput. Biol., Vol. 7, p. 203-214; Altschul, S. F. et al., 1990. Journal of Molecular Biology, Vol. 215, p. 403-410; and Pearson, W. R. et al., 1988, Proc. Natl. Acad. Sci. U.S.A, Vol. 85, p. 2444-2448).

The term "derivative" used herein is meant to include a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) without any limitation.

The "nucleic acid" used herein capable of specifically binding to a polynucleotide selected from the stomach cancer marker miRNAs described above is a synthesized or prepared nucleic acid and specifically includes a "nucleic acid probe" or a "primer". The "nucleic acid" is utilized directly or indirectly for detecting the presence or absence of stomach cancer in a subject, for diagnosing the presence or absence of stomach cancer, the severity of stomach cancer, the presence or absence of amelioration or the degree of amelioration of stomach cancer, or the therapeutic sensitivity of stomach cancer, or for screening for a candidate substance useful in the prevention, amelioration, or treatment of stomach cancer. The "nucleic acid" includes a nucleotide, an oligonucleotide, and a polynucleotide capable of specifically recognizing and binding to a transcript represented by any of SEQ ID NOs: 1 to 657 or a synthetic cDNA nucleic acid thereof in vivo, particularly, in a sample such as a body fluid (e.g., blood or urine), in relation to the development of stomach cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination". "measurement", "detection", or "decision support". The term "evaluation" used herein is meant to include diagnosis or evaluation support on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "P" or "P value" used herein refers to a probability at which a more extreme statistic than that actually calculated from data under null hypothesis is observed in a statistical test. Thus, smaller "P" or "P value" is regarded as being a more significant difference between subjects to be compared.

The term "sensitivity" used herein means a value of (the number of true positives)/(the number of true positives+the number of false negatives). High sensitivity allows stomach cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being stomach cancer patients, leading to reduction in burden on patients and reduction in medical expense.

The term "accuracy" used herein means a value of (the number of true positives+the number of true negatives)/(the total number of cases). The accuracy indicates the ratio of samples that identified correctly in the discriminant results to all samples, and serves as a primary index for evaluating detection performance.

The "sample" used herein that is subject to determination, detection, or diagnosis refers to a tissue and a biological material in which the expression of the gene of the present invention varies as stomach cancer develops, as stomach cancer progresses, or as therapeutic effects on stomach cancer are exerted. Specifically, the "sample" refers to a gastric tissue, a perigastric vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-4257 gene" or "hsa-miR-4257" used herein includes the hsa-miR-4257 gene (miRBase Accession No. MIMAT0016878) described in SEQ ID NO: 1, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. MI0015856, SEQ ID NO: 200) having a hairpin-like structure is known as a precursor of "hsa-miR-4257".

The term "hsa-miR-6726-5p gene" or "hsa-miR-6726-5p" used herein includes the hsa-miR-6726-5p gene (miRBase Accession No. MIMAT0027353) described in SEQ ID NO: 2, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 201) having a hairpin-like structure is known as a precursor of "hsa-miR-6726-5p".

The term "hsa-miR-1343-3p gene" or "hsa-miR-1343-3p" used herein includes the hsa-miR-1343-3p gene (miRBase Accession No. MIMAT0019776) described in SEQ ID NO: 3, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 202) having a hairpin-like structure is known as a precursor of "hsa-miR-1343-3p".

The term "hsa-miR-1247-3p gene" or "hsa-miR-1247-3p" used herein includes the hsa-miR-1247-3p gene (miRBase Accession No. MIMAT0022721) described in SEQ ID NO: 4, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 203) having a hairpin-like structure is known as a precursor of "hsa-miR-1247-3p".

The term "hsa-miR-6787-5p gene" or "hsa-miR-6787-5p" used herein includes the hsa-miR-6787-5p gene (miRBase Accession No. MIMAT0027474) described in SEQ ID NO: 5, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632. SEQ ID NO: 204) having a hairpin-like structure is known as a precursor of "hsa-miR-6787-5p".

The term "hsa-miR-6875-5p gene" or "hsa-miR-6875-5p" used herein includes the hsa-miR-6875-5p gene (miRBase Accession No. MIMAT0027650) described in SEQ ID NO: 6, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875" (miRBase Accession No. MI0022722, SEQ ID NO: 205) having a hairpin-like structure is known as a precursor of "hsa-miR-6875-5p".

The term "hsa-miR-1225-3p gene" or "hsa-miR-1225-3p" used herein includes the hsa-miR-1225-3p gene (miRBase Accession No. MIMAT0005573) described in SEQ ID NO: 7, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. MI0006311, SEQ ID NO: 206) having a hairpin-like structure is known as a precursor of "hsa-miR-1225-3p".

The term "hsa-miR-8063 gene" or "hsa-miR-8063" used herein includes the hsa-miR-8063 gene (miRBase Accession No. MIMAT0030990) described in SEQ ID NO: 8, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 207) having a hairpin-like structure is known as a precursor of "hsa-miR-8063".

The term "hsa-miR-6781-5p gene" or "hsa-miR-6781-5p" used herein includes the hsa-miR-6781-5p gene (miRBase Accession No. MIMAT0027462) described in SEQ ID NO: 9, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. MI0022626. SEQ ID NO: 208) having a hairpin-like structure is known as a precursor of "hsa-miR-6781-5p".

The term "hsa-miR-4746-3p gene" or "hsa-miR-4746-3p" used herein includes the hsa-miR-4746-3p gene (miRBase Accession No. MIMAT0019881) described in SEQ ID NO: 10, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 209) having a hairpin-like structure is known as a precursor of "hsa-miR-4746-3p".

The term "hsa-miR-1908-5p gene" or "hsa-miR-1908-5p" used herein includes the hsa-miR-1908-5p gene (miRBase Accession No. MIMAT0007881) described in SEQ ID NO: 11, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 210) having a hairpin-like structure is known as a precursor of "hsa-miR-1908-5p".

The term "hsa-miR-6756-5p gene" or "hsa-miR-6756-5p" used herein includes the hsa-miR-6756-5p gene (miRBase Accession No. MIMAT0027412) described in SEQ ID NO: 12, a homolog or an ortholog of a different organism species, and the like. The hsa-miR-6756-5p gene can be obtained by a method described in Ladewig E et al., 2012, Genome Res, Vol. 22, p. 1634-1645. Also, "hsa-mir-6756" (miRBase Accession No. MI0022601, SEQ ID NO: 211) having a hairpin-like structure is known as a precursor of "hsa-miR-6756-5p".

The term "hsa-miR-204-3p gene" or "hsa-miR-204-3p" used herein includes the hsa-miR-204-3p gene (miRBase Accession No. MIMAT0022693) described in SEQ ID NO: 13, a homolog or an ortholog of a different organism species, and the like. The hsa-miR-204-3p gene can be obtained by a method described in Lim L P et al., 2003, Science, Vol. 299, p. 1540. Also, "hsa-mir-204" (miRBase Accession No. MI0000284. SEQ ID NO: 212) having a hairpin-like structure is known as a precursor of "hsa-miR-204-3p".

The term "hsa-miR-4651 gene" or "hsa-miR-4651" used herein includes the hsa-miR-4651 gene (miRBase Accession No. MIMAT0019715) described in SEQ ID NO: 14, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 213) having a hairpin-like structure is known as a precursor of "hsa-miR-4651".

The term "hsa-miR-6757-5p gene" or "hsa-miR-6757-5p" used herein includes the hsa-miR-6757-5p gene (miRBase Accession No. MIMAT0027414) described in SEQ ID NO: 15, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. MI0022602, SEQ ID NO: 214) having a hairpin-like structure is known as a precursor of "hsa-miR-6757-5p".

The term "hsa-miR-6825-5p gene" or "hsa-miR-6825-5p" used herein includes the hsa-miR-6825-5p gene (miRBase Accession No. MIMAT0027550) described in SEQ ID NO: 16, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 215) having a hairpin-like structure is known as a precursor of "hsa-miR-6825-5p".

The term "hsa-miR-7108-5p gene" or "hsa-miR-7108-5p" used herein includes the hsa-miR-7108-5p gene (miRBase Accession No. MIMAT0028113) described in SEQ ID NO: 17, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959. SEQ ID NO: 216) having a hairpin-like structure is known as a precursor of "hsa-miR-7108-5p".

The term "hsa-miR-4792 gene" or "hsa-miR-4792" used herein includes the hsa-miR-4792 gene (miRBase Accession No. MIMAT0019964) described in SEQ ID NO: 18, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 217) having a hairpin-like structure is known as a precursor of "hsa-miR-4792".

The term "hsa-miR-7641 gene" or "hsa-miR-7641" used herein includes the hsa-miR-7641 gene (miRBase Accession No. MIMAT0029782) described in SEQ ID NO: 19, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1 and hsa-mir-7641-2" (miRBase Accession Nos. MI0024975 and MI0024976, SEQ ID NO: 218 and 219) having a hairpin-like structure are known as precursors of "hsa-miR-7641".

The term "hsa-miR-3188 gene" or "hsa-miR-3188" used herein includes the hsa-miR-3188 gene (miRBase Accession No. MIMAT0015070) described in SEQ ID NO: 20, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 220) having a hairpin-like structure is known as a precursor of "hsa-miR-3188".

The term "hsa-miR-3131 gene" or "hsa-miR-3131" used herein includes the hsa-miR-3131 gene (miRBase Accession No. MIMAT0014996) described in SEQ ID NO: 21, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 221) having a hairpin-like structure is known as a precursor of "hsa-miR-3131".

The term "hsa-miR-6780b-5p gene" or "hsa-miR-6780b-5p" used herein includes the hsa-miR-6780b-5p gene (miRBase Accession No. MIMAT0027572) described in SEQ ID NO: 22, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. MI0022681, SEQ ID NO: 222) having a hairpin-like structure is know % n as a precursor of "hsa-miR-6780b-5p".

The term "hsa-miR-8069 gene" or "hsa-miR-8069" used herein includes the hsa-miR-8069 gene (miRBase Accession No. MIMAT0030996) described in SEQ ID NO: 23, a homolog or an ortholog of a different organism species, and the like. The hsa-miR-8069 gene can be obtained by a method described in Wang H J et al., 2013, Shock, Vol. 39, p. 480-487. Also, "hsa-mir-8069" (miRBase Accession No. MI0025905, SEQ ID NO: 223) having a hairpin-like structure is known as a precursor of "hsa-miR-8069".

The term "hsa-miR-6840-3p gene" or "hsa-miR-6840-3p" used herein includes the hsa-miR-6840-3p gene (miRBase Accession No. MIMAT0027583) described in SEQ ID NO: 24, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 224) having a hairpin-like structure is known as a precursor of "hsa-miR-6840-3p".

The term "hsa-miR-8072 gene" or "hsa-miR-8072" used herein includes the hsa-miR-8072 gene (miRBase Accession No. MIMAT0030999) described in SEQ ID NO: 25, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 225) having a hairpin-like structure is known as a precursor of "hsa-miR-8072".

The term "hsa-miR-1233-5p gene" or "hsa-miR-1233-5p" used herein includes the hsa-miR-1233-5p gene (miRBase Accession No. MIMAT0022943) described in SEQ ID NO: 26, a homolog or an ortholog of a different organism species, and the like. The hsa-miR-1233-5p gene can be obtained by a method described in Berezikov E et al., 2007. Mol Cell, Vol. 28, p. 328-336. Also, "hsa-mir-1233-1 and hsa-mir-1233-2" (miRBase Accession Nos. MI0006323 and MI0015973, SEQ ID NOs: 226 and 227) having a hairpin-like structure are known as precursors of "hsa-miR-1233-5p".

The term "hsa-miR-6887-5p gene" or "hsa-miR-6887-5p" used herein includes the hsa-miR-6887-5p gene (miRBase Accession No. MIMAT0027674) described in SEQ ID NO: 27, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 228) having a hairpin-like structure is known as a precursor of "hsa-miR-6887-5p".

The term "hsa-miR-1231 gene" or "hsa-miR-1231" used herein includes the hsa-miR-1231 gene (miRBase Accession No. MIMAT0005586) described in SEQ ID NO: 28, a homolog or an ortholog of a different organism species, and the like. The hsa-miR-1231 gene can be obtained by a method described in Berezikov E et al., 2007, Mol Cell, Vol. 28, p. 328-336. Also, "hsa-mir-1231" (miRBase Accession No. MI0006321, SEQ ID NO: 229) having a hairpin-like structure is known as a precursor of "hsa-miR-1231".

The term "hsa-miR-5572 gene" or "hsa-miR-5572" used herein includes the hsa-miR-5572 gene (miRBase Accession No. MIMAT0022260) described in SEQ ID NO: 29, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 230) having a hairpin-like structure is known as a precursor of "hsa-miR-5572".

The term "hsa-miR-6738-5p gene" or "hsa-miR-6738-5p" used herein includes the hsa-miR-6738-5p gene (miRBase Accession No. MIMAT0027377) described in SEQ ID NO: 30, a homolog or an ortholog of a different organism species, and the like. The hsa-miR-6738-5p gene can be obtained by a method described in Ladewig E et al., 2012, Genome Res, Vol. 22, p. 1634-1645. Also, "hsa-mir-6738" (miRBase Accession No. MI0022583, SEQ ID NO: 231) having a hairpin-like structure is known as a precursor of "hsa-miR-6738-5p".

The term "hsa-miR-6784-5p gene" or "hsa-miR-6784-5p" used herein includes the hsa-miR-6784-5p gene (miRBase Accession No. MIMAT0027468) described in SEQ ID NO: 31, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 232) having a hairpin-like structure is known as a precursor of "hsa-miR-6784-5p".

The term "hsa-miR-6791-5p gene" or "hsa-miR-6791-5p" used herein includes the hsa-miR-6791-5p gene (miRBase Accession No. MIMAT0027482) described in SEQ ID NO: 32, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 233) having a hairpin-like structure is known as a precursor of "hsa-miR-6791-5p".

The term "hsa-miR-6749-5p gene" or "hsa-miR-6749-5p" used herein includes the hsa-miR-6749-5p gene (miRBase Accession No. MIMAT0027398) described in SEQ ID NO: 33, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594. SEQ ID NO: 234) having a hairpin-like structure is known as a precursor of "hsa-miR-6749-5p".

The term "hsa-miR-6741-5p gene" or "hsa-miR-6741-5p" used herein includes the hsa-miR-6741-5p gene (miRBase Accession No. MIMAT0027383) described in SEQ ID NO: 34, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 235) having a hairpin-like structure is known as a precursor of "hsa-miR-6741-5p".

The term "hsa-miR-128-1-5p gene" or "hsa-miR-128-1-5p" used herein includes the hsa-miR-128-1-5p gene (miRBase Accession No. MIMAT0026477) described in SEQ ID NO: 35, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 236) having a hairpin-like structure is known as a precursor of "hsa-miR-128-1-5p".

The term "hsa-miR-4419b gene" or "hsa-miR-4419b" used herein includes the hsa-miR-4419b gene (miRBase Accession No. MIMAT0019034) described in SEQ ID NO: 36, a homolog or an ortholog of a different organism species, and the like. The hsa-miR-4419b gene can be obtained by a method described in Jima D D et al., 2010, Blood, Vol. 116, e118-e127. Also, "hsa-mir-4419b" (miRBase Accession No. MI0016861, SEQ ID NO: 237) having a hairpin-like structure is known as a precursor of "hsa-miR-4419b".

The term "hsa-miR-6746-5p gene" or "hsa-miR-6746-5p" used herein includes the hsa-miR-6746-5p gene (miRBase Accession No. MIMAT0027392) described in SEQ ID NO: 37, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. MI0022591. SEQ ID NO: 238) having a hairpin-like structure is known as a precursor of "hsa-miR-6746-5p".

The term "hsa-miR-3184-5p gene" or "hsa-miR-3184-5p" used herein includes the hsa-miR-3184-5p gene (miRBase Accession No. MIMAT0015064) described in SEQ ID NO: 38, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 239) having a hairpin-like structure is known as a precursor of "hsa-miR-3184-5p".

The term "hsa-miR-3679-5p gene" or "hsa-miR-3679-5p" used herein includes the hsa-miR-3679-5p gene (miRBase Accession No. MIMAT0018104) described in SEQ ID NO: 39, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 240) having a hairpin-like structure is known as a precursor of "hsa-miR-3679-5p".

The term "hsa-miR-7110-5p gene" or "hsa-miR-7110-5p" used herein includes the hsa-miR-7110-5p gene (miRBase Accession No. MIMAT0028117) described in SEQ ID NO: 40, a homolog or an ortholog of a different organism species, and the like. The hsa-miR-7110-5p gene can be obtained by a method described in Ladewig E et al., 2012, Genome Res, Vol. 22, p. 1634-1645. Also, "hsa-mir-7110" (miRBase Accession No. MI0022961, SEQ ID NO: 241) having a hairpin-like structure is known as a precursor of "hsa-miR-7110-5p".

The term "hsa-miR-4516 gene" or "hsa-miR-4516" used herein includes the hsa-miR-4516 gene (miRBase Accession No. MIMAT0019053) described in SEQ ID NO: 41, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 242) having a hairpin-like structure is known as a precursor of "hsa-miR-4516".

The term "hsa-miR-6717-5p gene" or "hsa-miR-6717-5p" used herein includes the hsa-miR-6717-5p gene (miRBase Accession No. MIMAT0025846) described in SEQ ID NO: 42, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 243) having a hairpin-like structure is known as a precursor of "hsa-miR-6717-5p".

The term "hsa-miR-6826-5p gene" or "hsa-miR-6826-5p" used herein includes the hsa-miR-6826-5p gene (miRBase Accession No. MIMAT0027552) described in SEQ ID NO: 43, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. MI0022671, SEQ ID NO: 244) having a hairpin-like structure is known as a precursor of "hsa-miR-6826-5p".

The term "hsa-miR-4433b-3p gene" or "hsa-miR-4433b-3p" used herein includes the hsa-miR-4433b-3p gene (miRBase Accession No. MIMAT0030414) described in SEQ ID NO: 44, a homolog or an ortholog of a different organism species, and the like. The hsa-miR-4433b-3p gene can be obtained by a method described in Pie H et al., 2012, PLoS One, Vol. 7, e50746. Also, "hsa-mir-4433b" (miRBase Accession No. MI0025511, SEQ ID NO: 245) having a hairpin-like structure is known as a precursor of "hsa-miR-4433b-3p".

The term "hsa-miR-3679-3p gene" or "hsa-miR-3679-3p" used herein includes the hsa-miR-3679-3p gene (miRBase Accession No. MIMAT0018105) described in SEQ ID NO: 45, a homolog or an ortholog of a different organism species, and the like. The hsa-miR-3679-3p gene can be obtained by a method described in Creighton C J et al., 2010, PLoS One, Vol. 5, e9637. Also, "hsa-mir-3679" (miRBase Accession No. MI0016080, SEQ ID NO: 240) having a hairpin-like structure is known as a precursor of "hsa-miR-3679-3p".

The term "hsa-miR-3135b gene" or "hsa-miR-3135b" used herein includes the hsa-miR-3135b gene (miRBase Accession No. MIMAT0018985) described in SEQ ID NO: 46, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 246) having a hairpin-like structure is known as a precursor of "hsa-miR-3135b".

The term "hsa-miR-3622a-5p gene" or "hsa-miR-3622a-5p" used herein includes the hsa-miR-3622a-5p gene (miRBase Accession No. MIMAT0018003) described in SEQ ID NO: 47, a homolog or an ortholog of a different organism species, and the like. The hsa-miR-3622a-5p gene can be obtained by a method described in Witten D et al., 2010, BMC Biol, Vol. 8, p. 58. Also, "hsa-mir-3622a" (miRBase Accession No. MI0016013, SEQ ID NO: 247) having a hairpin-like structure is known as a precursor of "hsa-miR-3622a-5p".

The term "hsa-miR-711 gene" or "hsa-miR-711" used herein includes the hsa-miR-711 gene (miRBase Accession No. MIMAT0012734) described in SEQ ID NO: 48, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. MI0012488, SEQ ID NO: 248) having a hairpin-like structure is known as a precursor of "hsa-miR-711".

The term "hsa-miR-4467 gene" or "hsa-miR-4467" used herein includes the hsa-miR-4467 gene (miRBase Accession No. MIMAT0018994) described in SEQ ID NO: 49, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No.

MI0016818, SEQ ID NO: 249) having a hairpin-like structure is known as a precursor of "hsa-miR-4467".

The term "hsa-miR-6857-5p gene" or "hsa-miR-6857-5p" used herein includes the hsa-miR-6857-5p gene (miRBase Accession No. MIMAT0027614) described in SEQ ID NO: 50, a homolog or an ortholog of a different organism species, and the like. The hsa-miR-6857-5p gene can be obtained by a method described in Ladewig E et al., 2012, Genome Res, Vol. 22, p. 1634-1645. Also, "hsa-mir-6857" (miRBase Accession No. MI0022703, SEQ ID NO: 250) having a hairpin-like structure is known as a precursor of "hsa-miR-6857-5p".

The term "hsa-miR-6515-3p gene" or "hsa-miR-6515-3p" used herein includes the hsa-miR-6515-3p gene (miRBase Accession No. MIMAT0025487) described in SEQ ID NO: 51, a homolog or an ortholog of a different organism species, and the like. The hsa-miR-6515-3p gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 251) having a hairpin-like structure is known as a precursor of "hsa-miR-6515-3p".

The term "hsa-miR-1225-5p gene" or "hsa-miR-1225-5p" used herein includes the hsa-miR-1225-5p gene (miRBase Accession No. MIMAT0005572) described in SEQ ID NO: 52, a homolog or an ortholog of a different organism species, and the like. The hsa-miR-1225-5p gene can be obtained by a method described in Berezikov E et al., 2007, Mol Cell, Vol. 28, p. 328-336. Also, "hsa-mir-1225" (miRBase Accession No. MI0006311, SEQ ID NO: 206) having a hairpin-like structure is known as a precursor of "hsa-miR-1225-5p".

The term "hsa-miR-187-5p gene" or "hsa-miR-187-5p" used herein includes the hsa-miR-187-5p gene (miRBase Accession No. MIMAT0004561) described in SEQ ID NO: 53, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274. SEQ ID NO: 252) having a hairpin-like structure is known as a precursor of "hsa-miR-187-5p".

The term "hsa-miR-3185 gene" or "hsa-miR-3185" used herein includes the hsa-miR-3185 gene (miRBase Accession No. MIMAT0015065) described in SEQ ID NO: 54, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 253) having a hairpin-like structure is known as a precursor of "hsa-miR-3185".

The term "hsa-miR-642b-3p gene" or "hsa-miR-642b-3p" used herein includes the hsa-miR-642b-3p gene (miRBase Accession No. MIMAT0018444) described in SEQ ID NO: 55, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 254) having a hairpin-like structure is known as a precursor of "hsa-miR-642b-3p".

The term "hsa-miR-1249 gene" or "hsa-miR-1249" used herein includes the hsa-miR-1249 gene (miRBase Accession No. MIMAT0005901) described in SEQ ID NO: 56, a homolog or an ortholog of a different organism species, and the like. The hsa-miR-1249 gene can be obtained by a method described in Morin R D et al., 2008, Genome Res, Vol. 18, p. 610-621. Also, "hsa-mir-1249" (miRBase Accession No. MI0006384, SEQ ID NO: 255) having a hairpin-like structure is known as a precursor of "hsa-miR-1249".

The term "hsa-miR-744-5p gene" or "hsa-miR-744-5p" used herein includes the hsa-miR-744-5p gene (miRBase Accession No. MIMAT0004945) described in SEQ ID NO: 57, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 256) having a hairpin-like structure is known as a precursor of "hsa-miR-744-5p".

The term "hsa-miR-4442 gene" or "hsa-miR-4442" used herein includes the hsa-miR-4442 gene (miRBase Accession No. MIMAT0018960) described in SEQ ID NO: 58, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 257) having a hairpin-like structure is known as a precursor of "hsa-miR-4442".

The term "hsa-miR-1228-3p gene" or "hsa-miR-1228-3p" used herein includes the hsa-miR-1228-3p gene (miRBase Accession No. MIMAT0005583) described in SEQ ID NO: 59, a homolog or an ortholog of a different organism species, and the like. The hsa-miR-1228-3p gene can be obtained by a method described in Berezikov E et al., 2007, Mol Cell, Vol. 28, p. 328-336. Also, "hsa-mir-1228" (miRBase Accession No. MI0006318, SEQ ID NO: 258) having a hairpin-like structure is known as a precursor of "hsa-miR-1228-3p".

The term "hsa-miR-939-5p gene" or "hsa-miR-939-5p" used herein includes the hsa-miR-939-5p gene (miRBase Accession No. MIMAT0004982) described in SEQ ID NO: 60, a homolog or an ortholog of a different organism species, and the like. The hsa-miR-939-5p gene can be obtained by a method described in Lui W O et al., 2007, Cancer Res, Vol. 67, p. 6031-6043. Also, "hsa-mir-939" (miRBase Accession No. MI0005761, SEQ ID NO: 259) having a hairpin-like structure is known as a precursor of "hsa-miR-939-5p".

The term "hsa-miR-6845-5p gene" or "hsa-miR-6845-5p" used herein includes the hsa-miR-6845-5p gene (miRBase Accession No. MIMAT0027590) described in SEQ ID NO: 61, a homolog or an ortholog of a different organism species, and the like. The hsa-miR-6845-5p gene can be obtained by a method described in Ladewig E et al., 2012, Genome Res, Vol. 22, p. 1634-1645. Also, "hsa-mir-6845" (miRBase Accession No. MI0022691. SEQ ID NO: 260) having a hairpin-like structure is known as a precursor of "hsa-miR-6845-5p".

The term "hsa-miR-887-3p gene" or "hsa-miR-887-3p" used herein includes the hsa-miR-887-3p gene (miRBase Accession No. MIMAT0004951) described in SEQ ID NO: 62, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 261) having a hairpin-like structure is known as a precursor of "hsa-miR-887-3p".

The term "hsa-miR-7845-5p gene" or "hsa-miR-7845-5p" used herein includes the hsa-miR-7845-5p gene (miRBase Accession No. MIMAT0030420) described in SEQ ID NO: 63, a homolog or an ortholog of a different organism species, and the like. The hsa-miR-7845-5p gene can be obtained by a method described in Pie H et al., 2012, PLoS One, Vol. 7, e50746. Also, "hsa-mir-7845" (miRBase Accession No.

MI0025515, SEQ ID NO: 262) having a hairpin-like structure is known as a precursor of "hsa-miR-7845-5p".

The term "hsa-miR-6729-5p gene" or "hsa-miR-6729-5p" used herein includes the hsa-miR-6729-5p gene (miRBase Accession No. MIMAT0027359) described in SEQ ID NO: 64, a homolog or an ortholog of a different organism species, and the like. The hsa-miR-6729-5p gene can be obtained by a method described in Ladewig E et al., 2012, Genome Res, Vol. 22, p. 1634-1645. Also, "hsa-mir-6729" (miRBase Accession No. MI0022574, SEQ ID NO: 263) having a hairpin-like structure is known as a precursor of "hsa-miR-6729-5p".

The term "hsa-miR-4632-5p gene" or "hsa-miR-4632-5p" used herein includes the hsa-miR-4632-5p gene (miRBase Accession No. MIMAT0022977) described in SEQ ID NO: 65, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miRBase Accession No. MI0017259, SEQ ID NO: 264) having a hairpin-like structure is known as a precursor of "hsa-miR-4632-5p".

The term "hsa-miR-615-5p gene" or "hsa-miR-615-5p" used herein includes the hsa-miR-615-5p gene (miRBase Accession No. MIMAT0004804) described in SEQ ID NO: 66, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628. SEQ ID NO: 265) having a hairpin-like structure is known as a precursor of "hsa-miR-615-5p".

The term "hsa-miR-6724-5p gene" or "hsa-miR-6724-5p" used herein includes the hsa-miR-6724-5p gene (miRBase Accession No. MIMAT0025856) described in SEQ ID NO: 67, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 266) having a hairpin-like structure is known as a precursor of "hsa-miR-6724-5p".

The term "hsa-miR-4728-5p gene" or "hsa-miR-4728-5p" used herein includes the hsa-miR-4728-5p gene (miRBase Accession No. MIMAT0019849) described in SEQ ID NO: 68, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI0017365, SEQ ID NO: 267) having a hairpin-like structure is known as a precursor of "hsa-miR-4728-5p".

The term "hsa-miR-6732-5p gene" or "hsa-miR-6732-5p" used herein includes the hsa-miR-6732-5p gene (miRBase Accession No. MIMAT0027365) described in SEQ ID NO: 69, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. MI0022577. SEQ ID NO: 268) having a hairpin-like structure is known as a precursor of "hsa-miR-6732-5p".

The term "hsa-miR-6816-5p gene" or "hsa-miR-6816-5p" used herein includes the hsa-miR-6816-5p gene (miRBase Accession No. MIMAT0027532) described in SEQ ID NO: 70, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 269) having a hairpin-like structure is known as a precursor of "hsa-miR-6816-5p".

The term "hsa-miR-4695-5p gene" or "hsa-miR-4695-5p" used herein includes the hsa-miR-4695-5p gene (miRBase Accession No. MIMAT0019788) described in SEQ ID NO: 71, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 270) having a hairpin-like structure is known as a precursor of "hsa-miR-4695-5p".

The term "hsa-miR-6088 gene" or "hsa-miR-6088" used herein includes the hsa-miR-6088 gene (miRBase Accession No. MIMAT0023713) described in SEQ ID NO: 72, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 271) having a hairpin-like structure is known as a precursor of "hsa-miR-6088".

The term "hsa-miR-7975 gene" or "hsa-miR-7975" used herein includes the hsa-miR-7975 gene (miRBase Accession No. MIMAT0031178) described in SEQ ID NO: 73, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751. SEQ ID NO: 272) having a hairpin-like structure is known as a precursor of "hsa-miR-7975".

The term "hsa-miR-3197 gene" or "hsa-miR-3197" used herein includes the hsa-miR-3197 gene (miRBase Accession No. MIMAT0015082) described in SEQ ID NO: 74, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No. MI0014245, SEQ ID NO: 273) having a hairpin-like structure is known as a precursor of "hsa-miR-3197".

The term "hsa-miR-6125 gene" or "hsa-miR-6125" used herein includes the hsa-miR-6125 gene (miRBase Accession No. MIMAT0024598) described in SEQ ID NO: 75, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 274) having a hairpin-like structure is known as a precursor of "hsa-miR-6125".

The term "hsa-miR-4433-3p gene" or "hsa-miR-4433-3p" used herein includes the hsa-miR-4433-3p gene (miRBase Accession No. MIMAT0018949) described in SEQ ID NO: 76, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. MI0016773, SEQ ID NO: 275) having a hairpin-like structure is known as a precursor of "hsa-miR-4433-3p".

The term "hsa-miR-6727-5p gene" or "hsa-miR-6727-5p" used herein includes the hsa-miR-6727-5p gene (miRBase Accession No. MIMAT0027355) described in SEQ ID NO: 77, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. MI0022572. SEQ ID NO: 276) having a hairpin-like structure is known as a precursor of "hsa-miR-6727-5p".

The term "hsa-miR-4706 gene" or "hsa-miR-4706" used herein includes the hsa-miR-4706 gene (miRBase Accession No. MIMAT0019806) described in SEQ ID NO: 78, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miRBase Accession No. MI0017339, SEQ ID NO: 277) having a hairpin-like structure is known as a precursor of "hsa-miR-4706".

The term "hsa-miR-7847-3p gene" or "hsa-miR-7847-3p" used herein includes the hsa-miR-7847-3p gene (miRBase Accession No. MIMAT0030422) described in SEQ ID NO: 79, a homolog or an ortholog of a different organism species, and the like. The hsa-miR-7847-3p gene can be obtained by a method described in Pie H et al., 2012, PLoS One, Vol. 7, e50746. Also, "hsa-mir-7847" (miRBase Accession No. MI0025517, SEQ ID NO: 278) having a hairpin-like structure is known as a precursor of "hsa-miR-7847-3p".

The term "hsa-miR-6805-3p gene" or "hsa-miR-6805-3p" used herein includes the hsa-miR-6805-3p gene (miRBase Accession No. MIMAT0027511) described in SEQ ID NO: 80, a homolog or an ortholog of a different organism species, and the like. The hsa-miR-6805-3p gene can be obtained by a method described in Ladewig E et al., 2012, Genome Res, Vol. 22, p. 1634-1645. Also, "hsa-mir-6805" (miRBase Accession No. MI0022650, SEQ ID NO: 279) having a hairpin-like structure is known as a precursor of "hsa-miR-6805-3p".

The term "hsa-miR-6766-3p gene" or "hsa-miR-6766-3p" used herein includes the hsa-miR-6766-3p gene (miRBase Accession No. MIMAT0027433) described in SEQ ID NO: 81, a homolog or an ortholog of a different organism species, and the like. The hsa-miR-6766-3p gene can be obtained by a method described in Ladewig E et al., 2012, Genome Res, Vol. 22, p. 1634-1645. Also, "hsa-mir-6766" (miRBase Accession No. MI0022611. SEQ ID NO: 280) having a hairpin-like structure is known as a precursor of "hsa-miR-6766-3p".

The term "hsa-miR-1913 gene" or "hsa-miR-1913" used herein includes the hsa-miR-1913 gene (miRBase Accession No. MIMAT0007888) described in SEQ ID NO: 82, a homolog or an ortholog of a different organism species, and the like. The hsa-miR-1913 gene can be obtained by a method described in Bar M et al., 2008, Stem Cells, Vol. 26, p. 2496-2505. Also, "hsa-mir-1913" (miRBase Accession No. MI0008334, SEQ ID NO: 281) having a hairpin-like structure is known as a precursor of "hsa-miR-1913".

The term "hsa-miR-4649-5p gene" or "hsa-miR-4649-5p" used herein includes the hsa-miR-4649-5p gene (miRBase Accession No. MIMAT0019711) described in SEQ ID NO: 83, a homolog or an ortholog of a different organism species, and the like. The hsa-miR-4649-5p gene can be obtained by a method described in Persson H et al., 2011. Cancer Res, Vol. 71, p. 78-86. Also, "hsa-mir-4649" (miRBase Accession No. MI0017276, SEQ ID NO: 282) having a hairpin-like structure is known as a precursor of "hsa-miR-4649-5p".

The term "hsa-miR-602 gene" or "hsa-miR-602" used herein includes the hsa-miR-602 gene (miRBase Accession No. MIMAT0003270) described in SEQ ID NO: 84, a homolog or an ortholog of a different organism species, and the like. The hsa-miR-602 gene can be obtained by a method described in Cummins J M et al., 2006, Proc Natl Acad Sci USA, Vol. 103, p. 3687-3692. Also, "hsa-mir-602" (miRBase Accession No. MI0003615, SEQ ID NO: 283) having a hairpin-like structure is known as a precursor of "hsa-miR-602".

The term "hsa-miR-3663-3p gene" or "hsa-miR-3663-3p" used herein includes the hsa-miR-3663-3p gene (miRBase Accession No. MIMAT0018085) described in SEQ ID NO: 85, a homolog or an ortholog of a different organism species, and the like. The hsa-miR-3663-3p gene can be obtained by a method described in Liao J Y et al., 2010, PLoS One, Vol. 5, e10563. Also, "hsa-mir-3663" (miRBase Accession No. MI0016064, SEQ ID NO: 284) having a hairpin-like structure is known as a precursor of "hsa-miR-3663-3p".

The term "hsa-miR-6893-5p gene" or "hsa-miR-6893-5p" used herein includes the hsa-miR-6893-5p gene (miRBase Accession No. MIMAT0027686) described in SEQ ID NO: 86, a homolog or an ortholog of a different organism species, and the like. The hsa-miR-6893-5p gene can be obtained by a method described in Ladewig E et al., 2012, Genome Res, Vol. 22, p. 1634-1645. Also, "hsa-mir-6893" (miRBase Accession No. MI0022740, SEQ ID NO: 285) having a hairpin-like structure is known as a precursor of "hsa-miR-6893-5p".

The term "hsa-miR-6861-5p gene" or "hsa-miR-6861-5p" used herein includes the hsa-miR-6861-5p gene (miRBase Accession No. MIMAT0027623) described in SEQ ID NO: 87, a homolog or an ortholog of a different organism species, and the like. The hsa-miR-6861-5p gene can be obtained by a method described in Ladewig E et al., 2012, Genome Res, Vol. 22, p. 1634-1645. Also, "hsa-mir-6861" (miRBase Accession No. MI0022708, SEQ ID NO: 286) having a hairpin-like structure is known as a precursor of "hsa-miR-6861-5p".

The term "hsa-miR-4449 gene" or "hsa-miR-4449" used herein includes the hsa-miR-4449 gene (miRBase Accession No. MIMAT0018968) described in SEQ ID NO: 88, a homolog or an ortholog of a different organism species, and the like. The hsa-miR-4449 gene can be obtained by a method described in Jima D D et al., 2010, Blood, Vol. 116, e118-e127. Also, "hsa-mir-4449" (miRBase Accession No. MI0016792, SEQ ID NO: 287) having a hairpin-like structure is known as a precursor of "hsa-miR-4449".

The term "hsa-miR-6842-5p gene" or "hsa-miR-6842-5p" used herein includes the hsa-miR-6842-5p gene (miRBase Accession No. MIMAT0027586) described in SEQ ID NO: 89, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688. SEQ ID NO: 288) having a hairpin-like structure is known as a precursor of "hsa-miR-6842-5p".

The term "hsa-miR-4454 gene" or "hsa-miR-4454" used herein includes the hsa-miR-4454 gene (miRBase Accession No. MIMAT0018976) described in SEQ ID NO: 90, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 289) having a hairpin-like structure is known as a precursor of "hsa-miR-4454".

The term "hsa-miR-5195-3p gene" or "hsa-miR-5195-3p" used herein includes the hsa-miR-5195-3p gene (miRBase Accession No. MIMAT0021127) described in SEQ ID NO: 91, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 290) having a hairpin-like structure is known as a precursor of "hsa-miR-5195-3p".

The term "hsa-miR-663b gene" or "hsa-miR-663b" used herein includes the hsa-miR-663b gene (miRBase Accession No. MIMAT0005867) described in SEQ ID NO: 92, a homolog or an ortholog of a different organism species, and the like. The hsa-miR-663b gene can be obtained by a method described in Takada S et al., 2008, Leukemia. Vol. 22, p. 1274-1278. Also, "hsa-mir-663b" (miRBase Accession No. MI0006336, SEQ ID NO: 291) having a hairpin-like structure is known as a precursor of "hsa-miR-663b".

The term "hsa-miR-6765-5p gene" or "hsa-miR-6765-5p" used herein includes the hsa-miR-6765-5p gene (miRBase Accession No. MIMAT0027430) described in SEQ ID NO: 93, a homolog or an ortholog of a different organism species, and the like. The hsa-miR-6765-5p gene can be obtained by a method described in Ladewig E et al., 2012, Genome Res, Vol. 22, p. 1634-1645. Also, "hsa-mir-6765" (miRBase Accession No. MI0022610. SEQ ID NO: 292) having a hairpin-like structure is known as a precursor of "hsa-miR-6765-5p".

The term "hsa-miR-4513 gene" or "hsa-miR-4513" used herein includes the hsa-miR-4513 gene (miRBase Accession No. MIMAT0019050) described in SEQ ID NO: 94, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 293) having a hairpin-like structure is known as a precursor of "hsa-miR-4513".

The term "hsa-miR-614 gene" or "hsa-miR-614" used herein includes the hsa-miR-614 gene (miRBase Accession No. MIMAT0003282) described in SEQ ID NO: 95, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 294) having a hairpin-like structure is known as a precursor of "hsa-miR-614".

The term "hsa-miR-6785-5p gene" or "hsa-miR-6785-5p" used herein includes the hsa-miR-6785-5p gene (miRBase Accession No. MIMAT0027470) described in SEQ ID NO: 96, a homolog or an ortholog of a different organism species, and the like. The hsa-miR-6785-5p gene can be obtained by a method described in Ladewig E et al., 2012, Genome Res, Vol. 22, p. 1634-1645. Also, "hsa-mir-6785" (miRBase Accession No. MI0022630, SEQ ID NO: 295) having a hairpin-like structure is known as a precursor of "hsa-miR-6785-5p".

The term "hsa-miR-6777-5p gene" or "hsa-miR-6777-5p" used herein includes the hsa-miR-6777-5p gene (miRBase Accession No. MIMAT0027454) described in SEQ ID NO: 97, a homolog or an ortholog of a different organism species, and the like. The hsa-miR-6777-5p gene can be obtained by a method described in Ladewig E et al., 2012, Genome Res, Vol. 22, p. 1634-1645. Also, "hsa-mir-6777" (miRBase Accession No. MI0022622. SEQ ID NO: 296) having a hairpin-like structure is known as a precursor of "hsa-miR-6777-5p".

The term "hsa-miR-940 gene" or "hsa-miR-940" used herein includes the hsa-miR-940 gene (miRBase Accession No. MIMAT0004983) described in SEQ ID NO: 98, a homolog or an ortholog of a different organism species, and the like. The hsa-miR-940 gene can be obtained by a method described in Lui W O et al., 2007, Cancer Res, Vol. 67, p. 6031-6043. Also, "hsa-mir-940" (miRBase Accession No. MI0005762, SEQ ID NO: 297) having a hairpin-like structure is known as a precursor of "hsa-miR-940".

The term "hsa-miR-4741 gene" or "hsa-miR-4741" used herein includes the hsa-miR-4741 gene (miRBase Accession No. MIMAT0019871) described in SEQ ID NO: 99, a homolog or an ortholog of a different organism species, and the like. The hsa-miR-4741 gene can be obtained by a method described in Persson H et al., 2011, Cancer Res, Vol. 71, p. 78-86. Also, "hsa-mir-4741" (miRBase Accession No. MI0017379, SEQ ID NO: 298) having a hairpin-like structure is known as a precursor of "hsa-miR-4741".

The term "hsa-miR-6870-5p gene" or "hsa-miR-6870-5p" used herein includes the hsa-miR-6870-5p gene (miRBase Accession No. MIMAT0027640) described in SEQ ID NO: 100, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 299) having a hairpin-like structure is known as a precursor of "hsa-miR-6870-5p".

The term "hsa-miR-6131 gene" or "hsa-miR-6131" used herein includes the hsa-miR-6131 gene (miRBase Accession No. MIMAT0024615) described in SEQ ID NO: 101, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. MI0021276, SEQ ID NO: 300) having a hairpin-like structure is known as a precursor of "hsa-miR-6131".

The term "hsa-miR-150-3p gene" or "hsa-miR-150-3p" used herein includes the hsa-miR-150-3p gene (miRBase Accession No. MIMAT0004610) described in SEQ ID NO: 102, a homolog or an ortholog of a different organism species, and the like. The hsa-miR-150-3p gene can be obtained by a method described in Lagos-Quintana M et al., 2002. Curr Biol, Vol. 12, p. 735-739. Also, "hsa-mir-150" (miRBase Accession No. MI0000479, SEQ ID NO: 301) having a hairpin-like structure is known as a precursor of "hsa-miR-150-3p".

The term "hsa-miR-4707-5p gene" or "hsa-miR-4707-5p" used herein includes the hsa-miR-4707-5p gene (miRBase Accession No. MIMAT0019807) described in SEQ ID NO: 103, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 302) having a hairpin-like structure is known as a precursor of "hsa-miR-4707-5p".

The term "hsa-miR-1915-3p gene" or "hsa-miR-1915-3p" used herein includes the hsa-miR-1915-3p gene (miRBase Accession No. MIMAT0007892) described in SEQ ID NO: 104, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 303) having a hairpin-like structure is known as a precursor of "hsa-miR-1915-3p".

The term "hsa-miR-3937 gene" or "hsa-miR-3937" used herein includes the hsa-miR-3937 gene (miRBase Accession No. MIMAT0018352) described in SEQ ID NO: 105, a homolog or an ortholog of a different organism species, and the like. The hsa-miR-3937 gene can be obtained by a method described in Liao J Y et al., 2010, PLoS One, Vol. 5, e10563. Also, "hsa-mir-3937" (miRBase Accession No. MI0016593, SEQ ID NO: 304) having a hairpin-like structure is known as a precursor of "hsa-miR-3937".

The term "hsa-miR-937-5p gene" or "hsa-miR-937-5p" used herein includes the hsa-miR-937-5p gene (miRBase Accession No. MIMAT0022938) described in SEQ ID NO: 106, a homolog or an ortholog of a different organism species, and the like. The hsa-miR-937-5p gene can be obtained by a method described in Lui W O et al., 2007, Cancer Res, Vol. 67, p. 6031-6043. Also, "hsa-mir-937" (miRBase Accession No. MI0005759, SEQ ID NO: 305) having a hairpin-like structure is known as a precursor of "hsa-miR-937-5p".

The term "hsa-miR-4443 gene" or "hsa-miR-4443" used herein includes the hsa-miR-4443 gene (miRBase Accession No. MIMAT0018961) described in SEQ ID NO: 107, a homolog or an ortholog of a different organism species, and the like. The hsa-miR-4443 gene can be obtained by a method described in Jima D D et al., 2010, Blood, Vol. 116, e118-e127. Also, "hsa-mir-4443" (miRBase Accession No. MI0016786, SEQ ID NO: 306) having a hairpin-like structure is known as a precursor of "hsa-miR-4443".

The term "hsa-miR-1914-3p gene" or "hsa-miR-1914-3p" used herein includes the hsa-miR-1914-3p gene (miRBase Accession No. MIMAT0007890) described in SEQ ID NO: 108, a homolog or an ortholog of a different organism species, and the like. The hsa-miR-1914-3p gene can be obtained by a method described in Bar M et al., 2008, Stem Cells, Vol. 26, p. 2496-2505. Also, "hsa-mir-1914" (miRBase Accession No. MI0008335, SEQ ID NO: 307) having a hairpin-like structure is known as a precursor of "hsa-miR-1914-3p".

The term "hsa-miR-3620-5p gene" or "hsa-miR-3620-5p" used herein includes the hsa-miR-3620-5p gene (miRBase Accession No. MIMAT0022967) described in SEQ ID NO: 109, a homolog or an ortholog of a different organism species, and the like. The hsa-miR-3620-5p gene can be obtained by a method described in Witten D et al., 2010, BMC Biol, Vol. 8, p. 58. Also, "hsa-mir-3620" (miRBase Accession No. MI0016011, SEQ ID NO: 308) having a hairpin-like structure is known as a precursor of "hsa-miR-3620-5p".

The term "hsa-miR-1268b gene" or "hsa-miR-1268b" used herein includes the hsa-miR-1268b gene (miRBase Accession No. MIMAT0018925) described in SEQ ID NO: 110, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 309) having a hairpin-like structure is known as a precursor of "hsa-miR-1268b".

The term "hsa-miR-1227-5p gene" or "hsa-miR-1227-5p" used herein includes the hsa-miR-1227-5p gene (miRBase Accession No. MIMAT0022941) described in SEQ ID NO: 111, a homolog or an ortholog of a different organism species, and the like. The hsa-miR-1227-5p gene can be obtained by a method described in Berezikov E et al., 2007, Mol Cell, Vol. 28, p. 328-336. Also, "hsa-mir-1227" (miRBase Accession No. MI0006316, SEQ ID NO: 310) having a hairpin-like structure is known as a precursor of "hsa-miR-1227-5p".

The term "hsa-miR-6880-5p gene" or "hsa-miR-6880-5p" used herein includes the hsa-miR-6880-5p gene (miRBase Accession No. MIMAT0027660) described in SEQ ID NO: 112, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. MI0022727, SEQ ID NO: 311) having a hairpin-like structure is known as a precursor of "hsa-miR-6880-5p".

The term "hsa-miR-4417 gene" or "hsa-miR-4417" used herein includes the hsa-miR-4417 gene (miRBase Accession No. MIMAT0018929) described in SEQ ID NO: 113, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 312) having a hairpin-like structure is known as a precursor of "hsa-miR-4417".

The term "hsa-miR-6802-5p gene" or "hsa-miR-6802-5p" used herein includes the hsa-miR-6802-5p gene (miRBase Accession No. MIMAT0027504) described in SEQ ID NO: 114, a homolog or an ortholog of a different organism species, and the like. The hsa-miR-6802-5p gene can be obtained by a method described in Ladewig E et al., 2012, Genome Res, Vol. 22, p. 1634-1645. Also, "hsa-mir-6802" (miRBase Accession No. MI0022647, SEQ ID NO: 313) having a hairpin-like structure is known as a precursor of "hsa-miR-6802-5p".

The term "hsa-miR-6769a-5p gene" or "hsa-miR-6769a-5p" used herein includes the hsa-miR-6769a-5p gene (miRBase Accession No. MIMAT0027438) described in SEQ ID NO: 115, a homolog or an ortholog of a different organism species, and the like. The hsa-miR-6769a-5p gene can be obtained by a method described in Ladewig E et al., 2012, Genome Res, Vol. 22, p. 1634-1645. Also, "hsa-mir-6769a" (miRBase Accession No. MI0022614, SEQ ID NO: 314) having a hairpin-like structure is known as a precursor of "hsa-miR-6769a-5p".

The term "hsa-miR-663a gene" or "hsa-miR-663a" used herein includes the hsa-miR-663a gene (miRBase Accession No. MIMAT0003326) described in SEQ ID NO: 116, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 315) having a hairpin-like structure is known as a precursor of "hsa-miR-663a".

The term "hsa-miR-6721-5p gene" or "hsa-miR-6721-5p" used herein includes the hsa-miR-6721-5p gene (miRBase Accession No. MIMAT0025852) described in SEQ ID NO: 117, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 316) having a hairpin-like structure is known as a precursor of "hsa-miR-6721-5p".

The term "hsa-miR-4532 gene" or "hsa-miR-4532" used herein includes the hsa-miR-4532 gene (miRBase Accession No. MIMAT0019071) described in SEQ ID NO: 118, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. MI0016899, SEQ ID NO: 317) having a hairpin-like structure is known as a precursor of "hsa-miR-4532".

The term "hsa-miR-7977 gene" or "hsa-miR-7977" used herein includes the hsa-miR-7977 gene (miRBase Accession No. MIMAT0031180) described in SEQ ID NO: 119, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. MI0025753, SEQ ID NO: 318) having a hairpin-like structure is known as a precursor of "hsa-miR-7977".

The term "hsa-miR-92b-5p gene" or "hsa-miR-92b-5p" used herein includes the hsa-miR-92b-5p gene (miRBase Accession No. MIMAT0004792) described in SEQ ID NO: 120, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 319) having a hairpin-like structure is known as a precursor of "hsa-miR-92b-5p".

The term "hsa-miR-371a-5p gene" or "hsa-miR-371a-5p" used herein includes the hsa-miR-371a-5p gene (miRBase Accession No. MIMAT0004687) described in SEQ ID NO: 121, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 320) having a hairpin-like structure is known as a precursor of "hsa-miR-371a-5p".

The term "hsa-miR-6126 gene" or "hsa-miR-6126" used herein includes the hsa-miR-6126 gene (miRBase Accession No. MIMAT0024599) described in SEQ ID NO: 122, a homolog or an ortholog of a different organism species, and the like. The hsa-miR-6126 gene can be obtained by a method described in Smith J L et al., 2012, J Virol, Vol. 86, p. 5278-5287. Also, "hsa-mir-6126" (miRBase Accession No. MI0021260, SEQ ID NO: 321) having a hairpin-like structure is known as a precursor of "hsa-miR-6126".

The term "hsa-miR-4734 gene" or "hsa-miR-4734" used herein includes the hsa-miR-4734 gene (miRBase Accession No. MIMAT0019859) described in SEQ ID NO: 123, a homolog or an ortholog of a different organism species, and the like. The hsa-miR-4734 gene can be obtained by a method described in Persson H et al., 2011. Cancer Res, Vol. 71, p. 78-86. Also, "hsa-mir-4734" (miRBase Accession No. MI0017371, SEQ ID NO: 322) having a hairpin-like structure is known as a precursor of "hsa-miR-4734".

The term "hsa-miR-4665-3p gene" or "hsa-miR-4665-3p" used herein includes the hsa-miR-4665-3p gene (miRBase Accession No. MIMAT0019740) described in SEQ ID NO: 124, a homolog or an ortholog of a different organism species, and the like. The hsa-miR-4665-3p gene can be obtained by a method described in Persson H et al., 2011, Cancer Res, Vol. 71, p. 78-86. Also, "hsa-mir-4665" (miRBase Accession No. MI0017295, SEQ ID NO: 323) having a hairpin-like structure is known as a precursor of "hsa-miR-4665-3p".

The term "hsa-miR-423-5p gene" or "hsa-miR-423-5p" used herein includes the hsa-miR-423-5p gene (miRBase Accession No. MIMAT0004748) described in SEQ ID NO: 125, a homolog or an ortholog of a different organism species, and the like. The hsa-miR-423-5p gene can be obtained by a method described in Kasashima K et al., 2004, Biochem Biophys Res Commun, Vol. 322, p. 403-410. Also, "hsa-mir-423" (miRBase Accession No. MI0001445, SEQ ID NO: 324) having a hairpin-like structure is known as a precursor of "hsa-miR-423-5p".

The term "hsa-miR-1469 gene" or "hsa-miR-1469" used herein includes the hsa-miR-1469 gene (miRBase Accession No. MIMAT0007347) described in SEQ ID NO: 126, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 325) having a hairpin-like structure is known as a precursor of "hsa-miR-1469".

The term "hsa-miR-4675 gene" or "hsa-miR-4675" used herein includes the hsa-miR-4675 gene (miRBase Accession No. MIMAT0019757) described in SEQ ID NO: 127, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 326) having a hairpin-like structure is known as a precursor of "hsa-miR-4675".

The term "hsa-miR-1915-5p gene" or "hsa-miR-1915-5p" used herein includes the hsa-miR-1915-5p gene (miRBase Accession No. MIMAT0007891) described in SEQ ID NO: 128, a homolog or an ortholog of a different organism species, and the like. The hsa-miR-1915-5p gene can be obtained by a method described in Bar M et al., 2008, Stem Cells, Vol. 26, p. 2496-2505. Also, "hsa-mir-1915" (miRBase Accession No. MI0008336, SEQ ID NO: 303) having a hairpin-like structure is known as a precursor of "hsa-miR-1915-5p".

The term "hsa-miR-6716-5p gene" or "hsa-miR-6716-5p" used herein includes the hsa-miR-6716-5p gene (miRBase Accession No. MIMAT0025844) described in SEQ ID NO: 129, a homolog or an ortholog of a different organism species, and the like. The hsa-miR-6716-5p gene can be obtained by a method described in Li Y et al., 2012, Gene, Vol. 497, p. 330-335. Also, "hsa-mir-6716" (miRBase Accession No. MI0022550, SEQ ID NO: 327) having a hairpin-like structure is known as a precursor of "hsa-miR-6716-5p".

The term "hsa-miR-718 gene" or "hsa-miR-718" used herein includes the hsa-miR-718 gene (miRBase Accession No. MIMAT0012735) described in SEQ ID NO: 130, a homolog or an ortholog of a different organism species, and the like. The hsa-miR-718 gene can be obtained by a method described in Artzi S et al., 2008, BMC Bioinformatics, Vol. 9, p. 39. Also, "hsa-mir-718" (miRBase Accession No. MI0012489, SEQ ID NO: 328) having a hairpin-like structure is known as a precursor of "hsa-miR-718".

The term "hsa-miR-4281 gene" or "hsa-miR-4281" used herein includes the hsa-miR-4281 gene (miRBase Accession No. MIMAT0016907) described in SEQ ID NO: 131, a homolog or an ortholog of a different organism species, and the like. The hsa-miR-4281 gene can be obtained by a method described in Goff L A et al., 2009, PLoS One, Vol. 4, e7192. Also, "hsa-mir-4281" (miRBase Accession No. MI0015885, SEQ ID NO: 329) having a hairpin-like structure is known as a precursor of "hsa-miR-4281".

The term "hsa-miR-6820-5p gene" or "hsa-miR-6820-5p" used herein includes the hsa-miR-6820-5p gene (miRBase Accession No. MIMAT0027540) described in SEQ ID NO: 132, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 330) having a hairpin-like structure is known as a precursor of "hsa-miR-6820-5p".

The term "hsa-miR-6795-5p gene" or "hsa-miR-6795-5p" used herein includes the hsa-miR-6795-5p gene (miRBase Accession No. MIMAT0027490) described in SEQ ID NO: 133, a homolog or an ortholog of a different organism species, and the like. The hsa-miR-6795-5p gene can be obtained by a method described in Ladewig E et al., 2012, Genome Res, Vol. 22, p. 1634-1645. Also, "hsa-mir-6795" (miRBase Accession No. MI0022640, SEQ ID NO: 331) having a hairpin-like structure is known as a precursor of "hsa-miR-6795-5p".

The term "hsa-miR-6779-5p gene" or "hsa-miR-6779-5p" used herein includes the hsa-miR-6779-5p gene (miRBase Accession No. MIMAT0027458) described in SEQ ID NO: 134, a homolog or an ortholog of a different organism species, and the like. The hsa-miR-6779-5p gene can be obtained by a method described in Ladewig E et al., 2012, Genome Res, Vol. 22, p. 1634-1645. Also, "hsa-mir-6779" (miRBase Accession No. MI0022624, SEQ ID NO: 332) having a hairpin-like structure is known as a precursor of "hsa-miR-6779-5p".

The term "hsa-miR-7109-5p gene" or "hsa-miR-7109-5p" used herein includes the hsa-miR-7109-5p gene (miRBase Accession No. MIMAT0028115) described in SEQ ID NO: 135, a homolog or an ortholog of a different organism species, and the like. The hsa-miR-7109-5p gene can be obtained by a method described in Ladewig E et al., 2012, Genome Res, Vol. 22, p. 1634-1645. Also, "hsa-mir-7109" (miRBase Accession No. MI0022960, SEQ ID NO: 333) having a hairpin-like structure is known as a precursor of "hsa-miR-7109-5p".

The term "hsa-miR-6798-5p gene" or "hsa-miR-6798-5p" used herein includes the hsa-miR-6798-5p gene (miRBase Accession No. MIMAT0027496) described in SEQ ID NO: 136, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 334) having a hairpin-like structure is known as a precursor of "hsa-miR-6798-5p".

The term "hsa-miR-4648 gene" or "hsa-miR-4648" used herein includes the hsa-miR-4648 gene (miRBase Accession No. MIMAT0019710) described in SEQ ID NO: 137, a homolog or an ortholog of a different organism species, and the like. The hsa-miR-4648 gene can be obtained by a method described in Persson H et al., 2011, Cancer Res, Vol. 71, p. 78-86. Also, "hsa-mir-4648" (miRBase Accession No. MI0017275, SEQ ID NO: 335) having a hairpin-like structure is known as a precursor of "hsa-miR-4648".

The term "hsa-miR-8059 gene" or "hsa-miR-8059" used herein includes the hsa-miR-8059 gene (miRBase Accession No. MIMAT0030986) described in SEQ ID NO: 138, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 336) having a hairpin-like structure is known as a precursor of "hsa-miR-8059".

The term "hsa-miR-6765-3p gene" or "hsa-miR-6765-3p" used herein includes the hsa-miR-6765-3p gene (miRBase Accession No. MIMAT0027431) described in SEQ ID NO: 139, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 292) having a hairpin-like structure is known as a precursor of "hsa-miR-6765-3p".

The term "hsa-miR-6132 gene" or "hsa-miR-6132" used herein includes the hsa-miR-6132 gene (miRBase Accession No. MIMAT0024616) described in SEQ ID NO: 140, a homolog or an ortholog of a different organism species, and the like. The hsa-miR-6132 gene can be obtained by a method described in Dannemann M et al., 2012, Genome Biol Evol, Vol. 4, p. 552-564. Also, "hsa-mir-6132" (miRBase Accession No. MI0021277, SEQ ID NO: 337) having a hairpin-like structure is known as a precursor of "hsa-miR-6132".

The term "hsa-miR-4492 gene" or "hsa-miR-4492" used herein includes the hsa-miR-4492 gene (miRBase Accession No. MIMAT0019027) described in SEQ ID NO: 141, a homolog or an ortholog of a different organism species, and the like. The hsa-miR-4492 gene can be obtained by a method described in Jima D D et al., 2010, Blood, Vol. 116, e118-e127. Also, "hsa-mir-4492" (miRBase Accession No. MI0016854, SEQ ID NO: 338) having a hairpin-like structure is known as a precursor of "hsa-miR-4492".

The term "hsa-miR-7107-5p gene" or "hsa-miR-7107-5p" used herein includes the hsa-miR-7107-5p gene (miRBase Accession No. MIMAT0028111) described in SEQ ID NO: 142, a homolog or an ortholog of a different organism species, and the like. The hsa-miR-7107-5p gene can be obtained by a method described in Ladewig E et al., 2012, Genome Res, Vol. 22, p. 1634-1645. Also, "hsa-mir-7107" (miRBase Accession No. MI0022958, SEQ ID NO: 339) having a hairpin-like structure is known as a precursor of "hsa-miR-7107-5p".

The term "hsa-miR-3195 gene" or "hsa-miR-3195" used herein includes the hsa-miR-3195 gene (miRBase Accession No. MIMAT0015079) described in SEQ ID NO: 143, a homolog or an ortholog of a different organism species, and the like. The hsa-miR-3195 gene can be obtained by a method described in Stark M S et al., 2010, PLoS One, Vol. 5, e9685. Also, "hsa-mir-3195" (miRBase Accession No. MI0014240, SEQ ID NO: 340) having a hairpin-like structure is known as a precursor of "hsa-miR-3195".

The term "hsa-miR-3180 gene" or "hsa-miR-3180" used herein includes the hsa-miR-3180 gene (miRBase Accession No. MIMAT0018178) described in SEQ ID NO: 144, a homolog or an ortholog of a different organism species, and the like. The hsa-miR-3180 gene can be obtained by a method described in Creighton C J et al., 2010, PLoS One, Vol. 5, e9637. Also, "hsa-mir-3180-4 and hsa-mir-3180-5" (miRBase Accession Nos. MI0016408 and MI0016409, SEQ ID NOs: 341 and 342) having a hairpin-like structure are known as precursors of "hsa-miR-3180".

The term "hsa-miR-296-3p gene" or "hsa-miR-296-3p" used herein includes the hsa-miR-296-3p gene (miRBase Accession No. MIMAT0004679) described in SEQ ID NO: 145, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 343) having a hairpin-like structure is known as a precursor of "hsa-miR-296-3p".

The term "hsa-miR-564 gene" or "hsa-miR-564" used herein includes the hsa-miR-564 gene (miRBase Accession No. MIMAT0003228) described in SEQ ID NO: 146, a homolog or an ortholog of a different organism species, and the like. The hsa-miR-564 gene can be obtained by a method described in Cummins J M et al., 2006, Proc Natl Acad Sci USA, Vol. 103, p. 3687-3692. Also, "hsa-mir-564" (miRBase Accession No. MI0003570, SEQ ID NO: 344) having a hairpin-like structure is known as a precursor of "hsa-miR-564".

The term "hsa-miR-1268a gene" or "hsa-miR-1268a" used herein includes the hsa-miR-1268a gene (miRBase Accession No. MIMAT0005922) described in SEQ ID NO: 147, a homolog or an ortholog of a different organism species, and the like. The hsa-miR-1268a gene can be obtained by a method described in Morin R D et al., 2008, Genome Res, Vol. 18, p. 610-621. Also, "hsa-mir-1268a" (miRBase Accession No. MI0006405, SEQ ID NO: 345) having a hairpin-like structure is known as a precursor of "hsa-miR-1268a".

The term "hsa-miR-6848-5p gene" or "hsa-miR-6848-5p" used herein includes the hsa-miR-6848-5p gene (miRBase Accession No. MIMAT0027596) described in SEQ ID NO: 148, a homolog or an ortholog of a different organism species, and the like. The hsa-miR-6848-5p gene can be obtained by a method described in Ladewig E et al., 2012, Genome Res, Vol. 22, p. 1634-1645. Also, "hsa-mir-6848" (miRBase Accession No. MI0022694, SEQ ID NO: 346) having a hairpin-like structure is known as a precursor of "hsa-miR-6848-5p".

The term "hsa-miR-762 gene" or "hsa-miR-762" used herein includes the hsa-miR-762 gene (miRBase Accession No. MIMAT0010313) described in SEQ ID NO: 149, a homolog or an ortholog of a different organism species, and the like. The hsa-miR-762 gene can be obtained by a method described in Berezikov E et al., 2006, Genome Res, Vol. 16, p. 1289-1298. Also, "hsa-mir-762" (miRBase Accession No. MI0003892, SEQ ID NO: 347) having a hairpin-like structure is known as a precursor of "hsa-miR-762".

The term "hsa-miR-2861 gene" or "hsa-miR-2861" used herein includes the hsa-miR-2861 gene (miRBase Accession No. MIMAT0013802) described in SEQ ID NO: 150, a homolog or an ortholog of a different organism species, and the like. The hsa-miR-2861 gene can be obtained by a method described in Li H et al., 2009, J Clin Invest, Vol. 119, p. 3666-3677. Also, "hsa-mir-2861" (miRBase Accession No. MI0013006, SEQ ID NO: 348) having a hairpin-like structure is known as a precursor of "hsa-miR-2861".

The term "hsa-miR-1203 gene" or "hsa-miR-1203" used herein includes the hsa-miR-1203 gene (miRBase Accession No. MIMAT0005866) described in SEQ ID NO: 151, a homolog or an ortholog of a different organism species, and the like. The hsa-miR-1203 gene can be obtained by a method described in Marton S et al., 2008, Leukemia. Vol. 22, p. 330-338. Also, "hsa-mir-1203" (miRBase Accession No. MI0006335, SEQ ID NO: 349) having a hairpin-like structure is known as a precursor of "hsa-miR-1203".

The term "hsa-miR-1260b gene" or "hsa-miR-1260b" used herein includes the hsa-miR-1260b gene (miRBase Accession No. MIMAT0015041) described in SEQ ID NO: 152, a homolog or an ortholog of a different organism species, and the like. The hsa-miR-1260b gene can be obtained by a method described in Stark M S et al., 2010, PLoS One, Vol. 5, e9685. Also, "hsa-mir-1260b" (miRBase Accession No. MI0014197, SEQ ID NO: 350) having a hairpin-like structure is known as a precursor of "hsa-miR-1260b".

The term "hsa-miR-4476 gene" or "hsa-miR-4476" used herein includes the hsa-miR-4476 gene (miRBase Accession No. MIMAT0019003) described in SEQ ID NO: 153, a homolog or an ortholog of a different organism species, and the like. The hsa-miR-4476 gene can be obtained by a method described in Jima D D et al., 2010, Blood, Vol. 116, e118-e127. Also, "hsa-mir-4476" (miRBase Accession No. MI0016828, SEQ ID NO: 351) having a hairpin-like structure is known as a precursor of "hsa-miR-4476".

The term "hsa-miR-6885-5p gene" or "hsa-miR-6885-5p" used herein includes the hsa-miR-6885-5p gene (miRBase Accession No. MIMAT0027670) described in SEQ ID NO: 154, a homolog or an ortholog of a different organism species, and the like. The hsa-miR-6885-5p gene can be obtained by a method described in Ladewig E et al., 2012, Genome Res, Vol. 22, p. 1634-1645. Also, "hsa-mir-6885" (miRBase Accession No. MI0022732, SEQ ID NO: 352) having a hairpin-like structure is known as a precursor of "hsa-miR-6885-5p".

The term "hsa-miR-6769b-5p gene" or "hsa-miR-6769b-5p" used herein includes the hsa-miR-6769b-5p gene (miRBase Accession No. MIMAT0027620) described in SEQ ID NO: 155, a homolog or an ortholog of a different organism species, and the like. The hsa-miR-6769b-5p gene can be obtained by a method described in Ladewig E et al., 2012, Genome Res, Vol. 22, p. 1634-1645. Also, "hsa-mir-6769b" (miRBase Accession No. MI0022706. SEQ ID NO: 353) having a hairpin-like structure is known as a precursor of "hsa-miR-6769b-5p".

The term "hsa-miR-23b-3p gene" or "hsa-miR-23b-3p" used herein includes the hsa-miR-23b-3p gene (miRBase Accession No. MIMAT0000418) described in SEQ ID NO: 156, a homolog or an ortholog of a different organism species, and the like. The hsa-miR-23b-3p gene can be obtained by a method described in Lagos-Quintana M et al., 2002, Curr Biol, Vol. 12, p. 735-739. Also, "hsa-mir-23b" (miRBase Accession No. MI0000439, SEQ ID NO: 354) having a hairpin-like structure is known as a precursor of "hsa-miR-23b-3p".

The term "hsa-miR-1343-5p gene" or "hsa-miR-1343-5p" used herein includes the hsa-miR-1343-5p gene (miRBase Accession No. MIMAT0027038) described in SEQ ID NO: 157, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 202) having a hairpin-like structure is known as a precursor of "hsa-miR-1343-5p".

The term "hsa-miR-3621 gene" or "hsa-miR-3621" used herein includes the hsa-miR-3621 gene (miRBase Accession No. MIMAT0018002) described in SEQ ID NO: 158, a homolog or an ortholog of a different organism species, and the like. The hsa-miR-3621 gene can be obtained by a method described in Witten D et al., 2010. BMC Biol, Vol. 8, p. 58. Also, "hsa-mir-3621" (miRBase Accession No. MI0016012, SEQ ID NO: 355) having a hairpin-like structure is known as a precursor of "hsa-miR-3621".

The term "hsa-miR-4688 gene" or "hsa-miR-4688" used herein includes the hsa-miR-4688 gene (miRBase Accession No. MIMAT0019777) described in SEQ ID NO: 159, a homolog or an ortholog of a different organism species, and the like. The hsa-miR-4688 gene can be obtained by a method described in Persson H et al., 2011, Cancer Res, Vol. 71, p. 78-86. Also, "hsa-mir-4688" (miRBase Accession No. MI0017321, SEQ ID NO: 356) having a hairpin-like structure is known as a precursor of "hsa-miR-4688".

The term "hsa-miR-4286 gene" or "hsa-miR-4286" used herein includes the hsa-miR-4286 gene (miRBase Accession No. MIMAT0016916) described in SEQ ID NO: 160, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 357) having a hairpin-like structure is known as a precursor of "hsa-miR-4286".

The term "hsa-miR-4640-5p gene" or "hsa-miR-4640-5p" used herein includes the hsa-miR-4640-5p gene (miRBase Accession No. MIMAT0019699) described in SEQ ID NO:

161, a homolog or an ortholog of a different organism species, and the like. The hsa-miR-4640-5p gene can be obtained by a method described in Persson H et al., 2011, Cancer Res, Vol. 71, p. 78-86. Also, "hsa-mir-4640" (miRBase Accession No. MI0017267, SEQ ID NO: 358) having a hairpin-like structure is known as a precursor of "hsa-miR-4640-5p".

The term "hsa-miR-4739 gene" or "hsa-miR-4739" used herein includes the hsa-miR-4739 gene (miRBase Accession No. MIMAT0019868) described in SEQ ID NO: 162, a homolog or an ortholog of a different organism species, and the like. The hsa-miR-4739 gene can be obtained by a method described in Persson H et al., 2011, Cancer Res, Vol. 71, p. 78-86. Also, "hsa-mir-4739" (miRBase Accession No. MI0017377, SEQ ID NO: 359) having a hairpin-like structure is known as a precursor of "hsa-miR-4739".

The term "hsa-miR-1260a gene" or "hsa-miR-1260a" used herein includes the hsa-miR-1260a gene (miRBase Accession No. MIMAT0005911) described in SEQ ID NO: 163, a homolog or an ortholog of a different organism species, and the like. The hsa-miR-1260a gene can be obtained by a method described in Morin R D et al., 2008, Genome Res, Vol. 18, p. 610-621. Also, "hsa-mir-1260a" (miRBase Accession No. MI0006394, SEQ ID NO: 360) having a hairpin-like structure is known as a precursor of "hsa-miR-1260a".

The term "hsa-miR-4276 gene" or "hsa-miR-4276" used herein includes the hsa-miR-4276 gene (miRBase Accession No. MIMAT0016904) described in SEQ ID NO: 164, a homolog or an ortholog of a different organism species, and the like. The hsa-miR-4276 gene can be obtained by a method described in Goff L A et al., 2009, PLoS One, Vol. 4, e7192. Also, "hsa-mir-4276" (miRBase Accession No. MI0015882, SEQ ID NO: 361) having a hairpin-like structure is known as a precursor of "hsa-miR-4276".

The term "hsa-miR-7106-5p gene" or "hsa-miR-7106-5p" used herein includes the hsa-miR-7106-5p gene (miRBase Accession No. MIMAT0028109) described in SEQ ID NO: 165, a homolog or an ortholog of a different organism species, and the like. The hsa-miR-7106-5p gene can be obtained by a method described in Ladewig E et al., 2012, Genome Res, Vol. 22, p. 1634-1645. Also, "hsa-mir-7106" (miRBase Accession No. MI0022957. SEQ ID NO: 362) having a hairpin-like structure is known as a precursor of "hsa-miR-7106-5p".

The term "hsa-miR-128-2-5p gene" or "hsa-miR-128-2-5p" used herein includes the hsa-miR-128-2-5p gene (miRBase Accession No. MIMAT0031095) described in SEQ ID NO: 166, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No. MI0000727, SEQ ID NO: 363) having a hairpin-like structure is known as a precursor of "hsa-miR-128-2-5p".

The term "hsa-miR-125a-3p gene" or "hsa-miR-125a-3p" used herein includes the hsa-miR-125a-3p gene (miRBase Accession No. MIMAT0004602) described in SEQ ID NO: 167, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. MI0000469, SEQ ID NO: 364) having a hairpin-like structure is known as a precursor of "hsa-miR-125a-3p".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 168, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 365) having a hairpin-like structure is known as a precursor of "hsa-miR-92a-2-5p".

The term "hsa-miR-486-3p gene" or "hsa-miR-486-3p" used herein includes the hsa-miR-486-3p gene (miRBase Accession No. MIMAT0004762) described in SEQ ID NO: 169, a homolog or an ortholog of a different organism species, and the like. The hsa-miR-486-3p gene can be obtained by a method described in Fu H et al., 2005, FEBS Lett, Vol. 579, p. 3849-3854. Also, "hsa-mir-486 and hsa-mir-486-2" (miRBase Accession Nos. MI0002470 and MI0023622, SEQ ID NOs: 366 and 367) having a hairpin-like structure are known as precursors of "hsa-miR-486-3p".

The term "hsa-miR-3196 gene" or "hsa-miR-3196" used herein includes the hsa-miR-3196 gene (miRBase Accession No. MIMAT0015080) described in SEQ ID NO: 170, a homolog or an ortholog of a different organism species, and the like. The hsa-miR-3196 gene can be obtained by a method described in Stark M S et al., 2010, PLoS One, Vol. 5, e9685. Also, "hsa-mir-3196" (miRBase Accession No. MI0014241, SEQ ID NO: 368) having a hairpin-like structure is known as a precursor of "hsa-miR-3196".

The term "hsa-miR-211-3p gene" or "hsa-miR-211-3p" used herein includes the hsa-miR-211-3p gene (miRBase Accession No. MIMAT0022694) described in SEQ ID NO: 171, a homolog or an ortholog of a different organism species, and the like. The hsa-miR-211-3p gene can be obtained by a method described in Lim L P et al., 2003, Science, Vol. 299, p. 1540. Also, "hsa-mir-211" (miRBase Accession No. MI0000287, SEQ ID NO: 369) having a hairpin-like structure is known as a precursor of "hsa-miR-211-3p".

The term "hsa-miR-4271 gene" or "hsa-miR-4271" used herein includes the hsa-miR-4271 gene (miRBase Accession No. MIMAT0016901) described in SEQ ID NO: 172, a homolog or an ortholog of a different organism species, and the like. The hsa-miR-4271 gene can be obtained by a method described in Goff L A et al., 2009, PLoS One, Vol. 4, e7192. Also, "hsa-mir-4271" (miRBase Accession No. MI0015879, SEQ ID NO: 370) having a hairpin-like structure is known as a precursor of "hsa-miR-4271".

The term "hsa-miR-6851-5p gene" or "hsa-miR-6851-5p" used herein includes the hsa-miR-6851-5p gene (miRBase Accession No. MIMAT0027602) described in SEQ ID NO: 173, a homolog or an ortholog of a different organism species, and the like. The hsa-miR-6851-5p gene can be obtained by a method described in Ladewig E et al., 2012, Genome Res, Vol. 22, p. 1634-1645. Also, "hsa-mir-6851" (miRBase Accession No. MI0022697. SEQ ID NO: 371) having a hairpin-like structure is known as a precursor of "hsa-miR-6851-5p".

The term "hsa-miR-149-3p gene" or "hsa-miR-149-3p" used herein includes the hsa-miR-149-3p gene (miRBase Accession No. MIMAT0004609) described in SEQ ID NO: 174, a homolog or an ortholog of a different organism species, and the like. The hsa-miR-149-3p gene can be obtained by a method described in Lagos-Quintana M et al., 2002. Curr Biol, Vol. 12, p. 735-739. Also, "hsa-mir-149" (miRBase Accession No. MI0000478, SEQ ID NO: 372) having a hairpin-like structure is known as a precursor of "hsa-miR-149-3p".

The term "hsa-miR-4667-5p gene" or "hsa-miR-4667-5p" used herein includes the hsa-miR-4667-5p gene (miRBase Accession No. MIMAT0019743) described in SEQ ID NO: 175, a homolog or an ortholog of a different organism species, and the like. The hsa-miR-4667-5p gene can be obtained by a method described in Persson H et al., 2011, Cancer Res, Vol. 71, p. 78-86. Also, "hsa-mir-4667" (miRBase Accession No. MI0017297, SEQ ID NO: 373) having a hairpin-like structure is known as a precursor of "hsa-miR-4667-5p".

The term "hsa-miR-135a-3p gene" or "hsa-miR-135a-3p" used herein includes the hsa-miR-135a-3p gene (miRBase Accession No. MIMAT0004595) described in SEQ ID NO: 176, a homolog or an ortholog of a different organism species, and the like. The hsa-miR-135a-3p gene can be obtained by a method described in Lagos-Quintana M et al., 2002, Curr Biol, Vol. 12, p. 735-739. Also, "hsa-mir-135a-1" (miRBase Accession No. MI0000452, SEQ ID NO: 374) having a hairpin-like structure is known as a precursor of "hsa-miR-135a-3p".

The term "hsa-miR-4486 gene" or "hsa-miR-4486" used herein includes the hsa-miR-4486 gene (miRBase Accession No. MIMAT0019020) described in SEQ ID NO: 177, a homolog or an ortholog of a different organism species, and the like. The hsa-miR-4486 gene can be obtained by a method described in Jima D D et al., 2010, Blood, Vol. 116, e118-e127. Also, "hsa-mir-4486" (miRBase Accession No. MI0016847, SEQ ID NO: 375) having a hairpin-like structure is known as a precursor of "hsa-miR-4486".

The term "hsa-miR-4697-5p gene" or "hsa-miR-4697-5p" used herein includes the hsa-miR-4697-5p gene (miRBase Accession No. MIMAT0019791) described in SEQ ID NO: 178, a homolog or an ortholog of a different organism species, and the like. The hsa-miR-4697-5p gene can be obtained by a method described in Persson H et al., 2011, Cancer Res, Vol. 71, p. 78-86. Also, "hsa-mir-4697" (miRBase Accession No. MI0017330, SEQ ID NO: 376) having a hairpin-like structure is known as a precursor of "hsa-miR-4697-5p".

The term "hsa-miR-4725-3p gene" or "hsa-miR-4725-3p" used herein includes the hsa-miR-4725-3p gene (miRBase Accession No. MIMAT0019844) described in SEQ ID NO: 179, a homolog or an ortholog of a different organism species, and the like. The hsa-miR-4725-3p gene can be obtained by a method described in Persson H et al., 2011. Cancer Res, Vol. 71, p. 78-86. Also, "hsa-mir-4725" (miRBase Accession No. MI0017362, SEQ ID NO: 377) having a hairpin-like structure is known as a precursor of "hsa-miR-4725-3p".

The term "hsa-miR-6510-5p gene" or "hsa-miR-6510-5p" used herein includes the hsa-miR-6510-5p gene (miRBase Accession No. MIMAT0025476) described in SEQ ID NO: 180, a homolog or an ortholog of a different organism species, and the like. The hsa-miR-6510-5p gene can be obtained by a method described in Joyce C E et al., 2011, Hum Mol Genet, Vol. 20, p. 4025-4040. Also, "hsa-mir-6510" (miRBase Accession No. MI0022222, SEQ ID NO: 378) having a hairpin-like structure is known as a precursor of "hsa-miR-6510-5p".

The term "hsa-miR-5001-5p gene" or "hsa-miR-5001-5p" used herein includes the hsa-miR-5001-5p gene (miRBase Accession No. MIMAT0021021) described in SEQ ID NO: 181, a homolog or an ortholog of a different organism species, and the like. The hsa-miR-5001-5p gene can be obtained by a method described in Hansen T B et al., 2011, RNA Biol, Vol. 8, p. 378-383. Also, "hsa-mir-5001" (miRBase Accession No. MI0017867, SEQ ID NO: 379) having a hairpin-like structure is known as a precursor of "hsa-miR-5001-5p".

The term "hsa-miR-4673 gene" or "hsa-miR-4673" used herein includes the hsa-miR-4673 gene (miRBase Accession No. MIMAT0019755) described in SEQ ID NO: 182, a homolog or an ortholog of a different organism species, and the like. The hsa-miR-4673 gene can be obtained by a method described in Persson H et al., 2011, Cancer Res, Vol. 71, p. 78-86. Also, "hsa-mir-4673" (miRBase Accession No. MI0017304, SEQ ID NO: 380) having a hairpin-like structure is known as a precursor of "hsa-miR-4673".

The term "hsa-miR-4466 gene" or "hsa-miR-4466" used herein includes the hsa-miR-4466 gene (miRBase Accession No. MIMAT0018993) described in SEQ ID NO: 183, a homolog or an ortholog of a different organism species, and the like. The hsa-miR-4466 gene can be obtained by a method described in Jima D D et al., 2010. Blood, Vol. 116, e118-e127. Also, "hsa-mir-4466" (miRBase Accession No. MI0016817, SEQ ID NO: 381) having a hairpin-like structure is known as a precursor of "hsa-miR-4466".

The term "hsa-miR-23a-3p gene" or "hsa-miR-23a-3p" used herein includes the hsa-miR-23a-3p gene (miRBase Accession No. MIMAT0000078) described in SEQ ID NO: 184, a homolog or an ortholog of a different organism species, and the like. The hsa-miR-23a-3p gene can be obtained by a method described in Lagos-Quintana M et al., 2001, Science, Vol. 294, p. 853-858. Also, "hsa-mir-23a" (miRBase Accession No. MI0000079, SEQ ID NO: 382) having a hairpin-like structure is known as a precursor of "hsa-miR-23a-3p".

The term "hsa-miR-3656 gene" or "hsa-miR-3656" used herein includes the hsa-miR-3656 gene (miRBase Accession No. MIMAT0018076) described in SEQ ID NO: 185, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 383) having a hairpin-like structure is known as a precursor of "hsa-miR-3656".

The term "hsa-miR-6782-5p gene" or "hsa-miR-6782-5p" used herein includes the hsa-miR-6782-5p gene (miRBase Accession No. MIMAT0027464) described in SEQ ID NO: 186, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 384) having a hairpin-like structure is known as a precursor of "hsa-miR-6782-5p".

The term "hsa-miR-4689 gene" or "hsa-miR-4689" used herein includes the hsa-miR-4689 gene (miRBase Accession No. MIMAT0019778) described in SEQ ID NO: 187, a homolog or an ortholog of a different organism species, and the like. The hsa-miR-4689 gene can be obtained by a method described in Persson H et al., 2011. Cancer Res, Vol. 71, p. 78-86. Also, "hsa-mir-4689" (miRBase Accession No. MI0017322, SEQ ID NO: 385) having a hairpin-like structure is known as a precursor of "hsa-miR-4689".

The term "hsa-miR-451a gene" or "hsa-miR-451a" used herein includes the hsa-miR-451a gene (miRBase Accession No. MIMAT0001631) described in SEQ ID NO: 188, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 386) having a hairpin-like structure is known as a precursor of "hsa-miR-451a".

The term "hsa-miR-4446-3p gene" or "hsa-miR-4446-3p" used herein includes the hsa-miR-4446-3p gene (miRBase Accession No. MIMAT0018965) described in SEQ ID NO: 189, a homolog or an ortholog of a different organism species, and the like. The hsa-miR-4446-3p gene can be obtained by a method described in Jima D D et al., 2010, Blood, Vol. 116, e118-e127. Also, "hsa-mir-4446" (miRBase Accession No. MI0016789, SEQ ID NO: 387) having a hairpin-like structure is known as a precursor of "hsa-miR-4446-3p".

The term "hsa-miR-3180-3p gene" or "hsa-miR-3180-3p" used herein includes the hsa-miR-3180-3p gene (miRBase Accession No. MIMAT0015058) described in SEQ ID NO: 190, a homolog or an ortholog of a different organism species, and the like. The hsa-miR-3180-3p gene can be obtained by a method described in Creighton C J et al., 2010, PLoS One, Vol. 5, e9637. Also, "hsa-mir-3180-1, hsa-mir-3180-2, and hsa-mir-3180-3" (miRBase Accession Nos. MI0014214, MI0014215, and MI0014217, SEQ ID NOs: 388, 389, and 390) having a hairpin-like structure are known as precursors of "hsa-miR-3180-3p".

The term "hsa-miR-642a-3p gene" or "hsa-miR-642a-3p" used herein includes the hsa-miR-642a-3p gene (miRBase Accession No. MIMAT0020924) described in SEQ ID NO: 191, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692. Also, "hsa-mir-642a" (miRBase Accession No. MI0003657. SEQ ID NO: 391) having a hairpin-like structure is known as a precursor of "hsa-miR-642a-3p".

The term "hsa-miR-6889-5p gene" or "hsa-miR-6889-5p" used herein includes the hsa-miR-6889-5p gene (miRBase Accession No. MIMAT0027678) described in SEQ ID NO: 192, a homolog or an ortholog of a different organism species, and the like. The hsa-miR-6889-5p gene can be obtained by a method described in Ladewig E et al., 2012, Genome Res, Vol. 22, p. 1634-1645. Also, "hsa-mir-6889" (miRBase Accession No. MI0022736, SEQ ID NO: 392) having a hairpin-like structure is known as a precursor of "hsa-miR-6889-5p".

The term "hsa-miR-3178 gene" or "hsa-miR-3178" used herein includes the hsa-miR-3178 gene (miRBase Accession No. MIMAT0015055) described in SEQ ID NO: 193, a homolog or an ortholog of a different organism species, and the like. The hsa-miR-3178 gene can be obtained by a method described in Stark M S et al., 2010, PLoS One. Vol. 5, e9685. Also, "hsa-mir-3178" (miRBase Accession No. MI0014212, SEQ ID NO: 393) having a hairpin-like structure is known as a precursor of "hsa-miR-3178".

The term "hsa-miR-4665-5p gene" or "hsa-miR-4665-5p" used herein includes the hsa-miR-4665-5p gene (miRBase Accession No. MIMAT0019739) described in SEQ ID NO: 194, a homolog or an ortholog of a different organism species, and the like. The hsa-miR-4665-5p gene can be obtained by a method described in Persson H et al., 2011, Cancer Res, Vol. 71, p. 78-86. Also, "hsa-mir-4665" (miRBase Accession No. MI0017295, SEQ ID NO: 323) having a hairpin-like structure is known as a precursor of "hsa-miR-4665-5p".

The term "hsa-miR-6722-3p gene" or "hsa-miR-6722-3p" used herein includes the hsa-miR-6722-3p gene (miRBase Accession No. MIMAT0025854) described in SEQ ID NO: 195, a homolog or an ortholog of a different organism species, and the like. The hsa-miR-6722-3p gene can be obtained by a method described in Li Y et al., 2012, Gene, Vol. 497, p. 330-335. Also, "hsa-mir-6722" (miRBase Accession No. MI0022557, SEQ ID NO: 394) having a hairpin-like structure is known as a precursor of "hsa-miR-6722-3p".

The term "hsa-miR-30c-1-3p gene" or "hsa-miR-30c-1-3p" used herein includes the hsa-miR-30c-1-3p gene (miRBase Accession No. MIMAT0004674) described in SEQ ID NO: 196, a homolog or an ortholog of a different organism species, and the like. The hsa-miR-30c-1-3p gene can be obtained by a method described in Lagos-Quintana M et al., 2002, Curr Biol, Vol. 12, p. 735-739. Also, "hsa-mir-30c-1" (miRBase Accession No. MI0000736, SEQ ID NO: 395) having a hairpin-like structure is known as a precursor of "hsa-miR-30c-1-3p".

The term "hsa-miR-4507 gene" or "hsa-miR-4507" used herein includes the hsa-miR-4507 gene (miRBase Accession No. MIMAT0019044) described in SEQ ID NO: 197, a homolog or an ortholog of a different organism species, and the like. The hsa-miR-4507 gene can be obtained by a method described in Jima D D et al., 2010, Blood, Vol. 116, e118-e127. Also, "hsa-mir-4507" (miRBase Accession No. MI0016871, SEQ ID NO: 396) having a hairpin-like structure is known as a precursor of "hsa-miR-4507".

The term "hsa-miR-3141 gene" or "hsa-miR-3141" used herein includes the hsa-miR-3141 gene (miRBase Accession No. MIMAT0015010) described in SEQ ID NO: 198, a homolog or an ortholog of a different organism species, and the like. The hsa-miR-3141 gene can be obtained by a method described in Stark M S et al., 2010, PLoS One, Vol. 5, e9685. Also, "hsa-mir-3141" (miRBase Accession No. MI0014165, SEQ ID NO: 397) having a hairpin-like structure is known as a precursor of "hsa-miR-3141".

The term "hsa-miR-1199-5p gene" or "hsa-miR-1199-5p" used herein includes the hsa-miR-1199-5p gene (miRBase Accession No. MIMAT0031119) described in SEQ ID NO: 199, a homolog or an ortholog of a different organism species, and the like. The hsa-miR-1199-5p gene can be obtained by a method described in Salvi A et al., 2013, Int J Oncol, Vol. 42, p. 391-402. Also, "hsa-mir-1199" (miRBase Accession No. MI0020340, SEQ ID NO: 398) having a hairpin-like structure is known as a precursor of "hsa-miR-1199-5p".

The term "hsa-miR-6794-5p gene" or "hsa-miR-6794-5p" used herein includes the hsa-miR-6794-5p gene (miRBase Accession No. MIMAT0027488) described in SEQ ID NO: 635, a homolog or an ortholog of a different organism species, and the like. The hsa-miR-6794-5p gene can be obtained by a method described in Ladewig E et al., 2012, Genome Res, Vol. 22, p. 1634-1645. Also, "hsa-mir-6794" (miRBase Accession No. MI0022639, SEQ ID NO: 643) having a hairpin-like structure is known as a precursor of "hsa-miR-6794-5p".

The term "hsa-miR-6774-5p gene" or "hsa-miR-6774-5p" used herein includes the hsa-miR-6774-5p gene (miRBase Accession No. MIMAT0027448) described in SEQ ID NO: 636, a homolog or an ortholog of a different organism species, and the like. The hsa-miR-6774-5p gene can be obtained by a method described in Ladewig E et al., 2012, Genome Res, Vol. 22, p. 1634-1645. Also, "hsa-mir-6774" (miRBase Accession No. MI0022619. SEQ ID NO: 644) having a hairpin-like structure is known as a precursor of "hsa-miR-6774-5p".

The term "hsa-miR-4707-3p gene" or "hsa-miR-4707-3p" used herein includes the hsa-miR-4707-3p gene (miRBase Accession No. MIMAT0019808) described in SEQ ID NO:

637, a homolog or an ortholog of a different organism species, and the like. The hsa-miR-4707-3p gene can be obtained by a method described in Persson H et al., 2011, Cancer Res, Vol. 71, p. 78-86. Also, "hsa-mir-4707" (miR-Base Accession No. MI0017340, SEQ ID NO: 645) having a hairpin-like structure is known as a precursor of "hsa-miR-4707-3p".

The term "hsa-miR-4534 gene" or "hsa-miR-4534" used herein includes the hsa-miR-4534 gene (miRBase Accession No. MIMAT0019073) described in SEQ ID NO: 638, a homolog or an ortholog of a different organism species, and the like. The hsa-miR-4534 gene can be obtained by a method described in Jima D D et al., 2010, Blood., Vol. 116, e118-e127. Also, "hsa-mir-4534" (miRBase Accession No. MI0016901, SEQ ID NO: 646) having a hairpin-like structure is known as a precursor of "hsa-miR-4534".

The term "hsa-miR-4294 gene" or "hsa-miR-4294" used herein includes the hsa-miR-4294 gene (miRBase Accession No. MIMAT0016849) described in SEQ ID NO: 639, a homolog or an ortholog of a different organism species, and the like. The hsa-miR-4294 gene can be obtained by a method described in Goff L A et al., 2009, PLoS One., Vol. 4, e7192. Also, "hsa-mir-4294" (miRBase Accession No. MI0015827, SEQ ID NO: 647) having a hairpin-like structure is known as a precursor of "hsa-miR-4294".

The term "hsa-miR-6850-5p gene" or "hsa-miR-6850-5p" used herein includes the hsa-miR-6850-5p gene (miRBase Accession No. MIMAT0027600) described in SEQ ID NO: 640, a homolog or an ortholog of a different organism species, and the like. The hsa-miR-6850-5p gene can be obtained by a method described in Ladewig E et al., 2012, Genome Res., Vol. 22, p. 1634-1645. Also, "hsa-mir-6850" (miRBase Accession No. MI0022696. SEQ ID NO: 648) having a hairpin-like structure is known as a precursor of "hsa-miR-6850-5p".

The term "hsa-miR-6089 gene" or "hsa-miR-6089" used herein includes the hsa-miR-6089 gene (miRBase Accession No. MIMAT0023714) described in SEQ ID NO: 641, a homolog or an ortholog of a different organism species, and the like. The hsa-miR-6089 gene can be obtained by a method described in Yoo J K et al., 2012, Stem Cells Dev, Vol. 21, p. 2049-2057. Also, "hsa-mir-6089-1 and hsa-mir-6089-2" (miRBase Accession Nos. MI0020366 and MI0023563, SEQ ID NOs: 649 and 650) having a hairpin-like structure are known as precursors of "hsa-miR-6089".

The term "hsa-miR-671-5p gene" or "hsa-miR-671-5p" used herein includes the hsa-miR-671-5p gene (miRBase Accession No. MIMAT0003880) described in SEQ ID NO: 642, a homolog or an ortholog of a different organism species, and the like. The hsa-miR-671-5p gene can be obtained by a method described in Berezikov E et al., 2006, Genome Res, Vol. 16, p. 1289-1298. Also, "hsa-mir-671" (miRBase Accession No. MI0003760, SEQ ID NO: 651) having a hairpin-like structure is known as a precursor of "hsa-miR-671-5p".

A mature miRNA may become a variant due to the sequence cleaved shorter or longer by one to several flanking nucleotides or due to substitution of nucleotides when cleaved as the mature miRNA from its RNA precursor having a hairpin-like structure. This variant is called isomiR (Morin R D. et al., 2008, Genome Res., Vol. 18, p. 610-621). The miRBase Release 20 shows the nucleotide sequences represented by SEQ ID NOs: 1 to 199 and 635 to 642 as well as a large number of the nucleotide sequence variants and fragments represented by SEQ ID NOs: 399 to 634 and 652 to 657, called isomiRs. These variants can also be obtained as miRNAs having a nucleotide sequence represented by any of SEQ ID NOs: 1 to 199 and 635 to 642.

Specifically, among the variants of polynucleotides consisting of the nucleotide sequence represented by any of SEQ ID NOs: 3, 4, 11, 13, 14, 18, 20, 21, 26, 29, 35, 36, 39, 41, 42, 45, 46, 47, 48, 49, 51, 53, 54, 55, 56, 57, 58, 59, 60, 62, 65, 66, 67, 68, 71, 72, 73, 74, 75, 76, 78, 82, 83, 88, 90, 91, 92, 94, 95, 98, 99, 101, 102, 103, 104, 106, 107, 108, 109, 110, 113, 116, 117, 118, 120, 121, 122, 123, 125, 128, 129, 130, 131, 137, 140, 141, 143, 144, 145, 146, 147, 150, 152, 153, 156, 159, 160, 161, 162, 163, 166, 167, 168, 169, 170, 171, 172, 174, 175, 176, 177, 179, 180, 181, 182, 183, 184, 185, 187, 188, 189, 190, 191, 193, 194, 196, 197, 198, 637, 641 and 642 or a nucleotide sequence derived from the nucleotide sequence by the replacement of u with t according to the present invention, examples of the longest variants registered in the miRBase Release 20 include polynucleotides represented by SEQ ID NOs: 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 607, 609, 611, 613, 615, 617, 619, 621, 623, 625, 627, 629, 631, 633, 652, 654 and 656, respectively.

Also, among the variants of polynucleotides consisting of a nucleotide sequence represented by any of SEQ ID NOs: 3, 4, 11, 13, 14, 18, 20, 21, 26, 29, 35, 36, 39, 41, 42, 45, 46, 47, 48, 49, 51, 53, 54, 55, 56, 57, 58, 59, 60, 62, 65, 66, 67, 68, 71, 72, 73, 74, 75, 76, 78, 82, 83, 88, 90, 91, 92, 94, 95, 98, 99, 101, 102, 103, 104, 106, 107, 108, 109, 110, 113, 116, 117, 118, 120, 121, 122, 123, 125, 128, 129, 130, 131, 137, 140, 141, 143, 144, 145, 146, 147, 150, 152, 153, 156, 159, 160, 161, 162, 163, 166, 167, 168, 169, 170, 171, 172, 174, 175, 176, 177, 179, 180, 181, 182, 183, 184, 185, 187, 188, 189, 190, 191, 193, 194, 196, 197, 198, 637, 641 and 642 or a nucleotide sequence derived from the nucleotide sequence by the replacement of u with t according to the present invention, examples of the shortest variants registered in the miRBase Release 20 include polynucleotides having sequences represented by SEQ ID NOs: 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 653, 655 and 657, respectively. In addition to these variants and fragments, examples thereof include a large number of isomiR polynucleotides of SEQ ID NOs: 1 to 199 and 635 to 642 registered in the miRBase. Examples of the polynucleotide comprising a nucleotide sequence represented by any of SEQ ID NOs: 1 to 199 and 635 to 642 include a polynucleotide represented by any of SEQ ID NOs: 200 to 398 and 643 to 651, which are their respective precursors.

The terms and miRBase Accession Nos. (registration numbers) of the genes represented by SEQ ID NOs: 1 to 657 are shown in Table 1.

The term "capable of specifically binding" used herein means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-4257 | MIMAT0016878 |
| 2 | hsa-miR-6726-5p | MIMAT0027353 |
| 3 | hsa-miR-1343-3p | MIMAT0019776 |
| 4 | hsa-miR-1247-3p | MIMAT0022721 |
| 5 | hsa-miR-6787-5p | MIMAT0027474 |
| 6 | hsa-miR-6875-5p | MIMAT0027650 |
| 7 | hsa-miR-1225-3p | MIMAT0005573 |
| 8 | hsa-miR-8063 | MIMAT0030990 |
| 9 | hsa-miR-6781-5p | MIMAT0027462 |
| 10 | hsa-miR-4746-3p | MIMAT0019881 |
| 11 | hsa-miR-1908-5p | MIMAT0007881 |
| 12 | hsa-miR-6756-5p | MIMAT0027412 |
| 13 | hsa-miR-204-3p | MIMAT0022693 |
| 14 | hsa-miR-4651 | MIMAT0019715 |
| 15 | hsa-miR-6757-5p | MIMAT0027414 |
| 16 | hsa-miR-6825-5p | MIMAT0027550 |
| 17 | hsa-miR-7108-5p | MIMAT0028113 |
| 18 | hsa-miR-4792 | MIMAT0019964 |
| 19 | hsa-miR-7641 | MIMAT0029782 |
| 20 | hsa-miR-3188 | MIMAT0015070 |
| 21 | hsa-miR-3131 | MIMAT0014996 |
| 22 | hsa-miR-6780b-5p | MIMAT0027572 |
| 23 | hsa-miR-8069 | MIMAT0030996 |
| 24 | hsa-miR-6840-3p | MIMAT0027583 |
| 25 | hsa-miR-8072 | MIMAT0030999 |
| 26 | hsa-miR-1233-5p | MIMAT0022943 |
| 27 | hsa-miR-6887-5p | MIMAT0027674 |
| 28 | hsa-miR-1231 | MIMAT0005586 |
| 29 | hsa-miR-5572 | MIMAT0022260 |
| 30 | hsa-miR-6738-5p | MIMAT0027377 |
| 31 | hsa-miR-6784-5p | MIMAT0027468 |
| 32 | hsa-miR-6791-5p | MIMAT0027482 |
| 33 | hsa-miR-6749-5p | MIMAT0027398 |
| 34 | hsa-miR-6741-5p | MIMAT0027383 |
| 35 | hsa-miR-128-1-5p | MIMAT0026477 |
| 36 | hsa-miR-4419b | MIMAT0019034 |
| 37 | hsa-miR-6746-5p | MIMAT0027392 |
| 38 | hsa-miR-3184-5p | MIMAT0015064 |
| 39 | hsa-miR-3679-5p | MIMAT0018104 |
| 40 | hsa-miR-7110-5p | MIMAT0028117 |
| 41 | hsa-miR-4516 | MIMAT0019053 |
| 42 | hsa-miR-6717-5p | MIMAT0025846 |
| 43 | hsa-miR-6826-5p | MIMAT0027552 |
| 44 | hsa-miR-4433b-3p | MIMAT0030414 |
| 45 | hsa-miR-3679-3p | MIMAT0018105 |
| 46 | hsa-miR-3135b | MIMAT0018985 |
| 47 | hsa-miR-3622a-5p | MIMAT0018003 |
| 48 | hsa-miR-711 | MIMAT0012734 |
| 49 | hsa-miR-4467 | MIMAT0018994 |
| 50 | hsa-miR-6857-5p | MIMAT0027614 |
| 51 | hsa-miR-6515-3p | MIMAT0025487 |
| 52 | hsa-miR-1225-5p | MIMAT0005572 |
| 53 | hsa-miR-187-5p | MIMAT0004561 |
| 54 | hsa-miR-3185 | MIMAT0015065 |
| 55 | hsa-miR-642b-3p | MIMAT0018444 |
| 56 | hsa-miR-1249 | MIMAT0005901 |
| 57 | hsa-miR-744-5p | MIMAT0004945 |
| 58 | hsa-miR-4442 | MIMAT0018960 |
| 59 | hsa-miR-1228-3p | MIMAT0005583 |
| 60 | hsa-miR-939-5p | MIMAT0004982 |
| 61 | hsa-miR-6845-5p | MIMAT0027590 |
| 62 | hsa-miR-887-3p | MIMAT0004951 |
| 63 | hsa-miR-7845-5p | MIMAT0030420 |
| 64 | hsa-miR-6729-5p | MIMAT0027359 |
| 65 | hsa-miR-4632-5p | MIMAT0022977 |
| 66 | hsa-miR-615-5p | MIMAT0004804 |
| 67 | hsa-miR-6724-5p | MIMAT0025856 |
| 68 | hsa-miR-4728-5p | MIMAT0019849 |
| 69 | hsa-miR-6732-5p | MIMAT0027365 |
| 70 | hsa-miR-6816-5p | MIMAT0027532 |
| 71 | hsa-miR-4695-5p | MIMAT0019788 |
| 72 | hsa-miR-6088 | MIMAT0023713 |
| 73 | hsa-miR-7975 | MIMAT0031178 |
| 74 | hsa-miR-3197 | MIMAT0015082 |
| 75 | hsa-miR-6125 | MIMAT0024598 |
| 76 | hsa-miR-4433-3p | MIMAT0018949 |
| 77 | hsa-miR-6727-5p | MIMAT0027355 |
| 78 | hsa-miR-4706 | MIMAT0019806 |
| 79 | hsa-miR-7847-3p | MIMAT0030422 |
| 80 | hsa-miR-6805-3p | MIMAT0027511 |
| 81 | hsa-miR-6766-3p | MIMAT0027433 |
| 82 | hsa-miR-1913 | MIMAT0007888 |
| 83 | hsa-miR-4649-5p | MIMAT0019711 |
| 84 | hsa-miR-602 | MIMAT0003270 |
| 85 | hsa-miR-3663-3p | MIMAT0018085 |
| 86 | hsa-miR-6893-5p | MIMAT0027686 |
| 87 | hsa-miR-6861-5p | MIMAT0027623 |
| 88 | hsa-miR-4449 | MIMAT0018968 |
| 89 | hsa-miR-6842-5p | MIMAT0027586 |
| 90 | hsa-miR-4454 | MIMAT0018976 |
| 91 | hsa-miR-5195-3p | MIMAT0021127 |
| 92 | hsa-miR-663b | MIMAT0005867 |
| 93 | hsa-miR-6765-5p | MIMAT0027430 |
| 94 | hsa-miR-4513 | MIMAT0019050 |
| 95 | hsa-miR-614 | MIMAT0003282 |
| 96 | hsa-miR-6785-5p | MIMAT0027470 |
| 97 | hsa-miR-6777-5p | MIMAT0027454 |
| 98 | hsa-miR-940 | MIMAT0004983 |
| 99 | hsa-miR-4741 | MIMAT0019871 |
| 100 | hsa-miR-6870-5p | MIMAT0027640 |
| 101 | hsa-miR-6131 | MIMAT0024615 |
| 102 | hsa-miR-150-3p | MIMAT0004610 |
| 103 | hsa-miR-4707-5p | MIMAT0019807 |
| 104 | hsa-miR-1915-3p | MIMAT0007892 |
| 105 | hsa-miR-3937 | MIMAT0018352 |
| 106 | hsa-miR-937-5p | MIMAT0022938 |
| 107 | hsa-miR-4443 | MIMAT0018961 |
| 108 | hsa-miR-1914-3p | MIMAT0007890 |
| 109 | hsa-miR-3620-5p | MIMAT0022967 |
| 110 | hsa-miR-1268b | MIMAT0018925 |
| 111 | hsa-miR-1227-5p | MIMAT0022941 |
| 112 | hsa-miR-6880-5p | MIMAT0027660 |
| 113 | hsa-miR-4417 | MIMAT0018929 |
| 114 | hsa-miR-6802-5p | MIMAT0027504 |
| 115 | hsa-miR-6769a-5p | MIMAT0027438 |
| 116 | hsa-miR-663a | MIMAT0003326 |
| 117 | hsa-miR-6721-5p | MIMAT0025852 |
| 118 | hsa-miR-4532 | MIMAT0019071 |
| 119 | hsa-miR-7977 | MIMAT0031180 |
| 120 | hsa-miR-92b-5p | MIMAT0004792 |
| 121 | hsa-miR-371a-5p | MIMAT0004687 |
| 122 | hsa-miR-6126 | MIMAT0024599 |
| 123 | hsa-miR-4734 | MIMAT0019859 |
| 124 | hsa-miR-4665-3p | MIMAT0019740 |
| 125 | hsa-miR-423-5p | MIMAT0004748 |
| 126 | hsa-miR-1469 | MIMAT0007347 |
| 127 | hsa-miR-4675 | MIMAT0019757 |
| 128 | hsa-miR-1915-5p | MIMAT0007891 |
| 129 | hsa-miR-6716-5p | MIMAT0025844 |
| 130 | hsa-miR-718 | MIMAT0012735 |
| 131 | hsa-miR-4281 | MIMAT0016907 |
| 132 | hsa-miR-6820-5p | MIMAT0027540 |
| 133 | hsa-miR-6795-5p | MIMAT0027490 |
| 134 | hsa-miR-6779-5p | MIMAT0027458 |
| 135 | hsa-miR-7109-5p | MIMAT0028115 |
| 136 | hsa-miR-6798-5p | MIMAT0027496 |
| 137 | hsa-miR-4648 | MIMAT0019710 |
| 138 | hsa-miR-8059 | MIMAT0030986 |
| 139 | hsa-miR-6765-3p | MIMAT0027431 |
| 140 | hsa-miR-6132 | MIMAT0024616 |
| 141 | hsa-miR-4492 | MIMAT0019027 |
| 142 | hsa-miR-7107-5p | MIMAT0028111 |
| 143 | hsa-miR-3195 | MIMAT0015079 |
| 144 | hsa-miR-3180 | MIMAT0018178 |
| 145 | hsa-miR-296-3p | MIMAT0004679 |
| 146 | hsa-miR-564 | MIMAT0003228 |
| 147 | hsa-miR-1268a | MIMAT0005922 |
| 148 | hsa-miR-6848-5p | MIMAT0027596 |
| 149 | hsa-miR-762 | MIMAT0010313 |
| 150 | hsa-miR-2861 | MIMAT0013802 |

TABLE 1-continued

| SEQ ID NO: | Gene name | miRBase registration No. |
|---|---|---|
| 151 | hsa-miR-1203 | MIMAT0005866 |
| 152 | hsa-miR-1260b | MIMAT0015041 |
| 153 | hsa-miR-4476 | MIMAT0019003 |
| 154 | hsa-miR-6885-5p | MIMAT0027670 |
| 155 | hsa-miR-6769b-5p | MIMAT0027620 |
| 156 | hsa-miR-23b-3p | MIMAT0000418 |
| 157 | hsa-miR-1343-5p | MIMAT0027038 |
| 158 | hsa-miR-3621 | MIMAT0018002 |
| 159 | hsa-miR-4688 | MIMAT0019777 |
| 160 | hsa-miR-4286 | MIMAT0016916 |
| 161 | hsa-miR-4640-5p | MIMAT0019699 |
| 162 | hsa-miR-4739 | MIMAT0019868 |
| 163 | hsa-miR-1260a | MIMAT0005911 |
| 164 | hsa-miR-4276 | MIMAT0016904 |
| 165 | hsa-miR-7106-5p | MIMAT0028109 |
| 166 | hsa-miR-128-2-5p | MIMAT0031095 |
| 167 | hsa-miR-125a-3p | MIMAT0004602 |
| 168 | hsa-miR-92a-2-5p | MIMAT0004508 |
| 169 | hsa-miR-486-3p | MIMAT0004762 |
| 170 | hsa-miR-3196 | MIMAT0015080 |
| 171 | hsa-miR-211-3p | MIMAT0022694 |
| 172 | hsa-miR-4271 | MIMAT0016901 |
| 173 | hsa-miR-6851-5p | MIMAT0027602 |
| 174 | hsa-miR-149-3p | MIMAT0004609 |
| 175 | hsa-miR-4667-5p | MIMAT0019743 |
| 176 | hsa-miR-135a-3p | MIMAT0004595 |
| 177 | hsa-miR-4486 | MIMAT0019020 |
| 178 | hsa-miR-4697-5p | MIMAT0019791 |
| 179 | hsa-miR-4725-3p | MIMAT0019844 |
| 180 | hsa-miR-6510-5p | MIMAT0025476 |
| 181 | hsa-miR-5001-5p | MIMAT0021021 |
| 182 | hsa-miR-4673 | MIMAT0019755 |
| 183 | hsa-miR-4466 | MIMAT0018993 |
| 184 | hsa-miR-23a-3p | MIMAT0000078 |
| 185 | hsa-miR-3656 | MIMAT0018076 |
| 186 | hsa-miR-6782-5p | MIMAT0027464 |
| 187 | hsa-miR-4689 | MIMAT0019778 |
| 188 | hsa-miR-451a | MIMAT0001631 |
| 189 | hsa-miR-4446-3p | MIMAT0018965 |
| 190 | hsa-miR-3180-3p | MIMAT0015058 |
| 191 | hsa-miR-642a-3p | MIMAT0020924 |
| 192 | hsa-miR-6889-5p | MIMAT0027678 |
| 193 | hsa-miR-3178 | MIMAT0015055 |
| 194 | hsa-miR-4665-5p | MIMAT0019739 |
| 195 | hsa-miR-6722-3p | MIMAT0025854 |
| 196 | hsa-miR-30c-1-3p | MIMAT0004674 |
| 197 | hsa-miR-4507 | MIMAT0019044 |
| 198 | hsa-miR-3141 | MIMAT0015010 |
| 199 | hsa-miR-1199-5p | MIMAT0031119 |
| 200 | hsa-mir-4257 | MI0015856 |
| 201 | hsa-mir-6726 | MI0022571 |
| 202 | hsa-mir-1343 | MI0017320 |
| 203 | hsa-mir-1247 | MI0006382 |
| 204 | hsa-mir-6787 | MI0022632 |
| 205 | hsa-mir-6875 | MI0022722 |
| 206 | hsa-mir-1225 | MI0006311 |
| 207 | hsa-mir-8063 | MI0025899 |
| 208 | hsa-mir-6781 | MI0022626 |
| 209 | hsa-mir-4746 | MI0017385 |
| 210 | hsa-mir-1908 | MI0008329 |
| 211 | hsa-mir-6756 | MI0022601 |
| 212 | hsa-mir-204 | MI0000284 |
| 213 | hsa-mir-4651 | MI0017279 |
| 214 | hsa-mir-6757 | MI0022602 |
| 215 | hsa-mir-6825 | MI0022670 |
| 216 | hsa-mir-7108 | MI0022959 |
| 217 | hsa-mir-4792 | MI0017439 |
| 218 | hsa-mir-7641-1 | MI0024975 |
| 219 | hsa-mir-7641-2 | MI0024976 |
| 220 | hsa-mir-3188 | MI0014232 |
| 221 | hsa-mir-3131 | MI0014151 |
| 222 | hsa-mir-6780b | MI0022681 |
| 223 | hsa-mir-8069 | MI0025905 |
| 224 | hsa-mir-6840 | MI0022686 |
| 225 | hsa-mir-8072 | MI0025908 |
| 226 | hsa-mir-1233-1 | MI0006323 |
| 227 | hsa-mir-1233-2 | MI0015973 |
| 228 | hsa-mir-6887 | MI0022734 |
| 229 | hsa-mir-1231 | MI0006321 |
| 230 | hsa-mir-5572 | MI0019117 |
| 231 | hsa-mir-6738 | MI0022583 |
| 232 | hsa-mir-6784 | MI0022629 |
| 233 | hsa-mir-6791 | MI0022636 |
| 234 | hsa-mir-6749 | MI0022594 |
| 235 | hsa-mir-6741 | MI0022586 |
| 236 | hsa-mir-128-1 | MI0000447 |
| 237 | hsa-mir-4419b | MI0016861 |
| 238 | hsa-mir-6746 | MI0022591 |
| 239 | hsa-mir-3184 | MI0014226 |
| 240 | hsa-mir-3679 | MI0016080 |
| 241 | hsa-mir-7110 | MI0022961 |
| 242 | hsa-mir-4516 | MI0016882 |
| 243 | hsa-mir-6717 | MI0022551 |
| 244 | hsa-mir-6826 | MI0022671 |
| 245 | hsa-mir-4433 | MI0025511 |
| 246 | hsa-mir-3135b | MI0016809 |
| 247 | hsa-mir-3622a | MI0016013 |
| 248 | hsa-mir-711 | MI0012488 |
| 249 | hsa-mir-4467 | MI0016818 |
| 250 | hsa-mir-6857 | MI0022703 |
| 251 | hsa-mir-6515 | MI0022227 |
| 252 | hsa-mir-187 | MI0000274 |
| 253 | hsa-mir-3185 | MI0014227 |
| 254 | hsa-mir-642b | MI0016685 |
| 255 | hsa-mir-1249 | MI0006384 |
| 256 | hsa-mir-744 | MI0005559 |
| 257 | hsa-mir-4442 | MI0016785 |
| 258 | hsa-mir-1228 | MI0006318 |
| 259 | hsa-mir-939 | MI0005761 |
| 260 | hsa-mir-6845 | MI0022691 |
| 261 | hsa-mir-887 | MI0005562 |
| 262 | hsa-mir-7845 | MI0025515 |
| 263 | hsa-mir-6729 | MI0022574 |
| 264 | hsa-mir-4632 | MI0017259 |
| 265 | hsa-mir-615 | MI0003628 |
| 266 | hsa-mir-6724 | MI0022559 |
| 267 | hsa-mir-4728 | MI0017365 |
| 268 | hsa-mir-6732 | MI0022577 |
| 269 | hsa-mir-6816 | MI0022661 |
| 270 | hsa-mir-4695 | MI0017328 |
| 271 | hsa-mir-6088 | MI0020365 |
| 272 | hsa-mir-7975 | MI0025751 |
| 273 | hsa-mir-3197 | MI0014245 |
| 274 | hsa-mir-6125 | MI0021259 |
| 275 | hsa-mir-4433 | MI0016773 |
| 276 | hsa-mir-6727 | MI0022572 |
| 277 | hsa-mir-4706 | MI0017339 |
| 278 | hsa-mir-7847 | MI0025517 |
| 279 | hsa-mir-6805 | MI0022650 |
| 280 | hsa-mir-6766 | MI0022611 |
| 281 | hsa-mir-1913 | MI0008334 |
| 282 | hsa-mir-4649 | MI0017276 |
| 283 | hsa-mir-602 | MI0003615 |
| 284 | hsa-mir-3663 | MI0016064 |
| 285 | hsa-mir-6893 | MI0022740 |
| 286 | hsa-mir-6861 | MI0022708 |
| 287 | hsa-mir-4449 | MI0016792 |
| 288 | hsa-mir-6842 | MI0022688 |
| 289 | hsa-mir-4454 | MI0016800 |
| 290 | hsa-mir-5195 | MI0018174 |
| 291 | hsa-mir-663b | MI0006336 |
| 292 | hsa-mir-6765 | MI0022610 |
| 293 | hsa-mir-4513 | MI0016879 |
| 294 | hsa-mir-614 | MI0003627 |
| 295 | hsa-mir-6785 | MI0022630 |
| 296 | hsa-mir-6777 | MI0022622 |
| 297 | hsa-mir-940 | MI0005762 |
| 298 | hsa-mir-4741 | MI0017379 |
| 299 | hsa-mir-6870 | MI0022717 |
| 300 | hsa-mir-6131 | MI0021276 |
| 301 | hsa-mir-150 | MI0000479 |
| 302 | hsa-mir-4707 | MI0017340 |
| 303 | hsa-mir-1915 | MI0008336 |
| 304 | hsa-mir-3937 | MI0016593 |

TABLE 1-continued

| SEQ ID NO: | Gene name | miRBase registration No. |
|---|---|---|
| 305 | hsa-mir-937 | MI0005759 |
| 306 | hsa-mir-4443 | MI0016786 |
| 307 | hsa-mir-1914 | MI0008335 |
| 308 | hsa-mir-3620 | MI0016011 |
| 309 | hsa-mir-1268b | MI0016748 |
| 310 | hsa-mir-1227 | MI0006316 |
| 311 | hsa-mir-6880 | MI0022727 |
| 312 | hsa-mir-4417 | MI0016753 |
| 313 | hsa-mir-6802 | MI0022647 |
| 314 | hsa-mir-6769a | MI0022614 |
| 315 | hsa-mir-663a | MI0003672 |
| 316 | hsa-mir-6721 | MI0022556 |
| 317 | hsa-mir-4532 | MI0016899 |
| 318 | hsa-mir-7977 | MI0025753 |
| 319 | hsa-mir-92b | MI0003560 |
| 320 | hsa-mir-371a | MI0000779 |
| 321 | hsa-mir-6126 | MI0021260 |
| 322 | hsa-mir-4734 | MI0017371 |
| 323 | hsa-mir-4665 | MI0017295 |
| 324 | hsa-mir-423 | MI0001445 |
| 325 | hsa-mir-1469 | MI0007074 |
| 326 | hsa-mir-4675 | MI0017306 |
| 327 | hsa-mir-6716 | MI0022550 |
| 328 | hsa-mir-718 | MI0012489 |
| 329 | hsa-mir-4281 | MI0015885 |
| 330 | hsa-mir-6820 | MI0022665 |
| 331 | hsa-mir-6795 | MI0022640 |
| 332 | hsa-mir-6779 | MI0022624 |
| 333 | hsa-mir-7109 | MI0022960 |
| 334 | hsa-mir-6798 | MI0022643 |
| 335 | hsa-mir-4648 | MI0017275 |
| 336 | hsa-mir-8059 | MI0025895 |
| 337 | hsa-mir-6132 | MI0021277 |
| 338 | hsa-mir-4492 | MI0016854 |
| 339 | hsa-mir-7107 | MI0022958 |
| 340 | hsa-mir-3195 | MI0014240 |
| 341 | hsa-mir-3180-4 | MI0016408 |
| 342 | hsa-mir-3180-5 | MI0016409 |
| 343 | hsa-mir-296 | MI0000747 |
| 344 | hsa-mir-564 | MI0003570 |
| 345 | hsa-mir-1268a | MI0006405 |
| 346 | hsa-mir-6848 | MI0022694 |
| 347 | hsa-mir-762 | MI0003892 |
| 348 | hsa-mir-2861 | MI0013006 |
| 349 | hsa-mir-1203 | MI0006335 |
| 350 | hsa-mir-1260b | MI0014197 |
| 351 | hsa-mir-4476 | MI0016828 |
| 352 | hsa-mir-6885 | MI0022732 |
| 353 | hsa-mir-6769b | MI0022706 |
| 354 | hsa-mir-23b | MI0000439 |
| 355 | hsa-mir-3621 | MI0016012 |
| 356 | hsa-mir-4688 | MI0017321 |
| 357 | hsa-mir-4286 | MI0015894 |
| 358 | hsa-mir-4640 | MI0017267 |
| 359 | hsa-mir-4739 | MI0017377 |
| 360 | hsa-mir-1260a | MI0006394 |
| 361 | hsa-mir-4276 | MI0015882 |
| 362 | hsa-mir-7106 | MI0022957 |
| 363 | hsa-mir-128-2 | MI0000727 |
| 364 | hsa-mir-125a | MI0000469 |
| 365 | hsa-mir-92a-2 | MI0000094 |
| 366 | hsa-mir-486 | MI0002470 |
| 367 | hsa-mir-486-2 | MI0023622 |
| 368 | hsa-mir-3196 | MI0014241 |
| 369 | hsa-mir-211 | MI0000287 |
| 370 | hsa-mir-4271 | MI0015879 |
| 371 | hsa-mir-6851 | MI0022697 |
| 372 | hsa-mir-149 | MI0000478 |
| 373 | hsa-mir-4667 | MI0017297 |
| 374 | hsa-mir-135a-1 | MI0000452 |
| 375 | hsa-mir-4486 | MI0016847 |
| 376 | hsa-mir-4697 | MI0017330 |
| 377 | hsa-mir-4725 | MI0017362 |
| 378 | hsa-mir-6510 | MI0022222 |
| 379 | hsa-mir-5001 | MI0017867 |
| 380 | hsa-mir-4673 | MI0017304 |
| 381 | hsa-mir-4466 | MI0016817 |
| 382 | hsa-mir-23a | MI0000079 |
| 383 | hsa-mir-3656 | MI0016056 |
| 384 | hsa-mir-6782 | MI0022627 |
| 385 | hsa-mir-4689 | MI0017322 |
| 386 | hsa-mir-451a | MI0001729 |
| 387 | hsa-mir-4446 | MI0016789 |
| 388 | hsa-mir-3180-1 | MI0014214 |
| 389 | hsa-mir-3180-2 | MI0014215 |
| 390 | hsa-mir-3180-3 | MI0014217 |
| 391 | hsa-mir-642a | MI0003657 |
| 392 | hsa-mir-6889 | MI0022736 |
| 393 | hsa-mir-3178 | MI0014212 |
| 394 | hsa-mir-6722 | MI0022557 |
| 395 | hsa-mir-30c-1 | MI0000736 |
| 396 | hsa-mir-4507 | MI0016871 |
| 397 | hsa-mir-3141 | MI0014165 |
| 398 | hsa-mir-1199 | MI0020340 |
| 399 | isomiR example 1 of SEQ ID NO: 3 | — |
| 400 | isomiR example 2 of SEQ ID NO: 3 | — |
| 401 | isomiR example 1 of SEQ ID NO: 4 | — |
| 402 | isomiR example 2 of SEQ ID NO: 4 | — |
| 403 | isomiR example 1 of SEQ ID NO: 11 | — |
| 404 | isomiR example 2 of SEQ ID NO: 11 | — |
| 405 | isomiR example 1 of SEQ ID NO: 13 | — |
| 406 | isomiR example 2 of SEQ ID NO: 13 | — |
| 407 | isomiR example 1 of SEQ ID NO: 14 | — |
| 408 | isomiR example 2 of SEQ ID NO: 14 | — |
| 409 | isomiR example 1 of SEQ ID NO: 18 | — |
| 410 | isomiR example 2 of SEQ ID NO: 18 | — |
| 411 | isomiR example 1 of SEQ ID NO: 20 | — |
| 412 | isomiR example 2 of SEQ ID NO: 20 | — |
| 413 | isomiR example 1 of SEQ ID NO: 21 | — |
| 414 | isomiR example 2 of SEQ ID NO: 21 | — |
| 415 | isomiR example 1 of SEQ ID NO: 26 | — |
| 416 | isomiR example 2 of SEQ ID NO: 26 | — |
| 417 | isomiR example 1 of SEQ ID NO: 29 | — |
| 418 | isomiR example 2 of SEQ ID NO: 29 | — |
| 419 | isomiR example 1 of SEQ ID NO: 35 | — |
| 420 | isomiR example 2 of SEQ ID NO: 35 | — |
| 421 | isomiR example 1 of SEQ ID NO: 36 | — |
| 422 | isomiR example 2 of SEQ ID NO: 36 | — |
| 423 | isomiR example 1 of SEQ ID NO: 39 | — |
| 424 | isomiR example 2 of SEQ ID NO: 39 | — |
| 425 | isomiR example 1 of SEQ ID NO: 41 | — |
| 426 | isomiR example 2 of SEQ ID NO: 41 | — |
| 427 | isomiR example 1 of SEQ ID NO: 42 | — |
| 428 | isomiR example 2 of SEQ ID NO: 42 | — |
| 429 | isomiR example 1 of SEQ ID NO: 45 | — |
| 430 | isomiR example 2 of SEQ ID NO: 45 | — |
| 431 | isomiR example 1 of SEQ ID NO: 46 | — |
| 432 | isomiR example 2 of SEQ ID NO: 46 | — |
| 433 | isomiR example 1 of SEQ ID NO: 47 | — |
| 434 | isomiR example 2 of SEQ ID NO: 47 | — |
| 435 | isomiR example 1 of SEQ ID NO: 48 | — |
| 436 | isomiR example 2 of SEQ ID NO: 48 | — |
| 437 | isomiR example 1 of SEQ ID NO: 49 | — |
| 438 | isomiR example 2 of SEQ ID NO: 49 | — |
| 439 | isomiR example 1 of SEQ ID NO: 51 | — |
| 440 | isomiR example 2 of SEQ ID NO: 51 | — |
| 441 | isomiR example 1 of SEQ ID NO: 53 | — |
| 442 | isomiR example 2 of SEQ ID NO: 53 | — |
| 443 | isomiR example 1 of SEQ ID NO: 54 | — |
| 444 | isomiR example 2 of SEQ ID NO: 54 | — |
| 445 | isomiR example 1 of SEQ ID NO: 55 | — |
| 446 | isomiR example 2 of SEQ ID NO: 55 | — |
| 447 | isomiR example 1 of SEQ ID NO: 56 | — |
| 448 | isomiR example 2 of SEQ ID NO: 56 | — |
| 449 | isomiR example 1 of SEQ ID NO: 57 | — |
| 450 | isomiR example 2 of SEQ ID NO: 57 | — |
| 451 | isomiR example 1 of SEQ ID NO: 58 | — |
| 452 | isomiR example 2 of SEQ ID NO: 58 | — |
| 453 | isomiR example 1 of SEQ ID NO: 59 | — |
| 454 | isomiR example 2 of SEQ ID NO: 59 | — |
| 455 | isomiR example 1 of SEQ ID NO: 60 | — |
| 456 | isomiR example 2 of SEQ ID NO: 60 | — |
| 457 | isomiR example 1 of SEQ ID NO: 62 | — |
| 458 | isomiR example 2 of SEQ ID NO: 62 | — |

TABLE 1-continued

| SEQ ID NO: | Gene name | miRBase registration No. |
|---|---|---|
| 459 | isomiR example 1 of SEQ ID NO: 65 | — |
| 460 | isomiR example 2 of SEQ ID NO: 65 | — |
| 461 | isomiR example 1 of SEQ ID NO: 66 | — |
| 462 | isomiR example 2 of SEQ ID NO: 66 | — |
| 463 | isomiR example 1 of SEQ ID NO: 67 | — |
| 464 | isomiR example 2 of SEQ ID NO: 67 | — |
| 465 | isomiR example 1 of SEQ ID NO: 68 | — |
| 466 | isomiR example 2 of SEQ ID NO: 68 | — |
| 467 | isomiR example 1 of SEQ ID NO: 71 | — |
| 468 | isomiR example 2 of SEQ ID NO: 71 | — |
| 469 | isomiR example 1 of SEQ ID NO: 72 | — |
| 470 | isomiR example 2 of SEQ ID NO: 72 | — |
| 471 | isomiR example 1 of SEQ ID NO: 73 | — |
| 472 | isomiR example 2 of SEQ ID NO: 73 | — |
| 473 | isomiR example 1 of SEQ ID NO: 74 | — |
| 474 | isomiR example 2 of SEQ ID NO: 74 | — |
| 475 | isomiR example 1 of SEQ ID NO: 75 | — |
| 476 | isomiR example 2 of SEQ ID NO: 75 | — |
| 477 | isomiR example 1 of SEQ ID NO: 76 | — |
| 478 | isomiR example 2 of SEQ ID NO: 76 | — |
| 479 | isomiR example 1 of SEQ ID NO: 78 | — |
| 480 | isomiR example 2 of SEQ ID NO: 78 | — |
| 481 | isomiR example 1 of SEQ ID NO: 82 | — |
| 482 | isomiR example 2 of SEQ ID NO: 82 | — |
| 483 | isomiR example 1 of SEQ ID NO: 83 | — |
| 484 | isomiR example 2 of SEQ ID NO: 83 | — |
| 485 | isomiR example 1 of SEQ ID NO: 88 | — |
| 486 | isomiR example 2 of SEQ ID NO: 88 | — |
| 487 | isomiR example 1 of SEQ ID NO: 90 | — |
| 488 | isomiR example 2 of SEQ ID NO: 90 | — |
| 489 | isomiR example 1 of SEQ ID NO: 91 | — |
| 490 | isomiR example 2 of SEQ ID NO: 91 | — |
| 491 | isomiR example 1 of SEQ ID NO: 92 | — |
| 492 | isomiR example 2 of SEQ ID NO: 92 | — |
| 493 | isomiR example 1 of SEQ ID NO: 94 | — |
| 494 | isomiR example 2 of SEQ ID NO: 94 | — |
| 495 | isomiR example 1 of SEQ ID NO: 95 | — |
| 496 | isomiR example 2 of SEQ ID NO: 95 | — |
| 497 | isomiR example 1 of SEQ ID NO: 98 | — |
| 498 | isomiR example 2 of SEQ ID NO: 98 | — |
| 499 | isomiR example 1 of SEQ ID NO: 99 | — |
| 500 | isomiR example 2 of SEQ ID NO: 99 | — |
| 501 | isomiR example 1 of SEQ ID NO: 101 | — |
| 502 | isomiR example 2 of SEQ ID NO: 101 | — |
| 503 | isomiR example 1 of SEQ ID NO: 102 | — |
| 504 | isomiR example 2 of SEQ ID NO: 102 | — |
| 505 | isomiR example 1 of SEQ ID NO: 103 | — |
| 506 | isomiR example 2 of SEQ ID NO: 103 | — |
| 507 | isomiR example 1 of SEQ ID NO: 104 | — |
| 508 | isomiR example 2 of SEQ ID NO: 104 | — |
| 509 | isomiR example 1 of SEQ ID NO: 106 | — |
| 510 | isomiR example 2 of SEQ ID NO: 106 | — |
| 511 | isomiR example 1 of SEQ ID NO: 107 | — |
| 512 | isomiR example 2 of SEQ ID NO: 107 | — |
| 513 | isomiR example 1 of SEQ ID NO: 108 | — |
| 514 | isomiR example 2 of SEQ ID NO: 108 | — |
| 515 | isomiR example 1 of SEQ ID NO: 109 | — |
| 516 | isomiR example 2 of SEQ ID NO: 109 | — |
| 517 | isomiR example 1 of SEQ ID NO: 110 | — |
| 518 | isomiR example 2 of SEQ ID NO: 110 | — |
| 519 | isomiR example 1 of SEQ ID NO: 113 | — |
| 520 | isomiR example 2 of SEQ ID NO: 113 | — |
| 521 | isomiR example 1 of SEQ ID NO: 116 | — |
| 522 | isomiR example 2 of SEQ ID NO: 116 | — |
| 523 | isomiR example 1 of SEQ ID NO: 117 | — |
| 524 | isomiR example 2 of SEQ ID NO: 117 | — |
| 525 | isomiR example 1 of SEQ ID NO: 118 | — |
| 526 | isomiR example 2 of SEQ ID NO: 118 | — |
| 527 | isomiR example 1 of SEQ ID NO: 120 | — |
| 528 | isomiR example 2 of SEQ ID NO: 120 | — |
| 529 | isomiR example 1 of SEQ ID NO: 121 | — |
| 530 | isomiR example 2 of SEQ ID NO: 121 | — |
| 531 | isomiR example 1 of SEQ ID NO: 122 | — |
| 532 | isomiR example 2 of SEQ ID NO: 122 | — |
| 533 | isomiR example 1 of SEQ ID NO: 123 | — |
| 534 | isomiR example 2 of SEQ ID NO: 123 | — |
| 535 | isomiR example 1 of SEQ ID NO: 125 | — |
| 536 | isomiR example 2 of SEQ ID NO: 125 | — |
| 537 | isomiR example 1 of SEQ ID NO: 128 | — |
| 538 | isomiR example 2 of SEQ ID NO: 128 | — |
| 539 | isomiR example 1 of SEQ ID NO: 129 | — |
| 540 | isomiR example 2 of SEQ ID NO: 129 | — |
| 541 | isomiR example 1 of SEQ ID NO: 130 | — |
| 542 | isomiR example 2 of SEQ ID NO: 130 | — |
| 543 | isomiR example 1 of SEQ ID NO: 131 | — |
| 544 | isomiR example 2 of SEQ ID NO: 131 | — |
| 545 | isomiR example 1 of SEQ ID NO: 137 | — |
| 546 | isomiR example 2 of SEQ ID NO: 137 | — |
| 547 | isomiR example 1 of SEQ ID NO: 140 | — |
| 548 | isomiR example 2 of SEQ ID NO: 140 | — |
| 549 | isomiR example 1 of SEQ ID NO: 141 | — |
| 550 | isomiR example 2 of SEQ ID NO: 141 | — |
| 551 | isomiR example 1 of SEQ ID NO: 143 | — |
| 552 | isomiR example 2 of SEQ ID NO: 143 | — |
| 553 | isomiR example 1 of SEQ ID NO: 144 | — |
| 554 | isomiR example 2 of SEQ ID NO: 144 | — |
| 555 | isomiR example 1 of SEQ ID NO: 145 | — |
| 556 | isomiR example 2 of SEQ ID NO: 145 | — |
| 557 | isomiR example 1 of SEQ ID NO: 146 | — |
| 558 | isomiR example 2 of SEQ ID NO: 146 | — |
| 559 | isomiR example 1 of SEQ ID NO: 147 | — |
| 560 | isomiR example 2 of SEQ ID NO: 147 | — |
| 561 | isomiR example 1 of SEQ ID NO: 150 | — |
| 562 | isomiR example 2 of SEQ ID NO: 150 | — |
| 563 | isomiR example 1 of SEQ ID NO: 152 | — |
| 564 | isomiR example 2 of SEQ ID NO: 152 | — |
| 565 | isomiR example 1 of SEQ ID NO: 153 | — |
| 566 | isomiR example 2 of SEQ ID NO: 153 | — |
| 567 | isomiR example 1 of SEQ ID NO: 156 | — |
| 568 | isomiR example 2 of SEQ ID NO: 156 | — |
| 569 | isomiR example 1 of SEQ ID NO: 159 | — |
| 570 | isomiR example 2 of SEQ ID NO: 159 | — |
| 571 | isomiR example 1 of SEQ ID NO: 160 | — |
| 572 | isomiR example 2 of SEQ ID NO: 160 | — |
| 573 | isomiR example 1 of SEQ ID NO: 161 | — |
| 574 | isomiR example 2 of SEQ ID NO: 161 | — |
| 575 | isomiR example 1 of SEQ ID NO: 162 | — |
| 576 | isomiR example 2 of SEQ ID NO: 162 | — |
| 577 | isomiR example 1 of SEQ ID NO: 163 | — |
| 578 | isomiR example 2 of SEQ ID NO: 163 | — |
| 579 | isomiR example 1 of SEQ ID NO: 166 | — |
| 580 | isomiR example 2 of SEQ ID NO: 166 | — |
| 581 | isomiR example 1 of SEQ ID NO: 167 | — |
| 582 | isomiR example 2 of SEQ ID NO: 167 | — |
| 583 | isomiR example 1 of SEQ ID NO: 168 | — |
| 584 | isomiR example 2 of SEQ ID NO: 168 | — |
| 585 | isomiR example 1 of SEQ ID NO: 169 | — |
| 586 | isomiR example 2 of SEQ ID NO: 169 | — |
| 587 | isomiR example 1 of SEQ ID NO: 170 | — |
| 588 | isomiR example 2 of SEQ ID NO: 170 | — |
| 589 | isomiR example 1 of SEQ ID NO: 171 | — |
| 590 | isomiR example 2 of SEQ ID NO: 171 | — |
| 591 | isomiR example 1 of SEQ ID NO: 172 | — |
| 592 | isomiR example 2 of SEQ ID NO: 172 | — |
| 593 | isomiR example 1 of SEQ ID NO: 174 | — |
| 594 | isomiR example 2 of SEQ ID NO: 174 | — |
| 595 | isomiR example 1 of SEQ ID NO: 175 | — |
| 596 | isomiR example 2 of SEQ ID NO: 175 | — |
| 597 | isomiR example 1 of SEQ ID NO: 176 | — |
| 598 | isomiR example 2 of SEQ ID NO: 176 | — |
| 599 | isomiR example 1 of SEQ ID NO: 177 | — |
| 600 | isomiR example 2 of SEQ ID NO: 177 | — |
| 601 | isomiR example 1 of SEQ ID NO: 179 | — |
| 602 | isomiR example 2 of SEQ ID NO: 179 | — |
| 603 | isomiR example 1 of SEQ ID NO: 180 | — |
| 604 | isomiR example 2 of SEQ ID NO: 180 | — |
| 605 | isomiR example 1 of SEQ ID NO: 181 | — |
| 606 | isomiR example 2 of SEQ ID NO: 181 | — |
| 607 | isomiR example 1 of SEQ ID NO: 182 | — |
| 608 | isomiR example 2 of SEQ ID NO: 182 | — |
| 609 | isomiR example 1 of SEQ ID NO: 183 | — |
| 610 | isomiR example 2 of SEQ ID NO: 183 | — |
| 611 | isomiR example 1 of SEQ ID NO: 184 | — |
| 612 | isomiR example 2 of SEQ ID NO: 184 | — |

TABLE 1-continued

| SEQ ID NO: | Gene name | miRBase registration No. |
|---|---|---|
| 613 | isomiR example 1 of SEQ ID NO: 185 | — |
| 614 | isomiR example 2 of SEQ ID NO: 185 | — |
| 615 | isomiR example 1 of SEQ ID NO: 187 | — |
| 616 | isomiR example 2 of SEQ ID NO: 187 | — |
| 617 | isomiR example 1 of SEQ ID NO: 188 | — |
| 618 | isomiR example 2 of SEQ ID NO: 188 | — |
| 619 | isomiR example 1 of SEQ ID NO: 189 | — |
| 620 | isomiR example 2 of SEQ ID NO: 189 | — |
| 621 | isomiR example 1 of SEQ ID NO: 190 | — |
| 622 | isomiR example 2 of SEQ ID NO: 190 | — |
| 623 | isomiR example 1 of SEQ ID NO: 191 | — |
| 624 | isomiR example 2 of SEQ ID NO: 191 | — |
| 625 | isomiR example 1 of SEQ ID NO: 193 | — |
| 626 | isomiR example 2 of SEQ ID NO: 193 | — |
| 627 | isomiR example 1 of SEQ ID NO: 194 | — |
| 628 | isomiR example 2 of SEQ ID NO: 194 | — |
| 629 | isomiR example 1 of SEQ ID NO: 196 | — |
| 630 | isomiR example 2 of SEQ ID NO: 196 | — |
| 631 | isomiR example 1 of SEQ ID NO: 197 | — |
| 632 | isomiR example 2 of SEQ ID NO: 197 | — |
| 633 | isomiR example 1 of SEQ ID NO: 198 | — |
| 634 | isomiR example 2 of SEQ ID NO: 198 | — |
| 635 | hsa-miR-6794-5p | MIMAT0027488 |
| 636 | hsa-miR-6774-5p | MIMAT0027448 |
| 637 | hsa-miR-4707-3p | MIMAT0019808 |
| 638 | hsa-miR-4534 | MIMAT0019073 |
| 639 | hsa-miR-4294 | MIMAT0016849 |
| 640 | hsa-miR-6850-5p | MIMAT0027600 |
| 641 | hsa-miR-6089 | MIMAT0023714 |
| 642 | hsa-miR-671-5p | MIMAT0003880 |
| 643 | hsa-mir-6794 | MI0022639 |
| 644 | hsa-mir-6774 | MI0022619 |
| 645 | hsa-mir-4707 | MI0017340 |
| 646 | hsa-mir-4534 | MI0016901 |
| 647 | hsa-mir-4294 | MI0015827 |
| 648 | hsa-mir-6850 | MI0022696 |
| 649 | hsa-mir-6089-1 | MI0020366 |
| 650 | hsa-mir-6089-2 | MI0023563 |
| 651 | hsa-mir-671 | MI0003760 |
| 652 | isomiR example 1 of SEQ ID NO: 637 | — |
| 653 | isomiR example 2 of SEQ ID NO: 637 | — |
| 654 | isomiR example 1 of SEQ ID NO: 641 | — |
| 655 | isomiR example 2 of SEQ ID NO: 641 | — |
| 656 | isomiR example 1 of SEQ ID NO: 642 | — |
| 657 | isomiR example 2 of SEQ ID NO: 642 | — |

The present specification encompasses the contents described in the specifications and/or drawings of Japanese Patent Application Nos. 2014-123224 and 2015-071485 from which the present application claims priority.

Advantageous Effects of Invention

According to the present invention, stomach cancer can be detected easily and in high accuracy.

For example, the presence or absence of stomach cancer in a patient(s) can be easily detected by using, as an indicator(s), the measurement values of several miRNAs in blood, serum, and/or plasma of the patient(s), which can be collected with limited invasiveness.

BRIEF DESCRIPTION OF DRAWINGS

FIG. 1 This figure shows the relationship between the nucleotide sequences of hsa-miR-1225-3p represented by SEQ ID NO: 7 and hsa-miR-1225-5p represented by SEQ ID NO: 52, which are produced from a precursor hsa-mir-1225 represented by SEQ ID NO: 206.

DESCRIPTION OF EMBODIMENTS

Figure 2:
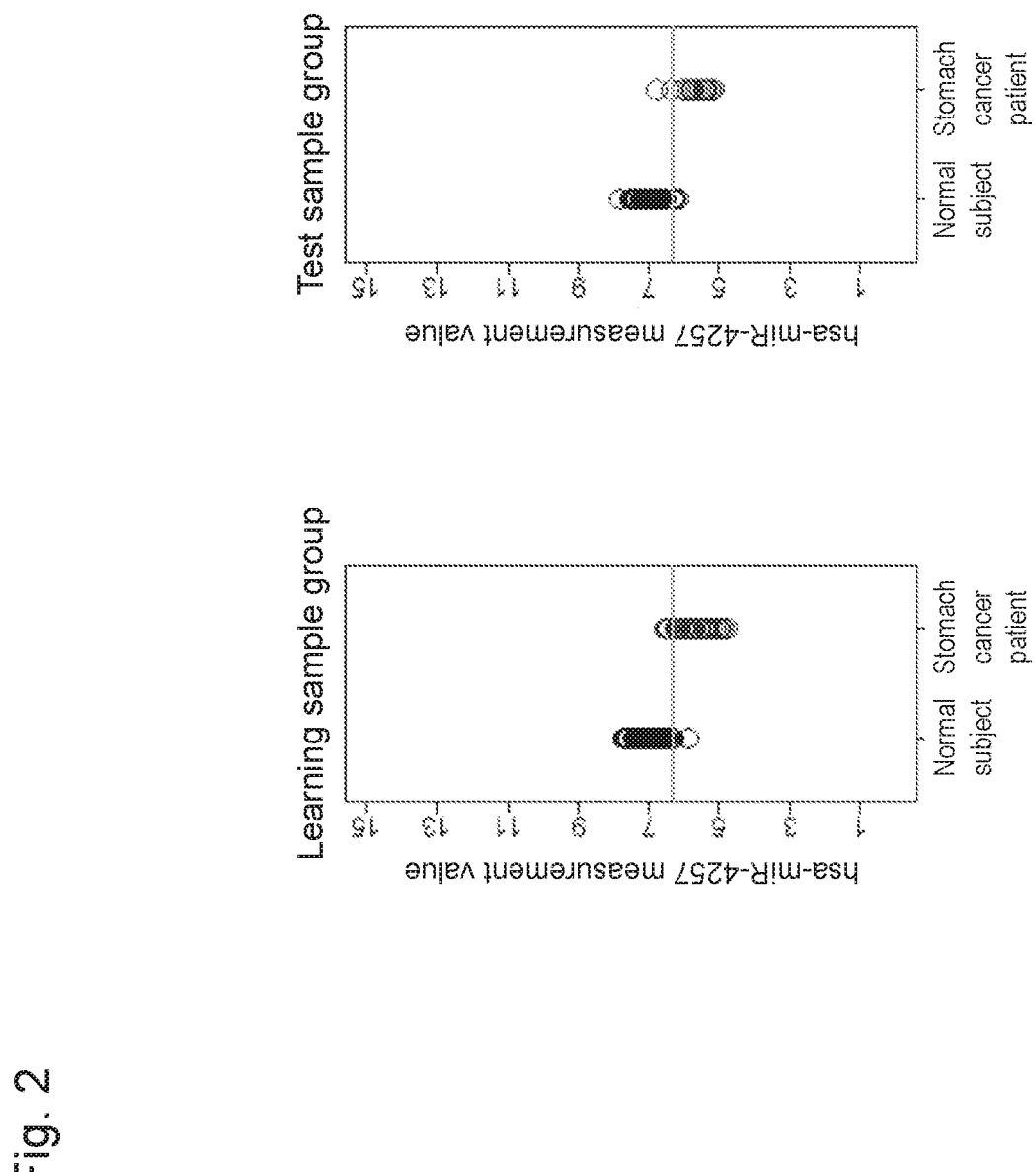
FIG. 2 Left diagram: the measurement values of hsa-miR-4257 (SEQ ID NO: 1) in healthy subjects (100 persons) and stomach cancer patients (34 persons) selected as a training cohort were each plotted on the ordinate. The horizontal line in the diagram depicts a threshold (6.29) that was optimized by Fisher's discriminant analysis and discriminated between the two groups. Right diagram: the measurement values of hsa-miR-4257 (SEQ ID NO: 1) in healthy subjects (50 persons) and stomach cancer patients (16 persons) selected as a validation cohort were each plotted on the ordinate. The horizontal line in the diagram depicts the threshold (6.29) that was set in the training cohort and discriminated between the two groups.

Hereinafter, the present invention will be further described in detail.

1. Target Nucleic Acid for Stomach Cancer

Primary target nucleic acids as a stomach cancer marker(s) for detecting the presence and/or absence of stomach cancer or stomach cancer cells using the nucleic acid probe(s) or the primer(s) for the detection of stomach cancer defined above according to the present invention comprises at least one or more miRNAs selected from the group consisting of hsa-miR-4257, hsa-miR-6726-5p, hsa-miR-1343-3p, hsa-miR-1247-3p, hsa-miR-6787-5p, hsa-miR-6875-5p, hsa-miR-1225-3p, hsa-miR-8063, hsa-miR-6781-5p, hsa-miR-4746-3p, hsa-miR-1908-5p, hsa-miR-6756-5p, hsa-miR-204-3p, hsa-miR-4651, hsa-miR-6757-5p, hsa-miR-6825-5p, hsa-miR-7108-5p, hsa-miR-4792, hsa-miR-7641, hsa-miR-3188, hsa-miR-3131, hsa-miR-6780b-5p, hsa-miR-8069, hsa-miR-6840-3p, hsa-miR-8072, hsa-miR-1233-5p, hsa-miR-6887-5p, hsa-miR-1231, hsa-miR-5572, hsa-miR-6738-5p, hsa-miR-6784-5p, hsa-miR-6791-5p, hsa-miR-6749-5p, hsa-miR-6741-5p, hsa-miR-128-1-5p, hsa-miR-4419b, hsa-miR-6746-5p, hsa-miR-3184-5p, hsa-miR-3679-5p, hsa-miR-7110-5p, hsa-miR-4516, hsa-miR-6717-5p, hsa-miR-6826-5p, hsa-miR-4433b-3p, hsa-miR-3679-3p, hsa-miR-3135b, hsa-miR-3622a-5p, hsa-miR-711, hsa-miR-4467, hsa-miR-6857-5p, hsa-miR-6515-3p, hsa-miR-1225-5p, hsa-miR-187-5p, hsa-miR-3185, hsa-miR-642b-3p, hsa-miR-1249, hsa-miR-744-5p, hsa-miR-4442, hsa-miR-1228-3p, hsa-miR-939-5p, hsa-miR-6845-5p, hsa-miR-887-3p, hsa-miR-7845-5p, hsa-miR-6729-5p, hsa-miR-4632-5p, hsa-miR-615-5p, hsa-miR-6724-5p, hsa-miR-4728-5p, hsa-miR-6732-5p, hsa-miR-6816-5p, hsa-miR-4695-5p, hsa-miR-6088, hsa-miR-7975, hsa-miR-3197, hsa-miR-6125, hsa-miR-4433-3p, hsa-miR-6727-5p, hsa-miR-4706, hsa-miR-7847-3p, hsa-miR-6805-3p, hsa-miR-6766-3p, hsa-miR-1913, hsa-miR-4649-5p, hsa-miR-602, hsa-miR-3663-3p, hsa-miR-6893-5p, hsa-miR-6861-5p, hsa-miR-4449, hsa-miR-6842-5p, hsa-miR-4454, hsa-miR-5195-3p, hsa-miR-663b, hsa-miR-6765-5p, hsa-miR-4513, hsa-miR-614, hsa-miR-6785-5p, hsa-miR-6777-5p, hsa-miR-940, hsa-miR-4741, hsa-miR-6870-5p, hsa-miR-6131, hsa-miR-150-3p, hsa-miR-4707-5p, hsa-miR-1915-3p, hsa-miR-3937, hsa-miR-937-5p, hsa-miR-4443, hsa-miR-1914-3p, hsa-miR-3620-5p, hsa-miR-1268b, hsa-miR-1227-5p, hsa-miR-6880-5p, hsa-miR-4417, hsa-miR-6802-5p, hsa-miR-6769a-5p, hsa-miR-663a, hsa-miR-6721-5p, hsa-miR-4532, hsa-miR-7977, hsa-miR-92b-5p, hsa-miR-371a-5p, hsa-miR-6126, hsa-miR-4734, hsa-miR-4665-3p, hsa-miR-423-5p, hsa-miR-1469, hsa-miR-4675, hsa-miR-1915-5p, hsa-miR-6716-5p, hsa-miR-718, hsa-miR-4281, hsa-miR-6820-5p, hsa-miR-6795-5p, hsa-miR-6779-5p, hsa-miR-7109-5p, hsa-miR-6798-5p, hsa-miR-4648, hsa-miR-8059, hsa-miR-6765-3p, hsa-miR-6132, hsa-miR-4492, hsa-miR-7107-5p, hsa-miR-3195, hsa-miR-3180, hsa-miR-296-3p, hsa-miR-564, hsa-miR-1268a, hsa-miR-6848-5p, hsa-miR-762, hsa-miR-2861, hsa-miR-1203, hsa-miR-1260b, hsa-miR-4476, hsa-miR-6885-5p, hsa-miR-6769b-5p, hsa-miR-23b-3p, hsa-miR-1343-5p, hsa-miR-3621, hsa-miR-4688, hsa-miR-4286, hsa-miR-4640-5p, hsa-miR-4739, hsa-miR-1260a, hsa-miR-4276, hsa-miR-7106, hsa-miR-6794-5p, hsa-miR-6774-5p, hsa-miR-4707-3p, hsa-miR-4534, hsa-miR-4294, hsa-miR-6850-5p, hsa-miR-6089 and hsa-miR-671-5p. Furthermore, at least one or more miRNAs selected from the group consisting of other stomach cancer markers that can be combined with these miRNAs, i.e., hsa-miR-128-2-5p, hsa-miR-125a-3p, hsa-miR-92a-2-5p, and hsa-miR-486-3p can also be preferably used as a target nucleic acid. Moreover, at least one or more miRNAs selected from the group consisting of other stomach cancer markers that can be combined with these miRNAs, i.e., hsa-miR-3196, hsa-miR-211-3p, hsa-miR-4271, hsa-miR-6851-5p, hsa-miR-149-3p, hsa-miR-4667-5p, hsa-miR-135a-3p, hsa-miR-4486, hsa-miR-4697-5p, hsa-miR-4725-3p, hsa-miR-6510-5p, hsa-miR-5001-5p, hsa-miR-4673, hsa-miR-4466, hsa-miR-23a-3p, hsa-miR-3656, hsa-miR-6782-5p, hsa-miR-4689, hsa-miR-451a, hsa-miR-4446-3p, hsa-miR-3180-3p, hsa-miR-642a-3p, hsa-miR-6889-5p, hsa-miR-3178, hsa-miR-4665-5p, hsa-miR-6722-3p, hsa-miR-30c-1-3p, hsa-miR-4507, hsa-miR-3141 and hsa-miR-1199-5p can also be preferably used as a target nucleic acid(s).

These miRNAs include, for example, a human gene comprising a nucleotide sequence represented by any of SEQ ID NOs: 1 to 199 and 635 to 642 (i.e., hsa-miR-4257, hsa-miR-6726-5p, hsa-miR-1343-3p, hsa-miR-1247-3p, hsa-miR-6787-5p, hsa-miR-6875-5p, hsa-miR-1225-3p, hsa-miR-8063, hsa-miR-6781-5p, hsa-miR-4746-3p, hsa-miR-1908-5p, hsa-miR-6756-5p, hsa-miR-204-3p, hsa-miR-4651, hsa-miR-6757-5p, hsa-miR-6825-5p, hsa-miR-7108-5p, hsa-miR-4792, hsa-miR-7641, hsa-miR-3188, hsa-miR-3131, hsa-miR-6780b-5p, hsa-miR-8069, hsa-miR-6840-3p, hsa-miR-8072, hsa-miR-1233-5p, hsa-miR-6887-5p, hsa-miR-1231, hsa-miR-5572, hsa-miR-6738-5p, hsa-miR-6784-5p, hsa-miR-6791-5p, hsa-miR-6749-5p, hsa-miR-6741-5p, hsa-miR-128-1-5p, hsa-miR-4419b, hsa-miR-6746-5p, hsa-miR-3184-5p, hsa-miR-3679-5p, hsa-miR-7110-5p, hsa-miR-4516, hsa-miR-6717-5p, hsa-miR-6826-5p, hsa-miR-4433b-3p, hsa-miR-3679-3p, hsa-miR-3135b, hsa-miR-3622a-5p, hsa-miR-711, hsa-miR-4467, hsa-miR-6857-5p, hsa-miR-6515-3p, hsa-miR-1225-5p, hsa-miR-187-5p, hsa-miR-3185, hsa-miR-642b-3p, hsa-miR-1249, hsa-miR-744-5p, hsa-miR-4442, hsa-miR-1228-3p, hsa-miR-939-5p, hsa-miR-6845-5p, hsa-miR-887-3p, hsa-miR-7845-5p, hsa-miR-6729-5p, hsa-miR-4632-5p, hsa-miR-615-5p, hsa-miR-6724-5p, hsa-miR-4728-5p, hsa-miR-6732-5p, hsa-miR-6816-5p, hsa-miR-4695-5p, hsa-miR-6088, hsa-miR-7975, hsa-miR-3197, hsa-miR-6125, hsa-miR-4433-3p, hsa-miR-6727-5p, hsa-miR-4706, hsa-miR-7847-3p, hsa-miR-6805-3p, hsa-miR-6766-3p, hsa-miR-1913, hsa-miR-4649-5p, hsa-miR-602, hsa-miR-3663-3p, hsa-miR-6893-5p, hsa-miR-6861-5p, hsa-miR-4449, hsa-miR-6842-5p, hsa-miR-4454, hsa-miR-51195-3p, hsa-miR-663b, hsa-miR-6765-5p, hsa-miR-4513, hsa-miR-614, hsa-miR-6785-5p, hsa-miR-6777-5p, hsa-miR-940, hsa-miR-4741, hsa-miR-6870-5p, hsa-miR-6131, hsa-miR-150-3p, hsa-miR-4707-5p, hsa-miR-1915-3p, hsa-miR-3937, hsa-miR-937-5p, hsa-miR-4443, hsa-miR-1914-3p, hsa-miR-3620-5p, hsa-miR-1268b, hsa-miR-1227-5p, hsa-miR-6880-5p, hsa-miR-4417, hsa-miR-6802-5p, hsa-miR-6769a-5p, hsa-miR-663a, hsa-miR-6721-5p, hsa-miR-4532, hsa-miR-7977, hsa-miR-92b-5p, hsa-miR-371a-5p, hsa-miR-6126, hsa-miR-4734, hsa-miR-4665-3p, hsa-miR-423-5p, hsa-miR-1469, hsa-miR-4675, hsa-miR-1915-5p, hsa-miR-6716-5p, hsa-miR-718, hsa-miR-281, hsa-miR-6820-5p, hsa-miR-6795-5p, hsa-miR-6779-5p, hsa-miR-7109-5p, hsa-miR-6798-5p, hsa-miR-4648, hsa-miR-8059, hsa-miR-6765-3p, hsa-miR-6132, hsa-miR-4492, hsa-miR-7107-5p, hsa-miR-3195, hsa-miR-3180, hsa-miR-296-3p, hsa-miR-564, hsa-miR-1268a, hsa-miR-6848-5p, hsa-miR-762, hsa-miR-2861, hsa-miR-1203, hsa-miR-1260b, hsa-miR-4476, hsa-miR-6885-5p, hsa-miR-6769b-5p, hsa-miR-23b-3p, hsa-miR-1343-5p, hsa-miR-3621, hsa-miR-4688, hsa-miR-4286, hsa-miR-4640-5p, hsa-miR-4739, hsa-miR-1260a, hsa-miR-4276, hsa-miR-7106, hsa-miR-6794-5p, hsa-miR-6774-5p, hsa-miR-4707-3p, hsa-miR-4534, hsa-miR-4294, hsa-miR-6850-5p, hsa-miR-6089, hsa-miR-671-5p, hsa-miR-128-2-5p, hsa-miR-125a-3p, hsa-miR-92a-2-5p, hsa-miR-486-3p, hsa-miR-3196, hsa-miR-211-3p, hsa-miR-4271, hsa-miR-6851-5p, hsa-miR-149-3p, hsa-miR-4667-5p, hsa-miR-135a-3p, hsa-miR-4486, hsa-miR-4697-5p, hsa-miR-4725-3p, hsa-miR-6510-5p, hsa-miR-5001-5p, hsa-miR-4673, hsa-miR-4466, hsa-miR-23a-3p, hsa-miR-3656, hsa-miR-6782-5p, hsa-miR-4689, hsa-miR-451a, hsa-miR-4446-3p, hsa-miR-3180-3p, hsa-miR-642a-3p, hsa-miR-6889-5p, hsa-miR-3178, hsa-miR-4665-5p, hsa-miR-6722-3p, hsa-miR-30c-1-3p, hsa-miR-4507, hsa-miR-3141 and hsa-miR-1199-5p, respectively), a congener thereof, a transcript thereof, and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 657 or a transcript thereof, more preferably the transcript, i.e., a miRNA or its precursor RNA (pri-miRNA or pre-miRNA).

The first target gene is the hsa-miR-4257 gene, a congener thereof, a transcript thereof, or a variant or a derivative thereof. None of the previously known reports show that change in the expression of the gene or the transcript thereof can serve as a marker for stomach cancer.

The second target gene is the hsa-miR-6726-5p gene, a congener thereof, a transcript thereof, or a variant or a derivative thereof. None of the previously known reports show that change in the expression of the gene or the transcript thereof can serve as a marker for stomach cancer.

The third target gene is the hsa-miR-1343-3p gene, a congener thereof, a transcript thereof, or a variant or a derivative thereof. None of the previously known reports show that change in the expression of the gene or the transcript thereof can serve as a marker for stomach cancer.

The fourth target gene is the hsa-miR-1247-3p gene, a congener thereof, a transcript thereof, or a variant or a derivative thereof. None of the previously known reports show that change in the expression of the gene or the transcript thereof can serve as a marker for stomach cancer.

The fifth target gene is the hsa-miR-6787-5p gene, a congener thereof, a transcript thereof, or a variant or a derivative thereof. None of the previously known reports show that change in the expression of the gene or the transcript thereof can serve as a marker for stomach cancer.

The sixth target gene is the hsa-miR-6875-5p gene, a congener thereof, a transcript thereof, or a variant or a derivative thereof. None of the previously known reports show that change in the expression of the gene or the transcript thereof can serve as a marker for stomach cancer.

The seventh target gene is the hsa-miR-1225-3p gene, a congener thereof, a transcript thereof, or a variant or a derivative thereof. None of the previously known reports show that change in the expression of the gene or the transcript thereof can serve as a marker for stomach cancer.

The eighth target gene is the hsa-miR-8063 gene, a congener thereof, a transcript thereof, or a variant or a derivative thereof. None of the previously known reports show that change in the expression of the gene or the transcript thereof can serve as a marker for stomach cancer.

The ninth target gene is the hsa-miR-6781-5p gene, a congener thereof, a transcript thereof, or a variant or a derivative thereof. None of the previously known reports show that change in the expression of the gene or the transcript thereof can serve as a marker for stomach cancer.

The 10th target gene is the hsa-miR-4746-3p gene, a congener thereof, a transcript thereof, or a variant or a derivative thereof. None of the previously known reports show that change in the expression of the gene or the transcript thereof can serve as a marker for stomach cancer.

The 11th target gene is the hsa-miR-1908-5p gene, a congener thereof, a transcript thereof, or a variant or a derivative thereof. None of the previously known reports show that change in the expression of the gene or the transcript thereof can serve as a marker for stomach cancer.

The 12th target gene is the hsa-miR-6756-5p gene, a congener thereof, a transcript thereof, or a variant or a derivative thereof. None of the previously known reports show that change in the expression of the gene or the transcript thereof can serve as a marker for stomach cancer.

The 13th target gene is the hsa-miR-204-3p gene, a congener thereof, a transcript thereof, or a variant or a derivative thereof. None of the previously known reports show that change in the expression of the gene or the transcript thereof can serve as a marker for stomach cancer.

The 14th target gene is the hsa-miR-4651 gene, a congener thereof, a transcript thereof, or a variant or a derivative thereof. None of the previously known reports show that change in the expression of the gene or the transcript thereof can serve as a marker for stomach cancer.

The 15th target gene is the hsa-miR-6757-5p gene, a congener thereof, a transcript thereof, or a variant or a derivative thereof. None of the previously known reports show that change in the expression of the gene or the transcript thereof can serve as a marker for stomach cancer.

The 16th target gene is the hsa-miR-6825-5p gene, a congener thereof, a transcript thereof, or a variant or a derivative thereof. None of the previously known reports show that change in the expression of the gene or the transcript thereof can serve as a marker for stomach cancer.

The 17th target gene is the hsa-miR-7108-5p gene, a congener thereof, a transcript thereof, or a variant or a derivative thereof. None of the previously known reports show that change in the expression of the gene or the transcript thereof can serve as a marker for stomach cancer.

The 18th target gene is the hsa-miR-4792 gene, a congener thereof, a transcript thereof, or a variant or a derivative thereof. None of the previously known reports show that change in the expression of the gene or the transcript thereof can serve as a marker for stomach cancer.

The 19th target gene is the hsa-miR-7641 gene, a congener thereof, a transcript thereof, or a variant or a derivative thereof. None of the previously known reports show that change in the expression of the gene or the transcript thereof can serve as a marker for stomach cancer.

The 20th target gene is the hsa-miR-3188 gene, a congener thereof, a transcript thereof, or a variant or a derivative thereof. None of the previously known reports show that change in the expression of the gene or the transcript thereof can serve as a marker for stomach cancer.

The 21st target gene is the hsa-miR-3131 gene, a congener thereof, a transcript thereof, or a variant or a derivative thereof. None of the previously known reports show that change in the expression of the gene or the transcript thereof can serve as a marker for stomach cancer.

The 22nd target gene is the hsa-miR-6780b-5p gene, a congener thereof, a transcript thereof, or a variant or a derivative thereof. None of the previously known reports show that change in the expression of the gene or the transcript thereof can serve as a marker for stomach cancer.

The 23rd target gene is the hsa-miR-8069 gene, a congener thereof, a transcript thereof, or a variant or a derivative thereof. None of the previously known reports show that change in the expression of the gene or the transcript thereof can serve as a marker for stomach cancer.

The 24th target gene is the hsa-miR-6840-3p gene, a congener thereof, a transcript thereof, or a variant or a derivative thereof. None of the previously known reports show that change in the expression of the gene or the transcript thereof can serve as a marker for stomach cancer.

The 25th target gene is the hsa-miR-8072 gene, a congener thereof, a transcript thereof, or a variant or a derivative thereof. None of the previously known reports show that change in the expression of the gene or the transcript thereof can serve as a marker for stomach cancer.

The 26th target gene is the hsa-miR-1233-5p gene, a congener thereof, a transcript thereof, or a variant or a derivative thereof. None of the previously known reports show that change in the expression of the gene or the transcript thereof can serve as a marker for stomach cancer.

The 27th target gene is the hsa-miR-6887-5p gene, a congener thereof, a transcript thereof, or a variant or a derivative thereof. None of the previously known reports show that change in the expression of the gene or the transcript thereof can serve as a marker for stomach cancer.

The 28th target gene is the hsa-miR-1231 gene, a congener thereof, a transcript thereof, or a variant or a derivative thereof. None of the previously known reports show that change in the expression of the gene or the transcript thereof can serve as a marker for stomach cancer.

The 29th target gene is the hsa-miR-5572 gene, a congener thereof, a transcript thereof, or a variant or a derivative thereof. None of the previously known reports show that change in the expression of the gene or the transcript thereof can serve as a marker for stomach cancer.

The 30th target gene is the hsa-miR-6738-5p gene, a congener thereof, a transcript thereof, or a variant or a derivative thereof. None of the previously known reports show that change in the expression of the gene or the transcript thereof can serve as a marker for stomach cancer.

The 31st target gene is the hsa-miR-6784-5p gene, a congener thereof, a transcript thereof, or a variant or a derivative thereof. None of the previously known reports show that change in the expression of the gene or the transcript thereof can serve as a marker for stomach cancer.

The 32nd target gene is the hsa-miR-6791-5p gene, a congener thereof, a transcript thereof, or a variant or a derivative thereof. None of the previously known reports show that change in the expression of the gene or the transcript thereof can serve as a marker for stomach cancer.

The 33rd target gene is the hsa-miR-6749-5p gene, a congener thereof, a transcript thereof, or a variant or a derivative thereof. None of the previously known reports show that change in the expression of the gene or the transcript thereof can serve as a marker for stomach cancer.

The 34th target gene is the hsa-miR-6741-5p gene, a congener thereof, a transcript thereof, or a variant or a derivative thereof. None of the previously known reports show that change in the expression of the gene or the transcript thereof can serve as a marker for stomach cancer.

The 35th target gene is the hsa-miR-128-1-5p gene, a congener thereof, a transcript thereof, or a variant or a derivative thereof. None of the previously known reports show that change in the expression of the gene or the transcript thereof can serve as a marker for stomach cancer.

The 36th target gene is the hsa-miR-4419b gene, a congener thereof, a transcript thereof, or a variant or a derivative thereof. None of the previously known reports show that change in the expression of the gene or the transcript thereof can serve as a marker for stomach cancer.

The 37th target gene is the hsa-miR-6746-5p gene, a congener thereof, a transcript thereof, or a variant or a derivative thereof. None of the previously known reports show that change in the expression of the gene or the transcript thereof can serve as a marker for stomach cancer.

The 38th target gene is the hsa-miR-3184-5p gene, a congener thereof, a transcript thereof, or a variant or a derivative thereof. None of the previously known reports show that change in the expression of the gene or the transcript thereof can serve as a marker for stomach cancer.

The 39th target gene is the hsa-miR-3679-5p gene, a congener thereof, a transcript thereof, or a variant or a derivative thereof. None of the previously known reports show that change in the expression of the gene or the transcript thereof can serve as a marker for stomach cancer.

The 40th target gene is the hsa-miR-7110-5p gene, a congener thereof, a transcript thereof, or a variant or a derivative thereof. None of the previously known reports show that change in the expression of the gene or the transcript thereof can serve as a marker for stomach cancer.

The 41st target gene is the hsa-miR-4516 gene, a congener thereof, a transcript thereof, or a variant or a derivative thereof. None of the previously known reports show that change in the expression of the gene or the transcript thereof can serve as a marker for stomach cancer.

The 42nd target gene is the hsa-miR-6717-5p gene, a congener thereof, a transcript thereof, or a variant or a derivative thereof. None of the previously known reports show that change in the expression of the gene or the transcript thereof can serve as a marker for stomach cancer.

The 43rd target gene is the hsa-miR-6826-5p gene, a congener thereof, a transcript thereof, or a variant or a derivative thereof. None of the previously known reports show that change in the expression of the gene or the transcript thereof can serve as a marker for stomach cancer.

The 44th target gene is the hsa-miR-4433b-3p gene, a congener thereof, a transcript thereof, or a variant or a derivative thereof. None of the previously known reports show that change in the expression of the gene or the transcript thereof can serve as a marker for stomach cancer.

The 45th target gene is the hsa-miR-3679-3p gene, a congener thereof, a transcript thereof, or a variant or a derivative thereof. None of the previously known reports show that change in the expression of the gene or the transcript thereof can serve as a marker for stomach cancer.

The 46th target gene is the hsa-miR-3135b gene, a congener thereof, a transcript thereof, or a variant or a derivative thereof. None of the previously known reports show that change in the expression of the gene or the transcript thereof can serve as a marker for stomach cancer.

The 47th target gene is the hsa-miR-3622a-5p gene, a congener thereof, a transcript thereof, or a variant or a derivative thereof. None of the previously known reports show that change in the expression of the gene or the transcript thereof can serve as a marker for stomach cancer.

The 48th target gene is the hsa-miR-711 gene, a congener thereof, a transcript thereof, or a variant or a derivative thereof. None of the previously known reports show that change in the expression of the gene or the transcript thereof can serve as a marker for stomach cancer.

The 49th target gene is the hsa-miR-4467 gene, a congener thereof, a transcript thereof, or a variant or a derivative thereof. None of the previously known reports show that change in the expression of the gene or the transcript thereof can serve as a marker for stomach cancer.

The 50th target gene is the hsa-miR-6857-5p gene, a congener thereof, a transcript thereof, or a variant or a derivative thereof. None of the previously known reports show that change in the expression of the gene or the transcript thereof can serve as a marker for stomach cancer.

The 51st target gene is the hsa-miR-6515-3p gene, a congener thereof, a transcript thereof, or a variant or a derivative thereof. None of the previously known reports show that change in the expression of the gene or the transcript thereof can serve as a marker for stomach cancer.

The 52nd target gene is the hsa-miR-1225-5p gene, a congener thereof, a transcript thereof, or a variant or a derivative thereof. None of the previously known reports show that change in the expression of the gene or the transcript thereof can serve as a marker for stomach cancer.

The 53rd target gene is the hsa-miR-187-5p gene, a congener thereof, a transcript thereof, or a variant or a derivative thereof. None of the previously known reports show that change in the expression of the gene or the transcript thereof can serve as a marker for stomach cancer.

The 54th target gene is the hsa-miR-3185 gene, a congener thereof, a transcript thereof, or a variant or a derivative thereof. None of the previously known reports show that change in the expression of the gene or the transcript thereof can serve as a marker for stomach cancer.

The 55th target gene is the hsa-miR-642b-3p gene, a congener thereof, a transcript thereof, or a variant or a derivative thereof. None of the previously known reports show that change in the expression of the gene or the transcript thereof can serve as a marker for stomach cancer.

The 56th target gene is the hsa-miR-1249 gene, a congener thereof, a transcript thereof, or a variant or a derivative thereof. None of the previously known reports show that change in the expression of the gene or the transcript thereof can serve as a marker for stomach cancer.

The 57th target gene is the hsa-miR-744-5p gene, a congener thereof, a transcript thereof, or a variant or a derivative thereof. None of the previously known reports show that change in the expression of the gene or the transcript thereof can serve as a marker for stomach cancer.

The 58th target gene is the hsa-miR-4442 gene, a congener thereof, a transcript thereof, or a variant or a derivative thereof. None of the previously known reports show that change in the expression of the gene or the transcript thereof can serve as a marker for stomach cancer.

The 59th target gene is the hsa-miR-1228-3p gene, a congener thereof, a transcript thereof, or a variant or a derivative thereof. None of the previously known reports show that change in the expression of the gene or the transcript thereof can serve as a marker for stomach cancer.

The 60th target gene is the hsa-miR-939-5p gene, a congener thereof, a transcript thereof, or a variant or a derivative thereof. None of the previously known reports show that change in the expression of the gene or the transcript thereof can serve as a marker for stomach cancer.

The 61st target gene is the hsa-miR-6845-5p gene, a congener thereof, a transcript thereof, or a variant or a derivative thereof. None of the previously known reports show that change in the expression of the gene or the transcript thereof can serve as a marker for stomach cancer.

The 62nd target gene is the hsa-miR-887-3p gene, a congener thereof, a transcript thereof, or a variant or a derivative thereof. None of the previously known reports show that change in the expression of the gene or the transcript thereof can serve as a marker for stomach cancer.

The 63rd target gene is the hsa-miR-7845-5p gene, a congener thereof, a transcript thereof, or a variant or a derivative thereof. None of the previously known reports show that change in the expression of the gene or the transcript thereof can serve as a marker for stomach cancer.

The 64th target gene is the hsa-miR-6729-5p gene, a congener thereof, a transcript thereof, or a variant or a derivative thereof. None of the previously known reports show that change in the expression of the gene or the transcript thereof can serve as a marker for stomach cancer.

The 65th target gene is the hsa-miR-4632-5p gene, a congener thereof, a transcript thereof, or a variant or a derivative thereof. None of the previously known reports show that change in the expression of the gene or the transcript thereof can serve as a marker for stomach cancer.

The 66th target gene is the hsa-miR-615-5p gene, a congener thereof, a transcript thereof, or a variant or a derivative thereof. None of the previously known reports show that change in the expression of the gene or the transcript thereof can serve as a marker for stomach cancer.

The 67th target gene is the hsa-miR-6724-5p gene, a congener thereof, a transcript thereof, or a variant or a derivative thereof. None of the previously known reports show that change in the expression of the gene or the transcript thereof can serve as a marker for stomach cancer.

The 68th target gene is the hsa-miR-4728-5p gene, a congener thereof, a transcript thereof, or a variant or a derivative thereof. None of the previously known reports show that change in the expression of the gene or the transcript thereof can serve as a marker for stomach cancer.

The 69th target gene is the hsa-miR-6732-5p gene, a congener thereof, a transcript thereof, or a variant or a derivative thereof. None of the previously known reports show that change in the expression of the gene or the transcript thereof can serve as a marker for stomach cancer.

The 70th target gene is the hsa-miR-6816-5p gene, a congener thereof, a transcript thereof, or a variant or a derivative thereof. None of the previously known reports show that change in the expression of the gene or the transcript thereof can serve as a marker for stomach cancer.

The 71st target gene is the hsa-miR-4695-5p gene, a congener thereof, a transcript thereof, or a variant or a derivative thereof. None of the previously known reports show that change in the expression of the gene or the transcript thereof can serve as a marker for stomach cancer.

The 72nd target gene is the hsa-miR-6088 gene, a congener thereof, a transcript thereof, or a variant or a derivative thereof. None of the previously known reports show that change in the expression of the gene or the transcript thereof can serve as a marker for stomach cancer.

The 73rd target gene is the hsa-miR-7975 gene, a congener thereof, a transcript thereof, or a variant or a derivative thereof. None of the previously known reports show that change in the expression of the gene or the transcript thereof can serve as a marker for stomach cancer.

The 74th target gene is the hsa-miR-3197 gene, a congener thereof, a transcript thereof, or a variant or a derivative thereof. None of the previously known reports show that change in the expression of the gene or the transcript thereof can serve as a marker for stomach cancer.

The 75th target gene is the hsa-miR-6125 gene, a congener thereof, a transcript thereof, or a variant or a derivative thereof. None of the previously known reports show that change in the expression of the gene or the transcript thereof can serve as a marker for stomach cancer.

The 76th target gene is the hsa-miR-4433-3p gene, a congener thereof, a transcript thereof, or a variant or a derivative thereof. None of the previously known reports show that change in the expression of the gene or the transcript thereof can serve as a marker for stomach cancer.

The 77th target gene is the hsa-miR-6727-5p gene, a congener thereof, a transcript thereof, or a variant or a derivative thereof. None of the previously known reports show that change in the expression of the gene or the transcript thereof can serve as a marker for stomach cancer.

The 78th target gene is the hsa-miR-4706 gene, a congener thereof, a transcript thereof, or a variant or a derivative thereof. None of the previously known reports show that change in the expression of the gene or the transcript thereof can serve as a marker for stomach cancer.

The 79th target gene is the hsa-miR-7847-3p gene, a congener thereof, a transcript thereof, or a variant or a derivative thereof. None of the previously known reports show that change in the expression of the gene or the transcript thereof can serve as a marker for stomach cancer.

The 80th target gene is the hsa-miR-6805-3p gene, a congener thereof, a transcript thereof, or a variant or a derivative thereof. None of the previously known reports show that change in the expression of the gene or the transcript thereof can serve as a marker for stomach cancer.

The 81st target gene is the hsa-miR-6766-3p gene, a congener thereof, a transcript thereof, or a variant or a derivative thereof. None of the previously known reports show that change in the expression of the gene or the transcript thereof can serve as a marker for stomach cancer.

The 82nd target gene is the hsa-miR-1913 gene, a congener thereof, a transcript thereof, or a variant or a derivative thereof. None of the previously known reports show that change in the expression of the gene or the transcript thereof can serve as a marker for stomach cancer.

The 83rd target gene is the hsa-miR-4649-5p gene, a congener thereof, a transcript thereof, or a variant or a derivative thereof. None of the previously known reports show that change in the expression of the gene or the transcript thereof can serve as a marker for stomach cancer.

The 84th target gene is the hsa-miR-602 gene, a congener thereof, a transcript thereof, or a variant or a derivative thereof. None of the previously known reports show that change in the expression of the gene or the transcript thereof can serve as a marker for stomach cancer.

The 85th target gene is the hsa-miR-3663-3p gene, a congener thereof, a transcript thereof, or a variant or a derivative thereof. None of the previously known reports show that change in the expression of the gene or the transcript thereof can serve as a marker for stomach cancer.

The 86th target gene is the hsa-miR-6893-5p gene, a congener thereof, a transcript thereof, or a variant or a derivative thereof. None of the previously known reports show that change in the expression of the gene or the transcript thereof can serve as a marker for stomach cancer.

The 87th target gene is the hsa-miR-6861-5p gene, a congener thereof, a transcript thereof, or a variant or a derivative thereof. None of the previously known reports show that change in the expression of the gene or the transcript thereof can serve as a marker for stomach cancer.

The 88th target gene is the hsa-miR-4449 gene, a congener thereof, a transcript thereof, or a variant or a derivative thereof. None of the previously known reports show that change in the expression of the gene or the transcript thereof can serve as a marker for stomach cancer.

The 89th target gene is the hsa-miR-6842-5p gene, a congener thereof, a transcript thereof, or a variant or a derivative thereof. None of the previously known reports show that change in the expression of the gene or the transcript thereof can serve as a marker for stomach cancer.

The 90th target gene is the hsa-miR-4454 gene, a congener thereof, a transcript thereof, or a variant or a derivative thereof. None of the previously known reports show that change in the expression of the gene or the transcript thereof can serve as a marker for stomach cancer.

The 91st target gene is the hsa-miR-5195-3p gene, a congener thereof, a transcript thereof, or a variant or a derivative thereof. None of the previously known reports show that change in the expression of the gene or the transcript thereof can serve as a marker for stomach cancer.

The 92nd target gene is the hsa-miR-663b gene, a congener thereof, a transcript thereof, or a variant or a derivative thereof. None of the previously known reports show that change in the expression of the gene or the transcript thereof can serve as a marker for stomach cancer.

The 93rd target gene is the hsa-miR-6765-5p gene, a congener thereof, a transcript thereof, or a variant or a derivative thereof. None of the previously known reports show that change in the expression of the gene or the transcript thereof can serve as a marker for stomach cancer.

The 94th target gene is the hsa-miR-4513 gene, a congener thereof, a transcript thereof, or a variant or a derivative thereof. None of the previously known reports show that change in the expression of the gene or the transcript thereof can serve as a marker for stomach cancer.

The 95th target gene is the hsa-miR-614 gene, a congener thereof, a transcript thereof, or a variant or a derivative thereof. None of the previously known reports show that change in the expression of the gene or the transcript thereof can serve as a marker for stomach cancer.

The 96th target gene is the hsa-miR-6785-5p gene, a congener thereof, a transcript thereof, or a variant or a derivative thereof. None of the previously known reports show that change in the expression of the gene or the transcript thereof can serve as a marker for stomach cancer.

The 97th target gene is the hsa-miR-6777-5p gene, a congener thereof, a transcript thereof, or a variant or a derivative thereof. None of the previously known reports show that change in the expression of the gene or the transcript thereof can serve as a marker for stomach cancer.

The 98th target gene is the hsa-miR-940 gene, a congener thereof, a transcript thereof, or a variant or a derivative thereof. None of the previously known reports show that change in the expression of the gene or the transcript thereof can serve as a marker for stomach cancer.

The 99th target gene is the hsa-miR-4741 gene, a congener thereof, a transcript thereof, or a variant or a derivative thereof. None of the previously known reports show that change in the expression of the gene or the transcript thereof can serve as a marker for stomach cancer.

The 100th target gene is the hsa-miR-6870-5p gene, a congener thereof, a transcript thereof, or a variant or a derivative thereof. None of the previously known reports show that change in the expression of the gene or the transcript thereof can serve as a marker for stomach cancer.

The 101st target gene is the hsa-miR-6131 gene, a congener thereof, a transcript thereof, or a variant or a derivative thereof. None of the previously known reports show that change in the expression of the gene or the transcript thereof can serve as a marker for stomach cancer.

The 102nd target gene is the hsa-miR-150-3p gene, a congener thereof, a transcript thereof, or a variant or a derivative thereof. None of the previously known reports show that change in the expression of the gene or the transcript thereof can serve as a marker for stomach cancer.

The 103rd target gene is the hsa-miR-4707-5p gene, a congener thereof, a transcript thereof, or a variant or a derivative thereof. None of the previously known reports show that change in the expression of the gene or the transcript thereof can serve as a marker for stomach cancer.

The 104th target gene is the hsa-miR-1915-3p gene, a congener thereof, a transcript thereof, or a variant or a derivative thereof. None of the previously known reports show that change in the expression of the gene or the transcript thereof can serve as a marker for stomach cancer.

The 105th target gene is the hsa-miR-3937 gene, a congener thereof, a transcript thereof, or a variant or a derivative thereof. None of the previously known reports show that change in the expression of the gene or the transcript thereof can serve as a marker for stomach cancer.

The 106th target gene is the hsa-miR-937-5p gene, a congener thereof, a transcript thereof, or a variant or a derivative thereof. None of the previously known reports show that change in the expression of the gene or the transcript thereof can serve as a marker for stomach cancer.

The 107th target gene is the hsa-miR-4443 gene, a congener thereof, a transcript thereof, or a variant or a derivative thereof. None of the previously known reports show that change in the expression of the gene or the transcript thereof can serve as a marker for stomach cancer.

The 108th target gene is the hsa-miR-1914-3p gene, a congener thereof, a transcript thereof, or a variant or a derivative thereof. None of the previously known reports show that change in the expression of the gene or the transcript thereof can serve as a marker for stomach cancer.

The 109th target gene is the hsa-miR-3620-5p gene, a congener thereof, a transcript thereof, or a variant or a derivative thereof. None of the previously known reports show that change in the expression of the gene or the transcript thereof can serve as a marker for stomach cancer.

The 110th target gene is the hsa-miR-1268b gene, a congener thereof, a transcript thereof, or a variant or a derivative thereof. None of the previously known reports show that change in the expression of the gene or the transcript thereof can serve as a marker for stomach cancer.

The 111th target gene is the hsa-miR-1227-5p gene, a congener thereof, a transcript thereof, or a variant or a derivative thereof. None of the previously known reports show that change in the expression of the gene or the transcript thereof can serve as a marker for stomach cancer.

The 112th target gene is the hsa-miR-6880-5p gene, a congener thereof, a transcript thereof, or a variant or a derivative thereof. None of the previously known reports show that change in the expression of the gene or the transcript thereof can serve as a marker for stomach cancer.

The 113th target gene is the hsa-miR-4417 gene, a congener thereof, a transcript thereof, or a variant or a derivative thereof. None of the previously known reports show that change in the expression of the gene or the transcript thereof can serve as a marker for stomach cancer.

The 114th target gene is the hsa-miR-6802-5p gene, a congener thereof, a transcript thereof, or a variant or a derivative thereof. None of the previously known reports show that change in the expression of the gene or the transcript thereof can serve as a marker for stomach cancer.

The 115th target gene is the hsa-miR-6769a-5p gene, a congener thereof, a transcript thereof, or a variant or a derivative thereof. None of the previously known reports show that change in the expression of the gene or the transcript thereof can serve as a marker for stomach cancer.

The 116th target gene is the hsa-miR-663a gene, a congener thereof, a transcript thereof, or a variant or a derivative thereof. None of the previously known reports show that change in the expression of the gene or the transcript thereof can serve as a marker for stomach cancer.

The 117th target gene is the hsa-miR-6721-5p gene, a congener thereof, a transcript thereof, or a variant or a derivative thereof. None of the previously known reports show that change in the expression of the gene or the transcript thereof can serve as a marker for stomach cancer.

The 118th target gene is the hsa-miR-4532 gene, a congener thereof, a transcript thereof, or a variant or a derivative thereof. None of the previously known reports show that change in the expression of the gene or the transcript thereof can serve as a marker for stomach cancer.

The 119th target gene is the hsa-miR-7977 gene, a congener thereof, a transcript thereof, or a variant or a derivative thereof. None of the previously known reports show that change in the expression of the gene or the transcript thereof can serve as a marker for stomach cancer.

The 120th target gene is the hsa-miR-92b-5p gene, a congener thereof, a transcript thereof, or a variant or a derivative thereof. None of the previously known reports show that change in the expression of the gene or the transcript thereof can serve as a marker for stomach cancer.

The 121st target gene is the hsa-miR-371a-5p gene, a congener thereof, a transcript thereof, or a variant or a derivative thereof. None of the previously known reports show that change in the expression of the gene or the transcript thereof can serve as a marker for stomach cancer.

The 122nd target gene is the hsa-miR-6126 gene, a congener thereof, a transcript thereof, or a variant or a derivative thereof. None of the previously known reports show that change in the expression of the gene or the transcript thereof can serve as a marker for stomach cancer.

The 123rd target gene is the hsa-miR-4734 gene, a congener thereof, a transcript thereof, or a variant or a derivative thereof. None of the previously known reports show that change in the expression of the gene or the transcript thereof can serve as a marker for stomach cancer.

The 124th target gene is the hsa-miR-4665-3p gene, a congener thereof, a transcript thereof, or a variant or a derivative thereof. None of the previously known reports show that change in the expression of the gene or the transcript thereof can serve as a marker for stomach cancer.

The 125th target gene is the hsa-miR-423-5p gene, a congener thereof, a transcript thereof, or a variant or a derivative thereof. None of the previously known reports show that change in the expression of the gene or the transcript thereof can serve as a marker for stomach cancer.

The 126th target gene is the hsa-miR-1469 gene, a congener thereof, a transcript thereof, or a variant or a derivative thereof. None of the previously known reports show that change in the expression of the gene or the transcript thereof can serve as a marker for stomach cancer.

The 127th target gene is the hsa-miR-4675 gene, a congener thereof, a transcript thereof, or a variant or a derivative thereof. None of the previously known reports show that change in the expression of the gene or the transcript thereof can serve as a marker for stomach cancer.

The 128th target gene is the hsa-miR-1915-5p gene, a congener thereof, a transcript thereof, or a variant or a derivative thereof. None of the previously known reports show that change in the expression of the gene or the transcript thereof can serve as a marker for stomach cancer.

The 129th target gene is the hsa-miR-6716-5p gene, a congener thereof, a transcript thereof, or a variant or a derivative thereof. None of the previously known reports show that change in the expression of the gene or the transcript thereof can serve as a marker for stomach cancer.

The 130th target gene is the hsa-miR-718 gene, a congener thereof, a transcript thereof, or a variant or a derivative thereof. None of the previously known reports show that change in the expression of the gene or the transcript thereof can serve as a marker for stomach cancer.

The 131st target gene is the hsa-miR-4281 gene, a congener thereof, a transcript thereof, or a variant or a derivative thereof. None of the previously known reports show that change in the expression of the gene or the transcript thereof can serve as a marker for stomach cancer.

The 132nd target gene is the hsa-miR-6820-5p gene, a congener thereof, a transcript thereof, or a variant or a derivative thereof. None of the previously known reports show that change in the expression of the gene or the transcript thereof can serve as a marker for stomach cancer.

The 133rd target gene is the hsa-miR-6795-5p gene, a congener thereof, a transcript thereof, or a variant or a derivative thereof. None of the previously known reports show that change in the expression of the gene or the transcript thereof can serve as a marker for stomach cancer.

The 134th target gene is the hsa-miR-6779-5p gene, a congener thereof, a transcript thereof, or a variant or a derivative thereof. None of the previously known reports show that change in the expression of the gene or the transcript thereof can serve as a marker for stomach cancer.

The 135th target gene is the hsa-miR-7109-5p gene, a congener thereof, a transcript thereof, or a variant or a derivative thereof. None of the previously known reports show that change in the expression of the gene or the transcript thereof can serve as a marker for stomach cancer.

The 136th target gene is the hsa-miR-6798-5p gene, a congener thereof, a transcript thereof, or a variant or a derivative thereof. None of the previously known reports show that change in the expression of the gene or the transcript thereof can serve as a marker for stomach cancer.

The 137th target gene is the hsa-miR-4648 gene, a congener thereof, a transcript thereof, or a variant or a derivative thereof. None of the previously known reports show that change in the expression of the gene or the transcript thereof can serve as a marker for stomach cancer.

The 138th target gene is the hsa-miR-8059 gene, a congener thereof, a transcript thereof, or a variant or a derivative thereof. None of the previously known reports show that change in the expression of the gene or the transcript thereof can serve as a marker for stomach cancer.

The 139th target gene is the hsa-miR-6765-3p gene, a congener thereof, a transcript thereof, or a variant or a derivative thereof. None of the previously known reports show that change in the expression of the gene or the transcript thereof can serve as a marker for stomach cancer.

The 140th target gene is the hsa-miR-6132 gene, a congener thereof, a transcript thereof, or a variant or a derivative thereof. None of the previously known reports show that change in the expression of the gene or the transcript thereof can serve as a marker for stomach cancer.

The 141st target gene is the hsa-miR-4492 gene, a congener thereof, a transcript thereof, or a variant or a derivative thereof. None of the previously known reports show that change in the expression of the gene or the transcript thereof can serve as a marker for stomach cancer.

The 142nd target gene is the hsa-miR-7107-5p gene, a congener thereof, a transcript thereof, or a variant or a derivative thereof. None of the previously known reports show that change in the expression of the gene or the transcript thereof can serve as a marker for stomach cancer.

The 143rd target gene is the hsa-miR-3195 gene, a congener thereof, a transcript thereof, or a variant or a derivative thereof. None of the previously known reports show that change in the expression of the gene or the transcript thereof can serve as a marker for stomach cancer.

The 144th target gene is the hsa-miR-3180 gene, a congener thereof, a transcript thereof, or a variant or a derivative thereof. None of the previously known reports show that change in the expression of the gene or the transcript thereof can serve as a marker for stomach cancer.

The 145th target gene is the hsa-miR-296-3p gene, a congener thereof, a transcript thereof, or a variant or a derivative thereof. None of the previously known reports show that change in the expression of the gene or the transcript thereof can serve as a marker for stomach cancer.

The 146th target gene is the hsa-miR-564 gene, a congener thereof, a transcript thereof, or a variant or a derivative thereof. None of the previously known reports show that change in the expression of the gene or the transcript thereof can serve as a marker for stomach cancer.

The 147th target gene is the hsa-miR-1268a gene, a congener thereof, a transcript thereof, or a variant or a derivative thereof. None of the previously known reports show that change in the expression of the gene or the transcript thereof can serve as a marker for stomach cancer.

The 148th target gene is the hsa-miR-6848-5p gene, a congener thereof, a transcript thereof, or a variant or a derivative thereof. None of the previously known reports show that change in the expression of the gene or the transcript thereof can serve as a marker for stomach cancer.

The 149th target gene is the hsa-miR-762 gene, a congener thereof, a transcript thereof, or a variant or a derivative thereof. None of the previously known reports show that change in the expression of the gene or the transcript thereof can serve as a marker for stomach cancer.

The 150th target gene is the hsa-miR-2861 gene, a congener thereof, a transcript thereof, or a variant or a derivative thereof. None of the previously known reports show that change in the expression of the gene or the transcript thereof can serve as a marker for stomach cancer.

The 151st target gene is the hsa-miR-1203 gene, a congener thereof, a transcript thereof, or a variant or a derivative thereof. None of the previously known reports show that change in the expression of the gene or the transcript thereof can serve as a marker for stomach cancer.

The 152nd target gene is the hsa-miR-1260b gene, a congener thereof, a transcript thereof, or a variant or a derivative thereof. None of the previously known reports show that change in the expression of the gene or the transcript thereof can serve as a marker for stomach cancer.

The 153rd target gene is the hsa-miR-4476 gene, a congener thereof, a transcript thereof, or a variant or a derivative thereof. None of the previously known reports show that change in the expression of the gene or the transcript thereof can serve as a marker for stomach cancer.

The 154th target gene is the hsa-miR-6885-5p gene, a congener thereof, a transcript thereof, or a variant or a derivative thereof. None of the previously known reports show that change in the expression of the gene or the transcript thereof can serve as a marker for stomach cancer.

The 155th target gene is the hsa-miR-6769b-5p gene, a congener thereof, a transcript thereof, or a variant or a derivative thereof. None of the previously known reports show that change in the expression of the gene or the transcript thereof can serve as a marker for stomach cancer.

The 156th target gene is the hsa-miR-23b-3p gene, a congener thereof, a transcript thereof, or a variant or a derivative thereof. None of the previously known reports show that change in the expression of the gene or the transcript thereof can serve as a marker for stomach cancer.

The 157th target gene is the hsa-miR-1343-5p gene, a congener thereof, a transcript thereof, or a variant or a derivative thereof. None of the previously known reports show that change in the expression of the gene or the transcript thereof can serve as a marker for stomach cancer.

The 158th target gene is the hsa-miR-3621 gene, a congener thereof, a transcript thereof, or a variant or a derivative thereof. None of the previously known reports show that change in the expression of the gene or the transcript thereof can serve as a marker for stomach cancer.

The 159th target gene is the hsa-miR-4688 gene, a congener thereof, a transcript thereof, or a variant or a derivative thereof. None of the previously known reports show that change in the expression of the gene or the transcript thereof can serve as a marker for stomach cancer.

The 160th target gene is the hsa-miR-4286 gene, a congener thereof, a transcript thereof, or a variant or a derivative thereof. None of the previously known reports show that change in the expression of the gene or the transcript thereof can serve as a marker for stomach cancer.

The 161st target gene is the hsa-miR-4640-5p gene, a congener thereof, a transcript thereof, or a variant or a derivative thereof. None of the previously known reports show that change in the expression of the gene or the transcript thereof can serve as a marker for stomach cancer.

The 162nd target gene is the hsa-miR-4739 gene, a congener thereof, a transcript thereof, or a variant or a derivative thereof. None of the previously known reports show that change in the expression of the gene or the transcript thereof can serve as a marker for stomach cancer.

The 163rd target gene is the hsa-miR-1260a gene, a congener thereof, a transcript thereof, or a variant or a derivative thereof. None of the previously known reports show that change in the expression of the gene or the transcript thereof can serve as a marker for stomach cancer.

The 164th target gene is the hsa-miR-4276 gene, a congener thereof, a transcript thereof, or a variant or a derivative thereof. None of the previously known reports show that change in the expression of the gene or the transcript thereof can serve as a marker for stomach cancer.

The 165th target gene is the hsa-miR-7106-5p gene, a congener thereof, a transcript thereof, or a variant or a derivative thereof. None of the previously known reports show that change in the expression of the gene or the transcript thereof can serve as a marker for stomach cancer.

The 166th target gene is the hsa-miR-128-2-5p gene, a congener thereof, a transcript thereof, or a variant or a derivative thereof. The previously known report shows that change in the expression of the hsa-miR-128b (hsa-miR-128-2-3p) gene, which is derived from the same precursor, or the transcript thereof can serve as a marker for stomach cancer (Patent Literature 2).

The 167th target gene is the hsa-miR-125a-3p gene, a congener thereof, a transcript thereof, or a variant or a derivative thereof. The previously known report shows that change in the expression of the gene or the transcript thereof can serve as a marker for stomach cancer (Patent Literature 1).

The 168th target gene is the hsa-miR-92a-2-5p gene, a congener thereof, a transcript thereof, or a variant or a derivative thereof. The previously known report shows that change in the expression of the hsa-miR-92-2 (hsa-miR-92a-2-3p) gene, which is derived from the same precursor, or the transcript thereof can serve as a marker for stomach cancer (Patent Literature 2).

The 169th target gene is the hsa-miR-486-3p gene, a congener thereof, a transcript thereof, or a variant or a derivative thereof. The previously known report shows that change in the expression of the hsa-miR-486-5p gene, which is derived from the same precursor, or the transcript thereof can serve as a marker for stomach cancer (Patent Literature 3).

The 170th target gene is the hsa-miR-3196 gene, a congener thereof, a transcript thereof, or a variant or a derivative thereof. None of the previously known reports show that change in the expression of the gene or the transcript thereof can serve as a marker for stomach cancer.

The 171st target gene is the hsa-miR-211-3p gene, a congener thereof, a transcript thereof, or a variant or a derivative thereof. The previously known report shows that change in the expression of the hsa-miR-211 (hsa-miR-211-5p) gene, which is derived from the same precursor, or the transcript thereof can serve as a marker for stomach cancer (Patent Literature 2).

The 172nd target gene is the hsa-miR-4271 gene, a congener thereof, a transcript thereof, or a variant or a derivative thereof. None of the previously known reports show that change in the expression of the gene or the transcript thereof can serve as a marker for stomach cancer.

The 173rd target gene is the hsa-miR-6851-5p gene, a congener thereof, a transcript thereof, or a variant or a derivative thereof. None of the previously known reports show that change in the expression of the gene or the transcript thereof can serve as a marker for stomach cancer.

The 174th target gene is the hsa-miR-149-3p gene, a congener thereof, a transcript thereof, or a variant or a derivative thereof. None of the previously known reports show that change in the expression of the gene or the transcript thereof can serve as a marker for stomach cancer.

The 175th target gene is the hsa-miR-4667-5p gene, a congener thereof, a transcript thereof, or a variant or a derivative thereof. None of the previously known reports show that change in the expression of the gene or the transcript thereof can serve as a marker for stomach cancer.

The 176th target gene is the hsa-miR-135a-3p gene, a congener thereof, a transcript thereof, or a variant or a derivative thereof. None of the previously known reports show that change in the expression of the gene or the transcript thereof can serve as a marker for stomach cancer.

The 177th target gene is the hsa-miR-4486 gene, a congener thereof, a transcript thereof, or a variant or a derivative thereof. None of the previously known reports show that change in the expression of the gene or the transcript thereof can serve as a marker for stomach cancer.

The 178th target gene is the hsa-miR-4697-5p gene, a congener thereof, a transcript thereof, or a variant or a derivative thereof. None of the previously known reports show that change in the expression of the gene or the transcript thereof can serve as a marker for stomach cancer.

The 179th target gene is the hsa-miR-4725-3p gene, a congener thereof, a transcript thereof, or a variant or a derivative thereof. None of the previously known reports show that change in the expression of the gene or the transcript thereof can serve as a marker for stomach cancer.

The 180th target gene is the hsa-miR-6510-5p gene, a congener thereof, a transcript thereof, or a variant or a derivative thereof. None of the previously known reports show that change in the expression of the gene or the transcript thereof can serve as a marker for stomach cancer.

The 181st target gene is the hsa-miR-5001-5p gene, a congener thereof, a transcript thereof, or a variant or a derivative thereof. None of the previously known reports show that change in the expression of the gene or the transcript thereof can serve as a marker for stomach cancer.

The 182nd target gene is the hsa-miR-4673 gene, a congener thereof, a transcript thereof, or a variant or a derivative thereof. None of the previously known reports show that change in the expression of the gene or the transcript thereof can serve as a marker for stomach cancer.

The 183rd target gene is the hsa-miR-4466 gene, a congener thereof, a transcript thereof, or a variant or a derivative thereof. None of the previously known reports show that change in the expression of the gene or the transcript thereof can serve as a marker for stomach cancer.

The 184th target gene is the hsa-miR-23a-3p gene, a congener thereof, a transcript thereof, or a variant or a derivative thereof. The previously known report shows that change in the expression of the gene or the transcript thereof can serve as a marker for stomach cancer (Patent Literature 2).

The 185th target gene is the hsa-miR-3656 gene, a congener thereof, a transcript thereof, or a variant or a derivative thereof. None of the previously known reports show that change in the expression of the gene or the transcript thereof can serve as a marker for stomach cancer.

The 186th target gene is the hsa-miR-6782-5p gene, a congener thereof, a transcript thereof, or a variant or a derivative thereof. None of the previously known reports show that change in the expression of the gene or the transcript thereof can serve as a marker for stomach cancer.

The 187th target gene is the hsa-miR-4689 gene, a congener thereof, a transcript thereof, or a variant or a derivative thereof. None of the previously known reports show that change in the expression of the gene or the transcript thereof can serve as a marker for stomach cancer.

The 188th target gene is the hsa-miR-451a gene, a congener thereof, a transcript thereof, or a variant or a derivative thereof. The previously known report shows that change in the expression of the gene or the transcript thereof can serve as a marker for stomach cancer (Patent Literature 3).

The 189th target gene is the hsa-miR-4446-3p gene, a congener thereof, a transcript thereof, or a variant or a derivative thereof. None of the previously known reports show that change in the expression of the gene or the transcript thereof can serve as a marker for stomach cancer.

The 190th target gene is the hsa-miR-3180-3p gene, a congener thereof, a transcript thereof, or a variant or a derivative thereof. None of the previously known reports show that change in the expression of the gene or the transcript thereof can serve as a marker for stomach cancer.

The 191st target gene is the hsa-miR-642a-3p gene, a congener thereof, a transcript thereof, or a variant or a derivative thereof. None of the previously known reports show that change in the expression of the gene or the transcript thereof can serve as a marker for stomach cancer.

The 192nd target gene is the hsa-miR-6889-5p gene, a congener thereof, a transcript thereof, or a variant or a derivative thereof. None of the previously known reports show that change in the expression of the gene or the transcript thereof can serve as a marker for stomach cancer.

The 193rd target gene is the hsa-miR-3178 gene, a congener thereof, a transcript thereof, or a variant or a derivative thereof. None of the previously known reports show that change in the expression of the gene or the transcript thereof can serve as a marker for stomach cancer.

The 194th target gene is the hsa-miR-4665-5p gene, a congener thereof, a transcript thereof, or a variant or a derivative thereof. None of the previously known reports show that change in the expression of the gene or the transcript thereof can serve as a marker for stomach cancer.

The 195th target gene is the hsa-miR-6722-3p gene, a congener thereof, a transcript thereof, or a variant or a derivative thereof. None of the previously known reports show that change in the expression of the gene or the transcript thereof can serve as a marker for stomach cancer.

The 196th target gene is the hsa-miR-30c-1-3p gene, a congener thereof, a transcript thereof, or a variant or a derivative thereof. The previously known report shows that change in the expression of the hsa-miR-30c (hsa-miR-30c-1-5p) gene, which is derived from the same precursor, or the transcript thereof can serve as a marker for stomach cancer (Patent Literature 2).

The 197th target gene is the hsa-miR-4507 gene, a congener thereof, a transcript thereof, or a variant or a derivative thereof. None of the previously known reports show that change in the expression of the gene or the transcript thereof can serve as a marker for stomach cancer.

The 198th target gene is the hsa-miR-3141 gene, a congener thereof, a transcript thereof, or a variant or a derivative thereof. None of the previously known reports show that change in the expression of the gene or the transcript thereof can serve as a marker for stomach cancer.

The 199th target gene is the hsa-miR-1199-5p gene, a congener thereof, a transcript thereof, or a variant or a derivative thereof. None of the previously known reports show that change in the expression of the gene or the transcript thereof can serve as a marker for stomach cancer.

The 200th target gene is the hsa-miR-6794-5p gene, a congener thereof, a transcript thereof, or a variant or a derivative thereof. None of the previously known reports show that change in the expression of the gene or the transcript thereof can serve as a marker for stomach cancer.

The 201st target gene is the hsa-miR-6774-5p gene, a congener thereof, a transcript thereof, or a variant or a derivative thereof. None of the previously known reports show that change in the expression of the gene or the transcript thereof can serve as a marker for stomach cancer.

The 202nd target gene is the hsa-miR-4707-3p gene, a congener thereof, a transcript thereof, or a variant or a derivative thereof. None of the previously known reports show that change in the expression of the gene or the transcript thereof can serve as a marker for stomach cancer.

The 203rd target gene is the hsa-miR-4534 gene, a congener thereof, a transcript thereof, or a variant or a derivative thereof. None of the previously known reports show that change in the expression of the gene or the transcript thereof can serve as a marker for stomach cancer.

The 204th target gene is the hsa-miR-4294 gene, a congener thereof, a transcript thereof, or a variant or a derivative thereof. None of the previously known reports show that change in the expression of the gene or the transcript thereof can serve as a marker for stomach cancer.

The 205th target gene is the hsa-miR-6850-5p gene, a congener thereof, a transcript thereof, or a variant or a derivative thereof. None of the previously known reports show that change in the expression of the gene or the transcript thereof can serve as a marker for stomach cancer.

The 206th target gene is the hsa-miR-6089 gene, a congener thereof, a transcript thereof, or a variant or a derivative thereof. None of the previously known reports show that change in the expression of the gene or the transcript thereof can serve as a marker for stomach cancer.

The 207th target gene is the hsa-miR-671-5p gene, a congener thereof, a transcript thereof, or a variant or a derivative thereof. None of the previously known reports show that change in the expression of the gene or the transcript thereof can serve as a marker for stomach cancer.

2. Nucleic Acid Probe or Primer for Detection of Stomach Cancer

In the present invention, a nucleic acid(s) capable of specifically binding to any of the target nucleic acid(s) as the stomach cancer marker(s) described above can be used as a nucleic acid(s), for example, a nucleic acid probe(s) or a primer(s), for the detection or diagnosis of stomach cancer.

In the present invention, the nucleic acid probe(s) or the primer(s) that can be used for detecting stomach cancer or for diagnosing stomach cancer enables qualitative and/or quantitative measurement of the presence, expression level, or abundance of any of the target nucleic acids as the stomach cancer markers described above, for example: human-derived hsa-miR-4257, hsa-miR-6726-5p, hsa-miR-1343-3p, hsa-miR-1247-3p, hsa-miR-6787-5p, hsa-miR-6875-5p, hsa-miR-1225-3p, hsa-miR-8063, hsa-miR-6781-5p, hsa-miR-4746-3p, hsa-miR-1908-5p, hsa-miR-6756-5p, hsa-miR-204-3p, hsa-miR-4651, hsa-miR-6757-5p, hsa-miR-6825-5p, hsa-miR-7108-5p, hsa-miR-4792, hsa-miR-7641, hsa-miR-3188, hsa-miR-3131, hsa-miR-6780b-5p, hsa-miR-8069, hsa-miR-6840-3p, hsa-miR-8072, hsa-miR-1233-5p, hsa-miR-6887-5p, hsa-miR-1231, hsa-miR-5572, hsa-miR-6738-5p, hsa-miR-6784-5p, hsa-miR-6791-5p, hsa-miR-6749-5p, hsa-miR-6741-5p, hsa-miR-128-1-5p, hsa-miR-4419b, hsa-miR-6746-5p, hsa-miR-3184-5p, hsa-miR-3679-5p, hsa-miR-7110-5p, hsa-miR-4516, hsa-miR-6717-5p, hsa-miR-6826-5p, hsa-miR-4433b-3p, hsa-miR-3679-3p, hsa-miR-3135b, hsa-miR-3622a-5p, hsa-miR-711, hsa-miR-4467, hsa-miR-6857-5p, hsa-miR-6515-3p, hsa-miR-1225-5p, hsa-miR-187-5p, hsa-miR-3185, hsa-miR-642b-3p, hsa-miR-1249, hsa-miR-744-5p, hsa-miR-4442, hsa-miR-1228-3p, hsa-miR-939-5p, hsa-miR-6845-5p, hsa-miR-887-3p, hsa-miR-7845-5p, hsa-miR-6729-5p, hsa-miR-4632-5p, hsa-miR-615-5p, hsa-miR-6724-5p, hsa-miR-4728-5p, hsa-miR-6732-5p, hsa-miR-6816-5p, hsa-miR-4695-5p, hsa-miR-6088, hsa-miR-7975, hsa-miR-3197, hsa-miR-6125, hsa-miR-4433-3p, hsa-miR-6727-5p, hsa-miR-4706, hsa-miR-7847-3p, hsa-miR-6805-3p, hsa-miR-6766-3p, hsa-miR-1913, hsa-miR-4649-5p, hsa-miR-602, hsa-miR-3663-3p, hsa-miR-6893-5p, hsa-miR-6861-5p, hsa-miR-4449, hsa-miR-6842-5p, hsa-miR-4454, hsa-miR-5195-3p, hsa-miR-663b, hsa-miR-6765-5p, hsa-miR-4513, hsa-miR-614, hsa-miR-6785-5p, hsa-miR-6777-5p, hsa-miR-940, hsa-miR-4741, hsa-miR-6870-5p, hsa-miR-6131, hsa-miR-150-3p, hsa-miR-4707-5p, hsa-miR-1915-3p, hsa-miR-3937, hsa-miR-937-5p, hsa-miR-4443, hsa-miR-1914-3p, hsa-miR-3620-5p, hsa-miR-1268b, hsa-miR-1227-5p, hsa-miR-6880-5p, hsa-miR-4417, hsa-miR-6802-5p, hsa-miR-6769a-5p, hsa-miR-663a, hsa-miR-6721-5p, hsa-miR-4532, hsa-miR-7977, hsa-miR-92b-5p, hsa-miR-371a-5p, hsa-miR-6126, hsa-miR-4734, hsa-miR-4665-3p, hsa-miR-423-5p, hsa-miR-1469, hsa-miR-4675, hsa-miR-1915-5p, hsa-miR-6716-5p, hsa-miR-718, hsa-miR-4281, hsa-miR-6820-5p, hsa-miR-6795-5p, hsa-miR-6779-5p, hsa-miR-7109-5p, hsa-miR-6798-5p, hsa-miR-4648, hsa-miR-8059, hsa-miR-6765-3p, hsa-miR-6132, hsa-miR-4492, hsa-miR-7107-5p, hsa-miR-3195, hsa-miR-3180, hsa-miR-296-3p, hsa-miR-564, hsa-miR-1268a, hsa-miR-6848-5p, hsa-miR-762, hsa-miR-2861, hsa-miR-1203, hsa-miR-1260b, hsa-miR-4476, hsa-miR-6885-5p, hsa-miR-6769b-5p, hsa-miR-23b-3p, hsa-miR-1343-5p, hsa-miR-3621, hsa-miR-4688, hsa-miR-4286, hsa-miR-4640-5p, hsa-miR-4739, hsa-miR-1260a, hsa-miR-4276, hsa-miR-7106, hsa-miR-6794-5p, hsa-miR-6774-5p, hsa-miR-4707-3p, hsa-miR-4534, hsa-miR-4294, hsa-miR-6850-5p, hsa-miR-6089 and hsa-miR-671-5p or a combination thereof, congeners thereof, transcripts thereof, or variants or derivatives thereof; and, optionally combined therewith, hsa-miR-128-2-5p, hsa-miR-125a-3p, hsa-miR-92a-2-5p, and hsa-miR-486-3p or a combination thereof, congeners thereof, transcripts thereof, or variants or derivatives thereof; and, optionally combined therewith, hsa-miR-3196, hsa-miR-211-3p, hsa-miR-4271, hsa-miR-6851-5p, hsa-miR-149-3p, hsa-miR-4667-5p, hsa-miR-135a-3p, hsa-miR-4486, hsa-miR-4697-5p, hsa-miR-4725-3p, hsa-miR-6510-5p, hsa-miR-5001-5p, hsa-miR-4673, hsa-miR-4466, hsa-miR-23a-3p, hsa-miR-3656, hsa-miR-6782-5p, hsa-miR-4689, hsa-miR-451a, hsa-miR-4446-3p, hsa-miR-3180-3p, hsa-miR-642a-3p, hsa-miR-6889-5p, hsa-miR-3178, hsa-miR-4665-5p, hsa-miR-6722-3p, hsa-miR-30c-1-3p, hsa-miR-4507, hsa-miR-3141 and hsa-miR-1199-5p or a combination thereof, congeners thereof, transcripts thereof, or variants or derivatives thereof.

The expression level of each target nucleic acid described above is increased or decreased (hereinafter, referred to as "increased/decreased") depending on the type of the target nucleic acid in a subject having stomach cancer as compared with a healthy subject. Hence, the nucleic acid of the present invention can be effectively used for measuring the expression level of the target nucleic acid described above in a body fluid derived from a subject (e.g., a human) suspected of having stomach cancer and a body fluid derived from a healthy subject and thereby detecting stomach cancer by the comparison thereof.

The nucleic acid probe(s) or the primer(s) that can be used in the present invention is a nucleic acid probe(s) capable of specifically binding to at least one polynucleotide consisting of a nucleotide sequence represented by any of SEQ ID NOs: 1 to 165 and 635 to 642, or a primer for amplifying at least one polynucleotide consisting of a nucleotide sequence represented by any of SEQ ID NOs: 1 to 165 and 635 to 642.

The nucleic acid probe(s) or the primer(s) that can be used in the present invention may further comprise a nucleic acid probe capable of specifically binding to at least one polynucleotide consisting of a nucleotide sequence represented by any of SEQ ID NOs: 166 to 169, or a primer for amplifying at least one polynucleotide consisting of a nucleotide sequence represented by any of SEQ ID NOs: 166 to 169.

The nucleic acid probe(s) or the primer(s) that can be used in the present invention may further comprise a nucleic acid probe capable of specifically binding to at least one polynucleotide consisting of a nucleotide sequence represented by any of SEQ ID NOs: 170 to 199, or a primer for amplifying at least one polynucleotide consisting of a nucleotide sequence represented by any of SEQ ID NOs: 170 to 199.

Specifically, these nucleic acid probes or primers comprise a combination of one or more polynucleotides selected from a group of polynucleotides comprising nucleotide sequences represented by any of SEQ ID NOs: 1 to 657, or nucleotide sequences derived from the nucleotide sequences by the replacement of u % with t, and a group of complementary polynucleotides thereof, a group of polynucleotides respectively hybridizing under stringent conditions (mentioned later) to DNAs consisting of nucleotide sequences complementary to these nucleotide sequences, and a group of complementary polynucleotides thereof, and a group of polynucleotides comprising 15 or more, preferably 17 or more consecutive nucleotides in the nucleotide sequences of these polynucleotide groups. These polynucleotides can be used as nucleic acid probes and primers for detecting the stomach cancer markers as target nucleic acids.

More specifically, examples of the nucleic acid probe(s) or the primer(s) that can be used in the present invention include one or more polynucleotides selected from the group consisting of the following polynucleotides (a) to (e):

(a) a polynucleotide consisting of a nucleotide sequence represented by any of SEQ ID NOs: 1 to 165 and 635 to 642 or a nucleotide sequence derived from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 165 and 635 to 642,
(c) a polynucleotide consisting of a nucleotide sequence complementary to a nucleotide sequence represented by any of SEQ ID NOs: 1 to 165 and 635 to 642, or a nucleotide sequence derived from the nucleotide sequence by the replacement of u with t, a variant thereof, a derivative thereof, or a fragment thereof comprising 15 or more consecutive nucleotides.
(d) a polynucleotide comprising a nucleotide sequence complementary to a nucleotide sequence represented by any of SEQ ID NOs: 1 to 165 and 635 to 642, or a nucleotide sequence derived from the nucleotide sequence by the replacement of u with t, and
(e) a polynucleotide hybridizing under stringent conditions to any of the polynucleotides (a) to (d).

In addition to at least one or more polynucleotides selected from the group consisting of the polynucleotides (a) to (e), the nucleic acid probe(s) or the primer(s) that can be used in the present invention may further comprise polynucleotides selected from the group consisting of the following polynucleotides (f) to (j):
(f) a polynucleotide consisting of a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides,
(g) a polynucleotide comprising a nucleotide sequence represented by any of SEQ ID NOs: 166 to 169,
(h) a polynucleotide consisting of a nucleotide sequence complementary to a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides,
(i) a polynucleotide comprising a nucleotide sequence complementary to a nucleotide sequence represented by any of SEQ ID NOs: 166 to 169 or a nucleotide sequence derived from the nucleotide sequence by the replacement of u with t, and
(j) a polynucleotide hybridizing under stringent conditions to any of the polynucleotides (f) to (i).

In addition to at least one or more polynucleotide(s) selected from the group consisting of the polynucleotides (a) to (j), the nucleic acid probe(s) or the primer(s) that can be used in the present invention may further comprise polynucleotides selected from the group consisting of the following polynucleotides (k) to (o):
(k) a polynucleotide consisting of a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides,
(l) a polynucleotide comprising a nucleotide sequence represented by any of SEQ ID NOs: 170 to 199,
(m) a polynucleotide consisting of a nucleotide sequence complementary to a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides,
(n) a polynucleotide comprising a nucleotide sequence complementary to a nucleotide sequence represented by any of SEQ ID NOs: 170 to 199 or a nucleotide sequence derived from the nucleotide sequence by the replacement of u with t, and
(o) a polynucleotide hybridizing under stringent conditions to any of the polynucleotides (k) to (n).

For the above-mentioned polynucleotides, the "fragment thereof comprising 15 or more consecutive nucleotides" can comprise, but not limited to, the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, or the like, in the nucleotide sequence of each polynucleotide.

These polynucleotides or fragments thereof used in the present invention may each be DNA or may each be RNA.

The polynucleotides that can be used in the present invention can each be prepared by use of a general technique such as a DNA recombination technique, PCR, or a method using an automatic DNA/RNA synthesizer.

The DNA recombination technique and the PCR method may employ a technique described in, for example, Ausubel et al., Current Protocols in Molecular Biology, John Willey & Sons, US (1993); and Sambrook et al., Molecular Cloning—A Laboratory Manual, Cold Spring Harbor Laboratory Press. US (1989).

The human-derived hsa-miR-4257, hsa-miR-6726-5p, hsa-miR-1343-3p, hsa-miR-1247-3p, hsa-miR-6787-5p, hsa-miR-6875-5p, hsa-miR-1225-3p, hsa-miR-8063, hsa-miR-6781-5p, hsa-miR-4746-3p, hsa-miR-1908-5p, hsa-miR-6756-5p, hsa-miR-204-3p, hsa-miR-4651, hsa-miR-6757-5p, hsa-miR-6825-5p, hsa-miR-7108-5p, hsa-miR-4792, hsa-miR-7641, hsa-miR-3188, hsa-miR-3131, hsa-miR-6780b-5p, hsa-miR-8069, hsa-miR-6840-3p, hsa-miR-8072, hsa-miR-1233-5p, hsa-miR-6887-5p, hsa-miR-1231, hsa-miR-5572, hsa-miR-6738-5p, hsa-miR-6784-5p, hsa-miR-6791-5p, hsa-miR-6749-5p, hsa-miR-6741-5p, hsa-miR-128-1-5p, hsa-miR-4419b, hsa-miR-6746-5p, hsa-miR-3184-5p, hsa-miR-3679-5p, hsa-miR-7110-5p, hsa-miR-4516, hsa-miR-6717-5p, hsa-miR-6826-5p, hsa-miR-4433b-3p, hsa-miR-3679-3p, hsa-miR-3135b, hsa-miR-3622a-5p, hsa-miR-711, hsa-miR-4467, hsa-miR-6857-5p, hsa-miR-6515-3p, hsa-miR-1225-5p, hsa-miR-187-5p, hsa-miR-3185, hsa-miR-642b-3p, hsa-miR-1249, hsa-miR-744-5p, hsa-miR-4442, hsa-miR-1228-3p, hsa-miR-939-5p, hsa-miR-6845-5p, hsa-miR-887-3p, hsa-miR-7845-5p, hsa-miR-6729-5p, hsa-miR-4632-5p, hsa-miR-615-5p, hsa-miR-6724-5p, hsa-miR-4728-5p, hsa-miR-6732-5p, hsa-miR-6816-5p, hsa-miR-4695-5p, hsa-miR-6088, hsa-miR-7975, hsa-miR-3197, hsa-miR-6125, hsa-miR-4433-3p, hsa-miR-6727-5p, hsa-miR-4706, hsa-miR-7847-3p, hsa-miR-6805-3p, hsa-miR-6766-3p, hsa-miR-1913, hsa-miR-4649-5p, hsa-miR-602, hsa-miR-3663-3p, hsa-miR-6893-5p, hsa-miR-6861-5p, hsa-miR-4449, hsa-miR-6842-5p, hsa-miR-4454, hsa-miR-5195-3p, hsa-miR-663b, hsa-miR-6765-5p, hsa-miR-4513, hsa-miR-614, hsa-miR-6785-5p, hsa-miR-6777-5p, hsa-miR-940, hsa-miR-4741, hsa-miR-6870-5p, hsa-miR-6131, hsa-miR-150-3p, hsa-miR-4707-5p, hsa-miR-1915-3p, hsa-miR-3937, hsa-miR-937-5p, hsa-miR-4443, hsa-miR-1914-3p, hsa-miR-3620-5p, hsa-miR-1268b, hsa-miR-1227-5p, hsa-miR-6880-5p, hsa-miR-4417, hsa-miR-6802-5p, hsa-miR-6769a-5p, hsa-miR-663a, hsa-miR-6721-5p, hsa-miR-4532, hsa-miR-7977, hsa-miR-92b-5p, hsa-miR-371a-5p, hsa-miR-6126, hsa-miR-4734, hsa-miR- 4665-3p, hsa-miR-423-5p, hsa-miR-1469, hsa-miR-4675, hsa-miR-1915-5p, hsa-miR-6716-5p, hsa-miR-718, hsa-miR-4281, hsa-miR-6820-5p, hsa-miR-6795-5p, hsa-miR-6779-5p, hsa-miR-7109-5p, hsa-miR-6798-5p, hsa-miR-4648, hsa-miR-8059, hsa-miR-6765-3p, hsa-miR-6132, hsa-miR-4492, hsa-miR-7107-5p, hsa-miR-3195, hsa-miR-3180, hsa-miR-296-3p, hsa-miR-564, hsa-miR-1268a, hsa-miR-6848-5p, hsa-miR-762, hsa-miR-2861, hsa-miR-1203, hsa-miR-1260b, hsa-miR-4476, hsa-miR-6885-5p, hsa-miR-6769b-5p, hsa-miR-23b-3p, hsa-miR-1343-5p, hsa-miR-3621, hsa-miR-4688, hsa-miR-4286, hsa-miR-4640-5p, hsa-miR-4739, hsa-miR-1260a, hsa-miR-4276, hsa-miR-7106, hsa-miR-6794-5p, hsa-miR-6774-5p, hsa-miR-4707-3p, hsa-miR-4534, hsa-miR-4294, hsa-miR-6850-5p, hsa-miR-6089 and hsa-miR-671-5p, hsa-miR-128-2-5p, hsa-miR-125a-3p, hsa-miR-92a-2-5p, hsa-miR-486-3p, hsa-miR-3196, hsa-miR-211-3p, hsa-miR-4271, hsa-miR-6851-5p, hsa-miR-149-3p, hsa-miR-4667-5p, hsa-miR-135a-3p, hsa-miR-4486, hsa-miR-4697-5p, hsa-miR-4725-3p, hsa-miR-6510-5p, hsa-miR-5001-5p, hsa-miR-4673, hsa-miR-4466, hsa-miR-23a-3p, hsa-miR-3656, hsa-miR-6782-5p, hsa-miR-4689, hsa-miR-451a, hsa-miR-4446-3p, hsa-miR-3180-3p, hsa-miR-642a-3p, hsa-miR-6889-5p, hsa-miR-3178, hsa-miR-4665-5p, hsa-miR-6722-3p, hsa-miR-30c-1-3p, hsa-miR-4507, hsa-miR-3141 and hsa-miR-1199-5p represented by SEQ ID NOs: 1 to 199 and 635 to 642 are known in the art, and their acquisition methods are also known as mentioned above. Therefore, each polynucleotide that can be used as a nucleic acid probe(s) or a primer(s) in the present invention can be prepared by cloning the gene.

Such a nucleic acid probe(s) or a primer(s) can be chemically synthesized using an automatic DNA synthesizer. In general, a phosphoramidite method is used in this synthesis, and single-stranded DNA up to approximately 100 nucleotides can be automatically synthesized by this method. The automatic DNA synthesizer is commercially available from, for example, Polygen GmbH, ABI, or Applied Biosystems, Inc.

Alternatively, the polynucleotide of the present invention can also be prepared by a cDNA cloning method. The cDNA cloning technique may employ, for example, microRNA Cloning Kit Wako.

In this context, the sequences of the nucleic acid probe(s) and the primer(s) for detecting the polynucleotide consisting of a nucleotide sequence represented by any of SEQ ID NOs: 1 to 199 and 635 to 642 do not exist as miRNAs or precursors thereof in the living body or in vivo. For example, the nucleotide sequences represented by SEQ ID NO: 7 and SEQ ID NO: 52 are produced from the precursor represented by SEQ ID NO: 206. This precursor has a hairpin-like structure as shown in FIG. 1, and the nucleotide sequences represented by SEQ ID NO: 7 and SEQ ID NO: 52 have mismatch sequences with each other. As such, a nucleotide sequence completely complementary to the nucleotide sequence represented by SEQ ID NO: 7 or SEQ ID NO: 52 is not naturally produced in vivo. Therefore, the nucleic acid probe and the primer for detecting the nucleotide sequence represented by any of SEQ ID NOs: 1 to 199 and 635 to 642 each have an artificial nucleotide sequence that does not exist in the living body or in vivo.

3. Kit or Device for Detection of Stomach Cancer

The present invention also provides a kit or a device for the detection of stomach cancer, comprising one or more polynucleotides (which may include a variant, a fragment, or a derivative thereof: hereinafter, also referred to as a polynucleotide for detection) that can be used as a nucleic acid probe(s) or a primer(s) in the present invention for measuring a target nucleic acid(s) as a stomach cancer marker(s).

The target nucleic acid(s) as a stomach cancer marker(s) according to the present invention is selected from the following group 1:
miR-4257, miR-6726-5p, miR-1343-3p, miR-1247-3p, miR-6787-5p, miR-6875-5p, miR-1225-3p, miR-8063, miR-6781-5p, miR-4746-3p, miR-1908-5p, miR-6756-5p, miR-204-3p, miR-4651, miR-6757-5p, miR-6825-5p, miR-7108-5p, miR-4792, miR-7641, miR-3188, miR-3131, miR-6780b-5p, miR-8069, miR-6840-3p, miR-8072, miR-1233-5p, miR-6887-5p, miR-1231, miR-5572, miR-6738-5p, miR-6784-5p, miR-6791-5p, miR-6749-5p, miR-6741-5p, miR-128-1-5p, miR-4419b, miR-6746-5p, miR-3184-5p, miR-3679-5p, miR-7110-5p, miR-4516, miR-6717-5p, miR-6826-5p, miR-4433b-3p, miR-3679-3p, miR-3135b, miR-3622a-5p, miR-711, miR-4467, miR-6857-5p, miR-6515-3p, miR-1225-5p, miR-187-5p, miR-3185, miR-642b-3p, miR-1249, miR-744-5p, miR-4442, miR-1228-3p, miR-939-5p, miR-6845-5p, miR-887-3p, miR-7845-5p, miR-6729-5p, miR-4632-5p, miR-615-5p, miR-6724-5p, miR-4728-5p, miR-6732-5p, miR-6816-5p, miR-4695-5p, miR-6088, miR-7975, miR-3197, miR-6125, miR-4433-3p, miR-6727-5p, miR-4706, miR-7847-3p, miR-6805-3p, miR-6766-3p, miR-1913, miR-4649-5p, miR-602, miR-3663-3p, miR-6893-5p, miR-6861-5p, miR-4449, miR-6842-5p, miR-4454, miR-5195-3p, miR-663b, miR-6765-5p, miR-4513, miR-614, miR-6785-5p, miR-6777-5p, miR-940, miR-4741, miR-6870-5p, miR-6131, miR-150-3p, miR-4707-5p, miR-1915-3p, miR-3937, miR-937-5p, miR-4443, miR-1914-3p, miR-3620-5p, miR-1268b, miR-1227-5p, miR-6880-5p, miR-4417, miR-6802-5p, miR-6769a-5p, miR-663a, miR-6721-5p, miR-4532, miR-7977, miR-92b-5p, miR-371a-5p, miR-6126, miR-4734, miR-4665-3p, miR-423-5p, miR-1469, miR-4675, miR-1915-5p, miR-6716-5p, miR-718, miR-4281, miR-6820-5p, miR-6795-5p, miR-6779-5p, miR-7109-5p, miR-6798-5p, miR-4648, miR-8059, miR-6765-3p, miR-6132, miR-4492, miR-7107-5p, miR-3195, miR-3180, miR-296-3p, miR-564, miR-1268a, miR-6848-5p, miR-762, miR-2861, miR-1203, miR-1260b, miR-4476, miR-6885-5p, miR-6769b-5p, miR-23b-3p, miR-1343-5p, miR-3621, miR-4688, miR-4286, miR-4640-5p, miR-4739, miR-1260a, miR-4276, miR-7106-5p, miR-6794-5p, miR-6774-5p, miR-4707-3p, miR-4534, miR-4294, miR-6850-5p, miR-6089 and miR-671-5p.

Additional target nucleic acid(s) that may be optionally used in the measurement is preferably selected from the following group 2: miR-128-2-5p, miR-125a-3p, miR-92a-2-5p, and miR-486-3p. Additional target nucleic acid(s) that may be optionally further used in the measurement is preferably selected from the following group 3: miR-3196, miR-211-3p, miR-4271, miR-6851-5p, miR-149-3p, miR-4667-5p, miR-135a-3p, miR-4486, miR-4697-5p, miR-4725-3p, miR-6510-5p, miR-5001-5p, miR-4673, miR-4466, miR-23a-3p, miR-3656, miR-6782-5p, miR-4689, miR-451a, miR-4446-3p, miR-3180-3p, miR-642a-3p, miR-6889-5p, miR-3178, miR-4665-5p, miR-6722-3p, miR-30c-1-3p, miR-4507, miR-3141 and miR-1199-5p.

The kit or the device of the present invention comprises a nucleic acid(s) capable of specifically binding to any of the target nucleic acids as the stomach cancer markers described above, preferably one or more polynucleotides selected from the nucleic acid probes or the primers described in the preceding Section 2, specifically, the polynucleotides described in the preceding Section 2 or variant(s) thereof.

Specifically, the kit or the device of the present invention can comprise at least one or more polynucleotides comprising (or consisting of) a nucleotide sequence represented by any of SEQ ID NOs: 1 to 165 and 635 to 642 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention can further comprise one or more polynucleotides comprising (or consisting of) a nucleotide sequence represented by any of SEQ ID NOs: 166 to 169 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The kit or the device of the present invention can further comprise one or more polynucleotides comprising (or consisting of) a nucleotide sequence represented by any of SEQ ID NOs: 170 to 199 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment(s) that can be contained in the kit or the device of the present invention is, for example, one or more, preferably two or more polynucleotides selected from the group consisting of the following polynucleotides (1) to (3):
(1) a polynucleotide comprising 15 or more consecutive nucleotides that are from a nucleotide sequence derived from a nucleotide sequence represented by any of SEQ ID NOs: 1 to 165 and 635 to 642 by the replacement of u with t, or a complementary sequence thereof;
(2) a polynucleotide comprising 15 or more consecutive nucleotides that are from a nucleotide sequence derived from a nucleotide sequence represented by any of SEQ ID NOs: 166 to 169 by the replacement of u with t, or a complementary sequence thereof; and
(3) a polynucleotide comprising 15 or more consecutive nucleotides that are from a nucleotide sequence derived from a nucleotide sequence represented by any of SEQ ID NOs: 170 to 199 by the replacement of u with t, or a complementary sequence thereof.

In a preferred embodiment, the polynucleotide is a polynucleotide consisting of a nucleotide sequence represented by any of SEQ ID NOs: 1 to 165 and 635 to 642 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 166 to 169 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 170 to 199 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide.

Specific examples of the aforementioned polynucleotide combination as target nucleic acids for the kit or the device of the present invention can include combinations of the polynucleotides consisting of nucleotide sequences represented by SEQ ID NOs shown in Table 1 (SEQ ID NOs: 1 to 199 and 635 to 642 corresponding to the miRNA markers in Table 1). However, these are given merely for illustrative purposes, and all of various other possible combinations are included in the present invention.

The combination of the target nucleic acids for the kit or the device for discriminating a stomach cancer patient from a healthy subject according to the present invention is desirably, for example, a combination of two or more polynucleotides consisting of the nucleotide sequences represented by SEQ ID NOs shown in Table 1. Usually, a combination of two of these polynucleotides can produce adequate performance.

The specific combination of two polynucleotides consisting of the nucleotide sequences or the complementary sequences thereof for discriminating a stomach cancer patient from a healthy subject is preferably a combination comprising at least one or more of the newly found polynucleotides consisting of the nucleotide sequences represented by SEQ ID NOs: 1 to 165 and 635 to 642, among the combinations of two of the aforementioned polynucleotides consisting of the nucleotide sequences represented by SEQ ID NOs: 1 to 199 and 635 to 642.

The combination of polynucleotides with cancer type specificity capable of discriminating a stomach cancer patient not only from a healthy subject but also from other cancer patients is preferably, for example, a combination of multiple polynucleotides comprising at least one polynucleotide selected from the group consisting of polynucleotides of SEQ ID NOs: 9, 13, 21, 27, 34, 36, 66, 75, 95, 98, 108, 130, 135, 143, 155, 183, 185, 187, 191, 193, 194, 635, 636, 637, 638, 639, 640, 641 and 642 (hereinafter, this group is referred to as "cancer type-specific polynucleotide group 1"), with any of the polynucleotides of the other SEQ ID NOs.

The combination of polynucleotides with cancer type specificity capable of discriminating a stomach cancer patient not only from a healthy subject but also from other cancer patients is more preferably a combination of multiple polynucleotides selected from the cancer type-specific polynucleotide group 1.

The combination of polynucleotides with cancer type specificity capable of discriminating a stomach cancer patient not only from a healthy subject but also from other cancer patients is more preferably a combination comprising at least one or more polynucleotides selected from the group consisting of polynucleotides of SEQ ID NOs: 21, 34, 36, 98, and 155 (hereinafter, this group is referred to as "cancer type-specific polynucleotide group 2") included in the cancer type-specific polynucleotide group 1, among the combinations of multiple polynucleotides selected from the cancer type-specific polynucleotide group 1.

The number of the polynucleotides with cancer type specificity may be 2, 3, 4, 5, 6, 7, 8, 9, 10 or more in the combination and is more preferably 6 or more in the combination. Usually, the combination of 6 of these polynucleotides can produce adequate performance.

Non-limiting examples of the combination of the polynucleotide consisting of the nucleotide sequence represented by SEQ ID NO: 21 or a complementary sequence thereof with polynucleotides consisting of nucleotide sequences represented by SEQ ID NOs of five polynucleotides selected from the cancer type-specific polynucleotide group 1 or complementary sequences thereof are listed below.

(1) a combination of SEQ ID NOs: 9, 21, 36, 98, 130, and 637 (markers: hsa-miR-6781-5p, hsa-miR-3131, hsa-miR-4419b, hsa-miR-940, hsa-miR-718, and hsa-miR-4707-3p);

(2) a combination of SEQ ID NOs: 9, 21, 34, 36, 98, and 637 (markers: hsa-miR-6781-5p, hsa-miR-3131, hsa-miR-6741-5p, hsa-miR-4419b, hsa-miR-940, and hsa-miR-4707-3p):

(3) a combination of SEQ ID NOs: 9, 21, 34, 36, 98, and 155 (markers: hsa-miR-6781-5p, hsa-miR-3131, hsa-miR-6741-5p, hsa-miR-4419b, hsa-miR-940, and hsa-miR-6769b-5p):

(4) a combination of SEQ ID NOs: 21, 36, 75, 98, 155, and 635 (markers: hsa-miR-3131, hsa-miR-4419b, hsa-miR-6125, hsa-miR-940, hsa-miR-6769b-5p, and hsa-miR-6794-5p); and (5) a combination of SEQ ID NOs: 9, 21, 36, 98, 108, and 155 (markers: hsa-miR-6781-5p, hsa-miR-3131, hsa-miR-4419b, hsa-miR-940, hsa-miR-1914-3p, and hsa-miR-6769b-5p).

Non-limiting examples of the combination of the polynucleotide consisting of the nucleotide sequence represented by SEQ ID NO: 34 or a complementary sequence thereof with polynucleotides consisting of nucleotide sequences represented by SEQ ID NOs of five polynucleotides selected from the cancer type-specific polynucleotide group 1 or complementary sequences thereof are further listed.

(1) a combination of SEQ ID NOs: 34, 36, 143, 155, 187, and 635 (markers: hsa-miR-6741-5p, hsa-miR-4419b, hsa-miR-3195, hsa-miR-6769b-5p, hsa-miR-4689, and hsa-miR-6794-5p):

(2) a combination of SEQ ID NOs: 9, 34, 36, 66, 98, and 187 (markers: hsa-miR-6781-5p, hsa-miR-6741-5p, hsa-miR-4419b, hsa-miR-615-5p, hsa-miR-940, and hsa-miR-4689);

(3) a combination of SEQ ID NOs: 9, 34, 36, 98, 187, and 637 (markers: hsa-miR-6781-5p, hsa-miR-6741-5p, hsa-miR-4419b, hsa-miR-940, hsa-miR-4689, and hsa-miR-4707-3p);

(4) a combination of SEQ ID NOs: 9, 34, 36, 98, 185, and 637 (markers: hsa-miR-6781-5p, hsa-miR-6741-5p, hsa-miR-4419b, hsa-miR-940, hsa-miR-3656, and hsa-miR-4707-3p); and (5) a combination of SEQ ID NOs: 9, 34, 36, 98, 637, and 639 (markers: hsa-miR-6781-5p, hsa-miR-6741-5p, hsa-miR-4419b, hsa-miR-940, hsa-miR-4707-3p, and hsa-miR-4294).

Non-limiting examples of the combination of the polynucleotide consisting of the nucleotide sequence represented by SEQ ID NO: 36 or a complementary sequence thereof with polynucleotides consisting of nucleotide sequences represented by SEQ ID NOs of five polynucleotides selected from the cancer type-specific polynucleotide group 1 or complementary sequences thereof are further listed.

(1) a combination of SEQ ID NOs: 9, 36, 98, 108, 638, and 639 (markers: hsa-miR-6781-5p, hsa-miR-4419b, hsa-miR-940, hsa-miR-1914-3p, hsa-miR-4534, and hsa-miR-4294);

(2) a combination of SEQ ID NOs: 36, 98, 155, 194, 635, and 642 (markers: hsa-miR-4419b, hsa-miR-940, hsa-miR-6769b-5p, hsa-miR-4665-5p, hsa-miR-6794-5p, and hsa-miR-671-5p);

(3) a combination of SEQ ID NOs: 9, 34, 36, 75, 98, and 637 (markers: hsa-miR-6781-5p, hsa-miR-6741-5p, hsa-miR-4419b, hsa-miR-6125, hsa-miR-940, and hsa-miR-4707-3p):

(4) a combination of SEQ ID NOs: 21, 36, 98, 155, 185, and 635 (markers: hsa-miR-3131, hsa-miR-4419b, hsa-miR-940, hsa-miR-6769b-5p, hsa-miR-3656, and hsa-miR-6794-5p); and (5) a combination of SEQ ID NOs: 9, 36, 98, 108, 155, and 635 (markers: hsa-miR-6781-5p, hsa-miR-4419b, hsa-miR-940, hsa-miR-1914-3p, hsa-miR-6769b-5p, and hsa-miR-6794-5p).

Non-limiting examples of the combination of the polynucleotide consisting of the nucleotide sequence represented by SEQ ID NO: 98 or a complementary sequence thereof with polynucleotides consisting of nucleotide sequences represented by SEQ ID NOs of five polynucleotides selected from the cancer type-specific polynucleotide group 1 or complementary sequences thereof are further listed.

(1) a combination of SEQ ID NOs: 9, 36, 98, 130, 194, and 637 (markers: hsa-miR-6781-5p, hsa-miR-4419b, hsa-miR-940, hsa-miR-718, hsa-miR-4665-5p, and hsa-miR-4707-3p);

(2) a combination of SEQ ID NOs: 21, 36, 98, 108, 155, and 635 (markers: hsa-miR-3131, hsa-miR-4419b, hsa-miR-940, hsa-miR-1914-3p, hsa-miR-6769b-5p, and hsa-miR-6794-5p);

(3) a combination of SEQ ID NOs: 9, 36, 98, 108, 155, and 639 (markers: hsa-miR-6781-5p, hsa-miR-449b, hsa-miR-940, hsa-miR-1914-3p, hsa-miR-6769b-5p, and hsa-miR-4294):

(4) a combination of SEQ ID NOs: 9, 36, 98, 155, 187, and 639 (markers: hsa-miR-6781-5p, hsa-miR-4419b, hsa-miR-940, hsa-miR-6769b-5p, hsa-miR-4689, and hsa-miR-4294); and (5) a combination of SEQ ID NOs: 9, 36, 98, 155, 187, and 637 (markers: hsa-miR-6781-5p, hsa-miR-4419b, hsa-miR-940, hsa-miR-6769b-5p, hsa-miR-4689, and hsa-miR-4707-3p).

Non-limiting examples of the combination of the polynucleotide consisting of the nucleotide sequence represented by SEQ ID NO: 155 or a complementary sequence thereof with polynucleotides consisting of nucleotide sequences represented by SEQ ID NOs of five polynucleotides selected from the cancer type-specific polynucleotide group 1 or complementary sequences thereof are further listed.

(1) a combination of SEQ ID NOs: 9, 36, 75, 98, 155, and 635 (markers: hsa-miR-6781-5p, hsa-miR-4419b, hsa-miR-6125, hsa-miR-940, hsa-miR-6769b-5p, and hsa-miR-6794-5p):

(2) a combination of SEQ ID NOs: 36, 98, 130, 155, 185, and 635 (markers: hsa-miR-4419b, hsa-miR-940, hsa-miR-718, hsa-miR-6769b-5p, hsa-miR-3656, and hsa-miR-6794-5p);

(3) a combination of SEQ ID NOs: 9, 13, 143, 155, 194, and 639 (markers: hsa-miR-6781-5p, hsa-miR-204-3p, hsa-miR-3195, hsa-miR-6769b-5p, hsa-miR-4665-5p, and hsa-miR-4294);

(4) a combination of SEQ ID NOs: 9, 13, 34, 36, 98, and 155 (markers: hsa-miR-6781-5p, hsa-miR-204-3p, hsa-miR-6741-5p, hsa-miR-4419b, hsa-miR-940, and hsa-miR-6769b-5p); and (5) a combination of SEQ ID NOs: 36, 98, 108, 155, 193, and 635 (markers: hsa-miR-4419b, hsa-miR-940, hsa-miR-1914-3p, hsa-miR-6769b-5p, hsa-miR-3178, and hsa-miR-6794-5p).

The kit or the device of the present invention can also comprise a polynucleotide(s) that is already known or that will be found in the future, to enable detection of stomach cancer, in addition to the polynucleotide(s) (which may include a variant(s), a fragment(s), and a derivative(s)) as described above according to the present invention.

The kit of the present invention can also comprise an antibody for measuring a marker(s) for stomach cancer examination known in the art, such as CEA, or CA19-9, in addition to the polynucleotide(s) according to the present invention as described above, and a variant(s) thereof or a fragment(s) thereof.

These polynucleotides contained in the kit of the present invention may be packaged in different containers either individually or in any combination.

The kit of the present invention may comprise a kit for extracting a nucleic acid(s) (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring target nucleic acids through the use of hybridization using this array.

The kit or the device of the present invention comprises nucleic acids capable of specifically binding to the polynucleotides of at least one or more, preferably at least two or more, more preferably at least three or more, most preferably at least five or more to all of the stomach cancer marker miRNAs, respectively, of the group 1 described above. The kit or the device of the present invention can optionally further comprise nucleic acids capable of specifically binding to the polynucleotides of at least one or more, preferably at least two or more, more preferably at least three or more, most preferably at least five or more to all of the stomach cancer marker miRNAs, respectively, of the group 2 described above. The kit or the device of the present invention can optionally further comprise nucleic acids capable of specifically binding to the polynucleotides of at least one or more, preferably at least two or more, more preferably at least three or more, most preferably at least five or more to all of the stomach cancer marker miRNAs, respectively, of the group 3 described above.

The kit or the device of the present invention can be used for detecting stomach cancer as described in the Section 4 below.

4. Method for Detecting Stomach Cancer

The present invention further provides a method for detecting stomach cancer, comprising using the kit or the device of the present invention (comprising the nucleic acid(s) that can be used in the present invention) described in the preceding Section 3 above to measure an expression level(s) of one or more stomach cancer-derived genes represented by: an expression level(s) of stomach cancer-derived gene(s) selected from the following group: miR-4257, miR-6726-5p, miR-1343-3p, miR-1247-3p, miR-6787-5p, miR-6875-5p, miR-1225-3p, miR-8063, miR-6781-5p, miR-4746-3p, miR-1908-5p, miR-6756-5p, miR-204-3p, miR-4651, miR-6757-5p, miR-6825-5p, miR-7108-5p, miR-4792, miR-7641, miR-3188, miR-3131, miR-6780b-5p, miR-8069, miR-6840-3p, miR-8072, miR-1233-5p, miR-6887-5p, miR-1231, miR-5572, miR-6738-5p, miR-6784-5p, miR-6791-5p, miR-6749-5p, miR-6741-5p, miR-128-1-5p, miR-4419b, miR-6746-5p, miR-3184-5p, miR-3679-5p, miR-7110-5p, miR-4516, miR-6717-5p, miR-6826-5p, miR-4433b-3p, miR-3679-3p, miR-3135b, miR-3622a-5p, miR-711, miR-4467, miR-6857-5p, miR-6515-3p, miR-1225-5p, miR-187-5p, miR-3185, miR-642b-3p, miR-1249, miR-744-5p, miR-4442, miR-1228-3p, miR-939-5p, miR-6845-5p, miR-887-3p, miR-7845-5p, miR-6729-5p, miR-4632-5p, miR-615-5p, miR-6724-5p, miR-4728-5p, miR-6732-5p, miR-6816-5p, miR-4695-5p, miR-6088, miR-7975, miR-3197, miR-6125, miR-4433-3p, miR-6727-5p, miR-4706, miR-7847-3p, miR-6805-3p, miR-6766-3p, miR-1913, miR-4649-5p, miR-602, miR-3663-3p, miR-6893-5p, miR-6861-5p, miR-4449, miR-6842-5p, miR-4454, miR-5195-3p, miR-663b, miR-6765-5p, miR-4513, miR-614, miR-6785-5p, miR-6777-5p, miR-940, miR-4741, miR-6870-5p, miR-6131, miR-150-3p, miR-4707-5p, miR-1915-3p, miR-3937, miR-937-5p, miR-4443, miR-1914-3p, miR-3620-5p, miR-1268b, miR-1227-5p, miR-6880-5p, miR-4417, miR-6802-5p, miR-6769a-5p, miR-663a, miR-6721-5p, miR-4532, miR-7977, miR-92b-5p, miR-371a-5p, miR-6126, miR-4734, miR-4665-3p, miR-423-5p, miR-1469, miR-4675, miR-1915-5p, miR-6716-5p, miR-718, miR-4281, miR-6820-5p, miR-6795-5p, miR-6779-5p, miR-7109-5p, miR-6798-5p, miR-4648, miR-8059, miR-6765-3p, miR-6132, miR-4492, miR-7107-5p, miR-3195, miR-3180, miR-296-3p, miR-564, miR-1268a, miR-6848-5p, miR-762, miR-2861, miR-1203, miR-1260b, miR-4476, miR-6885-5p, miR-6769b-5p, miR-23b-3p, miR-1343-5p, miR-3621, miR-4688, miR-4286, miR-4640-5p, miR-4739, miR-1260a, miR-4276, miR-7106-5p, miR-6794-5p, miR-6774-5p, miR-4707-3p, miR-4534, miR-4294, miR-6850-5p, miR-6089 and miR-671-5p; and optionally an expression level(s) of stomach cancer-derived gene(s) selected from the following group: miR-128-2-5p, miR-125a-3p, miR-92a-2-5p, and miR-486-3p; and optionally an expression level(s) of stomach cancer-derived gene(s) selected from the following group: miR-3196, miR-211-3p, miR-4271, miR-6851-5p, miR-149-3p, miR-4667-5p, miR-135a-3p, miR-4486, miR-4697-5p, miR-4725-3p, miR-6510-5p, miR-5001-5p, miR-4673, miR-4466, miR-23a-3p, miR-3656, miR-6782-5p, miR-4689, miR-451a, miR-4446-3p, miR-3180-3p, miR-642a-3p, miR-6889-5p, miR-3178, miR-4665-5p, miR-6722-3p, miR-30c-1-3p, miR-4507, miR-3141 and miR-1199-5p in a sample in vitro, further comparing, for example, the expression level(s) of the gene(s) in the sample (e.g., blood, serum, or plasma) collected from a subject suspected of having stomach cancer with a control expression level in the sample collected from a healthy subject (including a non-stomach cancer patient), and evaluating the subject as having stomach cancer when the expression level of the target nucleic acid is statistically significantly different between the samples.

This method of the present invention enables a limitedly invasive, early diagnosis of cancer with high sensitivity and specificity and thereby brings about early treatment and improved prognosis. In addition, exacerbation of the disease or the effectiveness of surgical, radiotherapeutic, and chemotherapeutic treatments can be monitored.

The method for extracting the stomach cancer-derived gene(s) from the sample such as blood, serum, or plasma according to the present invention is particularly preferably prepared by the addition of a reagent for RNA extraction in 3D-Gene(™) RNA extraction reagent from liquid sample kit (Toray Industries, Inc.). A general acidic phenol method (acid guanidinium-phenol-chloroform (AGPC)) may be used, or Trizol(™) (Life Technologies Corp.) may be used. The stomach cancer-derived gene(s) may be prepared by the addition of a reagent for RNA extraction containing acidic phenol, such as Trizol (Life Technologies Corp.) or Isogen (Nippon Gene Co., Ltd.). Alternatively, a kit such as miRNeasy(™) Mini Kit (Qiagen N.V.) may be used, though the method is not limited thereto.

The present invention also provides use of the kit or the device of the present invention for detecting in vitro an expression product(s) of a stomach cancer-derived miRNA gene(s) in a sample derived from a subject.

In the method of the present invention, the kit or the device described above comprises a single polynucleotide or any possible combination of polynucleotides that can be used in the present invention as described above.

In the detection or (genetic) diagnosis of stomach cancer according to the present invention, each polynucleotide contained in the kit or the device of the present invention can be used as a probe or a primer. In the case of using the polynucleotide as a primer, TaqMan(™) MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of stomach cancer or the detection of the presence or absence of stomach cancer. Specifically, the detection of stomach cancer using the kit or the device can be performed by detecting in vitro an expression level(s) of a gene(s) using the nucleic acid probe(s) or the primer(s) contained in the kit or the device in a sample such as blood, serum, plasma, or urine from a subject suspected of having stomach cancer. The subject suspected of having stomach cancer can be evaluated as having stomach cancer when the expression level(s) of a target miRNA marker(s) measured using polynucleotide(s) (including a variant(s), a fragment(s), and a derivative(s) thereof) consisting of a nucleotide sequence(s) represented by at least one or more of SEQ ID NOs: 1 to 165 and 635 to 642 or a complementary sequence(s) thereof, optionally a nucleotide sequence(s) represented by one or more of SEQ ID NOs: 166 to 169 or a complementary sequence(s) thereof, and optionally a nucleotide sequence(s) represented by one or more of SEQ ID NOs: 170 to 199 or a complementary sequence(s) thereof in the sample such as blood, serum, plasma, or urine of the subject is statistically significantly different from the expression level(s) thereof in the sample such as blood, serum, or plasma, or urine of a healthy subject.

The method of the present invention can be combined with gastric X-ray examination and gastroscopy as well as a diagnostic imaging method such as CT, PET, or MRI. The method of the present invention is capable of specifically detecting stomach cancer and can substantially discriminate stomach cancer from other cancers.

The method for detecting the absence of an expression product(s) of a stomach cancer-derived gene(s) or the presence of the expression product(s) of a stomach cancer-derived gene(s) in a sample using the kit or the device of the present invention comprises collecting a body fluid such as blood, serum, plasma, or urine of a subject, and measuring the expression level(s) of the target gene(s) contained therein using one or more polynucleotide(s) (including a variant(s), a fragment(s), and a derivative(s)) selected from the polynucleotide group of the present invention, to evaluate the presence or absence of stomach cancer or to detect stomach cancer. Using the method for detecting stomach cancer according to the present invention, for example, the presence or absence of amelioration of the disease or the degree of amelioration thereof in a stomach cancer patient to whom a therapeutic drug for the amelioration of the disease is administered can be also evaluated or diagnosed.

The method of the present invention can comprise, for example, the following steps (a), (b), and (c):

(a) contacting a sample derived from a subject with a polynucleotide(s) in the kit or the device of the present invention in vitro:

(b) measuring an expression level(s) of the target nucleic acid(s) in the sample using the polynucleotide(s) as a nucleic acid probe(s) or a primer(s); and (c) evaluating the presence or absence of stomach cancer (cells) in the subject on the basis of the result in the step (b).

Specifically, the present invention provides a method for detecting stomach cancer, comprising measuring an expression level(s) of a target nucleic acid(s) in a sample of a subject using a nucleic acid(s) capable of specifically binding to at least one or more (preferably at least two or more) polynucleotide(s) selected from the group consisting of miR-4257, miR-6726-5p, miR-1343-3p, miR-1247-3p, miR-6787-5p, miR-6875-5p, miR-1225-3p, miR-8063, miR-6781-5p, miR-4746-3p, miR-1908-5p, miR-6756-5p, miR-204-3p, miR-4651, miR-6757-5p, miR-6825-5p, miR-7108-5p, miR-4792, miR-7641, miR-3188, miR-3131, miR-6780b-5p, miR-8069, miR-6840-3p, miR-8072, miR-1233-5p, miR-6887-5p, miR-1231, miR-5572, miR-6738-5p, miR-6784-5p, miR-6791-5p, miR-6749-5p, miR-6741-5p, miR-128-1-5p, miR-4419b, miR-6746-5p, miR-3184-5p, miR-3679-5p, miR-7110-5p, miR-4516, miR-6717-5p, miR-6826-5p, miR-4433b-3p, miR-3679-3p, miR-3135b, miR-3622a-5p, miR-711, miR-4467, miR-6857-5p, miR-6515-3p, miR-1225-5p, miR-187-5p, miR-3185, miR-642b-3p, miR-1249, miR-744-5p, miR-4442, miR-1228-3p, miR-939-5p, miR-6845-5p, miR-887-3p, miR-7845-5p, miR-6729-5p, miR-4632-5p, miR-615-5p, miR-6724-5p, miR-4728-5p, miR-6732-5p, miR-6816-5p, miR-4695-5p, miR-6088, miR-7975, miR-3197, miR-6125, miR-4433-3p, miR-6727-5p, miR-4706, miR-7847-3p, miR-6805-3p, miR-6766-3p, miR-1913, miR-4649-5p, miR-602, miR-3663-3p, miR-6893-5p, miR-6861-5p, miR-4449, miR-6842-5p, miR-4454, miR-5195-3p, miR-663b, miR-6765-5p, miR-4513, miR-614, miR-6785-5p, miR-6777-5p, miR-940, miR-4741, miR-6870-5p, miR-6131, miR-150-3p, miR-4707-5p, miR-1915-3p, miR-3937, miR-937-5p, miR-4443, miR-1914-3p, miR-3620-5p, miR-1268b, miR-1227-5p, miR-6880-5p, miR-4417, miR-6802-5p, miR-6769a-5p, miR-663a, miR-6721-5p, miR-4532, miR-7977, miR-92b-5p, miR-371a-5p, miR-6126, miR-4734, miR-4665-3p, miR-423-5p, miR-1469, miR-4675, miR-1915-5p, miR-6716-5p, miR-718, miR-4281, miR-6820-5p, miR-6795-5p, miR-6779-5p, miR-7109-5p, miR-6798-5p, miR-4648, miR-8059, miR-6765-3p, miR-6132, miR-4492, miR-7107-5p, miR-3195, miR-3180, miR-296-3p, miR-564, miR-1268a, miR-6848-5p, miR-762, miR-2861, miR-1203, miR-1260b, miR-4476, miR-6885-5p, miR-6769b-5p, miR-23b-3p, miR-1343-5p, miR-3621, miR-4688, miR-4286, miR-4640-5p, miR-4739, miR-1260a, miR-4276, miR-7106-5p, miR-6794-5p, miR-6774-5p, miR-4707-3p, miR-4534, miR-4294, miR-6850-5p, miR-6089 and miR-671-5p and evaluating in vitro whether or not the subject has stomach cancer using the measured expression level(s) and a control expression level(s) of a healthy subject measured in the same way as above.

The term "evaluation" used herein is evaluation support based on results of in vitro examination, not physician's judgment.

As described above, as for the target nucleic acids in a preferred embodiment of the method of the present invention, specifically, miR-4257 is hsa-miR-4257, miR-6726-5p is hsa-miR-6726-5p, miR-1343-3p is hsa-miR-1343-3p, miR-1247-3p is hsa-miR-1247-3p, miR-6787-5p is hsa-miR-6787-5p, miR-6875-5p is hsa-miR-6875-5p, miR-1225-3p is hsa-miR-1225-3p, miR-8063 is hsa-miR-8063, miR-6781-5p is hsa-miR-6781-5p, miR-4746-3p is hsa-miR-4746-3p, miR-1908-5p is hsa-miR-1908-5p, miR-6756-5p is hsa-miR-6756-5p, miR-204-3p is hsa-miR-204-3p, miR-4651 is hsa-miR-4651, miR-6757-5p is hsa-miR-6757-5p, miR-6825-5p is hsa-miR-6825-5p, miR-7108-5p is hsa-miR-7108-5p, miR-4792 is hsa-miR-4792, miR-7641 is hsa-miR-7641, miR-3188 is hsa-miR-3188, miR-3131 is hsa-miR-3131, miR-6780b-5p is hsa-miR-6780b-5p, miR-8069 is hsa-miR-8069, miR-6840-3p is hsa-miR-6840-3p, miR-8072 is hsa-miR-8072, miR-1233-5p is hsa-miR-1233-5p, miR-6887-5p is hsa-miR-6887-5p, miR-1231 is hsa-miR-1231, miR-5572 is hsa-miR-5572, miR-6738-5p is hsa-miR-6738-5p, miR-6784-5p is hsa-miR-6784-5p, miR-6791-5p is hsa-miR-6791-5p, miR-6749-5p is hsa-miR-6749-5p, miR-6741-5p is hsa-miR-6741-5p, miR-128-1-5p is hsa-miR-128-1-5p, miR-4419b is hsa-miR-4419b, miR-6746-5p is hsa-miR-6746-5p, miR-3184-5p is hsa-miR-3184-5p, miR-3679-5p is hsa-miR-3679-5p, miR-7110-5p is hsa-miR-7110-5p, miR-4516 is hsa-miR-4516, miR-6717-5p is hsa-miR-6717-5p, miR-6826-5p is hsa-miR-6826-5p, miR-4433b-3p is hsa-miR-4433b-3p, miR-3679-3p is hsa-miR-3679-3p, miR-3135b is hsa-miR-3135b, miR-3622a-5p is hsa-miR-3622a-5p, miR-711 is hsa-miR-711, miR-4467 is hsa-miR-4467, miR-6857-5p is hsa-miR-6857-5p, miR-6515-3p is hsa-miR-6515-3p, miR-1225-5p is hsa-miR-1225-5p, miR-1187-5p is hsa-miR-1187-5p, miR-3185 is hsa-miR-3185, miR-642b-3p is hsa-miR-642b-3p, miR-1249 is hsa-miR-1249, miR-744-5p is hsa-miR-744-5p, miR-4442 is hsa-miR-4442, miR-1228-3p is hsa-miR-1228-3p, miR-939-5p is hsa-miR-939-5p, miR-6845-5p is hsa-miR-6845-5p, miR-887-3p is hsa-miR-887-3p, miR-7845-5p is hsa-miR-7845-5p, miR-6729-5p is hsa-miR-6729-5p, miR-4632-5p is hsa-miR-4632-5p, miR-615-5p is hsa-miR-615-5p, miR-6724-5p is hsa-miR-6724-5p, miR-4728-5p is hsa-miR-4728-5p, miR-6732-5p is hsa-miR-6732-5p, miR-6816-5p is hsa-miR-6816-5p, miR-4695-5p is hsa-miR-4695-5p, miR-6088 is hsa-miR-6088, miR-7975 is hsa-miR-7975, miR-3197 is hsa-miR-3197, miR-6125 is hsa-miR-6125, miR-4433-3p is hsa-miR-4433-3p, miR-6727-5p is hsa-miR-6727-5p, miR-4706 is hsa-miR-4706, miR-7847-3p is hsa-miR-7847-3p, miR-6805-3p is hsa-miR-6805-3p, miR-6766-3p is hsa-miR-6766-3p, miR-1913 is hsa-miR-1913, miR-4649-5p is hsa-miR-4649-5p, miR-602 is hsa-miR-602, miR-3663-3p is hsa-miR-3663-3p, miR-6893-5p is hsa-miR-6893-5p, miR-6861-5p is hsa-miR-6861-5p, miR-4449 is hsa-miR-4449, miR-6842-5p is hsa-miR-6842-5p, miR-4454 is hsa-miR-4454, miR-5195-3p is hsa-miR-5195-3p, miR-663b is hsa-miR-663b, miR-6765-5p is hsa-miR-6765-5p, miR-4513 is hsa-miR-4513, miR-614 is hsa-miR-614, miR-6785-5p is hsa-miR-6785-5p, miR-6777-5p is hsa-miR-6777-5p, miR-940 is hsa-miR-940, miR-4741 is hsa-miR-4741, miR-6870-5p is hsa-miR-6870-5p, miR-6131 is hsa-miR-6131, miR-150-3p is hsa-miR-150-3p, miR-4707-5p is hsa-miR-4707-5p, miR-1915-3p is hsa-miR-1915-3p, miR-3937 is hsa-miR-3937, miR-937-5p is hsa-miR-937-5p, miR-4443 is hsa-miR-4443, miR-1914-3p is hsa-miR-1914-3p, miR-3620-5p is hsa-miR-3620-5p, miR-1268b is hsa-miR-1268b, miR-1227-5p is hsa-miR-1227-5p, miR-6880-5p is hsa-miR-6880-5p, miR-4417 is hsa-miR-4417, miR-6802-5p is hsa-miR-6802-5p, miR-6769a-5p is hsa-miR-6769a-5p, miR-663a is hsa-miR-663a, miR-6721-5p is hsa-miR-6721-5p, miR-4532 is hsa-miR-4532, miR-7977 is hsa-miR-7977, miR-92b-5p is hsa-miR-92b-5p, miR-371a-5p is hsa-miR-371a-5p, miR-6126 is hsa-miR-6126, miR-4734 is hsa-miR-4734, miR-4665-3p is hsa-miR-4665-3p, miR-423-5p is hsa-miR-423-5p, miR-1469 is hsa-miR-1469, miR-4675 is hsa-miR-4675, miR-1915-5p is hsa-miR-1915-5p, miR-6716-5p is hsa-miR-6716-5p, miR-718 is hsa-miR-718, miR-4281 is hsa-miR-4281, miR-6820-5p is hsa-miR-6820-5p, miR-6795-5p is hsa-miR-6795-5p, miR-6779-5p is hsa-miR-6779-5p, miR-7109-5p is hsa-miR-7109-5p, miR-6798-5p is hsa-miR-6798-5p, miR-4648 is hsa-miR-4648, miR-8059 is hsa-miR-8059, miR-6765-3p is hsa-miR-6765-3p, miR-6132 is hsa-miR-6132, miR-4492 is hsa-miR-4492, miR-7107-5p is hsa-miR-7107-5p, miR-3195 is hsa-miR-3195, miR-3180 is hsa-miR-3180, miR-296-3p is hsa-miR-296-3p, miR-564 is hsa-miR-564, miR-1268a is hsa-miR-1268a, miR-6848-5p is hsa-miR-6848-5p, miR-762 is hsa-miR-762, miR-2861 is hsa-miR-2861, miR-1203 is hsa-miR-1203, miR-1260b is hsa-miR-1260b, miR-4476 is hsa-miR-4476, miR-6885-5p is hsa-miR-6885-5p, miR-6769b-5p is hsa-miR-6769b-5p, miR-23b-3p is hsa-miR-23b-3p, miR-1343-5p is hsa-miR-1343-5p, miR-3621 is hsa-miR-3621, miR-4688 is hsa-miR-4688, miR-4286 is hsa-miR-4286, miR-4640-5p is hsa-miR-4640-5p, miR-4739 is hsa-miR-4739, miR-1260a is hsa-miR-1260a, miR-4276 is hsa-miR-4276, miR-7106-5p is hsa-miR-7106-5p, miR-6794-5p is hsa-miR-6794-5p, miR-6774-5p is hsa-miR-6774-5p, miR-4707-3p is hsa-miR-4707-3p, miR-4534 is hsa-miR-4534, miR-294 is hsa-miR-4294, miR-6850-5p is hsa-miR-6850-5p, miR-6089 is hsa-miR-6089, and miR-671-5p is hsa-miR-671-5p.

In a preferred embodiment of the method of the present invention, specifically, the nucleic acid(s) (specifically, probe(s) or primer(s)) is selected from the group consisting of the following polynucleotides (a) to (e):
(a) a polynucleotide consisting of a nucleotide sequence represented by any of SEQ ID NOs: 1 to 165 and 635 to 642 or a nucleotide sequence derived from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 165 and 635 to 642,
(c) a polynucleotide consisting of a nucleotide sequence complementary to a nucleotide sequence represented by any of SEQ ID NOs: 1 to 165 and 635 to 642 or a nucleotide sequence derived from the nucleotide sequence by the replacement of u with t, a variant thereof, a derivative thereof, or a fragment thereof comprising 15 or more consecutive nucleotides.
(d) a polynucleotide comprising a nucleotide sequence complementary to a nucleotide sequence represented by any of SEQ ID NOs: 1 to 165 and 635 to 642 or a nucleotide sequence derived from the nucleotide sequence by the replacement of u with t, and
(e) a polynucleotide hybridizing under stringent conditions to any of the polynucleotides (a) to (d).

The method of the present invention can further employ a nucleic acid(s) capable of specifically binding to at least one or more polynucleotides selected from miR-128-2-5p, miR-125a-3p, miR-92a-2-5p, and miR-486-3p.

In a preferred embodiment, as for such a nucleic acid, specifically, miR-128-2-5p is hsa-miR-128-2-5p, miR-125a-3p is hsa-miR-125a-3p, miR-92a-2-5p is hsa-miR-92a-2-5p, and miR-486-3p is hsa-miR-486-3p.

In a preferred embodiment, such a nucleic acid(s) is specifically selected from the group consisting of the following polynucleotides (f) to (j):
(f) a polynucleotide consisting of a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides,
(g) a polynucleotide comprising a nucleotide sequence represented by any of SEQ ID NOs: 166 to 169.
(h) a polynucleotide consisting of a nucleotide sequence complementary to a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides,
(i) a polynucleotide comprising a nucleotide sequence complementary to a nucleotide sequence represented by any of SEQ ID NOs: 166 to 169 or a nucleotide sequence derived from the nucleotide sequence by the replacement of u with t, and
(j) a polynucleotide hybridizing under stringent conditions to any of the polynucleotides (f) to (i).

The method of the present invention can further employ a nucleic acid(s) capable of specifically binding to at least one or more polynucleotides selected from the group consisting of miR-3196, miR-211-3p, miR-4271, miR-6851-5p, miR-149-3p, miR-4667-5p, miR-135a-3p, miR-4486, miR-4697-5p, miR-4725-3p, miR-6510-5p, miR-5001-5p, miR-4673, miR-4466, miR-23a-3p, miR-3656, miR-6782-5p, miR-4689, miR-451a, miR-4446-3p, miR-3180-3p, miR-642a-3p, miR-6889-5p, miR-3178, miR-4665-5p, miR-6722-3p, miR-30c-1-3p, miR-4507, miR-3141, and miR-1199-5p.

In a preferred embodiment, as for such a nucleic acid, specifically, miR-3196 is hsa-miR-3196, miR-211-3p is hsa-miR-211-3p, miR-4271 is hsa-miR-4271, miR-6851-5p is hsa-miR-6851-5p, miR-149-3p is hsa-miR-149-3p, miR-4667-5p is hsa-miR-4667-5p, miR-135a-3p is hsa-miR-135a-3p, miR-4486 is hsa-miR-4486, miR-4697-5p is hsa-miR-4697-5p, miR-4725-3p is hsa-miR-4725-3p, miR-6510-5p is hsa-miR-6510-5p, miR-5001-5p is hsa-miR-5001-5p, miR-4673 is hsa-miR-4673, miR-4466 is hsa-miR-4466, miR-23a-3p is hsa-miR-23a-3p, miR-3656 is hsa-miR-3656, miR-6782-5p is hsa-miR-6782-5p, miR-4689 is hsa-miR-4689, miR-451a is hsa-miR-451a, miR-4446-3p is hsa-miR-4446-3p, miR-3180-3p is hsa-miR-3180-3p, miR-642a-3p is hsa-miR-642a-3p, miR-6889-5p is hsa-miR-6889-5p, miR-3178 is hsa-miR-3178, miR-4665-5p is hsa-miR-4665-5p, miR-6722-3p is hsa-miR-6722-3p, miR-30c-1-3p is hsa-miR-30c-1-3p, miR-4507 is hsa-miR-4507, miR-3141 is hsa-miR-3141, and miR-1199-5p is hsa-miR-1199-5p.

Specifically, the nucleic acid(s) further used is a polynucleotide(s) selected from the group consisting of the following polynucleotides (k) to (o):
(k) a polynucleotide consisting of a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides,
(l) a polynucleotide comprising a nucleotide sequence represented by any of SEQ ID NOs: 170 to 199.
(m) a polynucleotide consisting of a nucleotide sequence complementary to a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides,
(n) a polynucleotide comprising a nucleotide sequence complementary to a nucleotide sequence represented by any of SEQ ID NOs: 170 to 199 or a nucleotide sequence derived from the nucleotide sequence by the replacement of u with t, and
(o) a polynucleotide hybridizing under stringent conditions to any of the polynucleotides (k) to (n).

Examples of the sample used in the method of the present invention can include samples prepared from a living tissue (preferably a stomach tissue) or a body fluid such as blood, serum, plasma, or urine from the subject. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

The subject used herein refers to a mammal, for example, a human, a monkey, a mouse or a rat without any limitation, and is preferably a human.

The steps of the method of the present invention can be changed according to the type of the sample to be assayed.

In the case of using RNA as an analyte, the detection of stomach cancer (cells) can comprise, for example, the following steps (a), (b), and (c):

(a) binding RNA(s) prepared from the sample of the subject or a complementary polynucleotide(s) (cDNA(s)) transcribed therefrom to a polynucleotide(s) in the kit or the device of the present invention;

(b) measuring the sample-derived RNA or the cDNA(s) synthesized from the RNA, bound with the polynucleotide by hybridization using the polynucleotide as a nucleic acid probe(s) or by quantitative RT-PCR using the polynucleotide(s) as a primer(s); and (c) evaluating the presence or absence of stomach cancer (or stomach cancer-derived gene expression) on the basis of the measurement results of the step (b).

For example, various hybridization methods can be used for detecting, examining, evaluating, or diagnosing stomach cancer (or stomach cancer-derived gene expression) in vitro according to the present invention. For example, Northern blot, Southern blot. RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe(s) that can be used in the present invention. Specific examples thereof can include a method which comprises labeling the nucleic acid probe (or a complementary strand) with a radioisotope ($^{32}P$, $^{33}P$, $^{35}S$, etc.), a fluorescent material, or the like, hybridizing the labeled product with the tissue-derived RNA of the subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which comprises preparing cDNA from the tissue-derived RNA of the subject according to a routine method, hybridizing a pair of primers (consisting of a plus strand and a reverse strand binding to the cDNA) of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) of the present invention is attached to a substrate (solid phase) is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. The term "chip" used herein includes these arrays. 3D-Gene(™) Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label on nucleic acid probes using an image detector (examples thereof can include Typhoon 9410 (GE Healthcare) and 3D-Gene(™) scanner (Toray Industries. Inc.)).

The "stringent conditions" used herein are, as mentioned above, conditions under which a nucleic acid probe hybridizes to its target sequence to a larger extent (e.g., a measurement value equal to or larger than "(a mean of background measurement values)+(a standard deviation of the background measurement values)×2") than that for other sequences.

The stringent conditions are defined by hybridization and subsequent washing conditions. Examples of the hybridization conditions include, but not limited to, 30° C. to 60° C. for 1 to 24 hours in a solution containing SSC, a surfactant, formamide, dextran sulfate, a blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably involve 3 to 10×SSC and 0.1 to 1% SDS. Examples of the conditions for the washing, following the hybridization, which is another condition to define the stringent conditions, can include conditions involving continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using a polynucleotide fragment(s) in the kit of the present invention as a primer(s) include treatment for approximately 15 seconds to 1 minute at 5 to 10° C. plus a Tm value calculated from the sequence(s) of the primer(s), using a PCR buffer having composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan(™) MicroRNA Assays (Life Technologies Corp.); LNA(™)-based MicroRNA PCR (Exiqon); or Ncode(™) miRNA qRT-PCT kit (Invitrogen Corp.) may be used.

For the calculation of gene expression levels according to the present invention, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably $2^8$, more preferably $2^{10}$ or larger in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring a target gene or gene expression level(s) in a sample derived from a subject using the polynucleotide(s), the kit, or the device (e.g., chip) for detection of the present invention, or a combination thereof, preparing a discriminant (discriminant function) with gene expression levels in a sample derived from a stomach cancer patient and a sample derived from a healthy subject as supervising samples, and determining or evaluating the presence and/or absence of the stomach cancer-derived gene(s) in the sample.

Specifically, the present invention further provides the method comprising: a first step of measuring in vitro an expression level(s) of a target gene(s) (target nucleic acid) in multiple samples that were known to be able to determine or evaluate the presence and/or absence of the stomach cancer-derived gene(s) in the samples, using the polynucleotide(s), the kit, or the device (e.g., chip) for detection of the present invention, or a combination thereof; a second step of constructing a discriminant with the measurement values of the expression level(s) of the target gene(s) that was obtained in the first step as supervising samples; a third step of measuring in vitro an expression level(s) of the target gene(s) in a sample derived from a subject in the same way as in the first step; and a fourth step of substituting the measurement value(s) of the expression level(s) of the target gene(s) obtained in the third step into the discriminant obtained in the second step, and determining or evaluating the presence or absence of the stomach cancer-derived gene(s) in the sample on the basis of the results obtained from the discriminant, wherein the target gene(s) can be detected using the polynucleotide(s) or using a polynucleotide(s) for the detection, that was contained in the polynucleotide, the kit or the device (e.g., chip). In this context, the discriminant can be prepared by use of Fisher's discriminant analysis, nonlinear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In Formula 1, x represents an explanatory variable, w represents a coefficient of the explanatory variable, and w0 represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be substituted as explanatory variables into the discriminant to determine clusters on the basis of the signs of the discriminant scores.

The Fisher's discriminant analysis, one type of linear discriminant analysis, is a dimension reduction method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer., 2002). In the Fisher's discriminant analysis, direction w of projection is determined so as to maximize Formula 2. In Formula 2, µ represents an average input, ng represents the number of data associate with class g, and µg represents an average input of the data associate with class g. The numerator and the denominator are the interclass variance and the intraclass variance, respectively, when each data is projected in the direction of the vector w. Discriminant coefficient wi is determined by maximizing this ratio (Takafumi Kanamori et al., "Pattern Recognition", Kyoritsu Shuppan Co., Ltd. (2009); and Richard O. et al., Pattern Classification Second Edition., Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i: y_i = g} (w^T x_i - w^T \mu_g)(w^T x_i - w^T \mu_g)} \qquad \text{Formula 2}$$

$$\text{subject to } \mu = \sum_{i=1}^{n} \frac{x_i}{n}, \mu_g = \sum_{i: u_i = g}^{n} \frac{x_i}{n_g}$$

The Mahalanobis' distance is calculated according to Formula 3 in consideration of data correlation and can be used as nonlinear discriminant analysis for determining a cluster in which a data point belongs to, based on a short Mahalanobis' distance from the data point to that cluster. In Formula 3, µ represents a central vector of each cluster, and S-1 represents an inverse matrix of the variance-covariance matrix of the cluster. The central vector is calculated from explanatory variable x, and an average vector, a median value vector, or the like can be used.

$$D(x, \mu) = \{(x - \mu)^t S^{-1}(x - \mu)\}^{\frac{1}{2}} \quad \text{Formula 3}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be substituted as explanatory variables into the discriminant to determine classes. In this respect, the result of the discriminant analysis may be classes, may be a probability of data to be classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004). Nello Cristianini et al., Introduction to SVM, Kyoritsu Shuppan Co., Ltd. (2008)).

C-support vector classification (C-SVC), one type of SVM, comprises preparing a hyperplane by supervising a data set with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a stomach cancer patient group and a healthy subject group. For example, stomach tissue examination can be used for each subject to be confirmed either as a stomach cancer patient or a healthy subject.

Next, a data set consisting of comprehensive gene expression levels of serum-derived samples of the two divided groups (hereinafter, this data set is referred to as a training cohort) is prepared, and a C-SVC discriminant is determined by using genes that were found to differ clearly in their gene expression levels between the two groups as explanatory variables and using this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_a \frac{1}{2} a^T Q a - e^T a \quad \text{Formula 4}$$

subject to $y^T a = 0$, $0 \leq a_i \leq C$, $i = 1, \ldots, l$,

Formula 5 is a finally obtained discriminant, and a group in which the data point belongs to can be determined on the basis of the sign of a value obtained according to the discriminant. In this formula, x represents a support vector, y represents a label indicating the association of a group, a represents the corresponding coefficient, b represents a constant term, and K represents a kernel function.

$$f(x) = \text{sgn}\left(\sum_{i=1}^{l} y_i a_i K(x_i, x) + b\right) \quad \text{Formula 5}$$

For example, a RBF kernel defined by Formula 6 can be used as the kernel function. In this formula, x represents a support vector, and y represents a kernel parameter for adjusting the complexity of the hyperplane.

$$K(x_i, x_j) = \exp(-r\|x_i - x_j\|^2), r < 0 \quad \text{Formula 6}$$

In addition, an approach such as neural network, k-nearest neighbor algorithms, decision trees, or logistic regression analysis can be selected as a method for determining or evaluating the presence and/or absence of expression of a stomach cancer-derived target gene(s) in a sample derived from a subject, or for evaluating the expression level thereof by comparison with a control derived from a healthy subject.

The method of the present invention can comprise, for example, the following steps (a), (b), and (c):

(a) measuring an expression level(s) of a target gene(s) in tissues containing stomach cancer-derived genes derived from stomach cancer patients and/or samples already known to be tissues containing no stomach cancer-derived gene(s) derived from healthy subjects, using the polynucleotide(s), the kit, or the device (e.g., DNA chip) for detection according to the present invention;

(b) preparing the discriminants of Formulas 1 to 3, 5, and 6 described above from the measurement values of the expression level measured in the step (a); and (c) measuring an expression level(s) of the target gene(s) in a sample derived from a subject using the polynucleotide(s), the kit, or the device (e.g., DNA chip) for diagnosis (detection) according to the present invention, substituting the obtained measurement value(s) into the discriminants prepared in the step (b), and determining or evaluating the presence and/or absence of the stomach cancer-derived target gene(s) in the sample, or evaluating the expression level(s) thereof by comparison with a healthy subject-derived control, on the basis of the obtained results. In this context, in the discriminants of Formulas 1 to 3, 5, and 6, x represents an explanatory variable and includes a value obtained by measuring a polynucleotide(s) selected from the polynucleotides described in the Section 2 above, or any fragment thereof, etc. Specifically, the explanatory variable for discriminating a stomach cancer patient from a healthy subject according to the present invention is a gene expression level(s) selected from, for example, the following expression levels (1) to (3):

(1) a gene expression level(s) in the serum of a stomach cancer patient or a healthy subject measured by any DNA comprising 15 or more consecutive nucleotides in a nucleotide sequence represented by any of SEQ ID NOs: 1 to 165 and 635 to 642 or a complementary sequence thereof, (2) a gene expression level(s) in the serum of a stomach cancer patient or a healthy subject measured by any DNA comprising 15 or more consecutive nucleotides in a nucleotide sequence represented by any of SEQ ID NOs: 166 to 169 or a complementary sequence thereof, and (3) a gene expression level(s) in the serum of a stomach cancer patient or a healthy subject measured by any DNA comprising 15 or more consecutive nucleotides in a nucleotide sequence represented by any of SEQ ID NOs: 170 to 199 or a complementary sequence thereof.

As described above, for the method for determining or evaluating the presence and/or absence of a stomach cancer-derived gene(s) in a sample derived from a subject, the preparation of a discriminant requires a discriminant prepared in a training cohort. For enhancing the accuracy of the discriminant, it is necessary for the discriminant to use genes that show clear difference between two groups in the training cohort.

Each gene that is used for an explanatory variable in a discriminant is preferably determined as follows. First, comprehensive gene expression levels of a stomach cancer patient group and comprehensive gene expression levels of a healthy subject group in a training cohort are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the statistical test, the absolute value (fold change) of an expression ratio of a median value of each gene expression level between gene expression levels of a stomach cancer patient group and gene expression levels of a healthy subject group may be calculated to select a gene that is used for an explanatory variable in a discriminant. Alternatively, ROC curves may be prepared using gene expression levels of a stomach cancer patient group and a healthy subject group, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discriminant accuracy include a method of constructing a discriminant in every combination of genes that satisfy the significance level of P value, and a method of repetitively evaluating a discriminant while increasing the number of genes for use one by one in a descending order of difference in gene expression level (Furey T S. et al., 2000, Bioinformatics., Vol. 16, p. 906-14). A gene expression level of another independent stomach cancer patient or healthy subject is substituted as an explanatory variable into this discriminant to calculate discriminant results of the group to which this independent stomach cancer patient or healthy subject associate. Specifically, the found gene set for diagnosis and the discriminant constructed using the gene set for diagnosis can be evaluated in an independent sample cohort to find a more universal gene set for diagnosis capable of detecting stomach cancer and a more universal method for discriminating stomach cancer.

Split-sample method is preferably used for evaluating the discriminant performance (generality) of the discriminant. Specifically, a data set is divided into a training cohort and a validation cohort, and gene selection by a statistical test and discriminant preparation are performed in the training cohort. Accuracy, sensitivity, and specificity are calculated using a result of discriminating a validation cohort according to the discriminant and a true group to which the validation cohort associate, to evaluate the performance of the discriminant. On the other hand, instead of dividing a data set, the gene selection by a statistical test and discriminant preparation may be performed using all of samples, and accuracy, sensitivity, and specificity can be calculated by the discriminant analysis of a newly prepared samples for evaluation of the performance of the discriminant.

The present invention provides a polynucleotide(s) for detection or for disease diagnosis useful in the diagnosis and treatment of stomach cancer, a method for detecting stomach cancer using the polynucleotide(s), and a kit and a device for the detection of stomach cancer, comprising the polynucleotide(s). Particularly, in order to select a gene(s) for diagnosis and prepare a discriminant so as to exhibit accuracy beyond a stomach cancer diagnosis method using existing tumor markers CEA and CA19-9, a gene set for diagnosis and a discriminant for the method of the present invention, that exhibit accuracy beyond CEA and CA19-9, can be constructed, for example, by comparing expressed genes in serum derived from a patient confirmed to be negative using CEA and CA19-9 but finally found to have stomach cancer by detailed examination such as computed tomography using a contrast medium, with genes expressed in serum derived from a patient having no stomach cancer.

For example, the gene set for diagnosis is set to any combination selected from one or two or more of the polynucleotides based on a nucleotide sequence(s) represented by any of SEQ ID NOs: 1 to 165 and 635 to 642 or a complementary sequence(s) thereof as described above; and optionally one or two or more of the polynucleotides based on a nucleotide sequence(s) represented by any of SEQ ID NOs: 166 to 169 or a complementary sequence(s) thereof; and optionally one or two or more of the polynucleotides based on a nucleotide sequence represented by any of SEQ ID NOs: 170 to 199 or a complementary sequence thereof. Further, a discriminant is constructed using expression levels of the gene set for diagnosis in samples derived from class I stomach cancer patients and samples derived from class II healthy subjects as a result of tissue diagnosis. As a result, the presence or absence of stomach cancer-derived genes in an unknown sample can be determined with 100% accuracy at the maximum by measuring expression levels of the gene set for diagnosis in an unknown sample.

EXAMPLES

Hereinafter, the present invention will be described further specifically with reference to Examples below. However, the scope of the present invention is not intended to be limited by these Examples.

Reference Example 1

<Collection of Samples from Stomach Cancer Patient and Healthy Subject>

Serum was collected using VENOJECT II vacuum blood collecting tube VP-AS109K60 (Terumo Corp.) from each of 100 healthy subjects and 34 stomach cancer patients (19 cases with stage IA, 5 cases with stage IB, 2 cases with stage IIA, 2 cases with stage IIB, 3 cases with stage IIIA, and 3 cases with stage IIIC) with no primary cancer found in areas other than stomach cancer after acquisition of informed consent, and used as a training cohort. Likewise, serum was collected using VENOJECT II vacuum blood collecting tube VP-AS109K60 (Terumo Corp.) from each of 50 healthy subjects and 16 stomach cancer patients (9 cases with stage IA, 2 cases with stage B, 2 cases with stage IIA, 1 case with stage IIB, I case with stage IIIA, and 1 case with stage IIIC) with no primary cancer found in areas other than stomach cancer after acquisition of informed consent, and used as a validation cohort.

<Extraction of Total RNA>

Total RNA was obtained from 300 μL of the serum sample obtained from each of 200 persons in total of 150 healthy subjects and 50 stomach cancer patients included in the training cohort and the validation cohort, using a reagent for RNA extraction in 3D-Gene(™) RNA extraction reagent from liquid sample kit (Toray Industries, Inc.) according to the protocol provided by the manufacturer.

<Measurement of Gene Expression Level> miRNAs in the total RNA obtained from the serum samples of each of 200 persons in total of 150 healthy subjects and 50 stomach cancer patients included in the training cohort and the validation cohort were fluorescently labeled using 3D-Gene(™) miRNA Labeling kit (Toray Industries, Inc.) according to the protocol (ver 2.20) provided by the manufacturer. The oligo DNA chip used was 3D-Gene(™) Human miRNA Oligo chip (Toray Industries, Inc.) with attached probes having sequences complementary to 2,555 miRNAs among the miRNAs registered in miRBase Release 20. Hybridization between the miRNAs in the total RNA and the probes on the DNA chip under stringent conditions and washing following the hybridization were performed according to the protocol provided by the manufacturer. The DNA chip was scanned using 3D-Gene(™) scanner (Toray Industries, Inc.) to obtain images. Fluorescence intensity was digitized using 3D-Gene(™) Extraction (Toray Industries. Inc.). The digitized fluorescence intensity was converted to a logarithmic value having a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the sera were obtained in the 50 stomach cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/) and MASS package 7.3-30 (Venables. W. N. & Ripley, B. D. (2002) Modern Applied Statistics with S. Fourth Edition. Springer, New York. ISBN 0-387-95457-0).

Reference Example 2

<Collection of Sample from Patient with Cancer Other than Stomach Cancers>

Serum was collected using VENOJECT II vacuum blood collecting tube VP-AS109K60 (Terumo Corp.) from each of 63 pancreatic cancer patients, 65 bile duct cancer patients, 35 colorectal cancer patients, 32 liver cancer patients, and 17 benign pancreaticobiliary disease patients with no cancer found in other organs after acquisition of informed consent, and used as a training cohort together with the samples of 34 stomach cancer patients and 102 healthy subjects of Reference Example 1. Likewise, serum was collected using VENOJECT II vacuum blood collecting tube VP-AS109K60 (Terumo Corp.) from each of 37 pancreatic cancer patients, 33 bile duct cancer patients, 15 colorectal cancer patients, 20 liver cancer patients, and 4 benign pancreaticobiliary disease patients with no cancer found in other organs after acquisition of informed consent, and used as a validation cohort together with the samples of 16 stomach cancer patients with no cancer found in areas other than stomach cancer and 48 healthy subjects of Reference Example 1. Subsequent operations were conducted in the same way as in Reference Example 1.

Example 1

<Selection of Gene Markers Using the Training Cohort, and Method for Evaluating Stomach Cancer Discriminant Performance of Single Gene Marker Using the Validation Cohort>

In this Example, a gene marker for discriminating a stomach cancer patient from a healthy subject was selected from the training cohort and studied in samples of the validation cohort independent of the training cohort, for a method for evaluating the stomach cancer discriminant performance of each selected gene marker alone.

Specifically, first, the miRNA expression levels of the training cohort and the validation cohort obtained in the preceding Reference Examples were combined and normalized by quantile normalization.

Next, genes for diagnosis were selected using the training cohort. Here, in order to acquire diagnostic markers with higher reliability, only genes having the expression level of $2^6$ or higher in 50% or more of the samples in either of the stomach cancer patient group of the training cohort or the healthy subject group of the training cohort were selected. In order to further acquire statistically significant genes for discriminating a stomach cancer patient group from a healthy subject group, the P value obtained by two-tailed t-test assuming equal variance as to each gene expression level was corrected by the Bonferroni method, and genes that satisfied p<0.01 were acquired as gene markers for use in explanatory variables of a discriminant. The result is described in Table 2.

In this way, polynucleotides consisting of hsa-miR-4257, hsa-miR-6726-5p, hsa-miR-1343-3p, hsa-miR-1247-3p, hsa-miR-6787-5p, hsa-miR-6875-5p, hsa-miR-1225-3p, hsa-miR-8063, hsa-miR-6781-5p, hsa-miR-4746-3p, hsa-miR-1908-5p, hsa-miR-6756-5p, hsa-miR-204-3p, hsa-miR-4651, hsa-miR-6757-5p, hsa-miR-6825-5p, hsa-miR-7108-5p, hsa-miR-4792, hsa-miR-7641, hsa-miR-3188, hsa-miR-3131, hsa-miR-6780b-5p, hsa-miR-8069, hsa-miR-6840-3p, hsa-miR-8072, hsa-miR-1233-5p, hsa-miR-6887-5p, hsa-miR-1231, hsa-miR-5572, hsa-miR-6738-5p, hsa-miR-6784-5p, hsa-miR-6791-5p, hsa-miR-6749-5p, hsa-miR-6741-5p, hsa-miR-128-1-5p, hsa-miR-4419b, hsamiR-6746-5p, hsa-miR-3184-5p, hsa-miR-3679-5p, hsa-miR-7110-5p, hsa-miR-4516, hsa-miR-6717-5p, hsa-miR-6826-5p, hsa-miR-4433b-3p, hsa-miR-3679-3p, hsa-miR-3135b, hsa-miR-3622a-5p, hsa-miR-711, hsa-miR-4467, hsa-miR-6857-5p, hsa-miR-6515-3p, hsa-miR-1225-5p, hsa-miR-1187-5p, hsa-miR-3185, hsa-miR-642b-3p, hsa-miR-1249, hsa-miR-744-5p, hsa-miR-4442, hsa-miR-1228-3p, hsa-miR-939-5p, hsa-miR-6845-5p, hsa-miR-887-3p, hsa-miR-7845-5p, hsa-miR-6729-5p, hsa-miR-4632-5p, hsa-miR-615-5p, hsa-miR-6724-5p, hsa-miR-4728-5p, hsa-miR-6732-5p, hsa-miR-6806-5p, hsa-miR-4695-5p, hsa-miR-6088, hsa-miR-7975, hsa-miR-3197, hsa-miR-6125, hsa-miR-4433-3p, hsa-miR-6727-5p, hsa-miR-4706, hsa-miR-7847-3p, hsa-miR-6805-3p, hsa-miR-6766-3p, hsa-miR-1913, hsa-miR-4649-5p, hsa-miR-602, hsa-miR-3663-3p, hsa-miR-6893-5p, hsa-miR-6861-5p, hsa-miR-4449, hsa-miR-6842-5p, hsa-miR-4454, hsa-miR-51195-3p, hsa-miR-663b, hsa-miR-6765-5p, hsa-miR-4513, hsa-miR-614, hsa-miR-6785-5p, hsa-miR-6777-5p, hsa-miR-940, hsa-miR-4741, hsa-miR-6870-5p, hsa-miR-6131, hsa-miR-150-3p, hsa-miR-4707-5p, hsa-miR-1915-3p, hsa-miR-3937, hsa-miR-937-5p, hsa-miR-4443, hsa-miR-1914-3p, hsa-miR-3620-5p, hsa-miR-1268b, hsa-miR-1227-5p, hsa-miR-6880-5p, hsa-miR-4417, hsa-miR-6802-5p, hsa-miR-6769a-5p, hsa-miR-663a, hsa-miR-6721-5p, hsa-miR-4532, hsa-miR-7977, hsa-miR-92b-5p, hsa-miR-371a-5p, hsa-miR-6126, hsa-miR-4734, hsa-miR-4665-3p, hsa-miR-423-5p, hsa-miR-1469, hsa-miR-4675, hsa-miR-1915-5p, hsa-miR-6716-5p, hsa-miR-718, hsa-miR-4281, hsa-miR-6820-5p, hsa-miR-6795-5p, hsa-miR-6779-5p, hsa-miR-7109-5p, hsa-miR-6798-5p, hsa-miR-4648, hsa-miR-8059, hsa-miR-6765-3p, hsa-miR-6132, hsa-miR-4492, hsa-miR-7107-5p, hsa-miR-3195, hsa-miR-3180, hsa-miR-296-3p, hsa-miR-564, hsa-miR-1268a, hsa-miR-6848-5p, hsa-miR-762, hsa-miR-2861, hsa-miR-1203, hsa-miR-11260b, hsa-miR-4476, hsa-miR-6885-5p, hsa-miR-6769b-5p, hsa-miR-23b-3p, hsa-miR-1343-5p, hsa-miR-3621, hsa-miR-4688, hsa-miR-4286, hsa-miR-4640-5p, hsa-miR-4739, hsa-miR-1260a, hsa-miR-4276, hsa-miR-7106, hsa-miR-128-2-5p, hsa-miR-125a-3p, hsa-miR-92a-2-5p and hsa-miR-486-3p genes, and the nucleotide sequences of SEQ ID NOs: 1 to 169 related thereto were found.

Among them, genes newly found as markers for examining the presence or absence of stomach cancer are polynucleotides consisting of the nucleotide sequences represented by SEQ ID NOs: 1 to 165.

A discriminant for determining the presence or absence of stomach cancer was further prepared by Fisher's discriminant analysis with the expression levels of these genes as indicators. Specifically, any newly found polynucleotide consisting of a nucleotide sequence represented by any of SEQ ID NOs: 1 to 169 in the training cohort was applied for Formula 2 to construct a discriminant. Calculated accuracy, sensitivity, and specificity are shown in Table 3. In this respect, a discriminant coefficient and a constant term are shown in Table 4. In this context, all of the polynucleotides consisting of the nucleotide sequences represented by SEQ ID NOs: 1 to 169 were selected as markers capable of determining all of papillary adenocarcinoma, tubular adenocarcinoma (3 cases), low differentiated adenocarcinoma, signet-ring cell carcinoma, and mucinous carcinoma, which are main types of stomach cancer.

Next, accuracy, sensitivity, and specificity in the validation cohort were calculated using the discriminant thus prepared, and the discriminant performance of the selected polynucleotides was validated using independent samples (Table 3). For example, the expression level measurement value of the nucleotide sequence represented by SEQ ID NO: 1 was compared between the healthy subjects (100 persons) and the stomach cancer patients (34 persons) in the training cohort. As a result, the gene expression level measurement values were found to be significantly lower in the stomach cancer patient group than in the healthy subject group (see the left diagram of FIG. 2). These results were also reproducible in the healthy subjects (50 persons) and the stomach cancer patients (16 persons) in the validation cohort (see the right diagram of FIG. 2). Likewise, the results obtained about the other polynucleotides shown in SEQ ID NOs: 2 to 169 showed that the gene expression level measurement values were significantly lower (−) or higher (+) in the stomach cancer patient group than in the healthy subject group (Table 2). These results were able to be validated in the validation cohort. For example, as for this nucleotide sequence represented by SEQ ID NO: 1, the number of correctly or incorrectly identified samples in the detection of stomach cancer was calculated using the threshold (6.29) that was set in the training cohort and discriminated between the groups. As a result, 14 true positives, 49 true negatives, 1 false positive, and 2 false negatives were obtained. From these values, 95.5% accuracy, 87.5% sensitivity, and 98% specificity were obtained as the detection performance. In this way, the detection performance was calculated as to all of the polynucleotides shown in SEQ ID NOs: 1 to 169, and described in Table 3. The polynucleotides consisting of the nucleotide sequences represented by SEQ ID NOs: 1 to 169 shown in Table 3, exhibited sensitivity of 87.5%, 93.8%, 93.8%, 81.2%, 93.8%, 87.5%, 87.5%, 81.2%, 68.8%, 87.5%, 75.0%, 81.2%, 87.5%, 75.0%, 81.2%, 93.8%, 68.8%, 81.2%, 56.2%, 68.8%, 87.5%, 56.2%, 62.5%, 62.5%, 62.5%, 75.0%, 56.2%, 87.5%, 93.8%, 62.5%, 87.5%, 62.5%, 68.8%, 81.2%, 81.2%, 62.5%, 81.2%, 81.2%, 62.5%, 87.5%, 62.5%, 75.0%, 56.2%, 75.0%, 62.5%, 56.2%, 68.8%, 62.5%, 56.2%, 93.8%, 62.5%, 62.5%, 56.2%, 81.2%, 68.8%, 56.2%, 43.8%, 75%, 75.0%, 68.8%, 81.2%, 75.0%, 68.8%, 68.8%, 43.8%, 62.5%, 50.0%, 50.0%, 62.5%, 62.5%, 50.0%, 68.8%, 37.5%, 50.0%, 37.5%, 68.8%, 68.8%, 56.2%, 12.5%, 75.0%, 50.0%, 50.0%, 37.5%, 68.8%, 25.0%/6, 81.2%, 43.8%, 56.2%, 62.5%, 37.5%, 43.8%, 43.8%, 37.5%, 43.8%, 31.2%, 43.8%, 50.0%, 25%, 43.8%, 37.5%, 37.5%, 31.2%, 25.0%, 25.0%, 56.2%, 31.2%, 43.8%, 56.2%, 50.0%, 37.5%, 31.2%, 31.2%, 37.5%, 50.0%, 12.5%, 31.2%, 56.2%, 18.8%, 43.8%, 18.8%, 37.5%, 31.2%, 37.5%, 50.0%, 50.0%, 12.5%, 31.2%, 31.2%, 31.2%, 31.2%, 50.0%, 37.5%, 18.8%, 37.5%, 50.0%, 43.8%, 18.8%, 43.8%, 31.2%, 18.8%, 50.0%, 25.0%, 31.2%, 31.2%, 18.8%, 43.8%, 6.2%, 25.0%, 12.5%, 31.2%, 12.5%, 18.8%, 37.5%, 6.2%, 31.2%, 6.2%, 18.8%, 6.2%, 18.8%, 6.2%, 12.5%, 18.8%, 6.2%, 12.5%, 6.2%, 50.0%, 68.8%, 31.2%, and 25.0, respectively, in the validation cohort. As seen from Comparative Example mentioned later, the existing markers CEA and CA19-9 had sensitivity of 12.5% (when the abnormal value of CEA was defined as 5 ng/ml or higher) and 12.5% (when the abnormal value of CA19-9 was defined as 37 U/ml or higher), respectively, in the validation cohort, demonstrating that all of the polynucleotides consisting of the nucleotide sequences represented by SEQ ID NOs: 1 to 169 can discriminate, each alone, stomach cancer in the validation cohort with sensitivity beyond CEA and CA19-9.

For example, 4 polynucleotides consisting of the nucleotide sequences represented by SEQ ID NOs: 3, 5, 21, and 28 were able to correctly determine stomach cancer as to 9 stage IA stomach cancer samples contained in the validation cohort. Thus, these polynucleotides can detect even early stomach cancer and contribute to the early diagnosis of stomach cancer.

Example 2

<Method for Evaluating Stomach Cancer Discriminant Performance by Combination of Multiple Gene Markers Using Samples in the Validation Cohort>

In this Example, a method for evaluating stomach cancer discriminant performance by a combination of the gene markers selected in Example 1 was studied. Specifically, Fisher's discriminant analysis was conducted as to 14,190 combinations of two expression level measurement values comprising at least one or more of the expression level measurement values of the newly found polynucleotides consisting of the nucleotide sequences represented by SEQ ID NOs: 1 to 165 among any of the polynucleotides consisting of the nucleotide sequences represented by SEQ ID NOs: 1 to 169 selected in Example 1, to construct a discriminant for determining the presence or absence of stomach cancer. Next, accuracy, sensitivity, and specificity in the validation cohort were calculated using the discriminant thus prepared, and the discriminant performance of the selected polynucleotides was validated using the independent samples.

Figure 3:
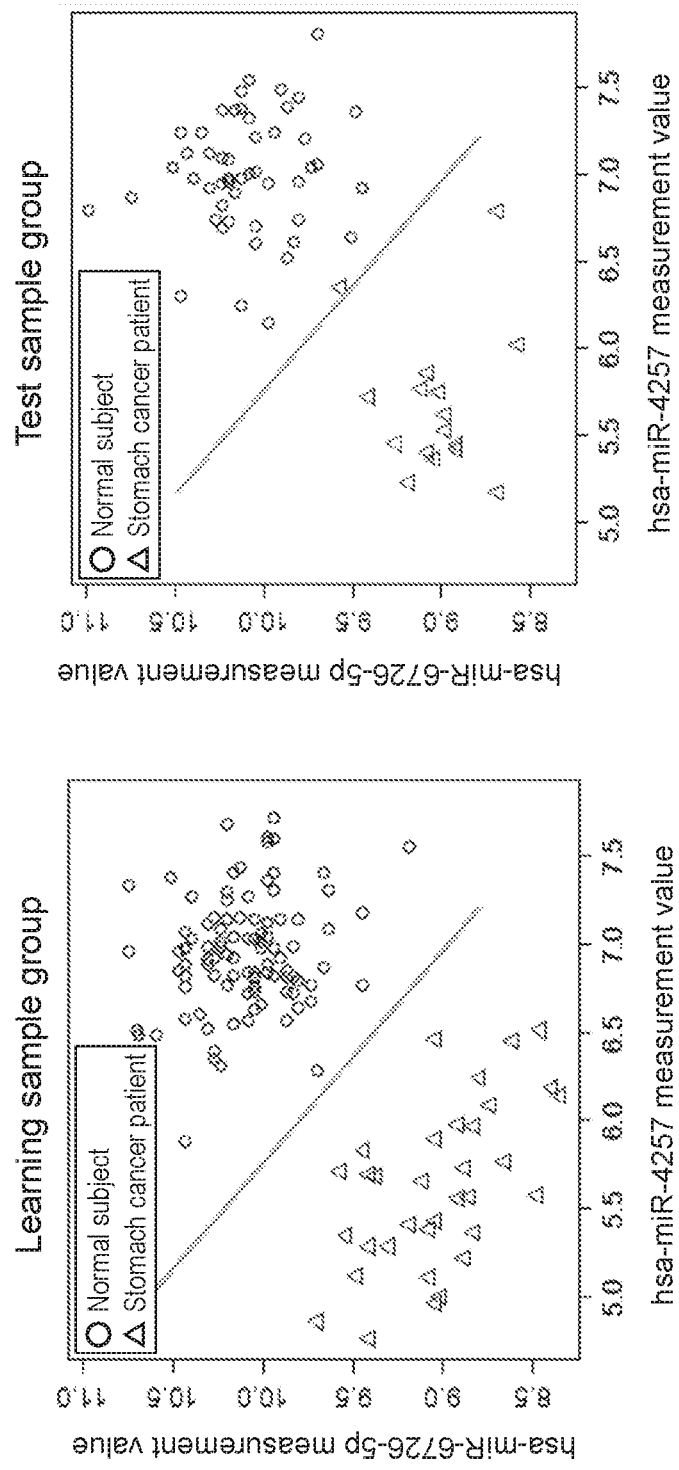
FIG. 3 Left diagram: the measurement values of hsa-miR-4257 (SEQ ID NO: 1) in healthy subjects (100 persons, circles) and stomach cancer patients (34 persons, triangles) selected as a training cohort were each plotted on the abscissa against their measurement values of hsa-miR-6726-5p (SEQ ID NO: 2) on the ordinate. The line in the diagram depicts a discriminant function (0=0.83x+y−14.78) that was optimized by Fisher's discriminant analysis and discriminated between the two groups. Right diagram: the measurement values of hsa-miR-4257 (SEQ ID NO: 1) in healthy subjects (50 persons, circles) and stomach cancer patients (16 persons, triangles) selected as a validation cohort were each plotted on the abscissa against their measurement values of hsa-miR-6726-5p (SEQ ID NO: 2) on the ordinate. The line in the diagram depicts the threshold (0=0.83x+y−14.78) that was set for the training cohort and discriminated between the two groups.

For example, the expression level measurement values of the nucleotide sequences represented by SEQ ID NO: 1 and SEQ ID NO: 2 were compared between the healthy subjects (100 persons) and the stomach cancer patients (34 persons) in the training cohort. As a result, a scatter diagram that significantly separated the expression level measurement values of the stomach cancer patient group from those of the healthy subject group was obtained (see the left diagram of FIG. 3). These results were also reproducible in the healthy subjects (50 persons) and the stomach cancer patients (16 persons) in the validation cohort (see the right diagram of FIG. 3). Likewise, a scatter diagram that significantly separated the gene expression level measurement values of the stomach cancer patient group from those of the healthy subject group was also obtained as to the other combinations of two expression level measurement values comprising at least one or more of the expression level measurement values of the newly found polynucleotides consisting of the nucleotide sequences represented by SEQ ID NOs: 1 to 165 among the polynucleotides consisting of the nucleotide sequences represented by SEQ ID NOs: 1 to 169. These results were able to be validated in the validation cohort. For example, as for these nucleotide sequences represented by SEQ ID NO: 1 and SEQ ID NO: 2, the number of samples that were correctly or incorrectly identified in the detection of stomach cancer was calculated using the function (0=0.83x+y−14.78) that was set in the training cohort and discriminated between the two groups. As a result, 15 true positives, 50 true negatives, 0 false positives, and 1 false negative were obtained. From these values, 98.5% accuracy, 93.8% sensitivity, and 100% specificity were obtained as the detection performance. In this way, the detection performance was calculated as to all of the combinations of two expression level measurement values comprising at least one or more of the expression level measurement values of any of the newly found polynucleotides consisting of the nucleotide sequences represented by SEQ ID NOs: 1 to 165 among the polynucleotides consisting of the nucleotide sequences represented by SEQ ID NOs: 1 to 169. Among them, 168 combinations comprising the expression level measurement value of the polynucleotide consisting of the nucleotide sequence represented by SEQ ID NO: 1 and the detection performance thereof were described in Table 6 as an example. For example, a combination of the expression level measurement values of the polynucleotides consisting of the nucleotide sequences represented by SEQ ID NOs: 1 and 14 exhibited sensitivity of 100% in the validation cohort. Also, all of combinations of two polynucleotides consisting of nucleotide sequences represented by SEQ ID NO: 1 and any of SEQ ID NOs: 2, 4, 14, 17, 22, 24, 27, 32, 39, 43, 46, 48, 53, 65, 66, 67, 78, 89, 91, 98, 99, 113, 116, 122, 129, 141, 144, 148, 150, 154, and 156 exhibited specificity of 100%. 14,159 combinations of the expression level measurement values of polynucleotides having sensitivity beyond the existing marker CEA or CA19-9 (both 12.5% in Table 5) were obtained in the validation cohort. All of the nucleotide sequences 1 to 165 described in Table 2 obtained in Example 1 were employed at least once in these combinations. These results demonstrated that the combined use of two of the polynucleotides consisting of the nucleotide sequences represented by SEQ ID NOs: 1 to 165 can also discriminate stomach cancer with excellent performance beyond the existing marker. Thus, the combinations of two expression level measurement values of the polynucleotides consisting of the nucleotide sequences also produced excellent stomach cancer detection sensitivity.

Markers for the detection of stomach cancer with better sensitivity are obtained by further combining 3, 4, 5, 6, 7, 8, 9, 10 or more of the expression level measurement values of the polynucleotides consisting of the nucleotide sequences represented by SEQ ID NOs: 1 to 169. For example, the newly found polynucleotides consisting of the nucleotide sequences represented by SEQ ID NOs: 1 to 165 among the polynucleotides consisting of the nucleotide sequences represented by SEQ ID NOs: 1 to 169 selected in Example 1 were measured to obtain their expression levels between the healthy subject group and the stomach cancer group in the validation cohort. All of the polynucleotides were ranked in the descending order of their P values based on the Student's t-test which indicates statistical significance of difference between groups (i.e., one having the lowest P value was ranked in the first place), and stomach cancer detection sensitivity was evaluated using combinations of one or more polynucleotides to which the polynucleotides were added one by one from the top to the bottom according to the rank. In short, the order in which the polynucleotides were combined in this evaluation is in reverse in terms of SEQ ID NOs from SEQ ID NO: 165 to SEQ ID NOs: 164, 163, ... shown in Table 2. As a result, the sensitivity in the validation cohort was 6.2% for 1 polynucleotide (SEQ ID NO: 165), 62.5% for 2 polynucleotides (SEQ ID NOs: 165 and 164), 68.8% for 4 polynucleotides (SEQ ID NOs: 162 to 165), 75.0% for 8 polynucleotides (SEQ ID NOs: 158 to 165), 87.5% for 13 polynucleotides (SEQ ID NOs: 153 to 165), 93.8% for 15 polynucleotides (SEQ ID NOs: 151 to 165), 100% for 23 polynucleotides (SEQ ID NOs: 143 to 165), 100% for 50 polynucleotides (SEQ ID NOs: 116 to 165), 100% for 80 polynucleotides (SEQ ID NOs: 86 to 165), 100% for 100 polynucleotides (SEQ ID NOs: 66 to 165), 100% for 150 polynucleotides (SEQ ID NOs: 16 to 165), and 100% for 165 polynucleotides (SEQ ID NOs: 1 to 165).

These results demonstrated that a combination of multiple polynucleotides can produce higher stomach cancer discriminant performance than that of each polynucleotide alone or a combination of a fewer number of polynucleotides. In this context, the combinations of multiple polynucleotides are not limited to the combinations of the polynucleotides added in the order of statistically significant difference as described above, and any combination of multiple polynucleotides can be used in the detection of stomach cancer.

From these results, it can be concluded that all of the polynucleotides consisting of the nucleotide sequences represented by SEQ ID NOs: 1 to 169 serve as excellent markers for the detection of stomach cancer.

TABLE 2

| SEQ ID NO: | Gene name | P value after Bonferroni correction | Expression level in stomach cancer patient relative to healthy subject |
|---|---|---|---|
| 1 | hsa-miR-4257 | 1.77.E−35 | − |
| 2 | hsa-miR-6726-5p | 1.21.E−34 | − |
| 3 | hsa-miR-1343-3p | 2.35.E−27 | − |
| 4 | hsa-miR-1247-3p | 1.41.E−25 | + |
| 5 | hsa-miR-6787-5p | 9.96.E−25 | − |
| 6 | hsa-miR-6875-5p | 3.18.E−23 | + |
| 7 | hsa-miR-1225-3p | 4.17.E−23 | + |
| 8 | hsa-miR-8063 | 1.39.E−22 | − |
| 9 | hsa-miR-6781-5p | 4.80.E−22 | + |
| 10 | hsa-miR-4746-3p | 7.08.E−22 | + |
| 11 | hsa-miR-1908-5p | 1.66.E−21 | + |
| 12 | hsa-miR-6756-5p | 2.78.E−21 | − |
| 13 | hsa-miR-204-3p | 3.60.E−21 | − |
| 14 | hsa-miR-4651 | 3.74.E−21 | − |
| 15 | hsa-miR-6757-5p | 5.50.E−21 | − |
| 16 | hsa-miR-6825-5p | 7.04.E−20 | + |
| 17 | hsa-miR-7108-5p | 8.87.E−20 | + |
| 18 | hsa-miR-4792 | 1.50.E−19 | + |
| 19 | hsa-miR-7641 | 2.77.E−19 | − |
| 20 | hsa-miR-3188 | 4.51.E−19 | + |
| 21 | hsa-miR-3131 | 1.03.E−18 | − |
| 22 | hsa-miR-6780b-5p | 1.44.E−18 | + |
| 23 | hsa-miR-8069 | 2.56.E−18 | + |
| 24 | hsa-miR-6840-3p | 3.01.E−18 | − |
| 25 | hsa-miR-8072 | 4.25.E−18 | + |
| 26 | hsa-miR-1233-5p | 2.25.E−17 | − |
| 27 | hsa-miR-6887-5p | 4.74.E−17 | − |
| 28 | hsa-miR-1231 | 5.08.E−17 | + |
| 29 | hsa-miR-5572 | 1.08.E−16 | + |
| 30 | hsa-miR-6738-5p | 1.16.E−16 | − |
| 31 | hsa-miR-6784-5p | 1.68.E−16 | + |
| 32 | hsa-miR-6791-5p | 3.16.E−16 | + |
| 33 | hsa-miR-6749-5p | 3.69.E−16 | − |
| 34 | hsa-miR-6741-5p | 5.38.E−16 | − |
| 35 | hsa-miR-128-1-5p | 1.67.E−15 | + |
| 36 | hsa-miR-4419b | 2.16.E−15 | − |
| 37 | hsa-miR-6746-5p | 2.49.E−15 | − |
| 38 | hsa-miR-3184-5p | 2.56.E−15 | + |
| 39 | hsa-miR-3679-5p | 2.88.E−15 | + |
| 40 | hsa-miR-7110-5p | 3.95.E−15 | + |
| 41 | hsa-miR-4516 | 4.43.E−15 | − |
| 42 | hsa-miR-6717-5p | 4.77.E−15 | − |
| 43 | hsa-miR-6826-5p | 4.94.E−15 | − |
| 44 | hsa-miR-4433-3p | 5.34.E−15 | + |
| 45 | hsa-miR-3679-3p | 2.55.E−14 | + |
| 46 | hsa-miR-3135b | 3.35.E−14 | − |
| 47 | hsa-miR-3622a-5p | 4.36.E−14 | − |
| 48 | hsa-miR-711 | 5.86.E−14 | + |
| 49 | hsa-miR-4467 | 7.26.E−14 | + |
| 50 | hsa-miR-6857-5p | 2.73.E−13 | + |
| 51 | hsa-miR-6515-3p | 3.28.E−13 | + |
| 52 | hsa-miR-1225-5p | 4.67.E−13 | + |
| 53 | hsa-miR-187-5p | 5.39.E−13 | − |
| 54 | hsa-miR-3185 | 6.80.E−13 | + |
| 55 | hsa-miR-642b-3p | 8.60.E−13 | − |
| 56 | hsa-miR-1249 | 1.16.E−12 | + |
| 57 | hsa-miR-744-5p | 2.15.E−12 | + |
| 58 | hsa-miR-4442 | 3.26.E−12 | − |
| 59 | hsa-miR-1228-3p | 4.54.E−12 | + |
| 60 | hsa-miR-939-5p | 7.77.E−12 | + |
| 61 | hsa-miR-6845-5p | 9.25.E−12 | + |
| 62 | hsa-miR-887-3p | 1.35.E−11 | + |
| 63 | hsa-miR-7845-5p | 1.81.E−11 | + |
| 64 | hsa-miR-6729-5p | 2.80.E−11 | + |
| 65 | hsa-miR-4632-5p | 6.45.E−11 | + |
| 66 | hsa-miR-615-5p | 7.56.E−11 | − |
| 67 | hsa-miR-6724-5p | 8.75.E−11 | + |
| 68 | hsa-miR-4728-5p | 1.05.E−10 | − |
| 69 | hsa-miR-6732-5p | 1.23.E−10 | + |
| 70 | hsa-miR-6816-5p | 1.35.E−10 | + |
| 71 | hsa-miR-4695-5p | 4.88.E−10 | + |
| 72 | hsa-miR-6088 | 5.46.E−10 | − |
| 73 | hsa-miR-7975 | 5.48.E−10 | − |
| 74 | hsa-miR-3197 | 5.56.E−10 | + |
| 75 | hsa-miR-6125 | 6.01.E−10 | + |
| 76 | hsa-miR-4433-3p | 6.04.E−10 | + |
| 77 | hsa-miR-6727-5p | 8.92.E−10 | − |
| 78 | hsa-miR-4706 | 1.09.E−09 | − |
| 79 | hsa-miR-7847-3p | 1.25.E−09 | − |
| 80 | hsa-miR-6805-3p | 1.57.E−09 | + |
| 81 | hsa-miR-6766-3p | 1.95.E−09 | + |
| 82 | hsa-miR-1913 | 2.12.E−09 | + |
| 83 | hsa-miR-4649-5p | 2.42.E−09 | − |
| 84 | hsa-miR-602 | 2.50.E−09 | + |
| 85 | hsa-miR-3663-3p | 2.83.E−09 | − |
| 86 | hsa-miR-6893-5p | 3.40.E−09 | − |
| 87 | hsa-miR-6861-5p | 3.53.E−09 | − |
| 88 | hsa-miR-4449 | 4.40.E−09 | + |
| 89 | hsa-miR-6842-5p | 4.48.E−09 | + |
| 90 | hsa-miR-4454 | 4.77.E−09 | − |
| 91 | hsa-miR-5195-3p | 6.01.E−09 | − |
| 92 | hsa-miR-663b | 9.12.E−09 | − |
| 93 | hsa-miR-6765-5p | 2.06.E−08 | + |
| 94 | hsa-miR-4513 | 2.61.E−08 | − |
| 95 | hsa-miR-614 | 4.92.E−08 | − |
| 96 | hsa-miR-6785-5p | 5.85.E−08 | − |
| 97 | hsa-miR-6777-5p | 6.02.E−08 | − |
| 98 | hsa-miR-940 | 8.08.E−08 | + |
| 99 | hsa-miR-4741 | 9.53.E−08 | + |
| 100 | hsa-miR-6870-5p | 1.07.E−07 | + |
| 101 | hsa-miR-6131 | 1.21.E−07 | − |
| 102 | hsa-miR-150-3p | 1.31.E−07 | − |
| 103 | hsa-miR-4707-5p | 1.70.E−07 | + |
| 104 | hsa-miR-1915-3p | 2.00.E−07 | + |
| 105 | hsa-miR-3937 | 2.17.E−07 | + |
| 106 | hsa-miR-937-5p | 2.85.E−07 | − |
| 107 | hsa-miR-4443 | 3.12.E−07 | + |
| 108 | hsa-miR-1914-3p | 3.23.E−07 | − |
| 109 | hsa-miR-3620-5p | 3.97.E−07 | + |
| 110 | hsa-miR-1268b | 5.51.E−07 | + |
| 111 | hsa-miR-1227-5p | 8.69.E−07 | + |
| 112 | hsa-miR-6880-5p | 9.59.E−07 | + |
| 113 | hsa-miR-4417 | 1.28.E−06 | + |
| 114 | hsa-miR-6802-5p | 1.30.E−06 | − |
| 115 | hsa-miR-6769a-5p | 1.32.E−06 | − |
| 116 | hsa-miR-663a | 1.42.E−06 | + |
| 117 | hsa-miR-6721-5p | 1.73.E−06 | + |
| 118 | hsa-miR-4532 | 2.01.E−06 | − |
| 119 | hsa-miR-7977 | 2.27.E−06 | − |
| 120 | hsa-miR-92b-5p | 2.37.E−06 | + |
| 121 | hsa-miR-371a-5p | 2.37.E−06 | − |
| 122 | hsa-miR-6126 | 2.47.E−06 | + |
| 123 | hsa-miR-4734 | 2.53.E−06 | + |
| 124 | hsa-miR-4665-3p | 2.71.E−06 | + |
| 125 | hsa-miR-423-5p | 4.04.E−06 | − |
| 126 | hsa-miR-1469 | 8.08.E−06 | + |
| 127 | hsa-miR-4675 | 8.36.E−06 | − |
| 128 | hsa-miR-1915-5p | 8.49.E−06 | + |
| 129 | hsa-miR-6716-5p | 9.56.E−06 | + |
| 130 | hsa-miR-718 | 1.59.E−05 | + |
| 131 | hsa-miR-4281 | 1.59.E−05 | − |
| 132 | hsa-miR-6820-5p | 1.88.E−05 | − |
| 133 | hsa-miR-6795-5p | 3.14.E−05 | − |
| 134 | hsa-miR-6779-5p | 3.55.E−05 | − |
| 135 | hsa-miR-7109-5p | 4.02.E−05 | − |
| 136 | hsa-miR-6798-5p | 4.28.E−05 | + |
| 137 | hsa-miR-4648 | 6.38.E−05 | + |
| 138 | hsa-miR-8059 | 7.15.E−05 | − |
| 139 | hsa-miR-6765-3p | 8.47.E−05 | − |
| 140 | hsa-miR-6132 | 1.28.E−04 | + |

TABLE 2-continued

| SEQ ID NO: | Gene name | P value after Bonferroni correction | Expression level in stomach cancer patient relative to healthy subject |
|---|---|---|---|
| 141 | hsa-miR-4492 | 1.51.E−04 | + |
| 142 | hsa-miR-7107-5p | 1.64.E−04 | − |
| 143 | hsa-miR-3195 | 1.73.E−04 | + |
| 144 | hsa-miR-3180 | 2.82.E−04 | + |
| 145 | hsa-miR-296-3p | 2.89.E−04 | − |
| 146 | hsa-miR-564 | 4.75.E−04 | − |
| 147 | hsa-miR-1268a | 5.55.E−04 | + |
| 148 | hsa-miR-6848-5p | 6.07.E−04 | + |
| 149 | hsa-miR-762 | 8.99.E−04 | + |
| 150 | hsa-miR-2861 | 1.57.E−03 | − |
| 151 | hsa-miR-1203 | 1.91.E−03 | + |
| 152 | hsa-miR-1260b | 2.01.E−03 | − |
| 153 | hsa-miR-4476 | 2.45.E−03 | − |
| 154 | hsa-miR-6885-5p | 2.83.E−03 | − |
| 155 | hsa-miR-6769b-5p | 2.84.E−03 | − |
| 156 | hsa-miR-23b-3p | 2.87.E−03 | − |
| 157 | hsa-miR-1343-5p | 3.95.E−03 | + |
| 158 | hsa-miR-3621 | 4.31.E−03 | − |
| 159 | hsa-miR-4688 | 4.77.E−03 | − |
| 160 | hsa-miR-4286 | 4.90.E−03 | − |
| 161 | hsa-miR-4640-5p | 6.06.E−03 | + |
| 162 | hsa-miR-4739 | 6.13.E−03 | + |
| 163 | hsa-miR-1260a | 7.24.E−03 | − |
| 164 | hsa-miR-4276 | 8.00.E−03 | + |
| 165 | hsa-miR-7106-5p | 9.50.E−03 | − |
| 166 | hsa-miR-128-2-5p | 1.79.E−09 | − |
| 167 | hsa-miR-125a-3p | 1.81.E−09 | − |
| 168 | hsa-miR-92a-2-5p | 2.01.E−05 | + |
| 169 | hsa-miR-486-3p | 2.60.E−03 | − |

TABLE 3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1 | 95.5 | 85.3 | 99.0 | 95.5 | 87.5 | 98.0 |
| 2 | 94.8 | 88.2 | 97.0 | 97.0 | 93.8 | 98.0 |
| 3 | 97.0 | 91.2 | 99.0 | 97.0 | 93.8 | 98.0 |
| 4 | 93.3 | 82.4 | 97.0 | 90.9 | 81.2 | 94.0 |
| 5 | 93.3 | 79.4 | 98.0 | 97.0 | 93.8 | 98.0 |
| 6 | 94.0 | 91.2 | 95.0 | 87.9 | 87.5 | 88.0 |
| 7 | 92.5 | 82.4 | 96.0 | 97.0 | 87.5 | 100.0 |
| 8 | 90.3 | 88.2 | 91.0 | 90.9 | 81.2 | 94.0 |
| 9 | 94.8 | 85.3 | 98.0 | 86.4 | 68.8 | 92.0 |
| 10 | 91.0 | 76.5 | 96.0 | 95.5 | 87.5 | 98.0 |
| 11 | 90.3 | 82.4 | 93.0 | 89.4 | 75.0 | 94.0 |
| 12 | 90.3 | 73.5 | 96.0 | 87.9 | 81.2 | 90.0 |
| 13 | 91.0 | 73.5 | 97.0 | 81.8 | 87.5 | 80.0 |
| 14 | 91.8 | 79.4 | 96.0 | 92.4 | 75.0 | 98.0 |
| 15 | 90.3 | 76.5 | 95.0 | 95.5 | 81.2 | 100.0 |
| 16 | 88.1 | 82.4 | 90.0 | 92.4 | 93.8 | 92.0 |
| 17 | 88.1 | 73.5 | 93.0 | 83.3 | 68.8 | 88.0 |
| 18 | 92.5 | 88.2 | 94.0 | 93.9 | 81.2 | 98.0 |
| 19 | 88.1 | 73.5 | 93.0 | 83.3 | 56.2 | 92.0 |
| 20 | 91.8 | 85.3 | 94.0 | 90.9 | 68.8 | 98.0 |
| 21 | 91.8 | 76.5 | 97.0 | 95.5 | 87.5 | 98.0 |
| 22 | 88.8 | 70.6 | 95.0 | 89.4 | 56.2 | 100.0 |
| 23 | 88.1 | 67.6 | 95.0 | 87.9 | 62.5 | 96.0 |
| 24 | 87.3 | 64.7 | 95.0 | 87.9 | 62.5 | 96.0 |
| 25 | 88.1 | 61.8 | 97.0 | 83.3 | 62.5 | 90.0 |
| 26 | 90.3 | 76.5 | 95.0 | 89.4 | 75.0 | 94.0 |
| 27 | 91.0 | 67.6 | 99.0 | 89.4 | 56.2 | 100.0 |
| 28 | 90.3 | 79.4 | 94.0 | 90.9 | 87.5 | 92.0 |
| 29 | 85.8 | 79.4 | 88.0 | 90.9 | 93.8 | 90.0 |
| 30 | 89.6 | 76.5 | 94.0 | 86.4 | 62.5 | 94.0 |
| 31 | 85.1 | 73.5 | 89.0 | 87.9 | 87.5 | 88.0 |
| 32 | 85.1 | 67.6 | 91.0 | 89.4 | 62.5 | 98.0 |
| 33 | 87.3 | 61.8 | 96.0 | 90.9 | 68.8 | 98.0 |
| 34 | 90.3 | 70.6 | 97.0 | 89.4 | 81.2 | 92.0 |
| 35 | 89.6 | 82.4 | 92.0 | 84.8 | 81.2 | 86.0 |
| 36 | 90.3 | 73.5 | 96.0 | 89.4 | 62.5 | 98.0 |
| 37 | 90.3 | 70.6 | 97.0 | 92.4 | 81.2 | 96.0 |
| 38 | 87.3 | 82.4 | 89.0 | 90.9 | 81.2 | 94.0 |
| 39 | 90.3 | 76.5 | 95.0 | 90.9 | 62.5 | 100.0 |
| 40 | 87.3 | 76.5 | 91.0 | 89.4 | 87.5 | 90.0 |
| 41 | 90.3 | 61.8 | 100.0 | 90.9 | 62.5 | 100.0 |
| 42 | 90.3 | 61.8 | 100.0 | 93.9 | 75.0 | 100.0 |
| 43 | 90.3 | 67.6 | 98.0 | 89.4 | 56.2 | 100.0 |
| 44 | 87.3 | 73.5 | 92.0 | 81.8 | 75.0 | 84.0 |
| 45 | 90.3 | 82.4 | 93.0 | 83.3 | 62.5 | 90.0 |
| 46 | 90.3 | 70.6 | 97.0 | 87.9 | 56.2 | 98.0 |
| 47 | 85.1 | 47.1 | 98.0 | 90.9 | 68.8 | 98.0 |
| 48 | 86.6 | 64.7 | 94.0 | 89.4 | 62.5 | 98.0 |
| 49 | 83.6 | 73.5 | 87.0 | 86.4 | 56.2 | 96.0 |
| 50 | 90.3 | 79.4 | 94.0 | 95.5 | 93.8 | 96.0 |
| 51 | 84.3 | 61.8 | 92.0 | 77.3 | 62.5 | 82.0 |
| 52 | 87.3 | 64.7 | 95.0 | 84.8 | 62.5 | 92.0 |
| 53 | 84.3 | 52.9 | 95.0 | 87.9 | 56.2 | 98.0 |
| 54 | 85.8 | 67.6 | 92.0 | 90.9 | 81.2 | 94.0 |
| 55 | 87.3 | 64.7 | 95.0 | 90.9 | 68.8 | 98.0 |
| 56 | 86.5 | 67.6 | 92.9 | 80.3 | 56.2 | 88.0 |
| 57 | 83.6 | 52.9 | 94.0 | 84.8 | 43.8 | 98.0 |
| 58 | 85.8 | 70.6 | 91.0 | 87.9 | 75.0 | 92.0 |
| 59 | 84.3 | 55.9 | 94.0 | 86.4 | 75.0 | 90.0 |
| 60 | 82.8 | 73.5 | 86.0 | 83.3 | 68.8 | 88.0 |
| 61 | 85.1 | 52.9 | 96.0 | 87.9 | 81.2 | 90.0 |
| 62 | 82.8 | 61.8 | 90.0 | 84.8 | 75.0 | 88.0 |
| 63 | 85.1 | 58.8 | 94.0 | 86.4 | 68.8 | 92.0 |
| 64 | 79.9 | 50.0 | 90.0 | 81.8 | 68.8 | 86.0 |
| 65 | 88.1 | 61.8 | 97.0 | 84.8 | 43.8 | 98.0 |
| 66 | 83.6 | 41.2 | 98.0 | 89.4 | 62.5 | 98.0 |
| 67 | 82.8 | 55.9 | 92.0 | 78.8 | 50.0 | 88.0 |
| 68 | 78.4 | 44.1 | 90.0 | 81.8 | 50.0 | 92.0 |
| 69 | 82.1 | 61.8 | 89.0 | 80.3 | 62.5 | 86.0 |
| 70 | 82.1 | 58.8 | 90.0 | 84.8 | 62.5 | 92.0 |
| 71 | 79.9 | 47.1 | 91.0 | 83.3 | 50.0 | 94.0 |
| 72 | 79.9 | 50.0 | 90.0 | 86.4 | 68.8 | 92.0 |
| 73 | 80.6 | 41.2 | 94.0 | 78.8 | 37.5 | 92.0 |
| 74 | 85.8 | 61.8 | 94.0 | 83.3 | 50.0 | 94.0 |
| 75 | 81.3 | 44.1 | 94.0 | 81.8 | 37.5 | 96.0 |
| 76 | 81.3 | 61.8 | 88.0 | 83.3 | 68.8 | 88.0 |
| 77 | 86.6 | 67.6 | 93.0 | 90.9 | 68.8 | 98.0 |
| 78 | 85.1 | 58.8 | 94.0 | 84.8 | 56.2 | 94.0 |
| 79 | 85.1 | 44.1 | 99.0 | 78.8 | 12.5 | 100.0 |
| 80 | 79.9 | 50.0 | 90.0 | 89.4 | 75.0 | 94.0 |
| 81 | 82.8 | 47.1 | 95.0 | 80.3 | 50.0 | 90.0 |
| 82 | 82.1 | 55.9 | 91.0 | 78.5 | 50.0 | 87.8 |
| 83 | 84.3 | 50.0 | 96.0 | 81.8 | 37.5 | 96.0 |
| 84 | 82.8 | 52.9 | 93.0 | 87.9 | 68.8 | 94.0 |
| 85 | 82.8 | 47.1 | 95.0 | 78.8 | 25.0 | 96.0 |
| 86 | 85.8 | 52.9 | 97.0 | 92.4 | 81.2 | 96.0 |
| 87 | 84.3 | 50.0 | 96.0 | 81.8 | 43.8 | 94.0 |
| 88 | 80.6 | 38.2 | 95.0 | 86.4 | 56.2 | 96.0 |
| 89 | 81.3 | 41.2 | 95.0 | 87.9 | 62.5 | 96.0 |
| 90 | 81.3 | 47.1 | 93.0 | 78.8 | 37.5 | 92.0 |
| 91 | 82.1 | 47.1 | 94.0 | 81.8 | 43.8 | 94.0 |
| 92 | 83.6 | 47.1 | 96.0 | 86.4 | 43.8 | 100.0 |
| 93 | 82.8 | 47.1 | 95.0 | 80.3 | 37.5 | 94.0 |
| 94 | 79.1 | 29.4 | 96.0 | 83.3 | 43.8 | 96.0 |
| 95 | 76.9 | 38.2 | 90.0 | 78.8 | 31.2 | 94.0 |
| 96 | 81.3 | 44.1 | 94.0 | 83.3 | 43.8 | 96.0 |
| 97 | 79.9 | 38.2 | 94.0 | 83.3 | 50.0 | 94.0 |
| 98 | 80.6 | 44.1 | 93.0 | 78.8 | 25.0 | 96.0 |
| 99 | 82.1 | 50.0 | 93.0 | 80.3 | 43.8 | 92.0 |
| 100 | 81.3 | 38.2 | 96.0 | 84.8 | 37.5 | 100.0 |
| 101 | 85.1 | 50.0 | 97.0 | 83.3 | 37.5 | 98.0 |
| 102 | 80.6 | 29.4 | 98.0 | 77.3 | 31.2 | 92.0 |
| 103 | 76.1 | 32.4 | 91.0 | 75.8 | 25.0 | 92.0 |
| 104 | 84.3 | 50.0 | 96.0 | 80.3 | 25.0 | 98.0 |
| 105 | 79.1 | 38.2 | 93.0 | 84.8 | 56.2 | 94.0 |
| 106 | 82.8 | 44.1 | 96.0 | 81.8 | 31.2 | 98.0 |
| 107 | 82.1 | 44.1 | 95.0 | 83.3 | 43.8 | 96.0 |
| 108 | 81.3 | 47.1 | 93.0 | 80.3 | 56.2 | 88.0 |

TABLE 3-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 109 | 79.9 | 38.2 | 94.0 | 81.8 | 50.0 | 92.0 |
| 110 | 74.6 | 32.4 | 89.0 | 72.7 | 37.5 | 84.0 |
| 111 | 81.3 | 44.1 | 94.0 | 75.8 | 31.2 | 90.0 |
| 112 | 82.8 | 47.1 | 95.0 | 80.3 | 31.2 | 96.0 |
| 113 | 81.3 | 35.3 | 97.0 | 81.8 | 37.5 | 96.0 |
| 114 | 86.6 | 52.9 | 98.0 | 86.4 | 50.0 | 98.0 |
| 115 | 79.1 | 38.2 | 93.0 | 75.8 | 12.5 | 96.0 |
| 116 | 81.3 | 41.2 | 95.0 | 78.8 | 31.2 | 94.0 |
| 117 | 76.9 | 38.2 | 90.0 | 80.3 | 56.2 | 88.0 |
| 118 | 81.3 | 38.2 | 96.0 | 75.8 | 18.8 | 94.0 |
| 119 | 78.4 | 35.3 | 93.0 | 81.8 | 43.8 | 94.0 |
| 120 | 78.4 | 38.2 | 92.0 | 78.8 | 18.8 | 98.0 |
| 121 | 79.1 | 35.3 | 94.0 | 75.8 | 37.5 | 88.0 |
| 122 | 78.4 | 38.2 | 92.0 | 81.8 | 31.2 | 98.0 |
| 123 | 78.4 | 32.4 | 94.0 | 80.3 | 37.5 | 94.0 |
| 124 | 87.3 | 52.9 | 99.0 | 86.4 | 50.0 | 98.0 |
| 125 | 76.9 | 32.4 | 92.0 | 75.8 | 50.0 | 84.0 |
| 126 | 78.4 | 29.4 | 95.0 | 71.2 | 12.5 | 90.0 |
| 127 | 80.6 | 41.2 | 94.0 | 83.3 | 31.2 | 100.0 |
| 128 | 79.9 | 32.4 | 96.0 | 78.8 | 31.2 | 94.0 |
| 129 | 77.6 | 26.5 | 95.0 | 77.3 | 31.2 | 92.0 |
| 130 | 76.1 | 26.5 | 93.0 | 75.8 | 31.2 | 90.0 |
| 131 | 78.4 | 35.3 | 93.0 | 84.8 | 50.0 | 96.0 |
| 132 | 80.6 | 29.4 | 98.0 | 77.3 | 37.5 | 90.0 |
| 133 | 79.9 | 23.5 | 99.0 | 80.3 | 18.8 | 100.0 |
| 134 | 75.4 | 32.4 | 90.0 | 83.3 | 37.5 | 98.0 |
| 135 | 73.9 | 23.5 | 91.0 | 80.3 | 50.0 | 90.0 |
| 136 | 78.4 | 44.1 | 90.0 | 74.2 | 43.8 | 84.0 |
| 137 | 73.9 | 20.6 | 92.0 | 80.3 | 18.8 | 100.0 |
| 138 | 79.1 | 29.4 | 96.0 | 81.8 | 43.8 | 94.0 |
| 139 | 82.1 | 41.2 | 96.0 | 80.3 | 31.2 | 96.0 |
| 140 | 79.9 | 29.4 | 97.0 | 78.8 | 18.8 | 98.0 |
| 141 | 79.1 | 32.4 | 95.0 | 81.8 | 50.0 | 92.0 |
| 142 | 75.4 | 29.4 | 91.0 | 75.8 | 25.0 | 92.0 |
| 143 | 78.4 | 38.2 | 92.0 | 77.3 | 31.2 | 92.0 |
| 144 | 79.9 | 32.4 | 96.0 | 81.8 | 31.2 | 98.0 |
| 145 | 81.2 | 27.3 | 99.0 | 77.3 | 18.8 | 96.0 |
| 146 | 81.3 | 35.3 | 97.0 | 84.8 | 43.8 | 98.0 |
| 147 | 73.1 | 14.7 | 93.0 | 71.2 | 6.2 | 92.0 |
| 148 | 77.6 | 23.5 | 96.0 | 78.8 | 25.0 | 96.0 |
| 149 | 77.6 | 23.5 | 96.0 | 72.3 | 12.5 | 91.8 |
| 150 | 77.6 | 23.5 | 96.0 | 80.3 | 31.2 | 96.0 |
| 151 | 74.6 | 14.7 | 95.0 | 78.8 | 12.5 | 100.0 |
| 152 | 79.9 | 32.4 | 96.0 | 75.8 | 18.8 | 94.0 |
| 153 | 76.1 | 20.6 | 95.0 | 78.8 | 37.5 | 92.0 |
| 154 | 81.3 | 32.4 | 98.0 | 75.8 | 6.2 | 98.0 |
| 155 | 76.9 | 20.6 | 96.0 | 81.8 | 31.2 | 98.0 |
| 156 | 79.1 | 23.5 | 98.0 | 72.7 | 6.2 | 94.0 |
| 157 | 82.1 | 35.3 | 98.0 | 80.3 | 18.8 | 100.0 |
| 158 | 74.6 | 11.8 | 96.0 | 74.2 | 6.2 | 96.0 |
| 159 | 77.6 | 20.6 | 97.0 | 78.8 | 18.8 | 98.0 |
| 160 | 75.4 | 20.6 | 94.0 | 71.2 | 6.2 | 92.0 |
| 161 | 78.4 | 26.5 | 96.0 | 78.8 | 12.5 | 100.0 |
| 162 | 79.1 | 20.6 | 99.0 | 78.8 | 18.8 | 98.0 |
| 163 | 76.1 | 20.6 | 95.0 | 72.7 | 6.2 | 94.0 |
| 164 | 76.9 | 14.7 | 98.0 | 78.8 | 12.5 | 100.0 |
| 165 | 74.6 | 8.8 | 97.0 | 75.8 | 6.2 | 98.0 |
| 166 | 85.1 | 52.9 | 96.0 | 87.9 | 50.0 | 100.0 |
| 167 | 85.8 | 50.0 | 98.0 | 89.4 | 68.8 | 96.0 |
| 168 | 80.6 | 41.2 | 94.0 | 77.3 | 31.2 | 92.0 |
| 169 | 80.6 | 32.4 | 97.0 | 81.8 | 25.0 | 100.0 |

TABLE 4

| SEQ ID NO: | Discriminant coefficient | Constant term |
|---|---|---|
| 1 | 2.731 | 17.177 |
| 2 | 3.324 | 31.765 |
| 3 | 1.836 | 12.851 |
| 4 | 4.010 | 25.699 |
| 5 | 3.767 | 31.391 |
| 6 | 3.829 | 35.096 |
| 7 | 3.144 | 17.990 |
| 8 | 2.726 | 21.913 |
| 9 | 5.443 | 57.639 |
| 10 | 2.686 | 18.095 |
| 11 | 4.398 | 51.318 |
| 12 | 5.286 | 43.176 |
| 13 | 1.921 | 24.270 |
| 14 | 5.407 | 58.548 |
| 15 | 2.820 | 19.731 |
| 16 | 2.197 | 14.682 |
| 17 | 4.707 | 43.642 |
| 18 | 2.022 | 13.892 |
| 19 | 1.268 | 8.665 |
| 20 | 3.417 | 21.034 |
| 21 | 2.266 | 15.207 |
| 22 | 3.039 | 27.590 |
| 23 | 7.728 | 99.955 |
| 24 | 3.052 | 26.321 |
| 25 | 5.366 | 66.791 |
| 26 | 2.810 | 30.883 |
| 27 | 2.291 | 13.933 |
| 28 | 3.580 | 23.815 |
| 29 | 2.466 | 16.690 |
| 30 | 3.715 | 25.964 |
| 31 | 3.866 | 49.046 |
| 32 | 4.847 | 44.998 |
| 33 | 4.518 | 44.908 |
| 34 | 4.174 | 28.253 |
| 35 | 2.781 | 21.080 |
| 36 | 2.163 | 12.587 |
| 37 | 2.399 | 14.923 |
| 38 | 2.387 | 19.533 |
| 39 | 2.662 | 18.538 |
| 40 | 1.844 | 14.656 |
| 41 | 4.162 | 54.280 |
| 42 | 1.861 | 10.860 |
| 43 | 1.882 | 10.852 |
| 44 | 3.955 | 32.182 |
| 45 | 3.509 | 21.353 |
| 46 | 2.764 | 21.183 |
| 47 | 2.237 | 12.508 |
| 48 | 3.474 | 29.057 |
| 49 | 2.348 | 23.412 |
| 50 | 1.601 | 8.585 |
| 51 | 4.385 | 29.783 |
| 52 | 3.501 | 25.951 |
| 53 | 2.121 | 20.821 |
| 54 | 2.398 | 17.081 |
| 55 | 2.333 | 21.669 |
| 56 | 3.979 | 23.944 |
| 57 | 2.618 | 18.423 |
| 58 | 3.487 | 32.829 |
| 59 | 4.222 | 26.720 |
| 60 | 2.479 | 18.929 |
| 61 | 3.944 | 38.152 |
| 62 | 2.371 | 17.392 |
| 63 | 2.987 | 20.097 |
| 64 | 9.232 | 116.333 |
| 65 | 4.246 | 34.038 |
| 66 | 1.900 | 12.014 |
| 67 | 4.891 | 49.041 |
| 68 | 5.062 | 35.194 |
| 69 | 3.378 | 28.973 |
| 70 | 4.587 | 46.523 |
| 71 | 4.446 | 33.529 |
| 72 | 3.367 | 33.945 |
| 73 | 2.155 | 21.186 |
| 74 | 2.768 | 26.384 |
| 75 | 5.220 | 62.722 |
| 76 | 3.883 | 28.652 |
| 77 | 5.643 | 71.747 |
| 78 | 3.610 | 27.579 |
| 79 | 2.457 | 15.182 |
| 80 | 2.520 | 19.029 |
| 81 | 3.853 | 22.961 |

TABLE 4-continued

| SEQ ID NO: | Discriminant coefficient | Constant term |
|---|---|---|
| 82 | 3.525 | 21.894 |
| 83 | 2.531 | 25.858 |
| 84 | 3.041 | 19.506 |
| 85 | 3.868 | 46.680 |
| 86 | 2.117 | 17.685 |
| 87 | 3.724 | 26.711 |
| 88 | 3.680 | 23.968 |
| 89 | 3.374 | 20.135 |
| 90 | 2.196 | 25.309 |
| 91 | 2.976 | 20.156 |
| 92 | 2.933 | 25.402 |
| 93 | 5.009 | 53.145 |
| 94 | 2.567 | 14.765 |
| 95 | 1.729 | 11.402 |
| 96 | 2.393 | 21.401 |
| 97 | 3.112 | 20.031 |
| 98 | 3.065 | 19.720 |
| 99 | 3.850 | 38.303 |
| 100 | 3.191 | 23.796 |
| 101 | 1.739 | 18.155 |
| 102 | 1.790 | 11.695 |
| 103 | 4.223 | 31.086 |
| 104 | 3.902 | 43.384 |
| 105 | 4.394 | 38.067 |
| 106 | 3.808 | 31.650 |
| 107 | 2.442 | 15.680 |
| 108 | 4.742 | 35.456 |
| 109 | 4.065 | 32.357 |
| 110 | 3.132 | 31.233 |
| 111 | 6.253 | 59.917 |
| 112 | 2.144 | 16.593 |
| 113 | 5.077 | 41.640 |
| 114 | 4.331 | 36.232 |
| 115 | 4.104 | 26.007 |
| 116 | 4.365 | 44.632 |
| 117 | 4.092 | 30.958 |
| 118 | 3.410 | 40.413 |
| 119 | 2.277 | 22.244 |
| 120 | 3.385 | 27.099 |
| 121 | 3.662 | 26.864 |
| 122 | 3.020 | 32.940 |
| 123 | 5.127 | 61.295 |
| 124 | 2.499 | 14.725 |
| 125 | 2.372 | 17.057 |
| 126 | 5.371 | 54.883 |
| 127 | 2.882 | 21.683 |
| 128 | 1.355 | 8.339 |
| 129 | 3.793 | 24.904 |
| 130 | 3.673 | 25.051 |
| 131 | 3.824 | 44.211 |
| 132 | 2.858 | 20.620 |
| 133 | 2.687 | 15.927 |
| 134 | 6.294 | 44.652 |
| 135 | 5.392 | 39.920 |
| 136 | 2.883 | 30.122 |
| 137 | 1.419 | 8.435 |
| 138 | 3.372 | 25.593 |
| 139 | 1.616 | 14.087 |
| 140 | 3.505 | 27.638 |
| 141 | 5.430 | 57.153 |
| 142 | 4.737 | 36.945 |
| 143 | 4.079 | 33.703 |
| 144 | 4.615 | 40.322 |
| 145 | 1.899 | 11.130 |
| 146 | 1.461 | 8.484 |
| 147 | 3.248 | 36.484 |
| 148 | 4.537 | 33.621 |
| 149 | 6.451 | 87.375 |
| 150 | 5.814 | 72.020 |
| 151 | 2.391 | 14.618 |
| 152 | 2.345 | 19.966 |
| 153 | 1.746 | 12.413 |
| 154 | 2.794 | 30.977 |
| 155 | 3.878 | 24.272 |
| 156 | 1.014 | 5.894 |
| 157 | 3.451 | 35.923 |
| 158 | 4.810 | 57.343 |
| 159 | 3.755 | 26.714 |
| 160 | 2.474 | 18.364 |
| 161 | 4.014 | 31.043 |
| 162 | 3.561 | 40.868 |
| 163 | 2.408 | 16.644 |
| 164 | 1.795 | 10.022 |
| 165 | 2.135 | 12.545 |
| 166 | 2.652 | 28.430 |
| 167 | 1.220 | 7.446 |
| 168 | 2.017 | 19.036 |
| 169 | 2.835 | 22.505 |

TABLE 5-1

Training cohort

| Sample name | Cancer stage | CEA | CA19-9 |
|---|---|---|---|
| SC03 | IA | 2.9(−) | 77.4(+) |
| SC04 | IA | 2.9(−) | 0.1(−) |
| SC05 | IA | 2.9(−) | 21.8(−) |
| SC06 | IA | 1.7(−) | 41.9(+) |
| SC07 | IB | 1.5(−) | 25.1(−) |
| SC09 | IA | 2.3(−) | 17.5(−) |
| SC10 | IIB | 1.2(−) | 10.0(−) |
| SC12 | IA | 3.3(−) | 8.5(−) |
| SC13 | IA | 3.4(−) | 8.2(−) |
| SC15 | IA | 3.7(−) | 6.3(−) |
| SC17 | IIB | 2.8(−) | 4.3(−) |
| SC18 | IB | 6.9(+) | 20.2(−) |
| SC19 | IA | 3.1(−) | 5.0(−) |
| SC20 | IIIC | 3.3(−) | 20.1(−) |
| SC23 | IB | 2.5(−) | 0.1(−) |
| SC24 | IA | 3.1(−) | 43.2(+) |
| SC25 | IIIA | 2.6(−) | 16.4(−) |
| SC26 | IA | 0.9(−) | 7.3(−) |
| SC27 | IA | 2.0(−) | 9.2(−) |
| SC29 | IIA | 1.3(−) | 35.6(−) |
| SC30 | IA | 2.8(−) | 0.1(−) |
| SC31 | IA | 2.4(−) | 14.0(−) |
| SC32 | IA | 4.0(−) | 10.5(−) |
| SC34 | IA | 2.4(−) | 17.0(−) |
| SC36 | IIIC | 1.5(−) | 14.1(−) |
| SC38 | IA | 4.8(−) | 47.6(+) |
| SC40 | IIA | 1.7(−) | 29.4(−) |
| SC41 | IA | 0.3(−) | 10.9(−) |
| SC42 | IIIA | 2.2(−) | 12.2(−) |
| SC45 | IIIC | 0.8(−) | 6.5(−) |
| SC47 | IB | 1.3(−) | 26.3(−) |
| SC48 | IIIA | 1.9(−) | 6.3(−) |
| SC49 | IA | 2.9(−) | 41.1(+) |
| SC50 | IB | 1.4(−) | 11.4(−) |

TABLE 5-2

Validation cohort

| Sample name | Cancer stage | CEA | CA19/9 |
|---|---|---|---|
| SC01 | IA | 3.7(−) | 0.1(−) |
| SC02 | IA | 4.9(−) | 65.2(+) |
| SC08 | IA | 1.1(−) | 9.9(−) |
| SC11 | IA | 1.8(−) | 9.4(−) |
| SC14 | IB | 2.0(−) | 26.1(−) |
| SC16 | IA | 3.1(−) | 9.5(−) |
| SC21 | IIA | 0.7(−) | 9.1(−) |
| SC22 | IA | 1.4(−) | 6.0(−) |
| SC28 | IA | 3.3(−) | 6.6(−) |
| SC33 | IIIA | 5.6(+) | 14.7(−) |
| SC35 | IA | 3.7(−) | 7.8(−) |
| SC37 | IIB | 4.2(−) | 0.1(−) |
| SC39 | IIIC | 17.5(+) | 7.0(−) |

TABLE 5-2-continued

| | Validation cohort | | |
|---|---|---|---|
| Sample name | Cancer stage | CEA | CA19/9 |
| SC43 | IIA | 4.6(−) | 10.1(−) |
| SC44 | IA | 1.8(−) | 5.8(−) |
| SC46 | IB | 2.7(−) | 37.1(+) |

For CEA, 5 ng/mL or lower was indicated as "−", and for A19-9, 37 U/mL or lower was indicated as "−", while values exceeding these were indicated as "+".

TABLE 6

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_2 | 100.0 | 100.0 | 100.0 | 98.5 | 93.8 | 100.0 |
| 1_3 | 97.8 | 94.1 | 99.0 | 95.5 | 87.5 | 98.0 |
| 1_4 | 98.5 | 94.1 | 100.0 | 98.5 | 93.8 | 100.0 |
| 1_5 | 96.3 | 88.2 | 99.0 | 95.5 | 87.5 | 98.0 |
| 1_6 | 97.0 | 91.2 | 99.0 | 93.9 | 87.5 | 96.0 |
| 1_7 | 96.3 | 91.2 | 98.0 | 95.5 | 87.5 | 98.0 |
| 1_8 | 95.5 | 88.2 | 98.0 | 95.5 | 87.5 | 98.0 |
| 1_9 | 97.0 | 91.2 | 99.0 | 95.5 | 87.5 | 98.0 |
| 1_10 | 97.0 | 91.2 | 99.0 | 95.5 | 87.5 | 98.0 |
| 1_11 | 96.3 | 88.2 | 99.0 | 95.5 | 87.5 | 98.0 |
| 1_12 | 96.3 | 88.2 | 99.0 | 93.9 | 87.5 | 96.0 |
| 1_13 | 100.0 | 100.0 | 100.0 | 93.9 | 93.8 | 94.0 |
| 1_14 | 97.8 | 94.1 | 99.0 | 100.0 | 100.0 | 100.0 |
| 1_15 | 95.5 | 85.3 | 99.0 | 95.5 | 87.5 | 98.0 |
| 1_16 | 96.3 | 88.2 | 99.0 | 95.5 | 87.5 | 98.0 |
| 1_17 | 96.3 | 91.2 | 98.0 | 95.5 | 81.2 | 100.0 |
| 1_18 | 96.3 | 88.2 | 99.0 | 95.5 | 87.5 | 98.0 |
| 1_19 | 100.0 | 100.0 | 100.0 | 95.5 | 87.5 | 98.0 |
| 1_20 | 96.3 | 88.2 | 99.0 | 95.5 | 87.5 | 98.0 |
| 1_21 | 95.5 | 85.3 | 99.0 | 95.5 | 87.5 | 98.0 |
| 1_22 | 97.8 | 91.2 | 100.0 | 95.5 | 81.2 | 100.0 |
| 1_23 | 99.3 | 97.1 | 100.0 | 95.5 | 87.5 | 98.0 |
| 1_24 | 96.3 | 88.2 | 99.0 | 97.0 | 87.5 | 100.0 |
| 1_25 | 99.3 | 97.1 | 100.0 | 95.5 | 87.5 | 98.0 |
| 1_26 | 96.3 | 88.2 | 99.0 | 93.9 | 87.5 | 96.0 |
| 1_27 | 96.3 | 88.2 | 99.0 | 97.0 | 87.5 | 100.0 |
| 1_28 | 96.3 | 88.2 | 99.0 | 97.0 | 93.8 | 98.0 |
| 1_29 | 95.5 | 88.2 | 98.0 | 95.5 | 87.5 | 98.0 |
| 1_30 | 95.5 | 88.2 | 98.0 | 95.5 | 87.5 | 98.0 |
| 1_31 | 96.3 | 88.2 | 99.0 | 93.9 | 87.5 | 96.0 |
| 1_32 | 96.3 | 88.2 | 99.0 | 97.0 | 87.5 | 100.0 |
| 1_33 | 96.3 | 88.2 | 99.0 | 95.5 | 87.5 | 98.0 |
| 1_34 | 96.3 | 88.2 | 99.0 | 95.5 | 87.5 | 98.0 |
| 1_35 | 96.3 | 88.2 | 99.0 | 95.5 | 87.5 | 98.0 |
| 1_36 | 96.3 | 88.2 | 99.0 | 95.5 | 87.5 | 98.0 |
| 1_37 | 96.3 | 88.2 | 99.0 | 95.5 | 87.5 | 98.0 |
| 1_38 | 96.3 | 88.2 | 99.0 | 95.5 | 87.5 | 98.0 |
| 1_39 | 96.3 | 88.2 | 99.0 | 97.0 | 87.5 | 100.0 |
| 1_40 | 95.5 | 88.2 | 98.0 | 95.5 | 87.5 | 98.0 |
| 1_41 | 95.5 | 85.3 | 99.0 | 95.5 | 87.5 | 98.0 |
| 1_42 | 95.5 | 85.3 | 99.0 | 95.5 | 87.5 | 98.0 |
| 1_43 | 95.5 | 85.3 | 99.0 | 97.0 | 87.5 | 100.0 |
| 1_44 | 95.5 | 88.2 | 98.0 | 93.9 | 87.5 | 96.0 |
| 1_45 | 97.8 | 94.1 | 99.0 | 95.5 | 87.5 | 98.0 |
| 1_46 | 97.0 | 91.2 | 99.0 | 97.0 | 87.5 | 100.0 |
| 1_47 | 97.0 | 94.1 | 98.0 | 97.0 | 93.8 | 98.0 |
| 1_48 | 96.3 | 88.2 | 99.0 | 97.0 | 87.5 | 100.0 |
| 1_49 | 97.8 | 91.2 | 100.0 | 93.9 | 87.5 | 96.0 |
| 1_50 | 95.5 | 85.3 | 99.0 | 95.5 | 87.5 | 98.0 |
| 1_51 | 98.5 | 97.1 | 99.0 | 95.5 | 87.5 | 98.0 |
| 1_52 | 95.5 | 85.3 | 99.0 | 95.5 | 87.5 | 98.0 |
| 1_53 | 95.5 | 85.3 | 99.0 | 97.0 | 87.5 | 100.0 |
| 1_54 | 95.5 | 85.3 | 99.0 | 95.5 | 87.5 | 98.0 |
| 1_55 | 96.3 | 88.2 | 99.0 | 95.5 | 87.5 | 98.0 |
| 1_56 | 97.7 | 94.1 | 99.0 | 95.5 | 87.5 | 98.0 |
| 1_57 | 97.8 | 91.2 | 100.0 | 97.0 | 93.8 | 98.0 |
| 1_58 | 95.5 | 88.2 | 98.0 | 93.9 | 87.5 | 96.0 |
| 1_59 | 97.0 | 94.1 | 98.0 | 93.9 | 87.5 | 96.0 |
| 1_60 | 94.8 | 85.3 | 98.0 | 95.5 | 87.5 | 98.0 |
| 1_61 | 95.5 | 85.3 | 99.0 | 97.0 | 93.8 | 98.0 |
| 1_62 | 96.3 | 88.2 | 99.0 | 95.5 | 87.5 | 98.0 |
| 1_63 | 96.3 | 88.2 | 99.0 | 95.5 | 87.5 | 98.0 |
| 1_64 | 96.3 | 88.2 | 99.0 | 95.5 | 87.5 | 98.0 |
| 1_65 | 96.3 | 88.2 | 99.0 | 97.0 | 87.5 | 100.0 |
| 1_66 | 97.0 | 91.2 | 99.0 | 97.0 | 87.5 | 100.0 |
| 1_67 | 95.5 | 88.2 | 98.0 | 97.0 | 87.5 | 100.0 |
| 1_68 | 95.5 | 85.3 | 99.0 | 95.5 | 87.5 | 98.0 |
| 1_69 | 95.5 | 88.2 | 98.0 | 95.5 | 87.5 | 98.0 |
| 1_70 | 96.3 | 88.2 | 99.0 | 95.5 | 87.5 | 98.0 |
| 1_71 | 96.3 | 88.2 | 99.0 | 95.5 | 87.5 | 98.0 |
| 1_72 | 95.5 | 85.3 | 99.0 | 95.5 | 87.5 | 98.0 |
| 1_73 | 95.5 | 85.3 | 99.0 | 95.5 | 87.5 | 98.0 |
| 1_74 | 95.5 | 85.3 | 99.0 | 95.5 | 87.5 | 98.0 |
| 1_75 | 98.5 | 94.1 | 100.0 | 95.5 | 87.5 | 98.0 |
| 1_76 | 95.5 | 85.3 | 99.0 | 93.9 | 87.5 | 96.0 |
| 1_77 | 95.5 | 85.3 | 99.0 | 95.5 | 87.5 | 98.0 |
| 1_78 | 96.3 | 88.2 | 99.0 | 98.5 | 93.8 | 100.0 |
| 1_79 | 97.0 | 91.2 | 99.0 | 95.5 | 87.5 | 98.0 |
| 1_80 | 95.5 | 88.2 | 98.0 | 95.5 | 87.5 | 98.0 |
| 1_81 | 97.0 | 91.2 | 99.0 | 95.5 | 87.5 | 98.0 |
| 1_82 | 95.5 | 85.3 | 99.0 | 95.4 | 87.5 | 98.0 |
| 1_83 | 96.3 | 88.2 | 99.0 | 95.5 | 87.5 | 98.0 |
| 1_84 | 94.8 | 82.4 | 99.0 | 95.5 | 87.5 | 98.0 |
| 1_85 | 96.3 | 88.2 | 99.0 | 95.5 | 87.5 | 98.0 |
| 1_86 | 99.3 | 97.1 | 100.0 | 95.5 | 93.8 | 96.0 |
| 1_87 | 95.5 | 85.3 | 99.0 | 95.5 | 87.5 | 98.0 |
| 1_88 | 96.3 | 88.2 | 99.0 | 95.5 | 87.5 | 98.0 |
| 1_89 | 96.3 | 88.2 | 99.0 | 97.0 | 87.5 | 100.0 |
| 1_90 | 95.5 | 85.3 | 99.0 | 95.5 | 87.5 | 98.0 |
| 1_91 | 96.3 | 91.2 | 98.0 | 97.0 | 87.5 | 100.0 |
| 1_92 | 96.3 | 88.2 | 99.0 | 95.5 | 87.5 | 98.0 |
| 1_93 | 96.3 | 88.2 | 99.0 | 95.5 | 87.5 | 98.0 |
| 1_94 | 96.3 | 88.2 | 99.0 | 95.5 | 87.5 | 98.0 |
| 1_95 | 96.3 | 88.2 | 99.0 | 95.5 | 87.5 | 98.0 |
| 1_96 | 95.5 | 85.3 | 99.0 | 95.5 | 87.5 | 98.0 |
| 1_97 | 97.0 | 91.2 | 99.0 | 95.5 | 87.5 | 98.0 |
| 1_98 | 95.5 | 91.2 | 97.0 | 97.0 | 87.5 | 100.0 |
| 1_99 | 95.5 | 85.3 | 99.0 | 97.0 | 87.5 | 100.0 |
| 1_100 | 96.3 | 88.2 | 99.0 | 95.5 | 87.5 | 98.0 |
| 1_101 | 96.3 | 88.2 | 99.0 | 95.5 | 87.5 | 98.0 |
| 1_102 | 99.3 | 97.1 | 100.0 | 97.0 | 93.8 | 98.0 |
| 1_103 | 95.5 | 85.3 | 99.0 | 95.5 | 87.5 | 98.0 |
| 1_104 | 95.5 | 85.3 | 99.0 | 93.9 | 87.5 | 96.0 |
| 1_105 | 95.5 | 85.3 | 99.0 | 95.5 | 87.5 | 98.0 |
| 1_106 | 96.3 | 88.2 | 99.0 | 95.5 | 87.5 | 98.0 |
| 1_107 | 96.3 | 88.2 | 99.0 | 95.5 | 87.5 | 98.0 |
| 1_108 | 97.0 | 91.2 | 99.0 | 93.9 | 87.5 | 96.0 |
| 1_109 | 95.5 | 85.3 | 99.0 | 95.5 | 87.5 | 98.0 |
| 1_110 | 96.3 | 88.2 | 99.0 | 95.5 | 87.5 | 98.0 |
| 1_111 | 96.3 | 88.2 | 99.0 | 95.5 | 87.5 | 98.0 |
| 1_112 | 95.5 | 85.3 | 99.0 | 95.5 | 87.5 | 98.0 |
| 1_113 | 97.0 | 91.2 | 99.0 | 98.5 | 93.8 | 100.0 |
| 1_114 | 95.5 | 85.3 | 99.0 | 95.5 | 87.5 | 98.0 |
| 1_115 | 95.5 | 85.3 | 99.0 | 95.5 | 87.5 | 98.0 |
| 1_116 | 96.3 | 91.2 | 98.0 | 98.5 | 93.8 | 100.0 |
| 1_117 | 96.3 | 88.2 | 99.0 | 95.5 | 87.5 | 98.0 |
| 1_118 | 96.3 | 88.2 | 99.0 | 95.5 | 87.5 | 98.0 |
| 1_119 | 95.5 | 85.3 | 99.0 | 95.5 | 87.5 | 98.0 |
| 1_120 | 97.0 | 91.2 | 99.0 | 95.5 | 87.5 | 98.0 |
| 1_121 | 96.3 | 88.2 | 99.0 | 95.5 | 87.5 | 98.0 |
| 1_122 | 96.3 | 88.2 | 99.0 | 97.0 | 87.5 | 100.0 |
| 1_123 | 97.8 | 91.2 | 100.0 | 97.0 | 93.8 | 98.0 |
| 1_124 | 95.5 | 85.3 | 99.0 | 95.5 | 87.5 | 98.0 |
| 1_125 | 98.5 | 94.1 | 100.0 | 97.0 | 93.8 | 98.0 |
| 1_126 | 97.0 | 91.2 | 99.0 | 97.0 | 93.8 | 98.0 |
| 1_127 | 96.3 | 88.2 | 99.0 | 95.5 | 87.5 | 98.0 |
| 1_128 | 96.3 | 88.2 | 99.0 | 95.5 | 87.5 | 98.0 |
| 1_129 | 97.0 | 91.2 | 99.0 | 97.0 | 87.5 | 100.0 |
| 1_130 | 96.3 | 88.2 | 99.0 | 95.5 | 87.5 | 98.0 |
| 1_131 | 96.3 | 88.2 | 99.0 | 95.5 | 87.5 | 98.0 |
| 1_132 | 97.0 | 91.2 | 99.0 | 95.5 | 87.5 | 98.0 |
| 1_133 | 96.3 | 88.2 | 99.0 | 95.5 | 87.5 | 98.0 |
| 1_134 | 96.3 | 88.2 | 99.0 | 95.5 | 87.5 | 98.0 |
| 1_135 | 96.3 | 88.2 | 99.0 | 97.0 | 93.8 | 98.0 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_136 | 95.5 | 85.3 | 99.0 | 95.5 | 87.5 | 98.0 |
| 1_137 | 95.5 | 85.3 | 99.0 | 97.0 | 93.8 | 98.0 |
| 1_138 | 96.3 | 88.2 | 99.0 | 95.5 | 87.5 | 98.0 |
| 1_139 | 95.5 | 85.3 | 99.0 | 95.5 | 87.5 | 98.0 |
| 1_140 | 97.0 | 91.2 | 99.0 | 95.5 | 87.5 | 98.0 |
| 1_141 | 95.5 | 85.3 | 99.0 | 98.5 | 93.8 | 100.0 |
| 1_142 | 97.8 | 91.2 | 100.0 | 93.9 | 87.5 | 96.0 |
| 1_143 | 95.5 | 85.3 | 99.0 | 95.5 | 87.5 | 98.0 |
| 1_144 | 96.3 | 88.2 | 99.0 | 97.0 | 87.5 | 100.0 |
| 1_145 | 96.2 | 87.9 | 99.0 | 95.5 | 87.5 | 98.0 |
| 1_146 | 99.3 | 97.1 | 100.0 | 97.0 | 93.8 | 98.0 |
| 1_147 | 96.3 | 88.2 | 99.0 | 95.5 | 87.5 | 98.0 |
| 1_148 | 96.3 | 88.2 | 99.0 | 98.5 | 93.8 | 100.0 |
| 1_149 | 95.5 | 85.3 | 99.0 | 95.4 | 87.5 | 98.0 |
| 1_150 | 97.0 | 91.2 | 99.0 | 97.0 | 87.5 | 100.0 |
| 1_151 | 95.5 | 88.2 | 98.0 | 95.5 | 87.5 | 98.0 |
| 1_152 | 95.5 | 85.3 | 99.0 | 95.5 | 87.5 | 98.0 |
| 1_153 | 99.3 | 97.1 | 100.0 | 97.0 | 93.8 | 98.0 |
| 1_154 | 96.3 | 88.2 | 99.0 | 97.0 | 87.5 | 100.0 |
| 1_155 | 96.3 | 88.2 | 99.0 | 95.5 | 87.5 | 98.0 |
| 1_156 | 96.3 | 88.2 | 99.0 | 97.0 | 87.5 | 100.0 |
| 1_157 | 96.3 | 88.2 | 99.0 | 97.0 | 93.8 | 98.0 |
| 1_158 | 95.5 | 85.3 | 99.0 | 95.5 | 87.5 | 98.0 |
| 1_159 | 95.5 | 85.3 | 99.0 | 95.5 | 87.5 | 98.0 |
| 1_160 | 95.5 | 85.3 | 99.0 | 95.5 | 87.5 | 98.0 |
| 1_161 | 95.5 | 85.3 | 99.0 | 95.5 | 87.5 | 98.0 |
| 1_162 | 96.3 | 88.2 | 99.0 | 95.5 | 87.5 | 98.0 |
| 1_163 | 95.5 | 85.3 | 99.0 | 95.5 | 87.5 | 98.0 |
| 1_164 | 96.3 | 88.2 | 99.0 | 95.5 | 87.5 | 98.0 |
| 1_165 | 97.8 | 94.1 | 99.0 | 95.5 | 87.5 | 98.0 |
| 1_166 | 96.3 | 88.2 | 99.0 | 95.5 | 87.5 | 98.0 |
| 1_167 | 98.5 | 97.1 | 99.0 | 97.0 | 93.8 | 98.0 |
| 1_168 | 97.0 | 91.2 | 99.0 | 95.5 | 87.5 | 98.0 |
| 1_169 | 96.3 | 88.2 | 99.0 | 95.5 | 87.5 | 98.0 |

Example 3

<Selection of Gene Markers Using all Samples and Method for Evaluating Stomach Cancer Discriminant Performance of Acquired Gene Markers>

In this Example, the samples of the training cohort and the validation cohort used in Examples 1 and 2 described above were integrated, and selection of a gene marker and evaluation of its stomach cancer discriminant performance were conducted using all of the samples.

Specifically, the expression levels in the sera of the 50 stomach cancer patients and the 150 healthy subject miRNAs obtained in the preceding Reference Examples were normalized by quantile normalization. In order to acquire diagnosis markers with higher reliability, only genes having a gene expression level of $2^6$ or higher in 50% or more of the samples in either of the stomach cancer patient group or the healthy subject group were selected in the gene marker selection. In order to further acquire statistical significance for discriminating a stomach cancer patient group from a healthy subject group, the P value obtained by two-tailed t-test assuming equal variance as to each gene expression level was corrected by the Bonferroni method, and genes that satisfied p<0.01 were selected as gene markers for use in explanatory variables of a discriminant and described in Table 7. In this way, hsa-miR-3196, hsa-miR-211-3p, hsa-miR-4271, hsa-miR-6851-5p, hsa-miR-149-3p, hsa-miR-4667-5p, hsa-miR-135a-3p, hsa-miR-4486, hsa-miR-4697-5p, hsa-miR-4725-3p, hsa-miR-6510-5p, hsa-miR-5001-5p, hsa-miR-4673, hsa-miR-4466, hsa-miR-23a-3p, hsa-miR-3656, hsa-miR-6782-5p, hsa-miR-4689, hsa-miR-451a, hsa-miR-4446-3p, hsa-miR-3180-3p, hsa-miR-642a-3p, hsa-miR-6889-5p, hsa-miR-3178, hsa-miR-4665-5p, hsa-miR-6722-3p, hsa-miR-30c-1-3p, hsa-miR-4507, hsa-miR-3141 and hsa-miR-1199-5p genes, and the nucleotide sequences of SEQ ID NOs: 170 to 199 related thereto were found in addition to the genes described in Table 2. As with the nucleotide sequences shown in SEQ ID NOs: 1 to 169, the results obtained about the polynucleotides shown in SEQ ID NOs: 170 to 199 also showed that the measurement values were significantly lower (−) or higher (+) in the stomach cancer patient group than in the healthy subject group (Table 7). These results were able to be validated in the validation cohort. Thus, the presence or absence of stomach cancer in the newly obtained samples can be determined by the methods described in Examples 1 and 2 by using, alone or in combination, the gene expression level measurement values described in Table 7.

TABLE 7

| SEQ ID NO: | Gene name | P value after Bonferroni correction | Expression level in stomach cancer patient relative to healthy subject |
|---|---|---|---|
| 1 | hsa-miR-4257 | 1.17.E−53 | − |
| 2 | hsa-miR-6726-5p | 1.13.E−52 | − |
| 3 | hsa-miR-1343-3p | 1.41.E−44 | − |
| 4 | hsa-miR-1247-3p | 5.94.E−35 | + |
| 5 | hsa-miR-6787-5p | 2.22.E−39 | − |
| 6 | hsa-miR-6875-5p | 1.92.E−30 | + |
| 7 | hsa-miR-1225-3p | 6.99.E−36 | + |
| 8 | hsa-miR-8063 | 7.15.E−31 | − |
| 9 | hsa-miR-6781-5p | 4.27.E−31 | + |
| 10 | hsa-miR-4746-3p | 1.93.E−35 | + |
| 11 | hsa-miR-1908-5p | 1.34.E−32 | + |
| 12 | hsa-miR-6756-5p | 2.25.E−28 | − |
| 13 | hsa-miR-204-3p | 5.11.E−30 | − |
| 14 | hsa-miR-4651 | 2.11.E−33 | − |
| 15 | hsa-miR-6757-5p | 2.11.E−34 | − |
| 16 | hsa-miR-6825-5p | 1.20.E−31 | + |
| 17 | hsa-miR-7108-5p | 3.88.E−25 | + |
| 18 | hsa-miR-4792 | 5.31.E−29 | + |
| 19 | hsa-miR-7641 | 1.72.E−27 | − |
| 20 | hsa-miR-3188 | 3.58.E−30 | + |
| 21 | hsa-miR-3131 | 3.98.E−33 | − |
| 22 | hsa-miR-6780b-5p | 4.88.E−28 | + |
| 23 | hsa-miR-8069 | 7.94.E−21 | + |
| 24 | hsa-miR-6840-3p | 4.43.E−23 | − |
| 25 | hsa-miR-8072 | 1.55.E−23 | + |
| 26 | hsa-miR-1233-5p | 3.51.E−26 | − |
| 27 | hsa-miR-6887-5p | 1.34.E−24 | − |
| 28 | hsa-miR-1231 | 9.31.E−26 | + |
| 29 | hsa-miR-5572 | 3.97.E−25 | + |
| 30 | hsa-miR-6738-5p | 2.02.E−21 | − |
| 31 | hsa-miR-6784-5p | 1.03.E−23 | + |
| 32 | hsa-miR-6791-5p | 2.63.E−22 | + |
| 33 | hsa-miR-6749-5p | 6.36.E−23 | − |
| 34 | hsa-miR-6741-5p | 6.07.E−23 | − |
| 35 | hsa-miR-128-1-5p | 3.13.E−20 | + |
| 36 | hsa-miR-4419b | 9.02.E−24 | − |
| 37 | hsa-miR-6746-5p | 1.60.E−25 | − |
| 38 | hsa-miR-3184-5p | 1.38.E−23 | + |
| 39 | hsa-miR-3679-5p | 6.33.E−26 | + |
| 40 | hsa-miR-7110-5p | 3.06.E−24 | + |
| 41 | hsa-miR-4516 | 1.26.E−23 | − |
| 42 | hsa-miR-6717-5p | 6.77.E−26 | − |
| 43 | hsa-miR-6826-5p | 8.66.E−25 | − |
| 44 | hsa-miR-4433b-3p | 5.71.E−19 | + |
| 45 | hsa-miR-3679-3p | 2.22.E−19 | + |
| 46 | hsa-miR-3135b | 7.59.E−15 | − |
| 47 | hsa-miR-3622a-5p | 4.66.E−24 | − |
| 48 | hsa-miR-711 | 9.88.E−22 | + |
| 49 | hsa-miR-4467 | 3.85.E−21 | + |
| 50 | hsa-miR-6857-5p | 1.03.E−19 | + |
| 51 | hsa-miR-6515-3p | 5.53.E−16 | + |

TABLE 7-continued

| SEQ ID NO: | Gene name | P value after Bonferroni correction | Expression level in stomach cancer patient relative to healthy subject |
|---|---|---|---|
| 52 | hsa-miR-1225-5p | 2.33.E−19 | + |
| 53 | hsa-miR-187-5p | 1.31.E−20 | − |
| 54 | hsa-miR-3185 | 1.30.E−19 | + |
| 55 | hsa-miR-642b-3p | 2.56.E−18 | − |
| 56 | hsa-miR-1249 | 5.41.E−19 | + |
| 57 | hsa-miR-744-5p | 9.41.E−20 | + |
| 58 | hsa-miR-4442 | 1.75.E−17 | − |
| 59 | hsa-miR-1228-3p | 1.10.E−19 | + |
| 60 | hsa-miR-939-5p | 1.54.E−16 | + |
| 61 | hsa-miR-6845-5p | 5.15.E−20 | + |
| 62 | hsa-miR-887-3p | 2.86.E−15 | + |
| 63 | hsa-miR-7845-5p | 3.21.E−16 | + |
| 64 | hsa-miR-6729-5p | 6.04.E−16 | + |
| 65 | hsa-miR-4632-5p | 7.17.E−16 | + |
| 66 | hsa-miR-615-5p | 3.13.E−17 | − |
| 67 | hsa-miR-6724-5p | 6.37.E−15 | + |
| 68 | hsa-miR-4728-5p | 1.26.E−16 | − |
| 69 | hsa-miR-6732-5p | 5.05.E−14 | + |
| 70 | hsa-miR-6816-5p | 8.52.E−17 | + |
| 71 | hsa-miR-4695-5p | 2.40.E−14 | + |
| 72 | hsa-miR-6088 | 7.13.E−16 | − |
| 73 | hsa-miR-7975 | 1.51.E−14 | − |
| 74 | hsa-miR-3197 | 5.56.E−16 | + |
| 75 | hsa-miR-6125 | 2.29.E−15 | + |
| 76 | hsa-miR-4433-3p | 1.66.E−13 | + |
| 77 | hsa-miR-6727-5p | 1.77.E−15 | − |
| 78 | hsa-miR-4706 | 2.89.E−15 | − |
| 79 | hsa-miR-7847-3p | 1.35.E−14 | − |
| 80 | hsa-miR-6805-3p | 5.87.E−17 | + |
| 81 | hsa-miR-6766-3p | 1.02.E−14 | + |
| 82 | hsa-miR-1913 | 6.53.E−14 | + |
| 83 | hsa-miR-4649-5p | 1.20.E−13 | − |
| 84 | hsa-miR-602 | 3.43.E−17 | + |
| 85 | hsa-miR-3663-3p | 2.10.E−13 | − |
| 86 | hsa-miR-6893-5p | 3.43.E−17 | − |
| 87 | hsa-miR-6861-5p | 4.41.E−14 | − |
| 88 | hsa-miR-4449 | 2.00.E−16 | + |
| 89 | hsa-miR-6842-5p | 1.49.E−15 | + |
| 90 | hsa-miR-4454 | 1.57.E−13 | − |
| 91 | hsa-miR-5195-3p | 6.87.E−14 | − |
| 92 | hsa-miR-663b | 1.51.E−12 | − |
| 93 | hsa-miR-6765-3p | 5.17.E−11 | + |
| 94 | hsa-miR-4513 | 3.77.E−14 | − |
| 95 | hsa-miR-614 | 1.11.E−11 | − |
| 96 | hsa-miR-6785-5p | 6.54.E−12 | − |
| 97 | hsa-miR-6777-5p | 2.92.E−14 | − |
| 98 | hsa-miR-940 | 1.38.E−13 | + |
| 99 | hsa-miR-4741 | 2.04.E−12 | + |
| 100 | hsa-miR-6870-5p | 4.12.E−14 | + |
| 101 | hsa-miR-6131 | 1.02.E−12 | − |
| 102 | hsa-miR-150-3p | 1.47.E−10 | − |
| 103 | hsa-miR-4707-5p | 8.76.E−12 | + |
| 104 | hsa-miR-1915-3p | 4.55.E−13 | + |
| 105 | hsa-miR-3937 | 6.01.E−12 | + |
| 106 | hsa-miR-937-5p | 3.22.E−11 | − |
| 107 | hsa-miR-4443 | 3.16.E−10 | + |
| 108 | hsa-miR-1914-3p | 7.61.E−11 | − |
| 109 | hsa-miR-3620-5p | 7.63.E−11 | + |
| 110 | hsa-miR-1268b | 2.01.E−09 | + |
| 111 | hsa-miR-1227-5p | 3.14.E−10 | + |
| 112 | hsa-miR-6880-5p | 3.80.E−09 | + |
| 113 | hsa-miR-4417 | 7.19.E−10 | + |
| 114 | hsa-miR-6802-5p | 4.37.E−11 | − |
| 115 | hsa-miR-6769a-5p | 3.34.E−09 | − |
| 116 | hsa-miR-663a | 7.98.E−11 | + |
| 117 | hsa-miR-6721-5p | 1.38.E−09 | + |
| 118 | hsa-miR-4532 | 9.58.E−08 | − |
| 119 | hsa-miR-7977 | 9.99.E−11 | − |
| 120 | hsa-miR-92b-5p | 1.77.E−08 | + |
| 121 | hsa-miR-371a-5p | 8.63.E−09 | − |
| 122 | hsa-miR-6126 | 1.93.E−10 | + |
| 123 | hsa-miR-4734 | 3.27.E−09 | + |
| 124 | hsa-miR-4665-3p | 6.99.E−14 | + |
| 125 | hsa-miR-423-5p | 1.58.E−08 | − |
| 126 | hsa-miR-1469 | 8.71.E−07 | + |
| 127 | hsa-miR-4675 | 2.67.E−10 | − |
| 128 | hsa-miR-1915-5p | 1.06.E−08 | − |
| 129 | hsa-miR-6716-5p | 7.56.E−09 | + |
| 130 | hsa-miR-718 | 1.99.E−09 | + |
| 131 | hsa-miR-4281 | 9.46.E−11 | − |
| 132 | hsa-miR-6820-5p | 1.42.E−08 | − |
| 133 | hsa-miR-6795-5p | 4.38.E−10 | − |
| 134 | hsa-miR-6779-5p | 2.99.E−08 | − |
| 135 | hsa-miR-7109-5p | 7.06.E−08 | − |
| 136 | hsa-miR-6798-5p | 7.93.E−07 | + |
| 137 | hsa-miR-4648 | 2.21.E−09 | + |
| 138 | hsa-miR-8059 | 1.44.E−08 | − |
| 139 | hsa-miR-6765-3p | 6.59.E−08 | − |
| 140 | hsa-miR-6132 | 3.82.E−06 | + |
| 141 | hsa-miR-4492 | 1.34.E−08 | + |
| 142 | hsa-miR-7107-5p | 1.84.E−06 | − |
| 143 | hsa-miR-3195 | 6.91.E−08 | + |
| 144 | hsa-miR-3180 | 1.11.E−07 | + |
| 145 | hsa-miR-296-3p | 2.56.E−06 | − |
| 146 | hsa-miR-564 | 1.32.E−07 | − |
| 147 | hsa-miR-1268a | 1.25.E−04 | + |
| 148 | hsa-miR-6848-5p | 2.82.E−06 | + |
| 149 | hsa-miR-762 | 5.66.E−04 | + |
| 150 | hsa-miR-2861 | 1.45.E−06 | − |
| 151 | hsa-miR-1203 | 7.90.E−07 | + |
| 152 | hsa-miR-1260b | 2.26.E−04 | − |
| 153 | hsa-miR-4476 | 5.95.E−06 | − |
| 154 | hsa-miR-6885-5p | 5.73.E−05 | − |
| 155 | hsa-miR-6769b-5p | 1.91.E−07 | − |
| 156 | hsa-miR-23b-3p | 1.38.E−05 | − |
| 157 | hsa-miR-1343-5p | 7.73.E−06 | + |
| 158 | hsa-miR-3621 | 3.64.E−05 | − |
| 159 | hsa-miR-4688 | 1.47.E−05 | − |
| 160 | hsa-miR-4286 | 3.79.E−03 | − |
| 161 | hsa-miR-4640-5p | 1.79.E−05 | + |
| 162 | hsa-miR-4739 | 2.45.E−05 | + |
| 163 | hsa-miR-1260a | 7.35.E−04 | − |
| 164 | hsa-miR-4276 | 3.45.E−07 | + |
| 165 | hsa-miR-7106-5p | 4.60.E−04 | − |
| 166 | hsa-miR-128-2-5p | 1.05.E−13 | − |
| 167 | hsa-miR-125a-3p | 2.30.E−15 | − |
| 168 | hsa-miR-92a-2-5p | 5.42.E−09 | + |
| 169 | hsa-miR-486-3p | 2.00.E−05 | − |
| 170 | hsa-miR-3196 | 2.06.E−06 | + |
| 171 | hsa-miR-211-3p | 2.03.E−05 | − |
| 172 | hsa-miR-4271 | 2.31.E−05 | − |
| 173 | hsa-miR-6851-5p | 2.68.E−05 | + |
| 174 | hsa-miR-149-3p | 2.75.E−05 | − |
| 175 | hsa-miR-4667-5p | 4.05.E−05 | + |
| 176 | hsa-miR-135a-3p | 4.28.E−05 | + |
| 177 | hsa-miR-4486 | 6.68.E−05 | + |
| 178 | hsa-miR-4697-5p | 7.18.E−05 | − |
| 179 | hsa-miR-4725-3p | 8.16.E−05 | + |
| 180 | hsa-miR-6510-5p | 8.18.E−05 | + |
| 181 | hsa-miR-5001-5p | 1.92.E−04 | − |
| 182 | hsa-miR-4673 | 2.32.E−04 | + |
| 183 | hsa-miR-4466 | 3.06.E−04 | − |
| 184 | hsa-miR-23a-3p | 5.28.E−04 | − |
| 185 | hsa-miR-3656 | 5.41.E−04 | + |
| 186 | hsa-miR-6782-5p | 7.05.E−04 | + |
| 187 | hsa-miR-4689 | 1.01.E−03 | − |
| 188 | hsa-miR-451a | 1.22.E−03 | − |
| 189 | hsa-miR-4446-3p | 1.51.E−03 | − |
| 190 | hsa-miR-3180-3p | 1.64.E−03 | + |
| 191 | hsa-miR-642a-3p | 1.80.E−03 | − |
| 192 | hsa-miR-6889-5p | 1.91.E−03 | + |
| 193 | hsa-miR-3178 | 2.08.E−03 | + |
| 194 | hsa-miR-4665-5p | 2.84.E−03 | − |
| 195 | hsa-miR-6722-3p | 3.22.E−03 | − |
| 196 | hsa-miR-30c-1-3p | 4.13.E−03 | + |
| 197 | hsa-miR-4507 | 6.12.E−03 | + |
| 198 | hsa-miR-3141 | 6.13.E−03 | + |
| 199 | hsa-miR-1199-5p | 7.28.E−03 | − |

Example 4

<Method for Evaluating Stomach Cancer-Specific Discriminant Performance by Combination of Multiple Gene Markers Using Samples of Validation Cohort>

In this Example, gene markers for diagnosis were selected by comparing gene expression levels of miRNAs in sera of stomach cancer patients with that of a control group consisting of healthy subjects, pancreatic cancer patients, bile duct cancer patients, colorectal cancer patients, liver cancer patients, and benign pancreaticobiliary disease patients in the same way as the method described in Example 1 using the gene markers selected in Example 1 with respect to the training cohort as the sample group described in Reference Example 2. The polynucleotides consisting of the nucleotide sequences represented by SEQ ID NOs: 635 to 642 thus selected were further combined therewith to study a method for evaluating stomach cancer-specific discriminant performance.

Specifically, first, the miRNA expression levels in the training cohort and the validation cohort obtained in Reference Example 2 mentioned above were combined and normalized by quantile normalization. Next, Fisher's discriminant analysis was conducted as to combinations of 1 to 6 expression level measurement values comprising at least one or more of the expression level measurement values of the polynucleotides consisting of the nucleotide sequences represented by SEQ ID NOs: 1 to 165 and 635 to 642, to construct a discriminant for determining the presence or absence of stomach cancer. Next, accuracy, sensitivity, and specificity in the validation cohort were calculated using the discriminant thus prepared, with the stomach cancer patient group as a positive sample group and, on the other hand, the healthy subject group, the pancreatic cancer patient group, the bile duct cancer patient group, the colorectal cancer patient group, the liver cancer patient group, and the benign pancreaticobiliary disease patient group as a negative sample groups. The discriminant performance of the selected polynucleotides was validated using the independent samples.

Most of polynucleotides consisting of the nucleotide sequences represented by any of these SEQ ID NOs (SEQ ID NOs: 1 to 165 and 635 to 642 corresponding to the miRNA markers of Table 1) or complementary sequences thereof mentioned above were able to provide relatively high accuracy, sensitivity, and specificity in the determination of the presence or absence of stomach cancer, and furthermore, were able to specifically discriminate stomach cancer from the other cancers. For example, among the combinations of multiple polynucleotides selected from the group consisting of polynucleotides consisting of the nucleotide sequences represented by SEQ ID NOs: 9, 13, 21, 27, 34, 36, 66, 75, 95, 98, 108, 130, 135, 143, 155, 183, 185, 187, 191, 193, 194, 635, 636, 637, 638, 639, 640, 641 and 642 or complementary sequences thereof (the cancer type-specific polynucleotide group 1) as polynucleotides capable of specifically binding to target markers, combinations comprising at least one or more polynucleotides selected from the group consisting of polynucleotides consisting of the nucleotide sequences represented by SEQ ID NOs: 21, 34, 36, 98, and 155 or complementary sequences thereof (the cancer type-specific polynucleotide group 2) included in the cancer type-specific polynucleotide group 1 were able to specifically discriminate stomach cancer from the other cancers with high accuracy.

The number of the aforementioned polynucleotides with cancer type specificity in the combination can be 2, 3, 4, 5, 6, 7, 8, 9, 10 or more for the combination. The combinations of 6 or more of these polynucleotides were able to exhibit discriminant accuracy of 80% or higher.

Specifically, the discriminant accuracy of the measurement using the polynucleotide consisting of the nucleotide sequence represented by SEQ ID NO: 21 or a complementary sequence thereof is shown in Table 8-1. The measurement using the polynucleotide consisting of the nucleotide sequence represented by SEQ ID NO: 21 or a complementary sequence thereof exhibited the highest accuracy of 79.8% in the training cohort and accuracy of 83.8% in the validation cohort. Also, for example, the measurement using the combinations of two polynucleotides comprising at least one polynucleotide consisting of the nucleotide sequence represented by SEQ ID NO: 21 or a complementary sequence thereof exhibited the highest accuracy of 82.4% in the training cohort and accuracy of 80.9% in the validation cohort. Furthermore, for example, the measurement using the combinations of three polynucleotides comprising at least one polynucleotide consisting of the nucleotide sequence represented by SEQ ID NO: 21 or a complementary sequence thereof exhibited the highest accuracy of 84.1% in the training cohort and accuracy of 83.8% in the validation cohort. Furthermore, for example, the measurement using the combinations of four polynucleotides comprising at least one polynucleotide consisting of the nucleotide sequence represented by SEQ ID NO: 21 or a complementary sequence thereof exhibited the highest accuracy of 85.9% in the training cohort and accuracy of 82.7% in the validation cohort. Furthermore, for example, the measurement using the combinations of five polynucleotides comprising at least one polynucleotide consisting of the nucleotide sequence represented by SEQ ID NO: 21 or a complementary sequence thereof exhibited the highest accuracy of 87.9% in the training cohort and accuracy of 88.4% in the validation cohort. Furthermore, for example, the measurement using the combinations of six polynucleotides comprising at least one polynucleotide consisting of the nucleotide sequence represented by SEQ ID NO: 21 or a complementary sequence thereof exhibited the highest accuracy of 87.0% in the training cohort and accuracy of 87.3% in the validation cohort.

Specifically, the discriminant accuracy of the measurement using the polynucleotide consisting of the nucleotide sequence represented by SEQ ID NO: 34 or a complementary sequence thereof is shown in Table 8-2. The measurement using the polynucleotide consisting of the nucleotide sequence represented by SEQ ID NO: 34 or a complementary sequence thereof exhibited the highest accuracy of 62.8% in the training cohort and accuracy of 60.7% in the validation cohort. Also, for example, the measurement using the combinations of two polynucleotides comprising at least one polynucleotide consisting of the nucleotide sequence represented by SEQ ID NO: 34 or a complementary sequence thereof exhibited the highest accuracy of 81.0% in the training cohort and accuracy of 82.1% in the validation cohort. Furthermore, for example, the measurement using the combinations of three polynucleotides comprising at least one polynucleotide consisting of the nucleotide sequence represented by SEQ ID NO: 34 or a complementary sequence thereof exhibited the highest accuracy of 84.4% in the training cohort and accuracy of 82.1% in the validation cohort. Furthermore, for example, the measurement using the combinations of four polynucleotides comprising at least one polynucleotide consisting of the nucleotide sequence represented by SEQ ID NO: 34 or a complementary sequence thereof exhibited the highest accuracy of 87.0% in the training cohort and accuracy of 88.4% in the validation cohort. Furthermore, for example, the measurement using the combinations of five polynucleotides comprising at least one polynucleotide consisting of the nucleotide sequence represented by SEQ ID NO: 34 or a complementary sequence thereof exhibited the highest accuracy of 88.2% in the training cohort and accuracy of 87.9% in the validation cohort. Furthermore, for example, the measurement using the combinations of six polynucleotides comprising at least one polynucleotide consisting of the nucleotide sequence represented by SEQ ID NO: 34 or a complementary sequence thereof exhibited the highest accuracy of 87.3% in the training cohort and accuracy of 88.4% in the validation cohort.

Specifically, the discriminant accuracy of the measurement using the polynucleotide consisting of the nucleotide sequence represented by SEQ ID NO: 36 or a complementary sequence thereof is shown in Table 8-3. The measurement using the polynucleotide consisting of the nucleotide sequence represented by SEQ ID NO: 36 or a complementary sequence thereof exhibited the highest accuracy of 78.7% in the training cohort and accuracy of 78.6% in the validation cohort. Also, for example, the measurement using the combinations of two polynucleotides comprising at least one polynucleotide consisting of the nucleotide sequence represented by SEQ ID NO: 36 or a complementary sequence thereof exhibited the highest accuracy of 82.7% in the training cohort and accuracy of 82.7% in the validation cohort. Furthermore, for example, the measurement using the combinations of three polynucleotides comprising at least one polynucleotide consisting of the nucleotide sequence represented by SEQ ID NO: 36 or a complementary sequence thereof exhibited the highest accuracy of 85.0% in the training cohort and accuracy of 86.7% in the validation cohort. Furthermore, for example, the measurement using the combinations of four polynucleotides comprising at least one polynucleotide consisting of the nucleotide sequence represented by SEQ ID NO: 36 or a complementary sequence thereof exhibited the highest accuracy of 87.0% in the training cohort and accuracy of 85.5% in the validation cohort. Furthermore, for example, the measurement using the combinations of five polynucleotides comprising at least one polynucleotide consisting of the nucleotide sequence represented by SEQ ID NO: 36 or a complementary sequence thereof exhibited the highest accuracy of 87.9% in the training cohort and accuracy of 86.1% in the validation cohort. Furthermore, for example, the measurement using the combinations of six polynucleotides comprising at least one polynucleotide consisting of the nucleotide sequence represented by SEQ ID NO: 36 or a complementary sequence thereof exhibited the highest accuracy of 87.3% in the training cohort and accuracy of 87.9% in the validation cohort.

Specifically, the discriminant accuracy of the measurement using the polynucleotide consisting of the nucleotide sequence represented by SEQ ID NO: 98 or a complementary sequence thereof is shown in Table 8-4. The measurement using the polynucleotide consisting of the nucleotide sequence represented by SEQ ID NO: 98 or a complementary sequence thereof exhibited the highest accuracy of 70.9% in the training cohort and accuracy of 70.5% in the validation cohort. Also, for example, the measurement using the combinations of two polynucleotides comprising at least one polynucleotide consisting of the nucleotide sequence represented by SEQ ID NO: 98 or a complementary sequence thereof exhibited the highest accuracy of 82.4% in the training cohort and accuracy of 82.1% in the validation cohort. Furthermore, for example, the measurement using the combinations of three polynucleotides comprising at least one polynucleotide consisting of the nucleotide sequence represented by SEQ ID NO: 98 or a complementary sequence thereof exhibited the highest accuracy of 84.1% in the training cohort and accuracy of 85.5% in the validation cohort. Furthermore, for example, the measurement using the combinations of four polynucleotides comprising at least one polynucleotide consisting of the nucleotide sequence represented by SEQ ID NO: 98 or a complementary sequence thereof exhibited the highest accuracy of 86.7% in the training cohort and accuracy of 89.6% in the validation cohort. Furthermore, for example, the measurement using the combinations of five polynucleotides comprising at least one polynucleotide consisting of the nucleotide sequence represented by SEQ ID NO: 98 or a complementary sequence thereof exhibited the highest accuracy of 88.2% in the training cohort and accuracy of 87.9% in the validation cohort. Furthermore, for example, the measurement using the combinations of six polynucleotides comprising at least one polynucleotide consisting of the nucleotide sequence represented by SEQ ID NO: 98 or a complementary sequence thereof exhibited the highest accuracy of 87.9% in the training cohort and accuracy of 88.4% in the validation cohort.

Specifically, the discriminant accuracy of the measurement using the polynucleotide consisting of the nucleotide sequence represented by SEQ ID NO: 155 or a complementary sequence thereof is shown in Table 8-5. The measurement using the polynucleotide consisting of the nucleotide sequence represented by SEQ ID NO: 155 or a complementary sequence thereof exhibited the highest accuracy of 67.1% in the training cohort and accuracy of 69.9% in the validation cohort. Also, for example, the measurement using the combinations of two polynucleotides comprising at least one polynucleotide consisting of the nucleotide sequence represented by SEQ ID NO: 155 or a complementary sequence thereof exhibited the highest accuracy of 81.6% in the training cohort and accuracy of 75.7% in the validation cohort. Furthermore, for example, the measurement using the combinations of three polynucleotides comprising at least one polynucleotide consisting of the nucleotide sequence represented by SEQ ID NO: 155 or a complementary sequence thereof exhibited the highest accuracy of 84.4% in the training cohort and accuracy of 85.0% in the validation cohort. Furthermore, for example, the measurement using the combinations of four polynucleotides comprising at least one polynucleotide consisting of the nucleotide sequence represented by SEQ ID NO: 155 or a complementary sequence thereof exhibited the highest accuracy of 87.0% in the training cohort and accuracy of 89.0% in the validation cohort. Furthermore, for example, the measurement using the combinations of five polynucleotides comprising at least one polynucleotide consisting of the nucleotide sequence represented by SEQ ID NO: 155 or a complementary sequence thereof exhibited the highest accuracy of 88.2% in the training cohort and accuracy of 87.3% in the validation cohort. Furthermore, for example, the measurement using the combinations of six polynucleotides comprising at least one polynucleotide consisting of the nucleotide sequence represented by SEQ ID NO: 155 or a complementary sequence thereof exhibited the highest accuracy of 88.2% in the training cohort and accuracy of 89.6% in the validation cohort.

Figure 4:
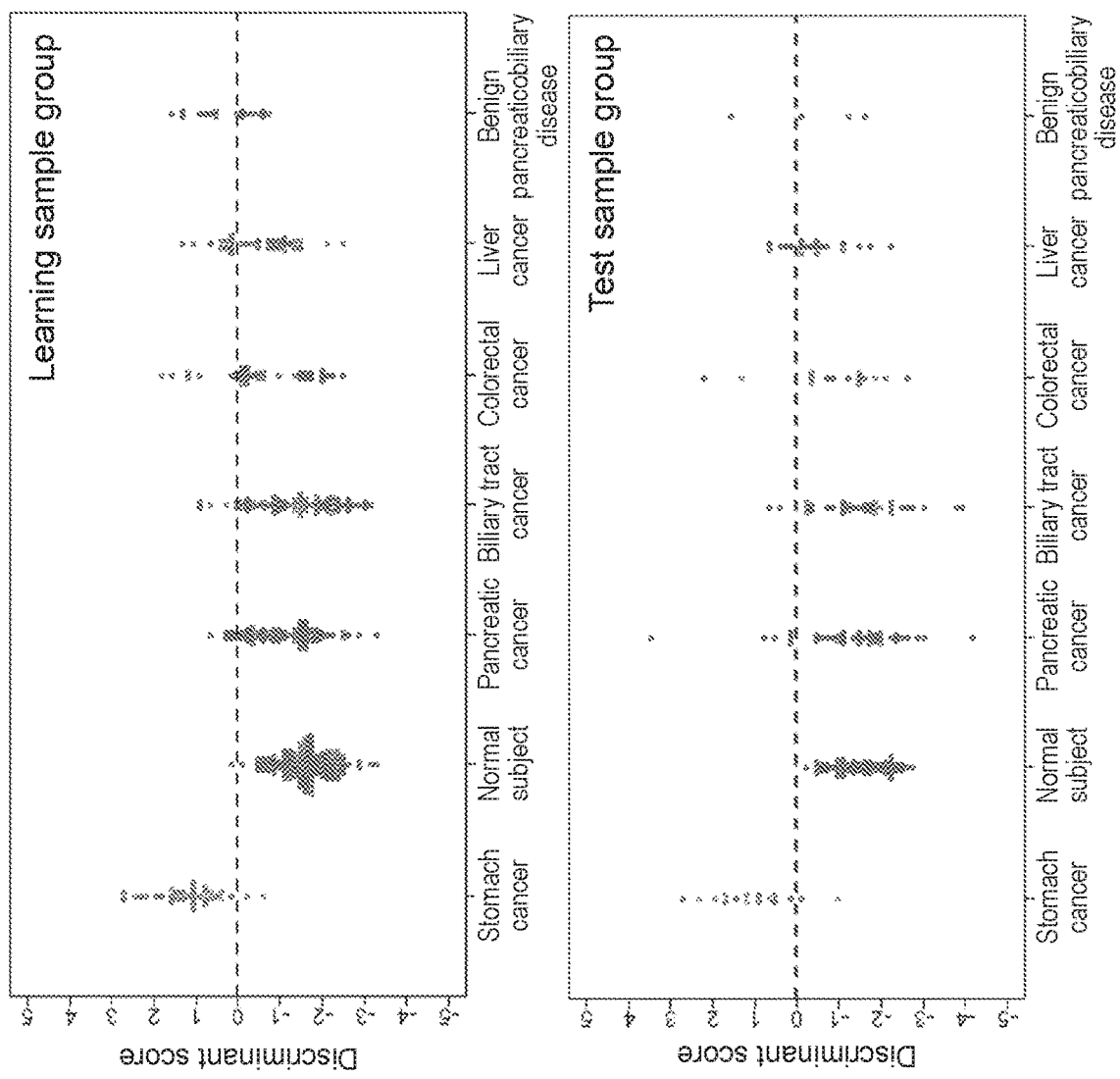
FIG. 4 Upper diagram: a discriminant (2.51×hsa-miR-6781-5p−0.63×hsa-miR-4419b+0.98×hsa-miR-940+0.63×hsa-miR-4294-0.70×hsa-miR-6769b-5p+0.85×hsa-miR-1914-3p−37.81) was prepared by use of Fisher's discriminant analysis from the measurement values of hsa-miR-6781-5p (SEQ ID NO: 9), hsa-miR-204-3p (SEQ ID NO: 13), hsa-miR-3195 (SEQ ID NO: 143), hsa-miR-6769b-5p (SEQ ID NO: 155), hsa-miR-4665-5p (SEQ ID NO: 194), and hsa-miR-4294 (SEQ ID NO: 639) in 34 stomach cancer patients, 102 healthy subjects, 63 pancreatic cancer patients, 65 bile duct cancer patients, 35 colorectal cancer patients, 32 liver cancer patients, and 17 benign pancreaticobiliary disease patients selected as a training cohort, and discriminant scores obtained from the discriminant were plotted on the ordinate against the sample groups on the abscissa. The dotted line in the diagram depicts a discriminant boundary that offered a discriminant score of 0 and discriminated between the groups. Lower diagram: discriminant scores obtained from the discriminant prepared from the training cohort as to the measurement values of hsa-miR-6781-5p (SEQ ID NO: 9), hsa-miR-204-3p (SEQ ID NO: 13), hsa-miR-3195 (SEQ ID NO: 143), hsa-miR-6769b-5p (SEQ ID NO: 155), hsa-miR-4665-5p (SEQ ID NO: 194), and hsa-miR-4294 (SEQ ID NO: 639) in 16 stomach cancer patients, 48 healthy subjects, 37 pancreatic cancer patients, 33 bile duct cancer patients, 15 colorectal cancer patients, 20 liver cancer patients, and 4 benign pancreaticobiliary disease patients selected as a validation cohort were plotted on the ordinate against the sample groups on the abscissa. The dotted line in the diagram depicts the discriminant boundary that offered a discriminant score of 0 and discriminated between both of the groups.

The expression level measurement values of the nucleotide sequences represented by SEQ ID NOs: 9, 13, 143, 155, 194, and 639 were compared among 34 stomach cancer patients, 102 healthy subjects, 63 pancreatic cancer patients, 65 bile duct cancer patients, 35 colorectal cancer patients, 32 liver cancer patients, and 17 benign pancreaticobiliary disease patients in the training cohort. As a result, a scatter diagram that significantly separated the discriminant score of the stomach cancer patient group from the discriminant scores of the other groups was obtained in the training cohort (see the upper diagram of FIG. 4). These results were also reproducible for the validation cohort (see the lower diagram of FIG. 4).

TABLE 8-1

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 21 | 79.8 | 82.4 | 79.6 | 83.8 | 81.2 | 84.1 |
| 9_21 | 82.4 | 97.1 | 80.8 | 80.9 | 81.2 | 80.9 |
| 9_21_34 | 84.1 | 91.2 | 83.4 | 83.8 | 75 | 84.7 |
| 9_21_34_36 | 85.9 | 91.2 | 85.3 | 82.7 | 68.8 | 84.1 |
| 9_21_34_36_98 | 87.9 | 97.1 | 86.9 | 88.4 | 81.2 | 89.2 |
| 9_21_36_98_130_637 | 83.6 | 100 | 81.8 | 85 | 87.5 | 84.7 |
| 9_21_34_36_98_637 | 87 | 94.1 | 86.3 | 87.3 | 87.5 | 87.3 |
| 9_21_34_36_98_155 | 86.7 | 97.1 | 85.6 | 89 | 81.2 | 89.8 |
| 21_36_75_98_155_635 | 83 | 97.1 | 81.5 | 87.9 | 87.5 | 87.9 |
| 9_21_36_98_108_155 | 86.7 | 100 | 85.3 | 86.7 | 81.2 | 87.3 |

TABLE 8-2

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 34 | 62.8 | 67.6 | 62.3 | 60.7 | 81.2 | 58.6 |
| 21_34 | 81 | 82.4 | 80.8 | 82.1 | 81.2 | 82.2 |
| 9_34_36 | 84.4 | 94.1 | 83.4 | 82.1 | 68.8 | 83.4 |
| 9_34_36_98 | 87 | 97.1 | 85.9 | 88.4 | 87.5 | 88.5 |
| 9_34_36_98_635 | 88.2 | 97.1 | 87.2 | 87.9 | 87.5 | 87.9 |
| 34_36_143_155_187_635 | 86.2 | 94.1 | 85.3 | 86.1 | 87.5 | 86 |
| 9_34_36_66_98_187 | 87.3 | 97.1 | 86.3 | 88.4 | 81.2 | 89.2 |
| 9_34_36_98_187_637 | 86.5 | 94.1 | 85.6 | 87.3 | 87.5 | 87.3 |
| 9_34_36_98_185_637 | 86.7 | 97.1 | 85.6 | 86.7 | 87.5 | 86.6 |
| 9_34_36_98_637_639 | 86.5 | 97.1 | 85.3 | 87.9 | 87.5 | 87.9 |

TABLE 8-3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 36 | 78.7 | 82.4 | 78.3 | 78.6 | 81.2 | 78.3 |
| 9_36 | 82.7 | 97.1 | 81.2 | 82.7 | 75 | 83.4 |
| 9_36_98 | 85 | 100 | 83.4 | 86.7 | 87.5 | 86.6 |
| 9_36_75_98 | 87 | 100 | 85.6 | 85.5 | 81.2 | 86 |
| 9_13_36_108_194 | 87.9 | 94.3 | 87.2 | 86.1 | 75 | 87.3 |
| 9_36_98_108_638_639 | 85.6 | 94.1 | 84.7 | 88.4 | 87.5 | 88.5 |
| 36_98_155_194_635_642 | 85.3 | 100 | 83.7 | 86.1 | 81.2 | 86.6 |
| 9_34_36_75_98_637 | 87.3 | 97.1 | 86.3 | 87.9 | 87.5 | 87.9 |
| 21_36_98_155_185_635 | 83.9 | 97.1 | 82.4 | 89 | 87.5 | 89.2 |
| 9_36_98_108_155_635 | 85.9 | 97.1 | 84.7 | 87.3 | 81.2 | 87.9 |

TABLE 8-4

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 98 | 70.9 | 64.7 | 71.6 | 70.5 | 62.5 | 71.3 |
| 36_98 | 82.4 | 88.2 | 81.8 | 82.1 | 75 | 82.8 |
| 9_98_639 | 84.1 | 91.2 | 83.4 | 85.5 | 81.2 | 86 |
| 9_36_98_194 | 86.7 | 97.1 | 85.6 | 89.6 | 81.2 | 90.4 |
| 9_98_130_135_639 | 88.2 | 97.1 | 87.2 | 87.9 | 100 | 86.6 |
| 9_36_98_130_194_637 | 87.3 | 100 | 85.9 | 89.6 | 87.5 | 89.8 |
| 21_36_98_108_155_635 | 85.6 | 94.1 | 84.7 | 89.6 | 87.5 | 89.8 |
| 9_36_98_108_155_639 | 87.9 | 97.1 | 86.9 | 88.4 | 87.5 | 88.5 |
| 9_36_98_155_187_639 | 87 | 97.1 | 85.9 | 88.4 | 93.8 | 87.9 |
| 9_36_98_155_187_637 | 85.9 | 100 | 84.3 | 85.5 | 81.2 | 86 |

TABLE 8-5

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 155 | 67.1 | 58.8 | 68.1 | 69.9 | 75 | 69.4 |
| 9_155 | 81.6 | 94.1 | 80.2 | 75.7 | 75 | 75.8 |
| 9_155_639 | 84.4 | 97.1 | 83.1 | 85 | 87.5 | 84.7 |
| 9_130_155639 | 87 | 91.2 | 86.6 | 89 | 100 | 87.9 |
| 9_34_130_155_639 | 88.2 | 91.2 | 87.9 | 87.3 | 93.8 | 86.6 |
| 9_36_75_98_155_635 | 85.6 | 100 | 84 | 86.1 | 81.2 | 86.6 |
| 36_98_130_155_185_635 | 85.9 | 94.1 | 85 | 86.1 | 87.5 | 86 |
| 9_13_143_155_194_639 | 88.2 | 94.1 | 87.5 | 89.6 | 87.5 | 89.8 |
| 9_13_34_36_98_155 | 87 | 97.1 | 85.9 | 89 | 81.2 | 89.8 |
| 36_98_108_155_193_635 | 85.3 | 94.1 | 84.3 | 86.7 | 81.2 | 87.3 |

Comparative Example 1

<Stomach Cancer Discriminant Performance of Existing Tumor Markers in Blood>

The concentrations of the existing tumor markers CEA and CA19-9 in blood were measured in the training cohort and the validation cohort obtained in the preceding Reference Examples. When the concentrations of these tumor markers in blood are higher than the reference values described in Kim. H. J. et al., Acta Oncologica, 2009, No. 48, p. 385 to 390 (CEA: 5 ng/mL, CA19-9: 37 U/mL), subjects are usually suspected of having cancer. Thus, whether or not the concentrations of CEA and CA19-9 in blood exceeded their reference values was confirmed for each sample, and the results were assessed for the ability of these tumor markers to detect cancer in stomach cancer patients. The sensitivity of each existing marker in the training cohort and the validation cohort was calculated. The results are shown in Table 5. The sensitivity of CEA and CA19-9 was as low as 2.9% in the training cohort, and was as low as 12.5% and 12.5%, respectively, in the validation cohort, demonstrating that neither of the markers are useful in the detection of stomach cancer (Table 5).

On the other hand, as shown above in Tables 3 and 6 of Examples 1 and 2, it can be concluded that in all of the polynucleotides consisting of the nucleotide sequences represented by SEQ ID NOs: 1 to 169 combinations of 1 or 2 polynucleotides exhibiting sensitivity beyond the existing stomach cancer markers are present, and thus such polynucleotides serve as excellent diagnosis markers.

As shown in these Examples and Comparative Example, the kit, etc., and the method of the present invention can detect stomach cancer with higher sensitivity than the existing tumor markers and therefore permit early detection and treatment of stomach cancer. As a result, improvement in survival rate resulting from reduction in the risk of recurrence, and a therapeutic option of stomach-conserving therapy can also be provided.

INDUSTRIAL APPLICABILITY

According to the present invention, stomach cancer can be effectively detected by a simple and inexpensive method. This enables early detection, diagnosis and treatment of stomach cancer. The method of the present invention can detect stomach cancer with limited invasiveness using the blood of a patient and therefore allows stomach cancer to be detected conveniently and rapidly.

All publications, patents, and patent applications cited herein are incorporated herein by reference in their entirety.

The invention claimed is:

1. A method for detecting stomach cancer comprising:

determining an expression level(s) of hsa-miR-4257 in a sample comprising blood, serum, or plasma from a human subject using a kit comprising a nucleic acid(s), as a primer(s) for PCR, or a probe(s) for Northern blot, Southern blot, or in situ hybridization, capable of specifically binding to hsa-miR-4257, wherein the determining comprises the following steps of:

(a) contacting hsa-miR-4257 in the sample or complementary polynucleotide(s) thereof prepared from hsa-miR-4257 with the nucleic acid(s);

(b) measuring an expression level of hsa-miR-4257 by quantitative RT-PCR using the nucleic acid(s) as the primer(s), or Northern blot, Southern blot, or in situ hybridization using the nucleic acids as the probe(s); and (c) comparing the expression level of hsa-miR-4257 measured in the step (b) with a control expression level of hsa-miR-4257 in a control sample from a healthy subject measured in the same way as in the step (b), wherein a lower expression level of hsa-miR-4257 in the sample comprising blood, serum, or plasma from the subject as compared to the control expression level is detected and is indicative that the subject has stomach cancer, and treating the subject for stomach cancer or performing a diagnostic procedure on the subject, wherein the treatment comprises surgery, radiotherapy, chemotherapy, or a combination thereof, and wherein the diagnostic procedure comprises gastric X-ray examination, gastroscopy, or imaging of the stomach.

2. A method for detecting stomach cancer comprising:
determining an expression level of hsa-miR-4257 in a sample comprising blood, serum, or plasma from a human subject using a device comprising a nucleic acid(s), as a probe(s), capable of specifically binding to hsa-miR-4257, wherein the determining comprises the following steps:
(a) binding hsa-miR-4257 in the sample or cDNA thereof prepared from hsa-miR-4257 to the nucleic acid(s) to measure an expression level of hsa-miR-4257 by hybridization using the nucleic acid(s); and
(b) comparing the expression level of hsa-miR-4257 measured in the step (a) with a control expression level of hsa-miR-4257 in a control sample from a healthy subject measured in the same way as in the step (a), wherein a lower expression level of hsa-miR-4257 in the sample comprising blood, serum, or plasma from the subject as compared to the control expression level is detected and is indicative that the subject has stomach cancer, and
treating the subject for stomach cancer or performing a diagnostic procedure on the subject, wherein the treatment comprises surgery, radiotherapy, chemotherapy, or a combination thereof, and wherein the diagnostic procedure comprises gastric X-ray examination, gastroscopy, or imaging of the stomach.

3. The method according to claim 1, wherein step (c) further comprises preparing a discriminant based on a formula.

4. The method according to claim 3, wherein the discriminant is compared to a threshold.

5. The method according to claim 2, wherein step (b) further comprises preparing a discriminant based on a formula.

6. The method according to claim 5, wherein the discriminant is compared to a threshold.

* * * * *

SEQUENCE LISTING

```
<160> NUMBER OF SEQ ID NOS: 657

<210> SEQ ID NO 1
<211> LENGTH: 18
<212> TYPE: RNA
<213> ORGANISM: Homo sapiens

<400> SEQUENCE: 1
ccagaggugg ggacugag                                                   18

<210> SEQ ID NO 2
<211> LENGTH: 21
<212> TYPE: RNA
<213> ORGANISM: Homo sapiens

<400> SEQUENCE: 2
cgggagcugg ggucugcagg u                                               21

<210> SEQ ID NO 3
<211> LENGTH: 22
<212> TYPE: RNA
<213> ORGANISM: Homo sapiens
```

```
<400> SEQUENCE: 3
cuccuggggc ccgcacucuc gc                                          22

<210> SEQ ID NO 4
<211> LENGTH: 24
<212> TYPE: RNA
<213> ORGANISM: Homo sapiens

<400> SEQUENCE: 4
ccccgggaac gucgagacug gagc                                        24

<210> SEQ ID NO 5
<211> LENGTH: 22
<212> TYPE: RNA
<213> ORGANISM: Homo sapiens

<400> SEQUENCE: 5 uggcggggu agagcuggcu gc                                           22

<210> SEQ ID NO 6
<211> LENGTH: 21
<212> TYPE: RNA
<213> ORGANISM: Homo sapiens

<400> SEQUENCE: 6
ugagggaccc aggacaggag a                                           21

<210> SEQ ID NO 7
<211> LENGTH: 22
<212> TYPE: RNA
<213> ORGANISM: Homo sapiens

<400> SEQUENCE: 7
ugagccccug ugccgccccc ag                                          22

<210> SEQ ID NO 8
<211> LENGTH: 22
<212> TYPE: RNA
<213> ORGANISM: Homo sapiens

<400> SEQUENCE: 8
ucaaaaucag gagucggggc uu                                          22

<210> SEQ ID NO 9
<211> LENGTH: 21
<212> TYPE: RNA
<213> ORGANISM: Homo sapiens

<400> SEQUENCE: 9
cgggccggag gucaagggcg u                                           21

<210> SEQ ID NO 10
<211> LENGTH: 21
<212> TYPE: RNA
<213> ORGANISM: Homo sapiens

<400> SEQUENCE: 10
agcggugcuc cugcgggccg a                                           21

<210> SEQ ID NO 11
<211> LENGTH: 21
<212> TYPE: RNA
```

<213> ORGANISM: Homo sapiens

<400> SEQUENCE: 11
cggcggggac ggcgauuggu c                                    21

<210> SEQ ID NO 12
<211> LENGTH: 23
<212> TYPE: RNA
<213> ORGANISM: Homo sapiens

<400> SEQUENCE: 12 agggugggc uggagguggg gcu                                   23

<210> SEQ ID NO 13
<211> LENGTH: 21
<212> TYPE: RNA
<213> ORGANISM: Homo sapiens

<400> SEQUENCE: 13
gcugggaagg caaagggacg u                                    21

<210> SEQ ID NO 14
<211> LENGTH: 20
<212> TYPE: RNA
<213> ORGANISM: Homo sapiens

<400> SEQUENCE: 14
cggggugggu gaggucgggc                                      20

<210> SEQ ID NO 15
<211> LENGTH: 22
<212> TYPE: RNA
<213> ORGANISM: Homo sapiens

<400> SEQUENCE: 15 uagggaugg aggccaggau ga                                    22

<210> SEQ ID NO 16
<211> LENGTH: 22
<212> TYPE: RNA
<213> ORGANISM: Homo sapiens

<400> SEQUENCE: 16 ugggaggug uggagucagc au                                    22

<210> SEQ ID NO 17
<211> LENGTH: 21
<212> TYPE: RNA
<213> ORGANISM: Homo sapiens

<400> SEQUENCE: 17
guguggccgg caggcggug g                                     21

<210> SEQ ID NO 18
<211> LENGTH: 18
<212> TYPE: RNA
<213> ORGANISM: Homo sapiens

<400> SEQUENCE: 18
cggugagcgc ucgcuggc                                        18

<210> SEQ ID NO 19
<211> LENGTH: 19

<212> TYPE: RNA
<213> ORGANISM: Homo sapiens

<400> SEQUENCE: 19
uugaucucgg aagcuaagc                                                    19

<210> SEQ ID NO 20
<211> LENGTH: 23
<212> TYPE: RNA
<213> ORGANISM: Homo sapiens

<400> SEQUENCE: 20
agaggcuuug ugcggauacg ggg                                               23

<210> SEQ ID NO 21
<211> LENGTH: 23
<212> TYPE: RNA
<213> ORGANISM: Homo sapiens

<400> SEQUENCE: 21
ucgaggacug guggaagggc cuu                                               23

<210> SEQ ID NO 22
<211> LENGTH: 23
<212> TYPE: RNA
<213> ORGANISM: Homo sapiens

<400> SEQUENCE: 22 ugggaaggc uuggcaggga aga                                                23

<210> SEQ ID NO 23
<211> LENGTH: 23
<212> TYPE: RNA
<213> ORGANISM: Homo sapiens

<400> SEQUENCE: 23
ggaugguugg gggcggucgg cgu                                               23

<210> SEQ ID NO 24
<211> LENGTH: 22
<212> TYPE: RNA
<213> ORGANISM: Homo sapiens

<400> SEQUENCE: 24
gcccaggacu uugugcgggg ug                                                22

<210> SEQ ID NO 25
<211> LENGTH: 20
<212> TYPE: RNA
<213> ORGANISM: Homo sapiens

<400> SEQUENCE: 25
ggcggcgggg agguaggcag                                                   20

<210> SEQ ID NO 26
<211> LENGTH: 22
<212> TYPE: RNA
<213> ORGANISM: Homo sapiens

<400> SEQUENCE: 26
agugggaggc cagggcacgg ca                                                22

<210> SEQ ID NO 27

```
<211> LENGTH: 23
<212> TYPE: RNA
<213> ORGANISM: Homo sapiens

<400> SEQUENCE: 27
uggggggaca gauggagagg aca                                              23

<210> SEQ ID NO 28
<211> LENGTH: 20
<212> TYPE: RNA
<213> ORGANISM: Homo sapiens

<400> SEQUENCE: 28
gugucugggc ggacagcugc                                                  20

<210> SEQ ID NO 29
<211> LENGTH: 21
<212> TYPE: RNA
<213> ORGANISM: Homo sapiens

<400> SEQUENCE: 29
guuggggugc aggggucugc u                                                21

<210> SEQ ID NO 30
<211> LENGTH: 23
<212> TYPE: RNA
<213> ORGANISM: Homo sapiens

<400> SEQUENCE: 30 cgaggggua g aagagcacag ggg                                             23

<210> SEQ ID NO 31
<211> LENGTH: 20
<212> TYPE: RNA
<213> ORGANISM: Homo sapiens

<400> SEQUENCE: 31
gccggggcuu ugggugaggg                                                  20

<210> SEQ ID NO 32
<211> LENGTH: 22
<212> TYPE: RNA
<213> ORGANISM: Homo sapiens

<400> SEQUENCE: 32
ccccuggggc ugggcaggcg ga                                               22

<210> SEQ ID NO 33
<211> LENGTH: 22
<212> TYPE: RNA
<213> ORGANISM: Homo sapiens

<400> SEQUENCE: 33
ucgggccugg gguuggggga gc                                               22

<210> SEQ ID NO 34
<211> LENGTH: 22
<212> TYPE: RNA
<213> ORGANISM: Homo sapiens

<400> SEQUENCE: 34
gugggugcug gugggagccg ug                                               22
```

```
<210> SEQ ID NO 35
<211> LENGTH: 23
<212> TYPE: RNA
<213> ORGANISM: Homo sapiens

<400> SEQUENCE: 35
cggggccgua gcacugucug aga                                       23

<210> SEQ ID NO 36
<211> LENGTH: 18
<212> TYPE: RNA
<213> ORGANISM: Homo sapiens

<400> SEQUENCE: 36
gaggcugaag gaagaugg                                             18

<210> SEQ ID NO 37
<211> LENGTH: 22
<212> TYPE: RNA
<213> ORGANISM: Homo sapiens

<400> SEQUENCE: 37
ccgggagaag gagguggccu gg                                        22

<210> SEQ ID NO 38
<211> LENGTH: 24
<212> TYPE: RNA
<213> ORGANISM: Homo sapiens

<400> SEQUENCE: 38
ugaggggccu cagaccgagc uuuu                                      24

<210> SEQ ID NO 39
<211> LENGTH: 23
<212> TYPE: RNA
<213> ORGANISM: Homo sapiens

<400> SEQUENCE: 39
ugaggauaug gcagggaagg gga                                       23

<210> SEQ ID NO 40
<211> LENGTH: 21
<212> TYPE: RNA
<213> ORGANISM: Homo sapiens

<400> SEQUENCE: 40 uggggugug gggagagaga g                                          21

<210> SEQ ID NO 41
<211> LENGTH: 17
<212> TYPE: RNA
<213> ORGANISM: Homo sapiens

<400> SEQUENCE: 41
gggagaaggg ucggggc                                              17

<210> SEQ ID NO 42
<211> LENGTH: 22
<212> TYPE: RNA
<213> ORGANISM: Homo sapiens

<400> SEQUENCE: 42
aggcgaugug gggauguaga ga                                        22
```

```
<210> SEQ ID NO 43
<211> LENGTH: 23
<212> TYPE: RNA
<213> ORGANISM: Homo sapiens

<400> SEQUENCE: 43
ucaauaggaa agagguggga ccu                                        23

<210> SEQ ID NO 44
<211> LENGTH: 21
<212> TYPE: RNA
<213> ORGANISM: Homo sapiens

<400> SEQUENCE: 44
caggaguggg ggugggacg u                                           21

<210> SEQ ID NO 45
<211> LENGTH: 22
<212> TYPE: RNA
<213> ORGANISM: Homo sapiens

<400> SEQUENCE: 45
cuucccccca guaaucuuca uc                                         22

<210> SEQ ID NO 46
<211> LENGTH: 22
<212> TYPE: RNA
<213> ORGANISM: Homo sapiens

<400> SEQUENCE: 46
ggcuggagcg agugcagugg ug                                         22

<210> SEQ ID NO 47
<211> LENGTH: 22
<212> TYPE: RNA
<213> ORGANISM: Homo sapiens

<400> SEQUENCE: 47
caggcacggg agcucaggug ag                                         22

<210> SEQ ID NO 48
<211> LENGTH: 22
<212> TYPE: RNA
<213> ORGANISM: Homo sapiens

<400> SEQUENCE: 48
gggacccagg gagagacgua ag                                         22

<210> SEQ ID NO 49
<211> LENGTH: 22
<212> TYPE: RNA
<213> ORGANISM: Homo sapiens

<400> SEQUENCE: 49
uggcggcggu aguuaugggc uu                                         22

<210> SEQ ID NO 50
<211> LENGTH: 22
<212> TYPE: RNA
<213> ORGANISM: Homo sapiens

<400> SEQUENCE: 50
uuggggauug ggucaggcca gu                                         22
```

```
<210> SEQ ID NO 51
<211> LENGTH: 20
<212> TYPE: RNA
<213> ORGANISM: Homo sapiens

<400> SEQUENCE: 51
ucucuucauc uaccccccag                                                    20

<210> SEQ ID NO 52
<211> LENGTH: 22
<212> TYPE: RNA
<213> ORGANISM: Homo sapiens

<400> SEQUENCE: 52
guggguacgg cccagugggg gg                                                 22

<210> SEQ ID NO 53
<211> LENGTH: 22
<212> TYPE: RNA
<213> ORGANISM: Homo sapiens

<400> SEQUENCE: 53
ggcuacaaca caggacccgg gc                                                 22

<210> SEQ ID NO 54
<211> LENGTH: 23
<212> TYPE: RNA
<213> ORGANISM: Homo sapiens

<400> SEQUENCE: 54
agaagaaggc ggucggucug cgg                                                23

<210> SEQ ID NO 55
<211> LENGTH: 22
<212> TYPE: RNA
<213> ORGANISM: Homo sapiens

<400> SEQUENCE: 55
agacacauuu ggagagggac cc                                                 22

<210> SEQ ID NO 56
<211> LENGTH: 22
<212> TYPE: RNA
<213> ORGANISM: Homo sapiens

<400> SEQUENCE: 56
acgcccuucc cccccuucuu ca                                                 22

<210> SEQ ID NO 57
<211> LENGTH: 22
<212> TYPE: RNA
<213> ORGANISM: Homo sapiens

<400> SEQUENCE: 57
ugcggggcua gggcuaacag ca                                                 22

<210> SEQ ID NO 58
<211> LENGTH: 17
<212> TYPE: RNA
<213> ORGANISM: Homo sapiens

<400> SEQUENCE: 58
```
gccggacaag agggagg                                                    17

<210> SEQ ID NO 59
<211> LENGTH: 20
<212> TYPE: RNA
<213> ORGANISM: Homo sapiens

<400> SEQUENCE: 59
ucacaccugc cucgccccccc                                                20

<210> SEQ ID NO 60
<211> LENGTH: 24
<212> TYPE: RNA
<213> ORGANISM: Homo sapiens

<400> SEQUENCE: 60
uggggagcug aggcucuggg ggug                                            24

<210> SEQ ID NO 61
<211> LENGTH: 19
<212> TYPE: RNA
<213> ORGANISM: Homo sapiens

<400> SEQUENCE: 61
cggggccaga gcagagagc                                                  19

<210> SEQ ID NO 62
<211> LENGTH: 22
<212> TYPE: RNA
<213> ORGANISM: Homo sapiens

<400> SEQUENCE: 62
gugaacgggc gccaucccga gg                                              22

<210> SEQ ID NO 63
<211> LENGTH: 21
<212> TYPE: RNA
<213> ORGANISM: Homo sapiens

<400> SEQUENCE: 63
aagggacagg gagggucgug g                                               21

<210> SEQ ID NO 64
<211> LENGTH: 22
<212> TYPE: RNA
<213> ORGANISM: Homo sapiens

<400> SEQUENCE: 64
ugggcgaggg cggcugagcg gc                                              22

<210> SEQ ID NO 65
<211> LENGTH: 23
<212> TYPE: RNA
<213> ORGANISM: Homo sapiens

<400> SEQUENCE: 65
gagggcagcg uggguguggc gga                                             23

<210> SEQ ID NO 66
<211> LENGTH: 22
<212> TYPE: RNA
<213> ORGANISM: Homo sapiens

<400> SEQUENCE: 66

-continued ggggguccccc ggugucucgga uc                                      22

<210> SEQ ID NO 67
<211> LENGTH: 23
<212> TYPE: RNA
<213> ORGANISM: Homo sapiens

<400> SEQUENCE: 67
cugggcccgc ggcgggcgug ggg                                       23

<210> SEQ ID NO 68
<211> LENGTH: 23
<212> TYPE: RNA
<213> ORGANISM: Homo sapiens

<400> SEQUENCE: 68
ugggagggga gaggcagcaa gca                                       23

<210> SEQ ID NO 69
<211> LENGTH: 20
<212> TYPE: RNA
<213> ORGANISM: Homo sapiens

<400> SEQUENCE: 69 uaggggugg caggcuggcc                                            20

<210> SEQ ID NO 70
<211> LENGTH: 21
<212> TYPE: RNA
<213> ORGANISM: Homo sapiens

<400> SEQUENCE: 70
uggggcgggg caggucccug c                                         21

<210> SEQ ID NO 71
<211> LENGTH: 22
<212> TYPE: RNA
<213> ORGANISM: Homo sapiens

<400> SEQUENCE: 71
caggaggcag ugggcgagca gg                                        22

<210> SEQ ID NO 72
<211> LENGTH: 20
<212> TYPE: RNA
<213> ORGANISM: Homo sapiens

<400> SEQUENCE: 72
agagaugaag cggggggggcg                                          20

<210> SEQ ID NO 73
<211> LENGTH: 18
<212> TYPE: RNA
<213> ORGANISM: Homo sapiens

<400> SEQUENCE: 73
auccuaguca cggcacca                                             18

<210> SEQ ID NO 74
<211> LENGTH: 23
<212> TYPE: RNA
<213> ORGANISM: Homo sapiens

```
<400> SEQUENCE: 74
ggaggcgcag gcucggaaag gcg                                          23

<210> SEQ ID NO 75
<211> LENGTH: 20
<212> TYPE: RNA
<213> ORGANISM: Homo sapiens

<400> SEQUENCE: 75
gcggaaggcg gagcggcgga                                              20

<210> SEQ ID NO 76
<211> LENGTH: 21
<212> TYPE: RNA
<213> ORGANISM: Homo sapiens

<400> SEQUENCE: 76
acaggagugg ggugggaca u                                             21

<210> SEQ ID NO 77
<211> LENGTH: 23
<212> TYPE: RNA
<213> ORGANISM: Homo sapiens

<400> SEQUENCE: 77
cucggggcag gcggcuggga gcg                                          23

<210> SEQ ID NO 78
<211> LENGTH: 25
<212> TYPE: RNA
<213> ORGANISM: Homo sapiens

<400> SEQUENCE: 78
agcggggagg aagugggcgc ugcuu                                        25

<210> SEQ ID NO 79
<211> LENGTH: 21
<212> TYPE: RNA
<213> ORGANISM: Homo sapiens

<400> SEQUENCE: 79
cguggaggac gaggaggagg c                                            21

<210> SEQ ID NO 80
<211> LENGTH: 23
<212> TYPE: RNA
<213> ORGANISM: Homo sapiens

<400> SEQUENCE: 80
uugcucugcu cccccgcccc cag                                          23

<210> SEQ ID NO 81
<211> LENGTH: 22
<212> TYPE: RNA
<213> ORGANISM: Homo sapiens

<400> SEQUENCE: 81
ugauugucuu cccccacccu ca                                           22

<210> SEQ ID NO 82
<211> LENGTH: 22
<212> TYPE: RNA
<213> ORGANISM: Homo sapiens
```

```
<400> SEQUENCE: 82 ucugccccu ccgcugcugc ca                                    22

<210> SEQ ID NO 83
<211> LENGTH: 24
<212> TYPE: RNA
<213> ORGANISM: Homo sapiens

<400> SEQUENCE: 83
ugggcgaggg gugggcucuc agag                                 24

<210> SEQ ID NO 84
<211> LENGTH: 23
<212> TYPE: RNA
<213> ORGANISM: Homo sapiens

<400> SEQUENCE: 84
gacacgggcg acagcugcgg ccc                                  23

<210> SEQ ID NO 85
<211> LENGTH: 23
<212> TYPE: RNA
<213> ORGANISM: Homo sapiens

<400> SEQUENCE: 85
ugagcaccac acaggccggg cgc                                  23

<210> SEQ ID NO 86
<211> LENGTH: 21
<212> TYPE: RNA
<213> ORGANISM: Homo sapiens

<400> SEQUENCE: 86
caggcaggug uaggguggag c                                    21

<210> SEQ ID NO 87
<211> LENGTH: 22
<212> TYPE: RNA
<213> ORGANISM: Homo sapiens

<400> SEQUENCE: 87 acugguagg uggggcucca gg                                    22

<210> SEQ ID NO 88
<211> LENGTH: 22
<212> TYPE: RNA
<213> ORGANISM: Homo sapiens

<400> SEQUENCE: 88
cgucccgggg cugcgcgagg ca                                   22

<210> SEQ ID NO 89
<211> LENGTH: 22
<212> TYPE: RNA
<213> ORGANISM: Homo sapiens

<400> SEQUENCE: 89
uggggguggu cucuagccaa gg                                   22

<210> SEQ ID NO 90
<211> LENGTH: 20
<212> TYPE: RNA
```

<213> ORGANISM: Homo sapiens

<400> SEQUENCE: 90
ggauccgagu cacggcacca                                                    20

<210> SEQ ID NO 91
<211> LENGTH: 21
<212> TYPE: RNA
<213> ORGANISM: Homo sapiens

<400> SEQUENCE: 91
auccaguucu cugaggggc u                                                   21

<210> SEQ ID NO 92
<211> LENGTH: 22
<212> TYPE: RNA
<213> ORGANISM: Homo sapiens

<400> SEQUENCE: 92
gguggcccgg ccgugccuga gg                                                 22

<210> SEQ ID NO 93
<211> LENGTH: 25
<212> TYPE: RNA
<213> ORGANISM: Homo sapiens

<400> SEQUENCE: 93
gugaggcggg gccaggaggg ugugu                                              25

<210> SEQ ID NO 94
<211> LENGTH: 22
<212> TYPE: RNA
<213> ORGANISM: Homo sapiens

<400> SEQUENCE: 94
agacugacgg cuggaggccc au                                                 22

<210> SEQ ID NO 95
<211> LENGTH: 23
<212> TYPE: RNA
<213> ORGANISM: Homo sapiens

<400> SEQUENCE: 95
gaacgccugu ucuugccagg ugg                                                23

<210> SEQ ID NO 96
<211> LENGTH: 22
<212> TYPE: RNA
<213> ORGANISM: Homo sapiens

<400> SEQUENCE: 96
ugggagggcg uggaugaugg ug                                                 22

<210> SEQ ID NO 97
<211> LENGTH: 23
<212> TYPE: RNA
<213> ORGANISM: Homo sapiens

<400> SEQUENCE: 97
acggggaguc aggcaguggu gga                                                23

<210> SEQ ID NO 98
<211> LENGTH: 21

<212> TYPE: RNA
<213> ORGANISM: Homo sapiens

<400> SEQUENCE: 98
aaggcagggc ccccgcuccc c                                              21

<210> SEQ ID NO 99
<211> LENGTH: 23
<212> TYPE: RNA
<213> ORGANISM: Homo sapiens

<400> SEQUENCE: 99
cgggcugucc ggaggggucg gcu                                            23

<210> SEQ ID NO 100
<211> LENGTH: 19
<212> TYPE: RNA
<213> ORGANISM: Homo sapiens

<400> SEQUENCE: 100 uggggagau ggggguuga                                                  19

<210> SEQ ID NO 101
<211> LENGTH: 19
<212> TYPE: RNA
<213> ORGANISM: Homo sapiens

<400> SEQUENCE: 101
ggcuggucag augggagug                                                 19

<210> SEQ ID NO 102
<211> LENGTH: 22
<212> TYPE: RNA
<213> ORGANISM: Homo sapiens

<400> SEQUENCE: 102
cugguacagg ccuggggac ag                                              22

<210> SEQ ID NO 103
<211> LENGTH: 23
<212> TYPE: RNA
<213> ORGANISM: Homo sapiens

<400> SEQUENCE: 103
gccccggcgc gggcgguuc ugg                                             23

<210> SEQ ID NO 104
<211> LENGTH: 20
<212> TYPE: RNA
<213> ORGANISM: Homo sapiens

<400> SEQUENCE: 104
ccccagggcg acgcggcggg                                                20

<210> SEQ ID NO 105
<211> LENGTH: 23
<212> TYPE: RNA
<213> ORGANISM: Homo sapiens

<400> SEQUENCE: 105
acaggcggcu guagcaaugg ggg                                            23

<210> SEQ ID NO 106

```
<211> LENGTH: 20
<212> TYPE: RNA
<213> ORGANISM: Homo sapiens

<400> SEQUENCE: 106
gugagucagg gugggcugg                                                  20

<210> SEQ ID NO 107
<211> LENGTH: 17
<212> TYPE: RNA
<213> ORGANISM: Homo sapiens

<400> SEQUENCE: 107
uuggaggcgu ggguuuu                                                    17

<210> SEQ ID NO 108
<211> LENGTH: 22
<212> TYPE: RNA
<213> ORGANISM: Homo sapiens

<400> SEQUENCE: 108
ggaggggucc cgcacuggga gg                                              22

<210> SEQ ID NO 109
<211> LENGTH: 22
<212> TYPE: RNA
<213> ORGANISM: Homo sapiens

<400> SEQUENCE: 109
gugggcuggg cugggcuggg cc                                              22

<210> SEQ ID NO 110
<211> LENGTH: 20
<212> TYPE: RNA
<213> ORGANISM: Homo sapiens

<400> SEQUENCE: 110
cgggcguggu ggugggggug                                                 20

<210> SEQ ID NO 111
<211> LENGTH: 17
<212> TYPE: RNA
<213> ORGANISM: Homo sapiens

<400> SEQUENCE: 111
guggggccag gcggugg                                                    17

<210> SEQ ID NO 112
<211> LENGTH: 22
<212> TYPE: RNA
<213> ORGANISM: Homo sapiens

<400> SEQUENCE: 112
ugguggagga agagggcagc uc                                              22

<210> SEQ ID NO 113
<211> LENGTH: 18
<212> TYPE: RNA
<213> ORGANISM: Homo sapiens

<400> SEQUENCE: 113
ggugggcuuc ccggaggg                                                   18
```

```
<210> SEQ ID NO 114
<211> LENGTH: 20
<212> TYPE: RNA
<213> ORGANISM: Homo sapiens

<400> SEQUENCE: 114
cuaggugggg ggcuugaagc                                               20

<210> SEQ ID NO 115
<211> LENGTH: 21
<212> TYPE: RNA
<213> ORGANISM: Homo sapiens

<400> SEQUENCE: 115
agguggguau ggaggagccc u                                             21

<210> SEQ ID NO 116
<211> LENGTH: 22
<212> TYPE: RNA
<213> ORGANISM: Homo sapiens

<400> SEQUENCE: 116
aggcggggcg ccgcgggacc gc                                            22

<210> SEQ ID NO 117
<211> LENGTH: 23
<212> TYPE: RNA
<213> ORGANISM: Homo sapiens

<400> SEQUENCE: 117
ugggcagggg cuuauuguag gag                                           23

<210> SEQ ID NO 118
<211> LENGTH: 17
<212> TYPE: RNA
<213> ORGANISM: Homo sapiens

<400> SEQUENCE: 118
ccccggggag cccggcg                                                  17

<210> SEQ ID NO 119
<211> LENGTH: 18
<212> TYPE: RNA
<213> ORGANISM: Homo sapiens

<400> SEQUENCE: 119
uucccagcca acgcacca                                                 18

<210> SEQ ID NO 120
<211> LENGTH: 22
<212> TYPE: RNA
<213> ORGANISM: Homo sapiens

<400> SEQUENCE: 120
agggacggga cgcggugcag ug                                            22

<210> SEQ ID NO 121
<211> LENGTH: 20
<212> TYPE: RNA
<213> ORGANISM: Homo sapiens

<400> SEQUENCE: 121
acucaaacug uggggggcacu                                              20
```

```
<210> SEQ ID NO 122
<211> LENGTH: 18
<212> TYPE: RNA
<213> ORGANISM: Homo sapiens

<400> SEQUENCE: 122
gugaaggccc ggcggaga                                                  18

<210> SEQ ID NO 123
<211> LENGTH: 22
<212> TYPE: RNA
<213> ORGANISM: Homo sapiens

<400> SEQUENCE: 123
gcugcgggcu gcggucaggg cg                                             22

<210> SEQ ID NO 124
<211> LENGTH: 26
<212> TYPE: RNA
<213> ORGANISM: Homo sapiens

<400> SEQUENCE: 124
cucggccgcg gcgcguagcc cccgcc                                         26

<210> SEQ ID NO 125
<211> LENGTH: 23
<212> TYPE: RNA
<213> ORGANISM: Homo sapiens

<400> SEQUENCE: 125
ugaggggcag agagcgagac uuu                                            23

<210> SEQ ID NO 126
<211> LENGTH: 22
<212> TYPE: RNA
<213> ORGANISM: Homo sapiens

<400> SEQUENCE: 126
cucggcgcgg ggcgcgggcu cc                                             22

<210> SEQ ID NO 127
<211> LENGTH: 22
<212> TYPE: RNA
<213> ORGANISM: Homo sapiens

<400> SEQUENCE: 127
ggggcuguga uugaccagca gg                                             22

<210> SEQ ID NO 128
<211> LENGTH: 22
<212> TYPE: RNA
<213> ORGANISM: Homo sapiens

<400> SEQUENCE: 128
accuugccuu gcugcccggg cc                                             22

<210> SEQ ID NO 129
<211> LENGTH: 20
<212> TYPE: RNA
<213> ORGANISM: Homo sapiens

<400> SEQUENCE: 129
ugggaauggg gguaagggcc                                                20
```

```
<210> SEQ ID NO 130
<211> LENGTH: 21
<212> TYPE: RNA
<213> ORGANISM: Homo sapiens

<400> SEQUENCE: 130
cuuccgcccc gccgggcguc g                                              21

<210> SEQ ID NO 131
<211> LENGTH: 18
<212> TYPE: RNA
<213> ORGANISM: Homo sapiens

<400> SEQUENCE: 131 ggucccggg gaggggggg                                                  18

<210> SEQ ID NO 132
<211> LENGTH: 19
<212> TYPE: RNA
<213> ORGANISM: Homo sapiens

<400> SEQUENCE: 132
ugcggcagag cuggguca                                                  19

<210> SEQ ID NO 133
<211> LENGTH: 24
<212> TYPE: RNA
<213> ORGANISM: Homo sapiens

<400> SEQUENCE: 133
uggggggaca ggaugagagg cugu                                           24

<210> SEQ ID NO 134
<211> LENGTH: 21
<212> TYPE: RNA
<213> ORGANISM: Homo sapiens

<400> SEQUENCE: 134
cugggagggg cugguuugg c                                               21

<210> SEQ ID NO 135
<211> LENGTH: 21
<212> TYPE: RNA
<213> ORGANISM: Homo sapiens

<400> SEQUENCE: 135
cuggggggag gagacccugc u                                              21

<210> SEQ ID NO 136
<211> LENGTH: 23
<212> TYPE: RNA
<213> ORGANISM: Homo sapiens

<400> SEQUENCE: 136 ccaggggau gggcgagcuu ggg                                             23

<210> SEQ ID NO 137
<211> LENGTH: 20
<212> TYPE: RNA
<213> ORGANISM: Homo sapiens

<400> SEQUENCE: 137
```

```
uguggggacug caaaugggag                                            20

<210> SEQ ID NO 138
<211> LENGTH: 22
<212> TYPE: RNA
<213> ORGANISM: Homo sapiens

<400> SEQUENCE: 138
ggggaacugu agaugaaaag gc                                          22

<210> SEQ ID NO 139
<211> LENGTH: 21
<212> TYPE: RNA
<213> ORGANISM: Homo sapiens

<400> SEQUENCE: 139
ucaccuggcu ggcccgccca g                                           21

<210> SEQ ID NO 140
<211> LENGTH: 19
<212> TYPE: RNA
<213> ORGANISM: Homo sapiens

<400> SEQUENCE: 140
agcagggcug gggauugca                                              19

<210> SEQ ID NO 141
<211> LENGTH: 17
<212> TYPE: RNA
<213> ORGANISM: Homo sapiens

<400> SEQUENCE: 141
ggggcugggc gcgcgcc                                                17

<210> SEQ ID NO 142
<211> LENGTH: 22
<212> TYPE: RNA
<213> ORGANISM: Homo sapiens

<400> SEQUENCE: 142
ucggccuggg gaggaggaag gg                                          22

<210> SEQ ID NO 143
<211> LENGTH: 17
<212> TYPE: RNA
<213> ORGANISM: Homo sapiens

<400> SEQUENCE: 143
cgcgccgggc ccgggu u                                               17

<210> SEQ ID NO 144
<211> LENGTH: 19
<212> TYPE: RNA
<213> ORGANISM: Homo sapiens

<400> SEQUENCE: 144
uggggcggag cuuccggag                                              19

<210> SEQ ID NO 145
<211> LENGTH: 22
<212> TYPE: RNA
<213> ORGANISM: Homo sapiens

<400> SEQUENCE: 145
```
gaggguuggg uggaggcucu cc                                            22

<210> SEQ ID NO 146
<211> LENGTH: 19
<212> TYPE: RNA
<213> ORGANISM: Homo sapiens

<400> SEQUENCE: 146
aggcacggug ucagcaggc                                                19

<210> SEQ ID NO 147
<211> LENGTH: 18
<212> TYPE: RNA
<213> ORGANISM: Homo sapiens

<400> SEQUENCE: 147
cgggcguggu gguggggg                                                 18

<210> SEQ ID NO 148
<211> LENGTH: 23
<212> TYPE: RNA
<213> ORGANISM: Homo sapiens

<400> SEQUENCE: 148 uggggcugg gaugggccau ggu                                            23

<210> SEQ ID NO 149
<211> LENGTH: 22
<212> TYPE: RNA
<213> ORGANISM: Homo sapiens

<400> SEQUENCE: 149
ggggcugggg ccggggccga gc                                            22

<210> SEQ ID NO 150
<211> LENGTH: 19
<212> TYPE: RNA
<213> ORGANISM: Homo sapiens

<400> SEQUENCE: 150
ggggccuggc gguggggcgg                                               19

<210> SEQ ID NO 151
<211> LENGTH: 21
<212> TYPE: RNA
<213> ORGANISM: Homo sapiens

<400> SEQUENCE: 151
cccggagcca ggaugcagcu c                                             21

<210> SEQ ID NO 152
<211> LENGTH: 19
<212> TYPE: RNA
<213> ORGANISM: Homo sapiens

<400> SEQUENCE: 152
aucccaccac ugccaccau                                                19

<210> SEQ ID NO 153
<211> LENGTH: 22
<212> TYPE: RNA
<213> ORGANISM: Homo sapiens

```
<400> SEQUENCE: 153
caggaaggau uuagggacag gc                                          22

<210> SEQ ID NO 154
<211> LENGTH: 25
<212> TYPE: RNA
<213> ORGANISM: Homo sapiens

<400> SEQUENCE: 154
aggggggcac ugcgcaagca aagcc                                       25

<210> SEQ ID NO 155
<211> LENGTH: 23
<212> TYPE: RNA
<213> ORGANISM: Homo sapiens

<400> SEQUENCE: 155 ugguggugg ggaggagaag ugc                                          23

<210> SEQ ID NO 156
<211> LENGTH: 21
<212> TYPE: RNA
<213> ORGANISM: Homo sapiens

<400> SEQUENCE: 156
aucacauugc cagggauuac c                                           21

<210> SEQ ID NO 157
<211> LENGTH: 22
<212> TYPE: RNA
<213> ORGANISM: Homo sapiens

<400> SEQUENCE: 157
uggggagcgg cccccgggug gg                                          22

<210> SEQ ID NO 158
<211> LENGTH: 20
<212> TYPE: RNA
<213> ORGANISM: Homo sapiens

<400> SEQUENCE: 158 cgcggucgg ggucugcagg                                              20

<210> SEQ ID NO 159
<211> LENGTH: 22
<212> TYPE: RNA
<213> ORGANISM: Homo sapiens

<400> SEQUENCE: 159
uaggggcagc agaggaccug gg                                          22

<210> SEQ ID NO 160
<211> LENGTH: 17
<212> TYPE: RNA
<213> ORGANISM: Homo sapiens

<400> SEQUENCE: 160
accccacucc ugguacc                                                17

<210> SEQ ID NO 161
<211> LENGTH: 23
<212> TYPE: RNA
<213> ORGANISM: Homo sapiens
```

```
<400> SEQUENCE: 161
ugggccaggg agcagcuggu ggg                                              23

<210> SEQ ID NO 162
<211> LENGTH: 25
<212> TYPE: RNA
<213> ORGANISM: Homo sapiens

<400> SEQUENCE: 162
aagggaggag gagcggaggg gcccu                                            25

<210> SEQ ID NO 163
<211> LENGTH: 18
<212> TYPE: RNA
<213> ORGANISM: Homo sapiens

<400> SEQUENCE: 163
aucccaccuc ugccacca                                                    18

<210> SEQ ID NO 164
<211> LENGTH: 17
<212> TYPE: RNA
<213> ORGANISM: Homo sapiens

<400> SEQUENCE: 164
cucagugacu caugugc                                                     17

<210> SEQ ID NO 165
<211> LENGTH: 20
<212> TYPE: RNA
<213> ORGANISM: Homo sapiens

<400> SEQUENCE: 165
ugggaggagg ggaucuuggg                                                  20

<210> SEQ ID NO 166
<211> LENGTH: 23
<212> TYPE: RNA
<213> ORGANISM: Homo sapiens

<400> SEQUENCE: 166
gggggccgau acacuguacg aga                                              23

<210> SEQ ID NO 167
<211> LENGTH: 22
<212> TYPE: RNA
<213> ORGANISM: Homo sapiens

<400> SEQUENCE: 167
acaggugagg uucuugggag cc                                               22

<210> SEQ ID NO 168
<211> LENGTH: 22
<212> TYPE: RNA
<213> ORGANISM: Homo sapiens

<400> SEQUENCE: 168
ggguggggau uuguugcauu ac                                               22

<210> SEQ ID NO 169
<211> LENGTH: 21
<212> TYPE: RNA
```

```
<213> ORGANISM: Homo sapiens

<400> SEQUENCE: 169
cggggcagcu caguacagga u                                              21

<210> SEQ ID NO 170
<211> LENGTH: 18
<212> TYPE: RNA
<213> ORGANISM: Homo sapiens

<400> SEQUENCE: 170
cggggcggca ggggccuc                                                  18

<210> SEQ ID NO 171
<211> LENGTH: 21
<212> TYPE: RNA
<213> ORGANISM: Homo sapiens

<400> SEQUENCE: 171
gcagggacag caaaggggug c                                              21

<210> SEQ ID NO 172
<211> LENGTH: 19
<212> TYPE: RNA
<213> ORGANISM: Homo sapiens

<400> SEQUENCE: 172
gggggaagaa aaggugggg                                                 19

<210> SEQ ID NO 173
<211> LENGTH: 23
<212> TYPE: RNA
<213> ORGANISM: Homo sapiens

<400> SEQUENCE: 173
aggagguggu acuaggggcc agc                                            23

<210> SEQ ID NO 174
<211> LENGTH: 21
<212> TYPE: RNA
<213> ORGANISM: Homo sapiens

<400> SEQUENCE: 174
agggagggac gggggcugug c                                              21

<210> SEQ ID NO 175
<211> LENGTH: 22
<212> TYPE: RNA
<213> ORGANISM: Homo sapiens

<400> SEQUENCE: 175
acuggggagc agaaggagaa cc                                             22

<210> SEQ ID NO 176
<211> LENGTH: 22
<212> TYPE: RNA
<213> ORGANISM: Homo sapiens

<400> SEQUENCE: 176
uauagggauu ggagccgugg cg                                             22

<210> SEQ ID NO 177
<211> LENGTH: 17
```

<210> SEQ ID NO 177
<211> LENGTH: (not shown)
<212> TYPE: RNA
<213> ORGANISM: Homo sapiens

<400> SEQUENCE: 177
gcugggcgag gcuggca                                                    17

<210> SEQ ID NO 178
<211> LENGTH: 22
<212> TYPE: RNA
<213> ORGANISM: Homo sapiens

<400> SEQUENCE: 178 aggggggcgca gucacugacg ug                                             22

<210> SEQ ID NO 179
<211> LENGTH: 22
<212> TYPE: RNA
<213> ORGANISM: Homo sapiens

<400> SEQUENCE: 179
uggggaaggc gucagugucg gg                                              22

<210> SEQ ID NO 180
<211> LENGTH: 22
<212> TYPE: RNA
<213> ORGANISM: Homo sapiens

<400> SEQUENCE: 180
cagcagggga gagagaggag uc                                              22

<210> SEQ ID NO 181
<211> LENGTH: 24
<212> TYPE: RNA
<213> ORGANISM: Homo sapiens

<400> SEQUENCE: 181
agggcuggac ucagcggcgg agcu                                            24

<210> SEQ ID NO 182
<211> LENGTH: 22
<212> TYPE: RNA
<213> ORGANISM: Homo sapiens

<400> SEQUENCE: 182
uccaggcagg agccggacug ga                                              22

<210> SEQ ID NO 183
<211> LENGTH: 18
<212> TYPE: RNA
<213> ORGANISM: Homo sapiens

<400> SEQUENCE: 183
gggugcgggc cggcgggg                                                   18

<210> SEQ ID NO 184
<211> LENGTH: 21
<212> TYPE: RNA
<213> ORGANISM: Homo sapiens

<400> SEQUENCE: 184
aucacauugc cagggauuuc c                                               21

<210> SEQ ID NO 185

```
<211> LENGTH: 17
<212> TYPE: RNA
<213> ORGANISM: Homo sapiens

<400> SEQUENCE: 185
ggcgggugcg ggggugg                                                    17

<210> SEQ ID NO 186
<211> LENGTH: 25
<212> TYPE: RNA
<213> ORGANISM: Homo sapiens

<400> SEQUENCE: 186 uaggguggg ggaauucagg ggugu                                            25

<210> SEQ ID NO 187
<211> LENGTH: 22
<212> TYPE: RNA
<213> ORGANISM: Homo sapiens

<400> SEQUENCE: 187
uugaggagac auggugggg cc                                               22

<210> SEQ ID NO 188
<211> LENGTH: 22
<212> TYPE: RNA
<213> ORGANISM: Homo sapiens

<400> SEQUENCE: 188
aaaccguuac cauuacugag uu                                              22

<210> SEQ ID NO 189
<211> LENGTH: 22
<212> TYPE: RNA
<213> ORGANISM: Homo sapiens

<400> SEQUENCE: 189
cagggcuggc agugacaugg gu                                              22

<210> SEQ ID NO 190
<211> LENGTH: 22
<212> TYPE: RNA
<213> ORGANISM: Homo sapiens

<400> SEQUENCE: 190
uggggcggag cuuccggagg cc                                              22

<210> SEQ ID NO 191
<211> LENGTH: 22
<212> TYPE: RNA
<213> ORGANISM: Homo sapiens

<400> SEQUENCE: 191
agacacauuu ggagagggaa cc                                              22

<210> SEQ ID NO 192
<211> LENGTH: 23
<212> TYPE: RNA
<213> ORGANISM: Homo sapiens

<400> SEQUENCE: 192
ucggggaguc ugggguccgg aau                                             23
```

```
<210> SEQ ID NO 193
<211> LENGTH: 17
<212> TYPE: RNA
<213> ORGANISM: Homo sapiens

<400> SEQUENCE: 193
ggggcgcggc cggaucg                                                    17

<210> SEQ ID NO 194
<211> LENGTH: 23
<212> TYPE: RNA
<213> ORGANISM: Homo sapiens

<400> SEQUENCE: 194 cuggggacg cgugagcgcg agc                                              23

<210> SEQ ID NO 195
<211> LENGTH: 22
<212> TYPE: RNA
<213> ORGANISM: Homo sapiens

<400> SEQUENCE: 195 ugcaggguc ggugggcca gg                                                22

<210> SEQ ID NO 196
<211> LENGTH: 22
<212> TYPE: RNA
<213> ORGANISM: Homo sapiens

<400> SEQUENCE: 196
cugggagagg guuguuuacu cc                                              22

<210> SEQ ID NO 197
<211> LENGTH: 20
<212> TYPE: RNA
<213> ORGANISM: Homo sapiens

<400> SEQUENCE: 197 cugguuggg cugggcuggg                                                  20

<210> SEQ ID NO 198
<211> LENGTH: 19
<212> TYPE: RNA
<213> ORGANISM: Homo sapiens

<400> SEQUENCE: 198
gagggcgggu ggaggagga                                                  19

<210> SEQ ID NO 199
<211> LENGTH: 20
<212> TYPE: RNA
<213> ORGANISM: Homo sapiens

<400> SEQUENCE: 199
ccugagcccg ggccgcgcag                                                 20

<210> SEQ ID NO 200
<211> LENGTH: 86
<212> TYPE: RNA
<213> ORGANISM: Homo sapiens

<400> SEQUENCE: 200
ggcuuagaaa caguccccuag guaggauuug gggaggagcu aagaagcccc uacagggccc    60
```
agaggugggg acugagccuu aguugg                                  86

<210> SEQ ID NO 201
<211> LENGTH: 61
<212> TYPE: RNA
<213> ORGANISM: Homo sapiens

<400> SEQUENCE: 201
gggggcggga gcugggucu gcagguucgc acugaugccu gcucgcccug ucucccgcua    60
g                                                                  61

<210> SEQ ID NO 202
<211> LENGTH: 84
<212> TYPE: RNA
<213> ORGANISM: Homo sapiens

<400> SEQUENCE: 202
gcuggcgucg gugcugggga gcggcccccg gguggccuc ugcucuggcc ccuccugggg    60
cccgcacucu cgcucuggge ccgc                                         84

<210> SEQ ID NO 203
<211> LENGTH: 136
<212> TYPE: RNA
<213> ORGANISM: Homo sapiens

<400> SEQUENCE: 203
ccgcuugccu cgcccagcgc agccccggcc gcugggcgca cccgucccgu ucgucccgg    60 acguugcucu cuaccccggg aacgucgaga cuggagcgcc cgaacugagc caccuucgcg  120
gaccccgaga gcggcg                                                 136

<210> SEQ ID NO 204
<211> LENGTH: 61
<212> TYPE: RNA
<213> ORGANISM: Homo sapiens

<400> SEQUENCE: 204
ucggcuggcg gggguagagc uggcugcagg cccggccccu cucagcugcu gcccucucca    60
g                                                                  61

<210> SEQ ID NO 205
<211> LENGTH: 72
<212> TYPE: RNA
<213> ORGANISM: Homo sapiens

<400> SEQUENCE: 205
gagucugagg gacccaggac aggagaaggc cuauggugau uugcauucuu ccugcccugg    60
cuccauccuc ag                                                      72

<210> SEQ ID NO 206
<211> LENGTH: 90
<212> TYPE: RNA
<213> ORGANISM: Homo sapiens

<400> SEQUENCE: 206 gugggguacgg cccaguggg gggagaggga cacgcccugg gcucugccca gggugcagcc    60
ggacugacug agccccugug ccgccccag                                    90

<210> SEQ ID NO 207
<211> LENGTH: 81

```
<212> TYPE: RNA
<213> ORGANISM: Homo sapiens

<400> SEQUENCE: 207
uagaggcagu ucaacagau guguagacuu uugauaugag aaauugguuu caaaaucagg    60
agucggggcu uuacugcuuu u                                             81

<210> SEQ ID NO 208
<211> LENGTH: 64
<212> TYPE: RNA
<213> ORGANISM: Homo sapiens

<400> SEQUENCE: 208
aaccccgggc cggaggucaa gggcgucgcu ucucccuaau guugccucuu uuccacggcc    60
ucag                                                                64

<210> SEQ ID NO 209
<211> LENGTH: 71
<212> TYPE: RNA
<213> ORGANISM: Homo sapiens

<400> SEQUENCE: 209
gugucugugc cggucccagg agaaccugca gaggcaucgg gucagcggug cuccugcggg    60
ccgacacuca c                                                        71

<210> SEQ ID NO 210
<211> LENGTH: 80
<212> TYPE: RNA
<213> ORGANISM: Homo sapiens

<400> SEQUENCE: 210
cgggaaugcc gcggcgggga cggcgauugg uccguaugug uggugccacc ggccgccggc    60
uccgccccgg cccccgcccc                                               80

<210> SEQ ID NO 211
<211> LENGTH: 63
<212> TYPE: RNA
<213> ORGANISM: Homo sapiens

<400> SEQUENCE: 211
acccuagggu ggggcuggag gugggcuga ggcugagucu ccuccccuu ccucccugcc     60 cag                                                                 63

<210> SEQ ID NO 212
<211> LENGTH: 110
<212> TYPE: RNA
<213> ORGANISM: Homo sapiens

<400> SEQUENCE: 212
ggcuacaguc uuucuucaug ugacucgugg acuucccuuu gucauccuau gccugagaau    60
auaugaagga ggcugggaag gcaaagggac guucaauugu caucacuggc              110

<210> SEQ ID NO 213
<211> LENGTH: 73
<212> TYPE: RNA
<213> ORGANISM: Homo sapiens

<400> SEQUENCE: 213
cggcgacggc ggggugggug aggucgggcc ccaagacucg gggguugccg ggcgccucag    60
```

```
uucaccgcgg ccg                                                         73

<210> SEQ ID NO 214
<211> LENGTH: 69
<212> TYPE: RNA
<213> ORGANISM: Homo sapiens

<400> SEQUENCE: 214
gggcuuaggg augggaggcc aggaugaaga uuaaucccua aucccaaca cuggccuugc       60 uaucccccag                                                             69

<210> SEQ ID NO 215
<211> LENGTH: 66
<212> TYPE: RNA
<213> ORGANISM: Homo sapiens

<400> SEQUENCE: 215
gggcaugggg aguguggag ucagcauggg gcuaggaggc cccgcgcuga cccgccuucu       60
ccgcag                                                                 66

<210> SEQ ID NO 216
<211> LENGTH: 87
<212> TYPE: RNA
<213> ORGANISM: Homo sapiens

<400> SEQUENCE: 216
guguggccgg caggcgggug ggcggggcg gccgguggga accccgcccc gccccgcgcc       60
cgcacucacc cgcccgucuc cccacag                                          87

<210> SEQ ID NO 217
<211> LENGTH: 74
<212> TYPE: RNA
<213> ORGANISM: Homo sapiens

<400> SEQUENCE: 217
gcagcccggu gagcgcucgc uggccuggca gucgucgga agaacagggc ggguggggcc       60
gcgcacaucu cugc                                                        74

<210> SEQ ID NO 218
<211> LENGTH: 61
<212> TYPE: RNA
<213> ORGANISM: Homo sapiens

<400> SEQUENCE: 218
ucucguuuga ucucggaagc uaagcagggu ugggccuggu aguacuugg augggaaacu       60 u                                                                      61

<210> SEQ ID NO 219
<211> LENGTH: 53
<212> TYPE: RNA
<213> ORGANISM: Homo sapiens

<400> SEQUENCE: 219
guuugaucuc ggaagcuaag cagggucggg ccugguuagu acuuggaugg gag             53

<210> SEQ ID NO 220
<211> LENGTH: 85
<212> TYPE: RNA
<213> ORGANISM: Homo sapiens

<400> SEQUENCE: 220
```

```
ggcgccuccu gcucugcugu gccgccaggg ccucccccuag cgcgccuucu ggagaggcuu    60
ugugcggaua cggggcugga ggccu                                          85

<210> SEQ ID NO 221
<211> LENGTH: 63
<212> TYPE: RNA
<213> ORGANISM: Homo sapiens

<400> SEQUENCE: 221
gagucgagga cugguggaag ggccuuuccc cucagaccaa ggcccuggcc ccagcuucuu    60
cuc                                                                  63

<210> SEQ ID NO 222
<211> LENGTH: 79
<212> TYPE: RNA
<213> ORGANISM: Homo sapiens

<400> SEQUENCE: 222
cagccugggg aaggcuuggc agggaagaca caugagcagu gccuccacuu cacgccucuc    60
ccuugucucc uuucccuag                                                 79

<210> SEQ ID NO 223
<211> LENGTH: 86
<212> TYPE: RNA
<213> ORGANISM: Homo sapiens

<400> SEQUENCE: 223
cgccugagcg ugcagcagga caucuuccug accugguaau aauuaggugu gaaggauggu    60 uggggggcggu cggcguaacu caggga                                        86

<210> SEQ ID NO 224
<211> LENGTH: 71
<212> TYPE: RNA
<213> ORGANISM: Homo sapiens

<400> SEQUENCE: 224
ugaccacccc cgggcaaaga ccugcagauc cccuguuaga gacgggccca ggacuuugug    60
cggggugccc a                                                         71

<210> SEQ ID NO 225
<211> LENGTH: 80
<212> TYPE: RNA
<213> ORGANISM: Homo sapiens

<400> SEQUENCE: 225
gcgucaagau ggcggcgggg agguaggcag agcaggacgc cgcugcugcc gccgccaccg    60
ccgccuccgc uccagucgcc                                                80

<210> SEQ ID NO 226
<211> LENGTH: 82
<212> TYPE: RNA
<213> ORGANISM: Homo sapiens

<400> SEQUENCE: 226
gugaguggga ggccagggca cggcaggggg agcugcaggg cuaugggagg ggccccagcg    60
ucugagcccu guccucccgc ag                                             82

<210> SEQ ID NO 227
```

```
<211> LENGTH: 82
<212> TYPE: RNA
<213> ORGANISM: Homo sapiens

<400> SEQUENCE: 227
gugaguggga ggccagggca cggcaggggg agcugcaggg cuaugggagg ggccccagcg    60
ucugagcccu guccucccgc ag                                             82

<210> SEQ ID NO 228
<211> LENGTH: 65
<212> TYPE: RNA
<213> ORGANISM: Homo sapiens

<400> SEQUENCE: 228
gagaaugggg ggacagaugg agaggacaca ggcuggcacu gagguccccu ccacuuuccu    60
ccuag                                                                65

<210> SEQ ID NO 229
<211> LENGTH: 92
<212> TYPE: RNA
<213> ORGANISM: Homo sapiens

<400> SEQUENCE: 229
gucagugucu gggcggacag cugcaggaaa gggaagacca aggcuugcug ucguccagu     60 cugccacccu acccgucug uucuugccac ag                                   92

<210> SEQ ID NO 230
<211> LENGTH: 137
<212> TYPE: RNA
<213> ORGANISM: Homo sapiens

<400> SEQUENCE: 230
agccagacaa gagggucaug gggagucacu gucaacccag agcaggcacu gccccugcga    60
ccagccuggg gcaucgguug ggugcaggg gucugcuggu gaugcuuucc aucucuuugc    120
uuuguccuga uuguagc                                                  137

<210> SEQ ID NO 231
<211> LENGTH: 64
<212> TYPE: RNA
<213> ORGANISM: Homo sapiens

<400> SEQUENCE: 231
gaaggcgagg gguagaagag cacagggguu cugauaaacc cuucugccug cauucuacuc    60
ccag                                                                 64

<210> SEQ ID NO 232
<211> LENGTH: 67
<212> TYPE: RNA
<213> ORGANISM: Homo sapiens

<400> SEQUENCE: 232
uacaggccgg ggcuuugggu gagggacccc cggagucugu cacggucuca ccccaacucu    60
gccccag                                                              67

<210> SEQ ID NO 233
<211> LENGTH: 67
<212> TYPE: RNA
<213> ORGANISM: Homo sapiens

<400> SEQUENCE: 233
```

```
ccagaccccu ggggcugggc aggcggaaag aggucugaac ugccucugcc uccuuggucu    60
ccggcag                                                              67

<210> SEQ ID NO 234
<211> LENGTH: 69
<212> TYPE: RNA
<213> ORGANISM: Homo sapiens

<400> SEQUENCE: 234
ggcccucggg ccuggggung ggggagcucu guccugucuc acucauugcu ccuccccugc    60
cuggcccag                                                            69

<210> SEQ ID NO 235
<211> LENGTH: 63
<212> TYPE: RNA
<213> ORGANISM: Homo sapiens

<400> SEQUENCE: 235
aaugggnggg ugcuggnggg agccgugccc uggccacuca uucggcucuc ucccucaccc    60
uag                                                                  63

<210> SEQ ID NO 236
<211> LENGTH: 82
<212> TYPE: RNA
<213> ORGANISM: Homo sapiens

<400> SEQUENCE: 236
ugagcuguug gauucggggc cguagcacug ucugagaggu uuacauuucu cacagugaac    60
cggucucuuu uucagcugcu uc                                             82

<210> SEQ ID NO 237
<211> LENGTH: 68
<212> TYPE: RNA
<213> ORGANISM: Homo sapiens

<400> SEQUENCE: 237
cucaggcuca guggugcaug cuuauagucc cagccacucu ggaggcugaa ggaagauggc    60
uugagccu                                                             68

<210> SEQ ID NO 238
<211> LENGTH: 63
<212> TYPE: RNA
<213> ORGANISM: Homo sapiens

<400> SEQUENCE: 238
cuugcccggg agaaggaggu ggccuggaga gcugcugucu ccagccgccg ccugucucca    60
cag                                                                  63

<210> SEQ ID NO 239
<211> LENGTH: 75
<212> TYPE: RNA
<213> ORGANISM: Homo sapiens

<400> SEQUENCE: 239
aagcaagacu gaggggccuc agaccgagcu uuuggaaaau agaaaagucu cgcucucugc    60
cccucagccu aacuu                                                     75

<210> SEQ ID NO 240
```

```
<211> LENGTH: 68
<212> TYPE: RNA
<213> ORGANISM: Homo sapiens

<400> SEQUENCE: 240
cguggugagg auauggcagg aagggagu uucccucuau ucccuucccc ccaguaaucu    60
ucaucaug                                                            68

<210> SEQ ID NO 241
<211> LENGTH: 86
<212> TYPE: RNA
<213> ORGANISM: Homo sapiens

<400> SEQUENCE: 241
ggggcugggg guguggggag agagagugca cagccagcuc agggauuaaa gcucuuucuc    60
ucucucucuc ucccacuucc cugcag                                         86

<210> SEQ ID NO 242
<211> LENGTH: 86
<212> TYPE: RNA
<213> ORGANISM: Homo sapiens

<400> SEQUENCE: 242
agggagaagg gucggggcag ggagggcagg gcaggcucug ggugggggg ucugugaguc    60 agccacggcu cugcccacgu cuccccc                                        86

<210> SEQ ID NO 243
<211> LENGTH: 73
<212> TYPE: RNA
<213> ORGANISM: Homo sapiens

<400> SEQUENCE: 243
cugguguuug aggcgaugug gggauguaga gacaacuucc cagucucauu uccucauccu    60
gccaggccac cau                                                       73

<210> SEQ ID NO 244
<211> LENGTH: 98
<212> TYPE: RNA
<213> ORGANISM: Homo sapiens

<400> SEQUENCE: 244
cuuggucaau aggaaagagg ugggaccucc uggcuuuucc ucugcagcau ggcucggacc    60
uagugcaaug uuuaagcucc ccucucuuuc cuguucag                            98

<210> SEQ ID NO 245
<211> LENGTH: 102
<212> TYPE: RNA
<213> ORGANISM: Homo sapiens

<400> SEQUENCE: 245
uguguucccu auccuccuua ugucccaccc ccacuccugu uugaauauuu caccagaaac    60
aggagugggg gguggggacgu aaggaggaug ggggaaagaa ca                      102

<210> SEQ ID NO 246
<211> LENGTH: 68
<212> TYPE: RNA
<213> ORGANISM: Homo sapiens

<400> SEQUENCE: 246
ugcccaggcu ggagcgagug cagguggugca gucaguccua gcucacugca gccucgaacu    60
```

```
                                               -continued ccugggcu                                                          68

<210> SEQ ID NO 247
<211> LENGTH: 83
<212> TYPE: RNA
<213> ORGANISM: Homo sapiens

<400> SEQUENCE: 247
aauagagggu gcacaggcac gggagcucag gugaggcagg gagcugagcu caccugaccu    60
cccaugccug ugcacccucu auu                                           83

<210> SEQ ID NO 248
<211> LENGTH: 76
<212> TYPE: RNA
<213> ORGANISM: Homo sapiens

<400> SEQUENCE: 248
acugacuuug agucucuccu cagggugcug caggcaaagc uggggaccca gggagagacg    60
uaagugaggg gagaug                                                   76

<210> SEQ ID NO 249
<211> LENGTH: 63
<212> TYPE: RNA
<213> ORGANISM: Homo sapiens

<400> SEQUENCE: 249
ugguggcggc gguaguuaug ggcuucucuu ucucaccagc agccccuggg ccgccgccuc    60
ccu                                                                 63

<210> SEQ ID NO 250
<211> LENGTH: 93
<212> TYPE: RNA
<213> ORGANISM: Homo sapiens

<400> SEQUENCE: 250
gcuuguuggg gauuggguca ggccaguguu caagggcccc uccucuagua cucccuguuu    60
guguucugcc acugacugag cuucuccca cag                                 93

<210> SEQ ID NO 251
<211> LENGTH: 57
<212> TYPE: RNA
<213> ORGANISM: Homo sapiens

<400> SEQUENCE: 251
cauuggaggg uguggaagac aucugggcca acucugaucu cuucaucuac cccccag       57

<210> SEQ ID NO 252
<211> LENGTH: 109
<212> TYPE: RNA
<213> ORGANISM: Homo sapiens

<400> SEQUENCE: 252
ggucgggcuc accaugacac agugugagac cucgggcuac aacacaggac ccgggcgcug    60
cucugacccc ucgugucuug uguugcagcc ggagggacgc agguccgca              109

<210> SEQ ID NO 253
<211> LENGTH: 68
<212> TYPE: RNA
<213> ORGANISM: Homo sapiens
```

<400> SEQUENCE: 253
gaauggaaga agaaggcggu cggucugcgg gagccaggcc gcagagccau ccgccuucug    60
uccauguc                                                              68

<210> SEQ ID NO 254
<211> LENGTH: 77
<212> TYPE: RNA
<213> ORGANISM: Homo sapiens

<400> SEQUENCE: 254
gaguugggag guucccucuc caaauguguc uugaucccccc accccaagac acauuuggag    60
agggacccuc ccaacuc                                                    77

<210> SEQ ID NO 255
<211> LENGTH: 66
<212> TYPE: RNA
<213> ORGANISM: Homo sapiens

<400> SEQUENCE: 255
gggaggaggg aggagauggg ccaaguuccc ucuggcugga acgcccuucc cccccuucuu    60
caccug                                                                66

<210> SEQ ID NO 256
<211> LENGTH: 98
<212> TYPE: RNA
<213> ORGANISM: Homo sapiens

<400> SEQUENCE: 256
uugggcaagg ugcggggcua gggcuaacag cagucuuacu gaagguuucc uggaaaccac    60
gcacaugcug uugccacuaa ccucaaccuu acucgguc                             98

<210> SEQ ID NO 257
<211> LENGTH: 67
<212> TYPE: RNA
<213> ORGANISM: Homo sapiens

<400> SEQUENCE: 257
gcgcccuccc ucucuccccg gugugcaaau gugugugugc gguguuaugc cggacaagag    60
ggaggug                                                               67

<210> SEQ ID NO 258
<211> LENGTH: 73
<212> TYPE: RNA
<213> ORGANISM: Homo sapiens

<400> SEQUENCE: 258
gugggcgggg gcaggugugu gguggguggu ggccugcggu gagcagggcc cucacaccug    60
ccucgccccc cag                                                        73

<210> SEQ ID NO 259
<211> LENGTH: 82
<212> TYPE: RNA
<213> ORGANISM: Homo sapiens

<400> SEQUENCE: 259
ugugggcagg gcccugggga gcugaggcuc uggggguggc cggggcugac ccugggccuc    60
ugcuccccag ugucugaccg cg                                              82

```
<210> SEQ ID NO 260
<211> LENGTH: 61
<212> TYPE: RNA
<213> ORGANISM: Homo sapiens

<400> SEQUENCE: 260
aacugcgggg ccagagcaga gagcccuugc acaccaccag ccucuccucc cugugcccca    60
g                                                                   61

<210> SEQ ID NO 261
<211> LENGTH: 79
<212> TYPE: RNA
<213> ORGANISM: Homo sapiens

<400> SEQUENCE: 261
gugcagaucc uugggagccc uguuagacuc uggauuuuac acuggagug aacgggcgcc    60 aucccgaggc uuugcacag                                                79

<210> SEQ ID NO 262
<211> LENGTH: 99
<212> TYPE: RNA
<213> ORGANISM: Homo sapiens

<400> SEQUENCE: 262
gcaagggaca gggagggucg uggcgacacu cgcgccagcu cccgggacgg cugggcucgg    60
gcuggucgcc gaccuccgac ccuccacuag augccuggc                          99

<210> SEQ ID NO 263
<211> LENGTH: 65
<212> TYPE: RNA
<213> ORGANISM: Homo sapiens

<400> SEQUENCE: 263
gagggugggc gagggcggcu gagcggcucc auccccggc cugcucaucc cccucgcccu    60
cucag                                                               65

<210> SEQ ID NO 264
<211> LENGTH: 61
<212> TYPE: RNA
<213> ORGANISM: Homo sapiens

<400> SEQUENCE: 264
gagggcagcg uggguguggc ggaggcaggc gugaccguuu ccgcccucu cgcugcucua    60 g                                                                   61

<210> SEQ ID NO 265
<211> LENGTH: 96
<212> TYPE: RNA
<213> ORGANISM: Homo sapiens

<400> SEQUENCE: 265
cucgggaggg gcgggagggg gguccccggu gcucggaucu cgagggugcu uauuguucgg    60
uccgagccug ggucucccuc uucccccaa cccccc                              96

<210> SEQ ID NO 266
<211> LENGTH: 92
<212> TYPE: RNA
<213> ORGANISM: Homo sapiens

<400> SEQUENCE: 266
```

```
cgcugcgcuu cugggcccgc ggcgggcgug gggcugcccg ggccggucga ccagcgcgcc    60
guagcucccg aggcccgagc cgcgacccgc gg                                  92
```

<210> SEQ ID NO 267
<211> LENGTH: 67
<212> TYPE: RNA
<213> ORGANISM: Homo sapiens

<400> SEQUENCE: 267

```
gugggagggg agaggcagca agcacacagg gccugggacu agcaugcuga ccucccuccu    60
gccccag                                                              67
```

<210> SEQ ID NO 268
<211> LENGTH: 60
<212> TYPE: RNA
<213> ORGANISM: Homo sapiens

<400> SEQUENCE: 268

```
aggccuaggg gguggcaggc uggccaucag uguggcuaa cccuguccuc ucccucccag    60
```

<210> SEQ ID NO 269
<211> LENGTH: 66
<212> TYPE: RNA
<213> ORGANISM: Homo sapiens

<400> SEQUENCE: 269

```
ccgagugggg cggggcaggu cccugcaggg acugugacac ugaaggaccu gcaccuucgc    60
ccacag                                                               66
```

<210> SEQ ID NO 270
<211> LENGTH: 74
<212> TYPE: RNA
<213> ORGANISM: Homo sapiens

<400> SEQUENCE: 270

```
ccugcaggag gcagugggcg agcaggcggg gcagcccaau gccaugggcc ugaucucacc    60
gcugccuccu uccc                                                      74
```

<210> SEQ ID NO 271
<211> LENGTH: 51
<212> TYPE: RNA
<213> ORGANISM: Homo sapiens

<400> SEQUENCE: 271

```
agagaugaag cgggggggcg gggucuugcu cuauugccua cgcugaucuc a             51
```

<210> SEQ ID NO 272
<211> LENGTH: 68
<212> TYPE: RNA
<213> ORGANISM: Homo sapiens

<400> SEQUENCE: 272

```
gugcaaagag caggaggaca ggggauuuau cucccaaggg aggucccug auccaguca     60 cggcacca                                                             68
```

<210> SEQ ID NO 273
<211> LENGTH: 73
<212> TYPE: RNA
<213> ORGANISM: Homo sapiens

<400> SEQUENCE: 273

```
ggcgagggga ggcgcaggcu cggaaaggcg cgcgaggcuc caggcuccuu cccgauccac    60
cgcucuccuc gcu                                                      73

<210> SEQ ID NO 274
<211> LENGTH: 96
<212> TYPE: RNA
<213> ORGANISM: Homo sapiens

<400> SEQUENCE: 274
gcucuggggc gugccgccgc cgucgcugcc accuccccua ccgcuagugg aagaagaugg    60
cggaaggcgg agcggcggau cuggacaccc agcggu                             96

<210> SEQ ID NO 275
<211> LENGTH: 81
<212> TYPE: RNA
<213> ORGANISM: Homo sapiens

<400> SEQUENCE: 275
cauccuccuu acgucccacc ccccacuccu guuucggug aaauauucaa acaggagugg     60 ggugggaca uaaggaggau a                                              81

<210> SEQ ID NO 276
<211> LENGTH: 65
<212> TYPE: RNA
<213> ORGANISM: Homo sapiens

<400> SEQUENCE: 276
gggugcucgg ggcaggcggc ugggagcggc ccucacauug auggcuccug ccaccuccuc    60
cgcag                                                               65

<210> SEQ ID NO 277
<211> LENGTH: 82
<212> TYPE: RNA
<213> ORGANISM: Homo sapiens

<400> SEQUENCE: 277
gcuacgggga gcgggagga aguggcgcu gcuucugcgu uaucuggaag gagcagccca      60
cuccuguccu gggcucugug gu                                            82

<210> SEQ ID NO 278
<211> LENGTH: 103
<212> TYPE: RNA
<213> ORGANISM: Homo sapiens

<400> SEQUENCE: 278
gugucggcug uggcgugacu gucccucugu gucccccacu aggccacugu cucaguggag    60
cguggaggac gaggaggagg ccguccacga gcaaugccag cau                    103

<210> SEQ ID NO 279
<211> LENGTH: 62
<212> TYPE: RNA
<213> ORGANISM: Homo sapiens

<400> SEQUENCE: 279
uggccuaggg ggcggcuugu ggaguguaug ggcugagccu ugcucugcuc cccgccccc     60 ag                                                                  62

<210> SEQ ID NO 280
```

```
<211> LENGTH: 72
<212> TYPE: RNA
<213> ORGANISM: Homo sapiens

<400> SEQUENCE: 280
augagcgggu gggagcagau cuuauugaga guuccuucuc cugcuccuga uugucuuccc    60
ccacccucac ag                                                       72

<210> SEQ ID NO 281
<211> LENGTH: 80
<212> TYPE: RNA
<213> ORGANISM: Homo sapiens

<400> SEQUENCE: 281
accucuaccu cccggcagag gaggcugcag aggcuggcuu ccaaaacuc ugcccccucc    60 gcugcugcca aguggcuggu                                               80

<210> SEQ ID NO 282
<211> LENGTH: 64
<212> TYPE: RNA
<213> ORGANISM: Homo sapiens

<400> SEQUENCE: 282
ucugggcgag ggugggcuc ucagagggc uggcaguacu gcucugaggc cugccucucc    60
ccag                                                               64

<210> SEQ ID NO 283
<211> LENGTH: 98
<212> TYPE: RNA
<213> ORGANISM: Homo sapiens

<400> SEQUENCE: 283 uucucaccc cgccugacac gggcgacagc ugcggcccgc uguucacu cgggccgagu    60 gcgucuccug ucaggcaagg gagagcagag ccccccug                          98

<210> SEQ ID NO 284
<211> LENGTH: 97
<212> TYPE: RNA
<213> ORGANISM: Homo sapiens

<400> SEQUENCE: 284
cccgggaccu ugguccaggc gcuggucugc guggugcucg gguggauaag ucugaucuga    60
gcaccacaca ggccgggcgc cgggaccaag ggggcuc                           97

<210> SEQ ID NO 285
<211> LENGTH: 69
<212> TYPE: RNA
<213> ORGANISM: Homo sapiens

<400> SEQUENCE: 285
ccgggcaggc agguguaggg uggagcccac uguggcuccu gacucagccc ugcugccuuc    60
accugccag                                                          69

<210> SEQ ID NO 286
<211> LENGTH: 64
<212> TYPE: RNA
<213> ORGANISM: Homo sapiens

<400> SEQUENCE: 286
gaggcacugg guaggugggg cuccagggcu ccugacaccu ggaccucucc ucccaggcc    60
```

```
caca                                                                64

<210> SEQ ID NO 287
<211> LENGTH: 66
<212> TYPE: RNA
<213> ORGANISM: Homo sapiens

<400> SEQUENCE: 287
agcagcccuc ggcggcccgg ggggcgggcg gcggugcccg ucccggggcu gcgcgaggca     60
caggcg                                                               66

<210> SEQ ID NO 288
<211> LENGTH: 65
<212> TYPE: RNA
<213> ORGANISM: Homo sapiens

<400> SEQUENCE: 288
agcccugggg guggucucua gccaaggcuc uggggucuca cccuuggcug gucucugcuc     60
cgcag                                                                65

<210> SEQ ID NO 289
<211> LENGTH: 55
<212> TYPE: RNA
<213> ORGANISM: Homo sapiens

<400> SEQUENCE: 289
ccggauccga gucacggcac caaauuucau gcguguccgu gugaagagac cacca          55

<210> SEQ ID NO 290
<211> LENGTH: 115
<212> TYPE: RNA
<213> ORGANISM: Homo sapiens

<400> SEQUENCE: 290
gagcaaaaac cagagaacaa caugggagcg uuccuaaccc cuaaggcaac uggaugggag     60
accugaccca uccaguucuc ugaggggcu cuugugucuu cuacaagguu guuca          115

<210> SEQ ID NO 291
<211> LENGTH: 115
<212> TYPE: RNA
<213> ORGANISM: Homo sapiens

<400> SEQUENCE: 291
ggugccgagg gccguccggc auccuaggcg ggucgcugcg guaccucccu ccugucugug     60 gcgguggau cccguggccg uguuuccug guggcccggc cgugccugag guuuc           115

<210> SEQ ID NO 292
<211> LENGTH: 87
<212> TYPE: RNA
<213> ORGANISM: Homo sapiens

<400> SEQUENCE: 292
gugaggcggg gccaggaggg uguguggcgu gggugcugcg gggccgucag ggugccugcg     60
ggacgcucac cuggcuggcc cgcccag                                        87

<210> SEQ ID NO 293
<211> LENGTH: 86
<212> TYPE: RNA
<213> ORGANISM: Homo sapiens
```

```
<400> SEQUENCE: 293
auucuaggug gggagacuga cggcuggagg cccauaagcu gucuaaaacu ucggccccca    60
gauuucuggu cucccacuu cagaac                                         86

<210> SEQ ID NO 294
<211> LENGTH: 90
<212> TYPE: RNA
<213> ORGANISM: Homo sapiens

<400> SEQUENCE: 294
ucuaagaaac gcaguggucu cugaagccug caggggcagg ccagcccugc acugaacgcc   60
uguucuugcc agguggcaga agguugcugc                                    90

<210> SEQ ID NO 295
<211> LENGTH: 81
<212> TYPE: RNA
<213> ORGANISM: Homo sapiens

<400> SEQUENCE: 295
cucccuggga gggcguggau gaugguggga gaggagcccc acuguggaag ucgaccccc    60 acaucgcccc accuucccca g                                             81

<210> SEQ ID NO 296
<211> LENGTH: 66
<212> TYPE: RNA
<213> ORGANISM: Homo sapiens

<400> SEQUENCE: 296
ucaagacggg gagucaggca gugguggaga uggagagccc ugagccucca cucuccuggc   60
ccccag                                                              66

<210> SEQ ID NO 297
<211> LENGTH: 94
<212> TYPE: RNA
<213> ORGANISM: Homo sapiens

<400> SEQUENCE: 297
gugaggugug ggcccggccc caggagcggg gccugggcag ccccgugugu ugaggaagga   60
aggcagggcc cccgcucccc gggccugacc ccac                               94

<210> SEQ ID NO 298
<211> LENGTH: 90
<212> TYPE: RNA
<213> ORGANISM: Homo sapiens

<400> SEQUENCE: 298 cgggcgggc gggguccggcc gccuccgagc ccggccggca gccccggcc uuaaagcgcg    60 ggcuguccgg aggggucggc uuucccaccg                                    90

<210> SEQ ID NO 299
<211> LENGTH: 60
<212> TYPE: RNA
<213> ORGANISM: Homo sapiens

<400> SEQUENCE: 299
caaggugggg gagauggggg uugaacuuca uuucucaugc ucaucccau cuccuuucag    60

<210> SEQ ID NO 300
<211> LENGTH: 109
```

-continued

```
<212> TYPE: RNA
<213> ORGANISM: Homo sapiens

<400> SEQUENCE: 300
ucccgcauuc ccucugcuuu ggucaggugg ugcccuccuu ccauggguag agccagagau    60
gguggguucu ggcuggucag augggagugg acagagaccc ggggguccuc              109

<210> SEQ ID NO 301
<211> LENGTH: 84
<212> TYPE: RNA
<213> ORGANISM: Homo sapiens

<400> SEQUENCE: 301
cuccccaugg cccugucucc caacccuugu accagugcug ggcucagacc cugguacagg    60 ccuggggac agggaccugg ggac                                            84

<210> SEQ ID NO 302
<211> LENGTH: 80
<212> TYPE: RNA
<213> ORGANISM: Homo sapiens

<400> SEQUENCE: 302
gguuccggag ccccggcgcg ggcggguucu gggguguaga cgcugcuggc cagcccgccc    60
cagccgaggu ucucggcacc                                                80

<210> SEQ ID NO 303
<211> LENGTH: 80
<212> TYPE: RNA
<213> ORGANISM: Homo sapiens

<400> SEQUENCE: 303
ugagaggccg caccuugccu ugcugcccgg gccgugcacc cgugggcccc agggcgacgc    60
ggcgggggcg gcccuagcga                                                80

<210> SEQ ID NO 304
<211> LENGTH: 106
<212> TYPE: RNA
<213> ORGANISM: Homo sapiens

<400> SEQUENCE: 304
agaagaaugc ccaaccagcc cucaguugcu acaguucccu guuguuucag cucgacaaca    60
acaggcggcu guagcaaugg ggggcuggau gggcaucuca augugc                   106

<210> SEQ ID NO 305
<211> LENGTH: 86
<212> TYPE: RNA
<213> ORGANISM: Homo sapiens

<400> SEQUENCE: 305
agcacugccc ccggugaguc agggugggge uggccccug cuucgugccc auccgcgcuc     60
ugacucucug cccaccugca ggagcu                                         86

<210> SEQ ID NO 306
<211> LENGTH: 53
<212> TYPE: RNA
<213> ORGANISM: Homo sapiens

<400> SEQUENCE: 306 ggugggguu ggaggcgugg guuuuagaac cuaucccuuu cuagcccuga gca            53
```

```
<210> SEQ ID NO 307
<211> LENGTH: 80
<212> TYPE: RNA
<213> ORGANISM: Homo sapiens

<400> SEQUENCE: 307
cgugugagcc cgcccugugc ccggcccacu ucugcuuccu cuuagcgcag gagggguccc      60
gcacugggag gggcccucac                                                  80

<210> SEQ ID NO 308
<211> LENGTH: 79
<212> TYPE: RNA
<213> ORGANISM: Homo sapiens

<400> SEQUENCE: 308 gugaggugggg ggccagcagg gagugggcug ggcugggcug ggccaaggua caaggccuca     60
cccugcaucc cgcacccag                                                   79

<210> SEQ ID NO 309
<211> LENGTH: 50
<212> TYPE: RNA
<213> ORGANISM: Homo sapiens

<400> SEQUENCE: 309
acccgggcgu gguggugggg gugggugccu guaauuccag cuaguuggga                 50

<210> SEQ ID NO 310
<211> LENGTH: 88
<212> TYPE: RNA
<213> ORGANISM: Homo sapiens

<400> SEQUENCE: 310
guggggccag gcgguggugg gcacugcugg ggugggcaca gcagccaugc agagcgggca      60
uuugaccccg ugccacccuu uuccccag                                         88

<210> SEQ ID NO 311
<211> LENGTH: 62
<212> TYPE: RNA
<213> ORGANISM: Homo sapiens

<400> SEQUENCE: 311 gagggugguug gaggaagagg gcagcuccca ugacugccug accgccuucu cuccucccc      60 ag                                                                     62

<210> SEQ ID NO 312
<211> LENGTH: 73
<212> TYPE: RNA
<213> ORGANISM: Homo sapiens

<400> SEQUENCE: 312
gaaaacaacc aggugggcuu cccggagggc ggaacaccca gccccagcau ccagggcuca      60
ccuaccacgu uug                                                         73

<210> SEQ ID NO 313
<211> LENGTH: 65
<212> TYPE: RNA
<213> ORGANISM: Homo sapiens

<400> SEQUENCE: 313
gagggcuagg uggggggcuu gaagcccga gaugccucac gucuucaccc cucucaccua       60
```

```
agcag                                                               65

<210> SEQ ID NO 314
<211> LENGTH: 73
<212> TYPE: RNA
<213> ORGANISM: Homo sapiens

<400> SEQUENCE: 314
aggccaggug gguauggagg agcccucaua uggcaguugg cgagggccca gugagcccu     60 cucugcucuc cag                                                      73

<210> SEQ ID NO 315
<211> LENGTH: 93
<212> TYPE: RNA
<213> ORGANISM: Homo sapiens

<400> SEQUENCE: 315
ccuuccggcg ucccaggcgg ggcgccgcgg gaccgcccuc gugucugugg cgguggaauc    60
ccgcggccgu guuuuccugg uggcccggcc aug                                93

<210> SEQ ID NO 316
<211> LENGTH: 87
<212> TYPE: RNA
<213> ORGANISM: Homo sapiens

<400> SEQUENCE: 316
cccucaucuc ugggcagggg cuuauuguag gagucucuga agagagcugu ggacugaccu    60
gcuuuaaccc uuccccaggu ucccauu                                       87

<210> SEQ ID NO 317
<211> LENGTH: 51
<212> TYPE: RNA
<213> ORGANISM: Homo sapiens

<400> SEQUENCE: 317
acagaccccg gggagcccgg cggugaagcu ccugguaucc uggguguucug a             51

<210> SEQ ID NO 318
<211> LENGTH: 49
<212> TYPE: RNA
<213> ORGANISM: Homo sapiens

<400> SEQUENCE: 318
uucccagcca acgcaccaaa aaugauaugg gucuguuguc uggagaaac               49

<210> SEQ ID NO 319
<211> LENGTH: 96
<212> TYPE: RNA
<213> ORGANISM: Homo sapiens

<400> SEQUENCE: 319
cgggccccgg gcgggcggga gggacgggac gcggugcagu guuguuuuuu ccccgccaa    60 uauugcacuc gucccggccu ccggcccccc cggccc                             96

<210> SEQ ID NO 320
<211> LENGTH: 67
<212> TYPE: RNA
<213> ORGANISM: Homo sapiens

<400> SEQUENCE: 320
```

<210> SEQ ID NO 321
<211> LENGTH: 89
<212> TYPE: RNA
<213> ORGANISM: Homo sapiens

<400> SEQUENCE: 321
agccugsugg aaagagaaga gcagggcagg gugaaggccc ggcggagaca cucugcccac    60
cccacacccu gccaugggc cacacagcu    89

<210> SEQ ID NO 322
<211> LENGTH: 70
<212> TYPE: RNA
<213> ORGANISM: Homo sapiens

<400> SEQUENCE: 322
cucgggcccg accgcgccgg cccgcaccuc ccggcccgga gcugcgggcu gcggucaggg    60
cgaucccggg    70

<210> SEQ ID NO 323
<211> LENGTH: 79
<212> TYPE: RNA
<213> ORGANISM: Homo sapiens

<400> SEQUENCE: 323
cucgaggugc uggggacgc gugagcgcga gccgcuuccu cacggcucgg ccgcggcgcg    60 uagccccgc cacaucggg    79

<210> SEQ ID NO 324
<211> LENGTH: 94
<212> TYPE: RNA
<213> ORGANISM: Homo sapiens

<400> SEQUENCE: 324
auaaaggaag uuaggcugag gggcagagag cgagacuuuu cuauuuucca aaagcucggu    60
cugaggcccc ucagucuugc uuccuaaccc gcgc    94

<210> SEQ ID NO 325
<211> LENGTH: 47
<212> TYPE: RNA
<213> ORGANISM: Homo sapiens

<400> SEQUENCE: 325
cucggcgcgg ggcgcgggcu ccggguuggg gcgagccaac gccgggg    47

<210> SEQ ID NO 326
<211> LENGTH: 77
<212> TYPE: RNA
<213> ORGANISM: Homo sapiens

<400> SEQUENCE: 326
caugagaaau ccugcugguc aaccauagcc cuggucagac ucuccggggc ugugauugac    60
cagcaggacu ucucaug    77

<210> SEQ ID NO 327
<211> LENGTH: 80
<212> TYPE: RNA
<213> ORGANISM: Homo sapiens

```
<400> SEQUENCE: 327
gagaggccaa gaccuuggga auggggguaa gggccuucug agcccagguc cgaacucucc    60
auuccucugc agagcgcucu                                                80

<210> SEQ ID NO 328
<211> LENGTH: 70
<212> TYPE: RNA
<213> ORGANISM: Homo sapiens

<400> SEQUENCE: 328
ggccgcggcg cgcaagaugg cggcgggccc gggcaccgcc ccuuccgccc cgccgggcgu    60
cgcacgaggc                                                          70

<210> SEQ ID NO 329
<211> LENGTH: 62
<212> TYPE: RNA
<213> ORGANISM: Homo sapiens

<400> SEQUENCE: 329
gcuggggguc ccccgacagu guggagcugg ggccgggucc ggggaggggg gguucugggc    60
ag                                                                  62

<210> SEQ ID NO 330
<211> LENGTH: 62
<212> TYPE: RNA
<213> ORGANISM: Homo sapiens

<400> SEQUENCE: 330
ccuucugcgg cagagcuggg gucaccagcc cucauguacu ugugacuucu ccccugccac    60
ag                                                                  62

<210> SEQ ID NO 331
<211> LENGTH: 68
<212> TYPE: RNA
<213> ORGANISM: Homo sapiens

<400> SEQUENCE: 331
aggguugggg ggacaggaug agaggcuguc uucauuccou cuugaccacc ccucguuucu    60
uccccccag                                                           68

<210> SEQ ID NO 332
<211> LENGTH: 64
<212> TYPE: RNA
<213> ORGANISM: Homo sapiens

<400> SEQUENCE: 332
gagcucuggg aggggcuggg uuuggcagga caguuuccaa gcccugcucu cucccaucuu    60
ccag                                                                64

<210> SEQ ID NO 333
<211> LENGTH: 65
<212> TYPE: RNA
<213> ORGANISM: Homo sapiens

<400> SEQUENCE: 333
gucuccuggg gggaggagac ccugcucucc cuggcagcaa gccucuccug cccuuccaga    60
uuagc                                                               65
```

<210> SEQ ID NO 334
<211> LENGTH: 67
<212> TYPE: RNA
<213> ORGANISM: Homo sapiens

<400> SEQUENCE: 334
ggcagccagg gggaugggcg agcuugggcc cauuccuuuc cuuacccuac cccccauccc    60
ccuguag                                                             67

<210> SEQ ID NO 335
<211> LENGTH: 72
<212> TYPE: RNA
<213> ORGANISM: Homo sapiens

<400> SEQUENCE: 335
ugugggacug caaaugggag cucagcaccu gccugccacc cacgcagacc agcccugcu    60 cuguucccac ag                                                       72

<210> SEQ ID NO 336
<211> LENGTH: 81
<212> TYPE: RNA
<213> ORGANISM: Homo sapiens

<400> SEQUENCE: 336
uacaggugca ggggaacugu agaugaaaag gcuuggcacu ugagggaaag ccucaguuca    60
uucucauuuu gcucaccugu u                                             81

<210> SEQ ID NO 337
<211> LENGTH: 109
<212> TYPE: RNA
<213> ORGANISM: Homo sapiens

<400> SEQUENCE: 337
ugcuauuguc uuacugcuac agcagggcug gggauugcag uauccgcugu ugcugcugcu    60
cccaguccug ccccugcugc uaccuagucc agccucaccg caucccaga              109

<210> SEQ ID NO 338
<211> LENGTH: 80
<212> TYPE: RNA
<213> ORGANISM: Homo sapiens

<400> SEQUENCE: 338
cugcagcgug cuucuccagg ccccgcgcgc ggacagacac acggacaagu cccgccaggg    60
gcugggcgcg cgccagccgg                                               80

<210> SEQ ID NO 339
<211> LENGTH: 80
<212> TYPE: RNA
<213> ORGANISM: Homo sapiens

<400> SEQUENCE: 339
ugccgucggc cuggggagga ggaagggcaa guccaaaggu auacaguugg ucguucauu    60 cucucuuuuu ggccuacaag                                               80

<210> SEQ ID NO 340
<211> LENGTH: 84
<212> TYPE: RNA
<213> ORGANISM: Homo sapiens

<400> SEQUENCE: 340

```
ccgcagccgc cgcgccgggc ccggguuggc cgcugacccc cgcggggccc ccggcggccg    60 gggcggggc gggggcugcc ccgg                                            84

<210> SEQ ID NO 341
<211> LENGTH: 153
<212> TYPE: RNA
<213> ORGANISM: Homo sapiens

<400> SEQUENCE: 341
gcuccgcccc acgucgcaug cgccccggga acgcgugggg cggagcuucc ggaggccccg    60
cucugcugcc gacccugugg agcggagggu gaagccuccg gaugccaguc ccucaucgcu   120
ggccuggucg cgcuguggcg aaggggggcgg agc                                153

<210> SEQ ID NO 342
<211> LENGTH: 153
<212> TYPE: RNA
<213> ORGANISM: Homo sapiens

<400> SEQUENCE: 342
gcuccgcccc acgucgcaug cgccccggga acgcgugggg cggagcuucc ggaggccccg    60
cccugcugcc gacccugugg agcggagggu gaagccuccg gaugccaguc ccucaucgcu   120
ggcccggucg cgcuguggcg aaggggcgg agc                                  153

<210> SEQ ID NO 343
<211> LENGTH: 80
<212> TYPE: RNA
<213> ORGANISM: Homo sapiens

<400> SEQUENCE: 343
aggacccuuc cagagggccc ccccucaauc cuguugugcc uaauucagag gguuggguggg   60 aggcucuccu gaagggcucu                                                80

<210> SEQ ID NO 344
<211> LENGTH: 94
<212> TYPE: RNA
<213> ORGANISM: Homo sapiens

<400> SEQUENCE: 344
cgggcagcgg gugccaggca cggugucagc aggcaacaug gccagagagc cggggccucc    60
gggcggcgcc guguccgcga ccgcguaccc ugac                                94

<210> SEQ ID NO 345
<211> LENGTH: 52
<212> TYPE: RNA
<213> ORGANISM: Homo sapiens

<400> SEQUENCE: 345
uagccgggcg ugguggugggg ggccuguggu cccagcuacu uuggaggcug ag            52

<210> SEQ ID NO 346
<211> LENGTH: 70
<212> TYPE: RNA
<213> ORGANISM: Homo sapiens

<400> SEQUENCE: 346
gucccugggg gcugggaugg gccauggugu gcucugaucc cccugugguc ucuggcccc     60 caggaacucc                                                           70
```

<210> SEQ ID NO 347
<211> LENGTH: 83
<212> TYPE: RNA
<213> ORGANISM: Homo sapiens

<400> SEQUENCE: 347
ggcccggcuc cgggucucgg cccguacagu ccggccggcc augcuggcgg ggcuggggcc    60
ggggccgagc ccgcggcggg gcc                                           83

<210> SEQ ID NO 348
<211> LENGTH: 90
<212> TYPE: RNA
<213> ORGANISM: Homo sapiens

<400> SEQUENCE: 348
ggcgccucug cagcuccggc uccccuggc cucucgggaa cuacaagucc caggggccu      60 ggcggugggc ggcgggcgga agaggcgggg                                    90

<210> SEQ ID NO 349
<211> LENGTH: 85
<212> TYPE: RNA
<213> ORGANISM: Homo sapiens

<400> SEQUENCE: 349
uccuccccgg agccaggaug cagcucaagc cacagcaggg uguuuagcgc ucuucagugg    60
cuccagauug uggcgcuggu gcagg                                         85

<210> SEQ ID NO 350
<211> LENGTH: 89
<212> TYPE: RNA
<213> ORGANISM: Homo sapiens

<400> SEQUENCE: 350
ucuccguuua ucccaccacu gccaccauua uugcuacugu ucagcaggug cugcuggugg    60
ugauggugau agucuggugg gggcggugg                                     89

<210> SEQ ID NO 351
<211> LENGTH: 70
<212> TYPE: RNA
<213> ORGANISM: Homo sapiens

<400> SEQUENCE: 351
aaaagccugu cccuaagucc cucccagccu uccagaguug gugccaggaa ggauuuaggg    60
acaggcuuug                                                          70

<210> SEQ ID NO 352
<211> LENGTH: 66
<212> TYPE: RNA
<213> ORGANISM: Homo sapiens

<400> SEQUENCE: 352
ccuggagggg ggcacugcgc aagcaaagcc agggacccug agaggcuuug cuuccugcuc    60
cccuag                                                              66

<210> SEQ ID NO 353
<211> LENGTH: 62
<212> TYPE: RNA
<213> ORGANISM: Homo sapiens

<400> SEQUENCE: 353

```
cuuccuggug ggugggagg agaagugccg uccucaugag ccccucucug ucccacccau    60
ag                                                                 62

<210> SEQ ID NO 354
<211> LENGTH: 97
<212> TYPE: RNA
<213> ORGANISM: Homo sapiens

<400> SEQUENCE: 354
cucaggugcu cuggcugcuu ggguuccugg caugcugauu ugugacuuaa gauuaaaauc   60
acauugccag ggauuaccac gcaaccacga ccuuggc                           97

<210> SEQ ID NO 355
<211> LENGTH: 85
<212> TYPE: RNA
<213> ORGANISM: Homo sapiens

<400> SEQUENCE: 355
gugagcugcu ggggacgcgg gucgggucu gcagggcggu gcggcagccg ccaccugacg    60
ccgcgccuuu gucugugucc cacag                                        85

<210> SEQ ID NO 356
<211> LENGTH: 83
<212> TYPE: RNA
<213> ORGANISM: Homo sapiens

<400> SEQUENCE: 356
gucuacuccc agggugccaa gcuguuucgu guucccuccc uaggggaucc cagguagggg   60
cagcagagga ccugggccug gac                                          83

<210> SEQ ID NO 357
<211> LENGTH: 93
<212> TYPE: RNA
<213> ORGANISM: Homo sapiens

<400> SEQUENCE: 357
uacuuauggc accccacucc ugguaccaua gucauaaguu aggagauguu agagcuguga   60
guaccaugac uuaaguguggug uggcuuaaac aug                             93

<210> SEQ ID NO 358
<211> LENGTH: 90
<212> TYPE: RNA
<213> ORGANISM: Homo sapiens

<400> SEQUENCE: 358
cugugggcug ggccagggag cagcuggugg gugggaagua agaucugacc uggacuccau   60
cccacccacc cccuguuucc uggcccacag                                   90

<210> SEQ ID NO 359
<211> LENGTH: 74
<212> TYPE: RNA
<213> ORGANISM: Homo sapiens

<400> SEQUENCE: 359
gggaggaaga agggaggagg agcggagggg cccuugucuu cccagagccu cucccuuccu   60
ccccuccccc uccc                                                    74

<210> SEQ ID NO 360
```

```
<211> LENGTH: 73
<212> TYPE: RNA
<213> ORGANISM: Homo sapiens

<400> SEQUENCE: 360
accuuuccag cucaucccac cucugccacc aaaacacuca ucgcggguc agagggagug    60 ccaaaaaagg uaa                                                      73

<210> SEQ ID NO 361
<211> LENGTH: 70
<212> TYPE: RNA
<213> ORGANISM: Homo sapiens

<400> SEQUENCE: 361
cacagucuga cucagugacu caugugcugg caguggccac guaaauagag cuacuguguc    60
ugaaagcaau                                                          70

<210> SEQ ID NO 362
<211> LENGTH: 65
<212> TYPE: RNA
<213> ORGANISM: Homo sapiens

<400> SEQUENCE: 362
gcuucuggga ggaggggauc uugggaguga ucccaacagc ugagcucccu gaaucccugu    60
cccag                                                               65

<210> SEQ ID NO 363
<211> LENGTH: 84
<212> TYPE: RNA
<213> ORGANISM: Homo sapiens

<400> SEQUENCE: 363
ugugcagugg aaggggggc cgauacacug uacgagagug aguagcaggu cucacaguga    60
accggucucu uucccuacug uguc                                          84

<210> SEQ ID NO 364
<211> LENGTH: 86
<212> TYPE: RNA
<213> ORGANISM: Homo sapiens

<400> SEQUENCE: 364
ugccagucuc uagguccug agacccuuua accugugagg acauccaggg ucacagguga    60
gguucuuggg agccuggcgu cuggcc                                        86

<210> SEQ ID NO 365
<211> LENGTH: 75
<212> TYPE: RNA
<213> ORGANISM: Homo sapiens

<400> SEQUENCE: 365
ucaucccugg gugggauuu guugcauuac uuguguucua uauaaaguau ugcacuuguc    60
ccggccugug gaaga                                                    75

<210> SEQ ID NO 366
<211> LENGTH: 68
<212> TYPE: RNA
<213> ORGANISM: Homo sapiens

<400> SEQUENCE: 366
gcauccugua cugagcugcc ccgaggcccu ucaugcugcc cagcucgggg cagcucagua    60
``` caggauac                                                              68

<210> SEQ ID NO 367
<211> LENGTH: 64
<212> TYPE: RNA
<213> ORGANISM: Homo sapiens

<400> SEQUENCE: 367
uccuguacug agcugccccg agcugggcag caugaagggc cucggggcag cucaguacag     60
gaug                                                                  64

<210> SEQ ID NO 368
<211> LENGTH: 64
<212> TYPE: RNA
<213> ORGANISM: Homo sapiens

<400> SEQUENCE: 368 ggguggggc ggggcggcag gggccucccc cagugccagg ccccauucug cuucucuccc      60
agcu                                                                  64

<210> SEQ ID NO 369
<211> LENGTH: 110
<212> TYPE: RNA
<213> ORGANISM: Homo sapiens

<400> SEQUENCE: 369
ucaccuggcc augugacuug ugggcuuccc uuugucaucc uucgccuagg gcucugagca     60
gggcagggac agcaaagggg ugcucaguug ucacuuccca cagcacggag               110

<210> SEQ ID NO 370
<211> LENGTH: 67
<212> TYPE: RNA
<213> ORGANISM: Homo sapiens

<400> SEQUENCE: 370
aaaucucucu ccauaucuuu ccugcagccc ccaggugggg gggaagaaaa gguggggaau     60
uagauuc                                                               67

<210> SEQ ID NO 371
<211> LENGTH: 67
<212> TYPE: RNA
<213> ORGANISM: Homo sapiens

<400> SEQUENCE: 371
cagggaggag gugguacuag gggccagcaa ccugauuacc ccucuuuggc ccuuuguacc     60
ccuccag                                                               67

<210> SEQ ID NO 372
<211> LENGTH: 89
<212> TYPE: RNA
<213> ORGANISM: Homo sapiens

<400> SEQUENCE: 372
gccggcgccc gagcucuggc uccgugucuu cacucccgug cuuguccgag gagggaggga     60
gggacggggg cugugcuggg gcagcugga                                       89

<210> SEQ ID NO 373
<211> LENGTH: 66
<212> TYPE: RNA

<213> ORGANISM: Homo sapiens

<400> SEQUENCE: 373
ugacugggga gcagaaggag aacccaagaa aagcugacuu ggaggucccu ccuucugucc    60
ccacag    66

<210> SEQ ID NO 374
<211> LENGTH: 90
<212> TYPE: RNA
<213> ORGANISM: Homo sapiens

<400> SEQUENCE: 374
aggccucgcu guucucuaug gcuuuuauu ccuaugugau cuacugcuc acucauauag    60 ggauuggagc cguggcgcac ggcggggaca    90

<210> SEQ ID NO 375
<211> LENGTH: 63
<212> TYPE: RNA
<213> ORGANISM: Homo sapiens

<400> SEQUENCE: 375
gcaugcuggg cgaggcuggc aucuagcaca ggcgguagau gcuugcucuu gccauugcaa    60
uga    63

<210> SEQ ID NO 376
<211> LENGTH: 78
<212> TYPE: RNA
<213> ORGANISM: Homo sapiens

<400> SEQUENCE: 376
gggcccagaa gggggcgcag ucacugacgu gaagggacca caucccgcuu caugucagug    60
acuccugccc cuuggucu    78

<210> SEQ ID NO 377
<211> LENGTH: 90
<212> TYPE: RNA
<213> ORGANISM: Homo sapiens

<400> SEQUENCE: 377
gugucucucu ggagacccug cagccuuccc acccaccagg gagcuuucca ugggcugugg    60
ggaaggcguc agugucgggu gagggaacac    90

<210> SEQ ID NO 378
<211> LENGTH: 54
<212> TYPE: RNA
<213> ORGANISM: Homo sapiens

<400> SEQUENCE: 378
agcagcaggg gagagagagg aguccucuag acaccgacuc ugucuccgc agau    54

<210> SEQ ID NO 379
<211> LENGTH: 100
<212> TYPE: RNA
<213> ORGANISM: Homo sapiens

<400> SEQUENCE: 379
agcucagggc ggcugcgcag agggcuggac ucagcggcgg agcuggcugc uggccucagu    60
ucugccucug uccagguccu ugugacccgc ccgcucuccu    100

```
<210> SEQ ID NO 380
<211> LENGTH: 59
<212> TYPE: RNA
<213> ORGANISM: Homo sapiens

<400> SEQUENCE: 380
guccaggcag gagccggacu ggaccucagg gaagaggcug acccggcccc ucuugcggc      59

<210> SEQ ID NO 381
<211> LENGTH: 54
<212> TYPE: RNA
<213> ORGANISM: Homo sapiens

<400> SEQUENCE: 381
acgcgggugc gggccggcgg gguagaagcc acccggcccg gcccggcccg gcga           54

<210> SEQ ID NO 382
<211> LENGTH: 73
<212> TYPE: RNA
<213> ORGANISM: Homo sapiens

<400> SEQUENCE: 382
ggccggcugg gguuccuggg gaugggauuu gcuuccuguc acaaaucaca uugccaggga     60
uuuccaaccg acc                                                        73

<210> SEQ ID NO 383
<211> LENGTH: 69
<212> TYPE: RNA
<213> ORGANISM: Homo sapiens

<400> SEQUENCE: 383
cuuucggcca gcgggacggc auccgaggug ggcuaggcuc gggcccgugg cgggugcggg     60
ggugggagg                                                             69

<210> SEQ ID NO 384
<211> LENGTH: 69
<212> TYPE: RNA
<213> ORGANISM: Homo sapiens

<400> SEQUENCE: 384 uggguaggg guggggaau ucaggggugu cgaacucaug gcugccaccu uuguguccccc      60 auccugcag                                                             69

<210> SEQ ID NO 385
<211> LENGTH: 70
<212> TYPE: RNA
<213> ORGANISM: Homo sapiens

<400> SEQUENCE: 385
gguuucuccu ugaggagaca uggugggggc cggucaggca gcccaugcca uguguccuca     60
uggagaggcc                                                            70

<210> SEQ ID NO 386
<211> LENGTH: 72
<212> TYPE: RNA
<213> ORGANISM: Homo sapiens

<400> SEQUENCE: 386
cuugggaaug gcaaggaaac cguuaccauu acugaguuua guaauggaa ugguucucuu      60 gcuauacccca ga                                                        72
```

```
<210> SEQ ID NO 387
<211> LENGTH: 67
<212> TYPE: RNA
<213> ORGANISM: Homo sapiens

<400> SEQUENCE: 387
cugguccauu ucccugccau ucccuuggcu ucaauuuacu cccagggcug gcagugacau    60
gggucaa                                                              67

<210> SEQ ID NO 388
<211> LENGTH: 94
<212> TYPE: RNA
<213> ORGANISM: Homo sapiens

<400> SEQUENCE: 388
cagugcgacg ggcggagcuu ccagacgcuc cgcccacgu cgcaugcgcc ccgggaaagc     60
guggggcgga gcuuccggag gccccgcccu gcug                                94

<210> SEQ ID NO 389
<211> LENGTH: 88
<212> TYPE: RNA
<213> ORGANISM: Homo sapiens

<400> SEQUENCE: 389
gcgacgggcg gagcuuccag acgcuccgcc ccacgucgca ugcgccccgg gaaagcgugg    60
ggcggagcuu ccggaggccc cgcccugc                                       88

<210> SEQ ID NO 390
<211> LENGTH: 94
<212> TYPE: RNA
<213> ORGANISM: Homo sapiens

<400> SEQUENCE: 390
cagugcgacg ggcggagcuu ccagacgcuc cgcccacgu cgcaugcgcc ccgggaaagc     60
guggggcgga gcuuccggag gccccgcccu gcug                                94

<210> SEQ ID NO 391
<211> LENGTH: 94
<212> TYPE: RNA
<213> ORGANISM: Homo sapiens

<400> SEQUENCE: 391
cagugcgacg ggcggagcuu ccagacgcuc cgcccacgu cgcaugcgcc ccgggaaagc     60
guggggcgga gcuuccggag gccccgcccu gcug                                94

<210> SEQ ID NO 392
<211> LENGTH: 59
<212> TYPE: RNA
<213> ORGANISM: Homo sapiens

<400> SEQUENCE: 392
cugugucggg gagucugggg uccggaauuc uccagagccu cugugccccu acuucccag     59

<210> SEQ ID NO 393
<211> LENGTH: 84
<212> TYPE: RNA
<213> ORGANISM: Homo sapiens

<400> SEQUENCE: 393
gaggcugggc ggggcgcggc cggaucgguc gagagcgucc uggcugauga cggucucccg    60
```

```
ugcccacgcc ccaaacgcag ucuc                                      84

<210> SEQ ID NO 394
<211> LENGTH: 78
<212> TYPE: RNA
<213> ORGANISM: Homo sapiens

<400> SEQUENCE: 394
ggccucaggc aggcgcaccc gaccacaugc auggcuggug gcggcgugca ggggucgggu    60
gggccaggcu gugggggcg                                                78

<210> SEQ ID NO 395
<211> LENGTH: 89
<212> TYPE: RNA
<213> ORGANISM: Homo sapiens

<400> SEQUENCE: 395
accaugcugu agugugugua aacauccuac acucucagcu gugagcucaa gguggcuggg    60
agaggguugu uuacuccuuc ugccaugga                                     89

<210> SEQ ID NO 396
<211> LENGTH: 52
<212> TYPE: RNA
<213> ORGANISM: Homo sapiens

<400> SEQUENCE: 396
ucugggcuga gccgagcugg guuaagccga gcuggguugg gcuggcugg gu             52

<210> SEQ ID NO 397
<211> LENGTH: 61
<212> TYPE: RNA
<213> ORGANISM: Homo sapiens

<400> SEQUENCE: 397
ucacccggug agggcgggug gaggaggagg guccccacca ucagccuuca cugggacggg    60
a                                                                   61

<210> SEQ ID NO 398
<211> LENGTH: 119
<212> TYPE: RNA
<213> ORGANISM: Homo sapiens

<400> SEQUENCE: 398
agccugcgcc ggagccgggg ccugagcccg ggccgcgcag gccgugaacu cgucgagcug    60
cgcgugcggc cggugcucaa ccugccgggu ccuggccccg cgcucccgcg cgcccugga   119

<210> SEQ ID NO 399
<211> LENGTH: 23
<212> TYPE: RNA
<213> ORGANISM: Homo sapiens

<400> SEQUENCE: 399
cuccuggggc ccgcacucuc gcu                                           23

<210> SEQ ID NO 400
<211> LENGTH: 18
<212> TYPE: RNA
<213> ORGANISM: Homo sapiens

<400> SEQUENCE: 400
```
cuccuggggc ccgcacuc                                                     18

<210> SEQ ID NO 401
<211> LENGTH: 22
<212> TYPE: RNA
<213> ORGANISM: Homo sapiens

<400> SEQUENCE: 401
ccgggaacgu cgagacugga gc                                                22

<210> SEQ ID NO 402
<211> LENGTH: 15
<212> TYPE: RNA
<213> ORGANISM: Homo sapiens

<400> SEQUENCE: 402
cgggaacguc gagac                                                        15

<210> SEQ ID NO 403
<211> LENGTH: 22
<212> TYPE: RNA
<213> ORGANISM: Homo sapiens

<400> SEQUENCE: 403
cgcggcgggg acggcgauug gu                                                22

<210> SEQ ID NO 404
<211> LENGTH: 17
<212> TYPE: RNA
<213> ORGANISM: Homo sapiens

<400> SEQUENCE: 404
cggcggggac ggcgauu                                                      17

<210> SEQ ID NO 405
<211> LENGTH: 24
<212> TYPE: RNA
<213> ORGANISM: Homo sapiens

<400> SEQUENCE: 405
gaggcuggga aggcaaaggg acgu                                              24

<210> SEQ ID NO 406
<211> LENGTH: 15
<212> TYPE: RNA
<213> ORGANISM: Homo sapiens

<400> SEQUENCE: 406
gaaggaggcu gggaa                                                        15

<210> SEQ ID NO 407
<211> LENGTH: 23
<212> TYPE: RNA
<213> ORGANISM: Homo sapiens

<400> SEQUENCE: 407
ggugggugag gucgggcccc aag                                               23

<210> SEQ ID NO 408
<211> LENGTH: 20
<212> TYPE: RNA
<213> ORGANISM: Homo sapiens

<400> SEQUENCE: 408

```
cgggguggu gaggucgggc                                              20

<210> SEQ ID NO 409
<211> LENGTH: 17
<212> TYPE: RNA
<213> ORGANISM: Homo sapiens

<400> SEQUENCE: 409
ggugagcgcu cgcuggc                                                17

<210> SEQ ID NO 410
<211> LENGTH: 15
<212> TYPE: RNA
<213> ORGANISM: Homo sapiens

<400> SEQUENCE: 410
cggugagcgc ucgcu                                                  15

<210> SEQ ID NO 411
<211> LENGTH: 26
<212> TYPE: RNA
<213> ORGANISM: Homo sapiens

<400> SEQUENCE: 411
ccuucuggag aggcuuugug cggaua                                      26

<210> SEQ ID NO 412
<211> LENGTH: 15
<212> TYPE: RNA
<213> ORGANISM: Homo sapiens

<400> SEQUENCE: 412
ccuucuggag aggcu                                                  15

<210> SEQ ID NO 413
<211> LENGTH: 24
<212> TYPE: RNA
<213> ORGANISM: Homo sapiens

<400> SEQUENCE: 413
ucgaggacug guggaagggc cuuu                                        24

<210> SEQ ID NO 414
<211> LENGTH: 16
<212> TYPE: RNA
<213> ORGANISM: Homo sapiens

<400> SEQUENCE: 414
ucgaggacug guggaa                                                 16

<210> SEQ ID NO 415
<211> LENGTH: 19
<212> TYPE: RNA
<213> ORGANISM: Homo sapiens

<400> SEQUENCE: 415
agugggaggc cagggcacg                                              19

<210> SEQ ID NO 416
<211> LENGTH: 15
<212> TYPE: RNA
<213> ORGANISM: Homo sapiens
```

```
<400> SEQUENCE: 416 aggggagcu gcagg                                              15

<210> SEQ ID NO 417
<211> LENGTH: 16
<212> TYPE: RNA
<213> ORGANISM: Homo sapiens

<400> SEQUENCE: 417
ugcuggugau gcuuuc                                            16

<210> SEQ ID NO 418
<211> LENGTH: 16
<212> TYPE: RNA
<213> ORGANISM: Homo sapiens

<400> SEQUENCE: 418
ugcuggugau gcuuuc                                            16

<210> SEQ ID NO 419
<211> LENGTH: 23
<212> TYPE: RNA
<213> ORGANISM: Homo sapiens

<400> SEQUENCE: 419
cggggccgua gcacugucug aga                                    23

<210> SEQ ID NO 420
<211> LENGTH: 20
<212> TYPE: RNA
<213> ORGANISM: Homo sapiens

<400> SEQUENCE: 420
cggggccgua gcacugucug                                        20

<210> SEQ ID NO 421
<211> LENGTH: 18
<212> TYPE: RNA
<213> ORGANISM: Homo sapiens

<400> SEQUENCE: 421
gaggcugaag gaagaugg                                          18

<210> SEQ ID NO 422
<211> LENGTH: 15
<212> TYPE: RNA
<213> ORGANISM: Homo sapiens

<400> SEQUENCE: 422
gaggcugaag gaaga                                             15

<210> SEQ ID NO 423
<211> LENGTH: 23
<212> TYPE: RNA
<213> ORGANISM: Homo sapiens

<400> SEQUENCE: 423
ugaggauaug gcagggaagg gga                                    23

<210> SEQ ID NO 424
<211> LENGTH: 19
<212> TYPE: RNA
<213> ORGANISM: Homo sapiens
```

```
<400> SEQUENCE: 424
ugaggauaug gcagggaag                                                    19

<210> SEQ ID NO 425
<211> LENGTH: 23
<212> TYPE: RNA
<213> ORGANISM: Homo sapiens

<400> SEQUENCE: 425
agggucgggg cagggagggc agg                                               23

<210> SEQ ID NO 426
<211> LENGTH: 15
<212> TYPE: RNA
<213> ORGANISM: Homo sapiens

<400> SEQUENCE: 426
gggagaaggg ucggg                                                        15

<210> SEQ ID NO 427
<211> LENGTH: 21
<212> TYPE: RNA
<213> ORGANISM: Homo sapiens

<400> SEQUENCE: 427
gaggcgaugu ggggauguag a                                                 21

<210> SEQ ID NO 428
<211> LENGTH: 20
<212> TYPE: RNA
<213> ORGANISM: Homo sapiens

<400> SEQUENCE: 428
cccagucuca uuuccucauc                                                   20

<210> SEQ ID NO 429
<211> LENGTH: 21
<212> TYPE: RNA
<213> ORGANISM: Homo sapiens

<400> SEQUENCE: 429 cuuccccca guaaucuuca u                                                  21

<210> SEQ ID NO 430
<211> LENGTH: 21
<212> TYPE: RNA
<213> ORGANISM: Homo sapiens

<400> SEQUENCE: 430 cuuccccca guaaucuuca u                                                  21

<210> SEQ ID NO 431
<211> LENGTH: 21
<212> TYPE: RNA
<213> ORGANISM: Homo sapiens

<400> SEQUENCE: 431
cccaggcugg agcgagugca g                                                 21

<210> SEQ ID NO 432
<211> LENGTH: 15
<212> TYPE: RNA
```

```
<213> ORGANISM: Homo sapiens

<400> SEQUENCE: 432
agcucacugc agccu                                                    15

<210> SEQ ID NO 433
<211> LENGTH: 22
<212> TYPE: RNA
<213> ORGANISM: Homo sapiens

<400> SEQUENCE: 433
caggcacggg agcucaggug ag                                            22

<210> SEQ ID NO 434
<211> LENGTH: 17
<212> TYPE: RNA
<213> ORGANISM: Homo sapiens

<400> SEQUENCE: 434
caggcacggg agcucag                                                  17

<210> SEQ ID NO 435
<211> LENGTH: 16
<212> TYPE: RNA
<213> ORGANISM: Homo sapiens

<400> SEQUENCE: 435
ggacccaggg agagac                                                   16

<210> SEQ ID NO 436
<211> LENGTH: 16
<212> TYPE: RNA
<213> ORGANISM: Homo sapiens

<400> SEQUENCE: 436
ggacccaggg agagac                                                   16

<210> SEQ ID NO 437
<211> LENGTH: 25
<212> TYPE: RNA
<213> ORGANISM: Homo sapiens

<400> SEQUENCE: 437
uggcggcggu aguuaugggc uucuc                                         25

<210> SEQ ID NO 438
<211> LENGTH: 25
<212> TYPE: RNA
<213> ORGANISM: Homo sapiens

<400> SEQUENCE: 438
uggcggcggu aguuaugggc uucuc                                         25

<210> SEQ ID NO 439
<211> LENGTH: 21
<212> TYPE: RNA
<213> ORGANISM: Homo sapiens

<400> SEQUENCE: 439
caacucugau cucuucaucu a                                             21

<210> SEQ ID NO 440
<211> LENGTH: 20
```

<212> TYPE: RNA
<213> ORGANISM: Homo sapiens

<400> SEQUENCE: 440
ucucuucauc uacccccag                      20

<210> SEQ ID NO 441
<211> LENGTH: 23
<212> TYPE: RNA
<213> ORGANISM: Homo sapiens

<400> SEQUENCE: 441
ggcuacaaca caggacccgg gcg                 23

<210> SEQ ID NO 442
<211> LENGTH: 21
<212> TYPE: RNA
<213> ORGANISM: Homo sapiens

<400> SEQUENCE: 442
ggcuacaaca caggacccgg g                   21

<210> SEQ ID NO 443
<211> LENGTH: 23
<212> TYPE: RNA
<213> ORGANISM: Homo sapiens

<400> SEQUENCE: 443
agaagaaggc ggucggucug cgg                 23

<210> SEQ ID NO 444
<211> LENGTH: 21
<212> TYPE: RNA
<213> ORGANISM: Homo sapiens

<400> SEQUENCE: 444
aagaaggcgg ucggucugcg g                   21

<210> SEQ ID NO 445
<211> LENGTH: 20
<212> TYPE: RNA
<213> ORGANISM: Homo sapiens

<400> SEQUENCE: 445
aagacacauu uggagaggga                     20

<210> SEQ ID NO 446
<211> LENGTH: 16
<212> TYPE: RNA
<213> ORGANISM: Homo sapiens

<400> SEQUENCE: 446
agacacauuu ggagag                         16

<210> SEQ ID NO 447
<211> LENGTH: 26
<212> TYPE: RNA
<213> ORGANISM: Homo sapiens

<400> SEQUENCE: 447
aggagggagg agaugggcca aguucc              26

<210> SEQ ID NO 448

```
<211> LENGTH: 15
<212> TYPE: RNA
<213> ORGANISM: Homo sapiens

<400> SEQUENCE: 448
gggaggaggg aggag                                               15

<210> SEQ ID NO 449
<211> LENGTH: 25
<212> TYPE: RNA
<213> ORGANISM: Homo sapiens

<400> SEQUENCE: 449
ugcggggcua gggcuaacag caguc                                    25

<210> SEQ ID NO 450
<211> LENGTH: 15
<212> TYPE: RNA
<213> ORGANISM: Homo sapiens

<400> SEQUENCE: 450
ugcggggcua gggcu                                               15

<210> SEQ ID NO 451
<211> LENGTH: 20
<212> TYPE: RNA
<213> ORGANISM: Homo sapiens

<400> SEQUENCE: 451
cuccccggug ugcaaaugug                                          20

<210> SEQ ID NO 452
<211> LENGTH: 15
<212> TYPE: RNA
<213> ORGANISM: Homo sapiens

<400> SEQUENCE: 452
gugugcggug uuaug                                               15

<210> SEQ ID NO 453
<211> LENGTH: 22
<212> TYPE: RNA
<213> ORGANISM: Homo sapiens

<400> SEQUENCE: 453
ccucacaccu gccucgcccc cc                                       22

<210> SEQ ID NO 454
<211> LENGTH: 15
<212> TYPE: RNA
<213> ORGANISM: Homo sapiens

<400> SEQUENCE: 454
ucacaccugc cucgc                                               15

<210> SEQ ID NO 455
<211> LENGTH: 24
<212> TYPE: RNA
<213> ORGANISM: Homo sapiens

<400> SEQUENCE: 455
uggggagcug aggcucuggg ggug                                     24
```

```
<210> SEQ ID NO 456
<211> LENGTH: 15
<212> TYPE: RNA
<213> ORGANISM: Homo sapiens

<400> SEQUENCE: 456
ggcccugggg agcug                                              15

<210> SEQ ID NO 457
<211> LENGTH: 27
<212> TYPE: RNA
<213> ORGANISM: Homo sapiens

<400> SEQUENCE: 457
gugaacgggc gccaucccga ggcuuug                                 27

<210> SEQ ID NO 458
<211> LENGTH: 16
<212> TYPE: RNA
<213> ORGANISM: Homo sapiens

<400> SEQUENCE: 458
gugaacgggc gccauc                                             16

<210> SEQ ID NO 459
<211> LENGTH: 21
<212> TYPE: RNA
<213> ORGANISM: Homo sapiens

<400> SEQUENCE: 459
gagggcagcg ugggugugc g                                        21

<210> SEQ ID NO 460
<211> LENGTH: 21
<212> TYPE: RNA
<213> ORGANISM: Homo sapiens

<400> SEQUENCE: 460
gagggcagcg uggguguggc g                                       21

<210> SEQ ID NO 461
<211> LENGTH: 23
<212> TYPE: RNA
<213> ORGANISM: Homo sapiens

<400> SEQUENCE: 461
gggggucccc ggugcucgga ucu                                     23

<210> SEQ ID NO 462
<211> LENGTH: 16
<212> TYPE: RNA
<213> ORGANISM: Homo sapiens

<400> SEQUENCE: 462
ucgggagggg cgggag                                             16

<210> SEQ ID NO 463
<211> LENGTH: 25
<212> TYPE: RNA
<213> ORGANISM: Homo sapiens

<400> SEQUENCE: 463
uucugggccc gcggcgggcg ugggg                                   25
```

<210> SEQ ID NO 464
<211> LENGTH: 15
<212> TYPE: RNA
<213> ORGANISM: Homo sapiens

<400> SEQUENCE: 464
cgcggcgggc guggg                                                        15

<210> SEQ ID NO 465
<211> LENGTH: 22
<212> TYPE: RNA
<213> ORGANISM: Homo sapiens

<400> SEQUENCE: 465
ugggagggga gaggcagcaa gc                                                22

<210> SEQ ID NO 466
<211> LENGTH: 22
<212> TYPE: RNA
<213> ORGANISM: Homo sapiens

<400> SEQUENCE: 466
ugggagggga gaggcagcaa gc                                                22

<210> SEQ ID NO 467
<211> LENGTH: 21
<212> TYPE: RNA
<213> ORGANISM: Homo sapiens

<400> SEQUENCE: 467
aggaggcagu gggcgagcag g                                                 21

<210> SEQ ID NO 468
<211> LENGTH: 21
<212> TYPE: RNA
<213> ORGANISM: Homo sapiens

<400> SEQUENCE: 468
aggaggcagu gggcgagcag g                                                 21

<210> SEQ ID NO 469
<211> LENGTH: 15
<212> TYPE: RNA
<213> ORGANISM: Homo sapiens

<400> SEQUENCE: 469
ugaagcgggg gggcg                                                        15

<210> SEQ ID NO 470
<211> LENGTH: 15
<212> TYPE: RNA
<213> ORGANISM: Homo sapiens

<400> SEQUENCE: 470
ugaagcgggg gggcg                                                        15

<210> SEQ ID NO 471
<211> LENGTH: 17
<212> TYPE: RNA
<213> ORGANISM: Homo sapiens

<400> SEQUENCE: 471
uccuagucac ggcacca                                                      17

<210> SEQ ID NO 472
<211> LENGTH: 17
<212> TYPE: RNA
<213> ORGANISM: Homo sapiens

<400> SEQUENCE: 472
uccuagucac ggcacca                                                   17

<210> SEQ ID NO 473
<211> LENGTH: 23
<212> TYPE: RNA
<213> ORGANISM: Homo sapiens

<400> SEQUENCE: 473
ggaggcgcag gcucggaaag gcg                                            23

<210> SEQ ID NO 474
<211> LENGTH: 15
<212> TYPE: RNA
<213> ORGANISM: Homo sapiens

<400> SEQUENCE: 474
gcaggcucgg aaagg                                                     15

<210> SEQ ID NO 475
<211> LENGTH: 23
<212> TYPE: RNA
<213> ORGANISM: Homo sapiens

<400> SEQUENCE: 475
cuaguggaag aagauggcgg aag                                            23

<210> SEQ ID NO 476
<211> LENGTH: 15
<212> TYPE: RNA
<213> ORGANISM: Homo sapiens

<400> SEQUENCE: 476
uaguggaaga agaug                                                     15

<210> SEQ ID NO 477
<211> LENGTH: 23
<212> TYPE: RNA
<213> ORGANISM: Homo sapiens

<400> SEQUENCE: 477
acaggagugg ggugggaca uaa                                             23

<210> SEQ ID NO 478
<211> LENGTH: 20
<212> TYPE: RNA
<213> ORGANISM: Homo sapiens

<400> SEQUENCE: 478
acaggagugg ggugggaca                                                 20

<210> SEQ ID NO 479
<211> LENGTH: 25
<212> TYPE: RNA
<213> ORGANISM: Homo sapiens

<400> SEQUENCE: 479

```
agcggggagg aagugggcgc ugcuu                                       25

<210> SEQ ID NO 480
<211> LENGTH: 21
<212> TYPE: RNA
<213> ORGANISM: Homo sapiens

<400> SEQUENCE: 480
agcggggagg aagugggcgc u                                           21

<210> SEQ ID NO 481
<211> LENGTH: 22
<212> TYPE: RNA
<213> ORGANISM: Homo sapiens

<400> SEQUENCE: 481
ccggcagagg aggcugcaga gg                                          22

<210> SEQ ID NO 482
<211> LENGTH: 19
<212> TYPE: RNA
<213> ORGANISM: Homo sapiens

<400> SEQUENCE: 482
ccggcagagg aggcugcag                                              19

<210> SEQ ID NO 483
<211> LENGTH: 15
<212> TYPE: RNA
<213> ORGANISM: Homo sapiens

<400> SEQUENCE: 483
ucugggcgag gggug                                                  15

<210> SEQ ID NO 484
<211> LENGTH: 15
<212> TYPE: RNA
<213> ORGANISM: Homo sapiens

<400> SEQUENCE: 484
ucugggcgag gggug                                                  15

<210> SEQ ID NO 485
<211> LENGTH: 26
<212> TYPE: RNA
<213> ORGANISM: Homo sapiens

<400> SEQUENCE: 485
gucccggggc ugcgcgaggc acaggc                                      26

<210> SEQ ID NO 486
<211> LENGTH: 15
<212> TYPE: RNA
<213> ORGANISM: Homo sapiens

<400> SEQUENCE: 486
ggcccggggg gcggg                                                  15

<210> SEQ ID NO 487
<211> LENGTH: 21
<212> TYPE: RNA
<213> ORGANISM: Homo sapiens

<400> SEQUENCE: 487
```

```
cggauccgag ucacggcacc a                                              21

<210> SEQ ID NO 488
<211> LENGTH: 15
<212> TYPE: RNA
<213> ORGANISM: Homo sapiens

<400> SEQUENCE: 488
ggauccgagu cacgg                                                     15

<210> SEQ ID NO 489
<211> LENGTH: 21
<212> TYPE: RNA
<213> ORGANISM: Homo sapiens

<400> SEQUENCE: 489
auccaguucu cugagggggc u                                              21

<210> SEQ ID NO 490
<211> LENGTH: 21
<212> TYPE: RNA
<213> ORGANISM: Homo sapiens

<400> SEQUENCE: 490
auccaguucu cugagggggc u                                              21

<210> SEQ ID NO 491
<211> LENGTH: 23
<212> TYPE: RNA
<213> ORGANISM: Homo sapiens

<400> SEQUENCE: 491
ggcccggccg ugccugaggu uuc                                            23

<210> SEQ ID NO 492
<211> LENGTH: 15
<212> TYPE: RNA
<213> ORGANISM: Homo sapiens

<400> SEQUENCE: 492
ggcgguggga ucccg                                                     15

<210> SEQ ID NO 493
<211> LENGTH: 18
<212> TYPE: RNA
<213> ORGANISM: Homo sapiens

<400> SEQUENCE: 493
ucuagguggg gagacuga                                                  18

<210> SEQ ID NO 494
<211> LENGTH: 16
<212> TYPE: RNA
<213> ORGANISM: Homo sapiens

<400> SEQUENCE: 494
guggggagac ugacgg                                                    16

<210> SEQ ID NO 495
<211> LENGTH: 17
<212> TYPE: RNA
<213> ORGANISM: Homo sapiens
```

```
<400> SEQUENCE: 495
ugcaggggca ggccagc                                                   17

<210> SEQ ID NO 496
<211> LENGTH: 17
<212> TYPE: RNA
<213> ORGANISM: Homo sapiens

<400> SEQUENCE: 496
ugcagggcca ggccagc                                                   17

<210> SEQ ID NO 497
<211> LENGTH: 25
<212> TYPE: RNA
<213> ORGANISM: Homo sapiens

<400> SEQUENCE: 497
aaggcagggc ccccgcuccc cgggc                                          25

<210> SEQ ID NO 498
<211> LENGTH: 15
<212> TYPE: RNA
<213> ORGANISM: Homo sapiens

<400> SEQUENCE: 498
guguguugag gaagg                                                     15

<210> SEQ ID NO 499
<211> LENGTH: 26
<212> TYPE: RNA
<213> ORGANISM: Homo sapiens

<400> SEQUENCE: 499
gcgggcuguc cggaggggguc ggcuuu                                        26

<210> SEQ ID NO 500
<211> LENGTH: 16
<212> TYPE: RNA
<213> ORGANISM: Homo sapiens

<400> SEQUENCE: 500
gcuguccgga gggguc                                                    16

<210> SEQ ID NO 501
<211> LENGTH: 20
<212> TYPE: RNA
<213> ORGANISM: Homo sapiens

<400> SEQUENCE: 501
ggcuggucag augggagugg                                                20

<210> SEQ ID NO 502
<211> LENGTH: 20
<212> TYPE: RNA
<213> ORGANISM: Homo sapiens

<400> SEQUENCE: 502
ggcuggucag augggagugg                                                20

<210> SEQ ID NO 503
<211> LENGTH: 24
<212> TYPE: RNA
<213> ORGANISM: Homo sapiens
```

```
<400> SEQUENCE: 503
cugguacagg ccuggggac aggg                                              24

<210> SEQ ID NO 504
<211> LENGTH: 18
<212> TYPE: RNA
<213> ORGANISM: Homo sapiens

<400> SEQUENCE: 504
cugguacagg ccuggggg                                                    18

<210> SEQ ID NO 505
<211> LENGTH: 23
<212> TYPE: RNA
<213> ORGANISM: Homo sapiens

<400> SEQUENCE: 505
gccccggcgc gggcggguuc ugg                                              23

<210> SEQ ID NO 506
<211> LENGTH: 16
<212> TYPE: RNA
<213> ORGANISM: Homo sapiens

<400> SEQUENCE: 506
ggagccccgg cgcggg                                                      16

<210> SEQ ID NO 507
<211> LENGTH: 20
<212> TYPE: RNA
<213> ORGANISM: Homo sapiens

<400> SEQUENCE: 507
ccccagggcg acgcggcggg                                                  20

<210> SEQ ID NO 508
<211> LENGTH: 15
<212> TYPE: RNA
<213> ORGANISM: Homo sapiens

<400> SEQUENCE: 508
cgcggcgggg gcggc                                                       15

<210> SEQ ID NO 509
<211> LENGTH: 21
<212> TYPE: RNA
<213> ORGANISM: Homo sapiens

<400> SEQUENCE: 509
gugagucagg gugggcugg c                                                 21

<210> SEQ ID NO 510
<211> LENGTH: 21
<212> TYPE: RNA
<213> ORGANISM: Homo sapiens

<400> SEQUENCE: 510
gugagucagg gugggcugg c                                                 21

<210> SEQ ID NO 511
<211> LENGTH: 21
<212> TYPE: RNA
```

<213> ORGANISM: Homo sapiens

<400> SEQUENCE: 511
guuggaggcg ugguuuuag a                    21

<210> SEQ ID NO 512
<211> LENGTH: 15
<212> TYPE: RNA
<213> ORGANISM: Homo sapiens

<400> SEQUENCE: 512
guuggaggcg ugggu                          15

<210> SEQ ID NO 513
<211> LENGTH: 23
<212> TYPE: RNA
<213> ORGANISM: Homo sapiens

<400> SEQUENCE: 513 aggaggggguc ccgcacuggg agg                23

<210> SEQ ID NO 514
<211> LENGTH: 15
<212> TYPE: RNA
<213> ORGANISM: Homo sapiens

<400> SEQUENCE: 514
ugggaggggc ccuca                          15

<210> SEQ ID NO 515
<211> LENGTH: 23
<212> TYPE: RNA
<213> ORGANISM: Homo sapiens

<400> SEQUENCE: 515
gugggcuggg cugggcuggg cca                 23

<210> SEQ ID NO 516
<211> LENGTH: 15
<212> TYPE: RNA
<213> ORGANISM: Homo sapiens

<400> SEQUENCE: 516
gggcugggcu gggcu                          15

<210> SEQ ID NO 517
<211> LENGTH: 24
<212> TYPE: RNA
<213> ORGANISM: Homo sapiens

<400> SEQUENCE: 517
cgggcguggu gguggggug ggug                 24

<210> SEQ ID NO 518
<211> LENGTH: 15
<212> TYPE: RNA
<213> ORGANISM: Homo sapiens

<400> SEQUENCE: 518
cgggcguggu ggugg                          15

<210> SEQ ID NO 519
<211> LENGTH: 18

<212> TYPE: RNA
<213> ORGANISM: Homo sapiens

<400> SEQUENCE: 519 gguggcuuc ccggaggg                                                  18

<210> SEQ ID NO 520
<211> LENGTH: 15
<212> TYPE: RNA
<213> ORGANISM: Homo sapiens

<400> SEQUENCE: 520 gguggcuuc ccgga                                                     15

<210> SEQ ID NO 521
<211> LENGTH: 26
<212> TYPE: RNA
<213> ORGANISM: Homo sapiens

<400> SEQUENCE: 521 cgguggauc ccgcggccgu guuuuc                                         26

<210> SEQ ID NO 522
<211> LENGTH: 15
<212> TYPE: RNA
<213> ORGANISM: Homo sapiens

<400> SEQUENCE: 522
ggggcgccgc gggac                                                    15

<210> SEQ ID NO 523
<211> LENGTH: 25
<212> TYPE: RNA
<213> ORGANISM: Homo sapiens

<400> SEQUENCE: 523
ugggcagggg cuuauuguag gaguc                                         25

<210> SEQ ID NO 524
<211> LENGTH: 19
<212> TYPE: RNA
<213> ORGANISM: Homo sapiens

<400> SEQUENCE: 524
ugggcagggg cuuauugua                                                19

<210> SEQ ID NO 525
<211> LENGTH: 20
<212> TYPE: RNA
<213> ORGANISM: Homo sapiens

<400> SEQUENCE: 525
ccccggggag cccggcggug                                               20

<210> SEQ ID NO 526
<211> LENGTH: 15
<212> TYPE: RNA
<213> ORGANISM: Homo sapiens

<400> SEQUENCE: 526
accccgggga gcccg                                                    15

<210> SEQ ID NO 527

```
<211> LENGTH: 26
<212> TYPE: RNA
<213> ORGANISM: Homo sapiens

<400> SEQUENCE: 527
agggacggga cgcggugcag uguugu                                         26

<210> SEQ ID NO 528
<211> LENGTH: 15
<212> TYPE: RNA
<213> ORGANISM: Homo sapiens

<400> SEQUENCE: 528
ggcgggcggg aggga                                                     15

<210> SEQ ID NO 529
<211> LENGTH: 22
<212> TYPE: RNA
<213> ORGANISM: Homo sapiens

<400> SEQUENCE: 529
acucaaacug uggggcacu uu                                              22

<210> SEQ ID NO 530
<211> LENGTH: 19
<212> TYPE: RNA
<213> ORGANISM: Homo sapiens

<400> SEQUENCE: 530
acucaaacug uggggcac                                                  19

<210> SEQ ID NO 531
<211> LENGTH: 16
<212> TYPE: RNA
<213> ORGANISM: Homo sapiens

<400> SEQUENCE: 531
gugaaggccc ggcgga                                                    16

<210> SEQ ID NO 532
<211> LENGTH: 15
<212> TYPE: RNA
<213> ORGANISM: Homo sapiens

<400> SEQUENCE: 532
gugaaggccc ggcgg                                                     15

<210> SEQ ID NO 533
<211> LENGTH: 24
<212> TYPE: RNA
<213> ORGANISM: Homo sapiens

<400> SEQUENCE: 533
gcugcgggcu gcggucaggg cgau                                           24

<210> SEQ ID NO 534
<211> LENGTH: 20
<212> TYPE: RNA
<213> ORGANISM: Homo sapiens

<400> SEQUENCE: 534
gcugcgggcu gcggucaggg                                                20
```

-continued

```
<210> SEQ ID NO 535
<211> LENGTH: 30
<212> TYPE: RNA
<213> ORGANISM: Homo sapiens

<400> SEQUENCE: 535
ugaggggcag agagcgagac uuuucuauuu                                    30

<210> SEQ ID NO 536
<211> LENGTH: 15
<212> TYPE: RNA
<213> ORGANISM: Homo sapiens

<400> SEQUENCE: 536
ugaggggcag agagc                                                    15

<210> SEQ ID NO 537
<211> LENGTH: 23
<212> TYPE: RNA
<213> ORGANISM: Homo sapiens

<400> SEQUENCE: 537
caccuugccu ugcugcccgg gcc                                           23

<210> SEQ ID NO 538
<211> LENGTH: 22
<212> TYPE: RNA
<213> ORGANISM: Homo sapiens

<400> SEQUENCE: 538
caccuugccu ugcugcccgg gc                                            22

<210> SEQ ID NO 539
<211> LENGTH: 21
<212> TYPE: RNA
<213> ORGANISM: Homo sapiens

<400> SEQUENCE: 539
ugggaauggg gguaagggcc u                                             21

<210> SEQ ID NO 540
<211> LENGTH: 15
<212> TYPE: RNA
<213> ORGANISM: Homo sapiens

<400> SEQUENCE: 540
cuucugagcc caggu                                                    15

<210> SEQ ID NO 541
<211> LENGTH: 15
<212> TYPE: RNA
<213> ORGANISM: Homo sapiens

<400> SEQUENCE: 541
ggcggcgggc ccggg                                                    15

<210> SEQ ID NO 542
<211> LENGTH: 15
<212> TYPE: RNA
<213> ORGANISM: Homo sapiens

<400> SEQUENCE: 542
ggcggcgggc ccggg                                                    15
```

```
<210> SEQ ID NO 543
<211> LENGTH: 16
<212> TYPE: RNA
<213> ORGANISM: Homo sapiens

<400> SEQUENCE: 543 cuggggqucc cccgac                                                      16

<210> SEQ ID NO 544
<211> LENGTH: 15
<212> TYPE: RNA
<213> ORGANISM: Homo sapiens

<400> SEQUENCE: 544
guguggagcu ggggc                                                       15

<210> SEQ ID NO 545
<211> LENGTH: 22
<212> TYPE: RNA
<213> ORGANISM: Homo sapiens

<400> SEQUENCE: 545 uguggqacug caaaugggag cu                                               22

<210> SEQ ID NO 546
<211> LENGTH: 22
<212> TYPE: RNA
<213> ORGANISM: Homo sapiens

<400> SEQUENCE: 546 uguggqacug caaaugggag cu                                               22

<210> SEQ ID NO 547
<211> LENGTH: 23
<212> TYPE: RNA
<213> ORGANISM: Homo sapiens

<400> SEQUENCE: 547
acagcagggc uggggauugc agu                                              23

<210> SEQ ID NO 548
<211> LENGTH: 19
<212> TYPE: RNA
<213> ORGANISM: Homo sapiens

<400> SEQUENCE: 548
ugcugcuccc aguccugcc                                                   19

<210> SEQ ID NO 549
<211> LENGTH: 17
<212> TYPE: RNA
<213> ORGANISM: Homo sapiens

<400> SEQUENCE: 549
aggggcuggg cgcgcgc                                                     17

<210> SEQ ID NO 550
<211> LENGTH: 15
<212> TYPE: RNA
<213> ORGANISM: Homo sapiens

<400> SEQUENCE: 550
caggggcugg gcgcg                                                       15
```

```
<210> SEQ ID NO 551
<211> LENGTH: 17
<212> TYPE: RNA
<213> ORGANISM: Homo sapiens

<400> SEQUENCE: 551
ggggcggggg cggggc                                                    17

<210> SEQ ID NO 552
<211> LENGTH: 15
<212> TYPE: RNA
<213> ORGANISM: Homo sapiens

<400> SEQUENCE: 552
cgcgccgggc ccggg                                                     15

<210> SEQ ID NO 553
<211> LENGTH: 23
<212> TYPE: RNA
<213> ORGANISM: Homo sapiens

<400> SEQUENCE: 553 ugggcggag cuuccggagg ccc                                             23

<210> SEQ ID NO 554
<211> LENGTH: 16
<212> TYPE: RNA
<213> ORGANISM: Homo sapiens

<400> SEQUENCE: 554
aucgcuggcc uggucg                                                    16

<210> SEQ ID NO 555
<211> LENGTH: 22
<212> TYPE: RNA
<213> ORGANISM: Homo sapiens

<400> SEQUENCE: 555 gagguuggg uggaggcucu cc                                              22

<210> SEQ ID NO 556
<211> LENGTH: 15
<212> TYPE: RNA
<213> ORGANISM: Homo sapiens

<400> SEQUENCE: 556 gagguuggg uggag                                                      15

<210> SEQ ID NO 557
<211> LENGTH: 18
<212> TYPE: RNA
<213> ORGANISM: Homo sapiens

<400> SEQUENCE: 557
cuccgggcgg cgccgugu                                                  18

<210> SEQ ID NO 558
<211> LENGTH: 18
<212> TYPE: RNA
<213> ORGANISM: Homo sapiens

<400> SEQUENCE: 558
```
cuccgggcgg cgccgugu                                                     18

<210> SEQ ID NO 559
<211> LENGTH: 21
<212> TYPE: RNA
<213> ORGANISM: Homo sapiens

<400> SEQUENCE: 559
gccgggcgug guggugggggg c                                                21

<210> SEQ ID NO 560
<211> LENGTH: 15
<212> TYPE: RNA
<213> ORGANISM: Homo sapiens

<400> SEQUENCE: 560
uagccgggcg uggug                                                        15

<210> SEQ ID NO 561
<211> LENGTH: 16
<212> TYPE: RNA
<213> ORGANISM: Homo sapiens

<400> SEQUENCE: 561
ggcggugggc ggcggg                                                       16

<210> SEQ ID NO 562
<211> LENGTH: 15
<212> TYPE: RNA
<213> ORGANISM: Homo sapiens

<400> SEQUENCE: 562
ggccucucgg gaacu                                                        15

<210> SEQ ID NO 563
<211> LENGTH: 20
<212> TYPE: RNA
<213> ORGANISM: Homo sapiens

<400> SEQUENCE: 563
aucccaccac ugccaccauu                                                   20

<210> SEQ ID NO 564
<211> LENGTH: 15
<212> TYPE: RNA
<213> ORGANISM: Homo sapiens

<400> SEQUENCE: 564
aucccaccac ugcca                                                        15

<210> SEQ ID NO 565
<211> LENGTH: 25
<212> TYPE: RNA
<213> ORGANISM: Homo sapiens

<400> SEQUENCE: 565
caggaaggau uuagggacag gcuuu                                             25

<210> SEQ ID NO 566
<211> LENGTH: 19
<212> TYPE: RNA
<213> ORGANISM: Homo sapiens

<400> SEQUENCE: 566

| | |
|---|---|
| caggaaggau uuagggaca | 19 |

<210> SEQ ID NO 567
<211> LENGTH: 26
<212> TYPE: RNA
<213> ORGANISM: Homo sapiens

<400> SEQUENCE: 567

| | |
|---|---|
| aaaaucacau ugccagggau uaccac | 26 |

<210> SEQ ID NO 568
<211> LENGTH: 15
<212> TYPE: RNA
<213> ORGANISM: Homo sapiens

<400> SEQUENCE: 568

| | |
|---|---|
| aaucacauug ccagg | 15 |

<210> SEQ ID NO 569
<211> LENGTH: 23
<212> TYPE: RNA
<213> ORGANISM: Homo sapiens

<400> SEQUENCE: 569

| | |
|---|---|
| uaggggcagc agaggaccug ggc | 23 |

<210> SEQ ID NO 570
<211> LENGTH: 20
<212> TYPE: RNA
<213> ORGANISM: Homo sapiens

<400> SEQUENCE: 570

| | |
|---|---|
| uaggggcagc agaggaccug | 20 |

<210> SEQ ID NO 571
<211> LENGTH: 22
<212> TYPE: RNA
<213> ORGANISM: Homo sapiens

<400> SEQUENCE: 571

| | |
|---|---|
| accccacucc ugguaccaua gu | 22 |

<210> SEQ ID NO 572
<211> LENGTH: 15
<212> TYPE: RNA
<213> ORGANISM: Homo sapiens

<400> SEQUENCE: 572

| | |
|---|---|
| accccacucc uggua | 15 |

<210> SEQ ID NO 573
<211> LENGTH: 25
<212> TYPE: RNA
<213> ORGANISM: Homo sapiens

<400> SEQUENCE: 573

| | |
|---|---|
| cugggccagg gagcagcugg ugggu | 25 |

<210> SEQ ID NO 574
<211> LENGTH: 20
<212> TYPE: RNA
<213> ORGANISM: Homo sapiens

```
<400> SEQUENCE: 574
ugggccaggg agcagcuggu                                              20

<210> SEQ ID NO 575
<211> LENGTH: 23
<212> TYPE: RNA
<213> ORGANISM: Homo sapiens

<400> SEQUENCE: 575
aagggaggag gagcggaggg gcc                                          23

<210> SEQ ID NO 576
<211> LENGTH: 15
<212> TYPE: RNA
<213> ORGANISM: Homo sapiens

<400> SEQUENCE: 576
gggaggagga gcgga                                                   15

<210> SEQ ID NO 577
<211> LENGTH: 20
<212> TYPE: RNA
<213> ORGANISM: Homo sapiens

<400> SEQUENCE: 577
aucccaccuc ugccaccaaa                                              20

<210> SEQ ID NO 578
<211> LENGTH: 15
<212> TYPE: RNA
<213> ORGANISM: Homo sapiens

<400> SEQUENCE: 578
aucccaccuc ugcca                                                   15

<210> SEQ ID NO 579
<211> LENGTH: 23
<212> TYPE: RNA
<213> ORGANISM: Homo sapiens

<400> SEQUENCE: 579
gggggccgau acacuguacg aga                                          23

<210> SEQ ID NO 580
<211> LENGTH: 20
<212> TYPE: RNA
<213> ORGANISM: Homo sapiens

<400> SEQUENCE: 580
gggggccgau acacuguacg                                              20

<210> SEQ ID NO 581
<211> LENGTH: 23
<212> TYPE: RNA
<213> ORGANISM: Homo sapiens

<400> SEQUENCE: 581
cacaggugag guucuuggga gcc                                          23

<210> SEQ ID NO 582
<211> LENGTH: 15
<212> TYPE: RNA
<213> ORGANISM: Homo sapiens
```

-continued

```
<400> SEQUENCE: 582
acaggugagg uucuu                                                      15

<210> SEQ ID NO 583
<211> LENGTH: 25
<212> TYPE: RNA
<213> ORGANISM: Homo sapiens

<400> SEQUENCE: 583
ggguggggau uguugcauu acuug                                            25

<210> SEQ ID NO 584
<211> LENGTH: 20
<212> TYPE: RNA
<213> ORGANISM: Homo sapiens

<400> SEQUENCE: 584
ggguggggau uguugcauu                                                  20

<210> SEQ ID NO 585
<211> LENGTH: 23
<212> TYPE: RNA
<213> ORGANISM: Homo sapiens

<400> SEQUENCE: 585
cggggcagcu caguacagga uac                                             23

<210> SEQ ID NO 586
<211> LENGTH: 15
<212> TYPE: RNA
<213> ORGANISM: Homo sapiens

<400> SEQUENCE: 586
agcucaguac aggau                                                      15

<210> SEQ ID NO 587
<211> LENGTH: 17
<212> TYPE: RNA
<213> ORGANISM: Homo sapiens

<400> SEQUENCE: 587
gcggggcggc aggggcc                                                    17

<210> SEQ ID NO 588
<211> LENGTH: 15
<212> TYPE: RNA
<213> ORGANISM: Homo sapiens

<400> SEQUENCE: 588
gggggcgggg cggca                                                      15

<210> SEQ ID NO 589
<211> LENGTH: 22
<212> TYPE: RNA
<213> ORGANISM: Homo sapiens

<400> SEQUENCE: 589
ggcagggaca gcaaaggggu gc                                              22

<210> SEQ ID NO 590
<211> LENGTH: 18
<212> TYPE: RNA
```

```
<213> ORGANISM: Homo sapiens

<400> SEQUENCE: 590
gcagggacag caaagggg                                                    18

<210> SEQ ID NO 591
<211> LENGTH: 16
<212> TYPE: RNA
<213> ORGANISM: Homo sapiens

<400> SEQUENCE: 591
ugggggggaa gaaaag                                                      16

<210> SEQ ID NO 592
<211> LENGTH: 16
<212> TYPE: RNA
<213> ORGANISM: Homo sapiens

<400> SEQUENCE: 592
ugggggggaa gaaaag                                                      16

<210> SEQ ID NO 593
<211> LENGTH: 23
<212> TYPE: RNA
<213> ORGANISM: Homo sapiens

<400> SEQUENCE: 593
gagggaggga cgggggcugu gcu                                              23

<210> SEQ ID NO 594
<211> LENGTH: 15
<212> TYPE: RNA
<213> ORGANISM: Homo sapiens

<400> SEQUENCE: 594
gaggagggag ggagg                                                       15

<210> SEQ ID NO 595
<211> LENGTH: 24
<212> TYPE: RNA
<213> ORGANISM: Homo sapiens

<400> SEQUENCE: 595
ugacugggga gcagaaggag aacc                                             24

<210> SEQ ID NO 596
<211> LENGTH: 15
<212> TYPE: RNA
<213> ORGANISM: Homo sapiens

<400> SEQUENCE: 596
gacuggggag cagaa                                                       15

<210> SEQ ID NO 597
<211> LENGTH: 22
<212> TYPE: RNA
<213> ORGANISM: Homo sapiens

<400> SEQUENCE: 597
auauagggau uggagccgug gc                                               22

<210> SEQ ID NO 598
<211> LENGTH: 20
```

```
<212> TYPE: RNA
<213> ORGANISM: Homo sapiens

<400> SEQUENCE: 598
auauagggau uggagccgug                                              20

<210> SEQ ID NO 599
<211> LENGTH: 19
<212> TYPE: RNA
<213> ORGANISM: Homo sapiens

<400> SEQUENCE: 599
gcugggcgag gcuggcauc                                               19

<210> SEQ ID NO 600
<211> LENGTH: 17
<212> TYPE: RNA
<213> ORGANISM: Homo sapiens

<400> SEQUENCE: 600
gcugggcgag gcuggca                                                 17

<210> SEQ ID NO 601
<211> LENGTH: 23
<212> TYPE: RNA
<213> ORGANISM: Homo sapiens

<400> SEQUENCE: 601 ugggaaggc gucagugucg ggu                                           23

<210> SEQ ID NO 602
<211> LENGTH: 16
<212> TYPE: RNA
<213> ORGANISM: Homo sapiens

<400> SEQUENCE: 602 ugggaaggc gucagu                                                   16

<210> SEQ ID NO 603
<211> LENGTH: 21
<212> TYPE: RNA
<213> ORGANISM: Homo sapiens

<400> SEQUENCE: 603
cagcagggga gagagaggag u                                            21

<210> SEQ ID NO 604
<211> LENGTH: 20
<212> TYPE: RNA
<213> ORGANISM: Homo sapiens

<400> SEQUENCE: 604
cagcagggga gagagaggag                                              20

<210> SEQ ID NO 605
<211> LENGTH: 26
<212> TYPE: RNA
<213> ORGANISM: Homo sapiens

<400> SEQUENCE: 605
agggcuggac ucagcggcgg agcugg                                       26

<210> SEQ ID NO 606
```

```
<211> LENGTH: 17
<212> TYPE: RNA
<213> ORGANISM: Homo sapiens

<400> SEQUENCE: 606
gcggcggagc uggcugc                                                    17

<210> SEQ ID NO 607
<211> LENGTH: 24
<212> TYPE: RNA
<213> ORGANISM: Homo sapiens

<400> SEQUENCE: 607
caggcaggag ccggacugga ccuc                                            24

<210> SEQ ID NO 608
<211> LENGTH: 21
<212> TYPE: RNA
<213> ORGANISM: Homo sapiens

<400> SEQUENCE: 608
uccaggcagg agccggacug g                                               21

<210> SEQ ID NO 609
<211> LENGTH: 19
<212> TYPE: RNA
<213> ORGANISM: Homo sapiens

<400> SEQUENCE: 609
gggugcgggc cggcggggu                                                  19

<210> SEQ ID NO 610
<211> LENGTH: 15
<212> TYPE: RNA
<213> ORGANISM: Homo sapiens

<400> SEQUENCE: 610
ugcgggccgg cgggg                                                      15

<210> SEQ ID NO 611
<211> LENGTH: 27
<212> TYPE: RNA
<213> ORGANISM: Homo sapiens

<400> SEQUENCE: 611
aucacauugc cagggauuuc caaccga                                         27

<210> SEQ ID NO 612
<211> LENGTH: 15
<212> TYPE: RNA
<213> ORGANISM: Homo sapiens

<400> SEQUENCE: 612
aaucacauug ccagg                                                      15

<210> SEQ ID NO 613
<211> LENGTH: 19
<212> TYPE: RNA
<213> ORGANISM: Homo sapiens

<400> SEQUENCE: 613
uggcgggugc gggggugg                                                   19
```

```
<210> SEQ ID NO 614
<211> LENGTH: 15
<212> TYPE: RNA
<213> ORGANISM: Homo sapiens

<400> SEQUENCE: 614
uggcgggugc ggggg                                                    15

<210> SEQ ID NO 615
<211> LENGTH: 21
<212> TYPE: RNA
<213> ORGANISM: Homo sapiens

<400> SEQUENCE: 615
uugaggagac auguggggg c                                              21

<210> SEQ ID NO 616
<211> LENGTH: 15
<212> TYPE: RNA
<213> ORGANISM: Homo sapiens

<400> SEQUENCE: 616
uugaggagac auggu                                                    15

<210> SEQ ID NO 617
<211> LENGTH: 27
<212> TYPE: RNA
<213> ORGANISM: Homo sapiens

<400> SEQUENCE: 617
aaaccguuac cauuacugag uuuagua                                       27

<210> SEQ ID NO 618
<211> LENGTH: 15
<212> TYPE: RNA
<213> ORGANISM: Homo sapiens

<400> SEQUENCE: 618
gaaaccguua ccauu                                                    15

<210> SEQ ID NO 619
<211> LENGTH: 23
<212> TYPE: RNA
<213> ORGANISM: Homo sapiens

<400> SEQUENCE: 619
ccagggcugg cagugacaug ggu                                           23

<210> SEQ ID NO 620
<211> LENGTH: 19
<212> TYPE: RNA
<213> ORGANISM: Homo sapiens

<400> SEQUENCE: 620
cagggcuggc agugacaug                                                19

<210> SEQ ID NO 621
<211> LENGTH: 23
<212> TYPE: RNA
<213> ORGANISM: Homo sapiens

<400> SEQUENCE: 621
uggggcggag cuuccggagg ccc                                           23
```

<210> SEQ ID NO 622
<211> LENGTH: 15
<212> TYPE: RNA
<213> ORGANISM: Homo sapiens

<400> SEQUENCE: 622
gccccgggaa agcgu                                              15

<210> SEQ ID NO 623
<211> LENGTH: 24
<212> TYPE: RNA
<213> ORGANISM: Homo sapiens

<400> SEQUENCE: 623
agacacauuu ggagagggaa ccuc                                    24

<210> SEQ ID NO 624
<211> LENGTH: 16
<212> TYPE: RNA
<213> ORGANISM: Homo sapiens

<400> SEQUENCE: 624
agacacauuu ggagag                                             16

<210> SEQ ID NO 625
<211> LENGTH: 24
<212> TYPE: RNA
<213> ORGANISM: Homo sapiens

<400> SEQUENCE: 625
gaucggucga gagcguccug gcug                                    24

<210> SEQ ID NO 626
<211> LENGTH: 15
<212> TYPE: RNA
<213> ORGANISM: Homo sapiens

<400> SEQUENCE: 626
gcugggcggg gcgcg                                              15

<210> SEQ ID NO 627
<211> LENGTH: 23
<212> TYPE: RNA
<213> ORGANISM: Homo sapiens

<400> SEQUENCE: 627 cuggggacg cgugagcgcg agc                                      23

<210> SEQ ID NO 628
<211> LENGTH: 21
<212> TYPE: RNA
<213> ORGANISM: Homo sapiens

<400> SEQUENCE: 628 cuggggacg cgugagcgcg a                                        21

<210> SEQ ID NO 629
<211> LENGTH: 27
<212> TYPE: RNA
<213> ORGANISM: Homo sapiens

<400> SEQUENCE: 629
caagguggcu gggagagggu uguuuac                                 27

```
<210> SEQ ID NO 630
<211> LENGTH: 15
<212> TYPE: RNA
<213> ORGANISM: Homo sapiens

<400> SEQUENCE: 630
gugagcucaa ggugg                                                     15

<210> SEQ ID NO 631
<211> LENGTH: 29
<212> TYPE: RNA
<213> ORGANISM: Homo sapiens

<400> SEQUENCE: 631
gcuggguuaa gccgagcugg guugggcug                                      29

<210> SEQ ID NO 632
<211> LENGTH: 19
<212> TYPE: RNA
<213> ORGANISM: Homo sapiens

<400> SEQUENCE: 632
cuggguuggg cugggcugg                                                 19

<210> SEQ ID NO 633
<211> LENGTH: 19
<212> TYPE: RNA
<213> ORGANISM: Homo sapiens

<400> SEQUENCE: 633
gagggcgggu ggaggagga                                                 19

<210> SEQ ID NO 634
<211> LENGTH: 15
<212> TYPE: RNA
<213> ORGANISM: Homo sapiens

<400> SEQUENCE: 634
gcggguggag gagga                                                     15

<210> SEQ ID NO 635
<211> LENGTH: 20
<212> TYPE: RNA
<213> ORGANISM: Homo sapiens

<400> SEQUENCE: 635 caggggggacu gggggugagc                                               20

<210> SEQ ID NO 636
<211> LENGTH: 25
<212> TYPE: RNA
<213> ORGANISM: Homo sapiens

<400> SEQUENCE: 636
acuugggcag gagggacccu guaug                                          25

<210> SEQ ID NO 637
<211> LENGTH: 22
<212> TYPE: RNA
<213> ORGANISM: Homo sapiens

<400> SEQUENCE: 637
``` agcccgccc cagccgagguu cu          22

<210> SEQ ID NO 638
<211> LENGTH: 17
<212> TYPE: RNA
<213> ORGANISM: Homo sapiens

<400> SEQUENCE: 638
ggauggagga ggggucu                17

<210> SEQ ID NO 639
<211> LENGTH: 17
<212> TYPE: RNA
<213> ORGANISM: Homo sapiens

<400> SEQUENCE: 639
gggagucuac agcaggg                17

<210> SEQ ID NO 640
<211> LENGTH: 22
<212> TYPE: RNA
<213> ORGANISM: Homo sapiens

<400> SEQUENCE: 640
gugcggaacg cuggccgggg cg          22

<210> SEQ ID NO 641
<211> LENGTH: 24
<212> TYPE: RNA
<213> ORGANISM: Homo sapiens

<400> SEQUENCE: 641
ggaggccggg gugggggcggg gcgg       24

<210> SEQ ID NO 642
<211> LENGTH: 23
<212> TYPE: RNA
<213> ORGANISM: Homo sapiens

<400> SEQUENCE: 642
aggaagcccu ggaggggcug gag         23

<210> SEQ ID NO 643
<211> LENGTH: 68
<212> TYPE: RNA
<213> ORGANISM: Homo sapiens

<400> SEQUENCE: 643
gggcgcaggg ggacuggggg ugagcaggcc cagaacccag cucgugcuca cucucagucc    60
cucccuag                                                             68

<210> SEQ ID NO 644
<211> LENGTH: 70
<212> TYPE: RNA
<213> ORGANISM: Homo sapiens

<400> SEQUENCE: 644
ugugcacuug ggcaggaggg acccuguaug ucuccccgca gcaccgucau cgugcccuc     60 uuguccacag                                                           70

<210> SEQ ID NO 645
<211> LENGTH: 80

```
<212> TYPE: RNA
<213> ORGANISM: Homo sapiens

<400> SEQUENCE: 645
gguuccggag ccccggcgcg ggcggguucu gggguguaga cgcugcuggc cagcccgccc    60
cagccgaggu ucucggcacc                                                80

<210> SEQ ID NO 646
<211> LENGTH: 60
<212> TYPE: RNA
<213> ORGANISM: Homo sapiens

<400> SEQUENCE: 646
ugugaaugac ccccuuccag agccaaaauc accagggaug gaggaggggu cuugggguacu   60

<210> SEQ ID NO 647
<211> LENGTH: 76
<212> TYPE: RNA
<213> ORGANISM: Homo sapiens

<400> SEQUENCE: 647
ccgaugccuc gggagucuac agcagggcca ugucugugag ggcccaaggg ugcauguguc    60
ucccagguuu cggugc                                                    76

<210> SEQ ID NO 648
<211> LENGTH: 61
<212> TYPE: RNA
<213> ORGANISM: Homo sapiens

<400> SEQUENCE: 648
gugcggaacg cuggccgggg cgggagggga agggacgccc ggccggaacg ccgcacucac    60
g                                                                    61

<210> SEQ ID NO 649
<211> LENGTH: 64
<212> TYPE: RNA
<213> ORGANISM: Homo sapiens

<400> SEQUENCE: 649
ccccgggccc ggcguucccu ccccuuccgu gcgccagugg aggccggggu ggggcggggc    60
gggg                                                                 64

<210> SEQ ID NO 650
<211> LENGTH: 64
<212> TYPE: RNA
<213> ORGANISM: Homo sapiens

<400> SEQUENCE: 650
ccccgggccc ggcguucccu ccccuuccgu gcgccagugg aggccggggu ggggcggggc    60
gggg                                                                 64

<210> SEQ ID NO 651
<211> LENGTH: 118
<212> TYPE: RNA
<213> ORGANISM: Homo sapiens

<400> SEQUENCE: 651
gcaggugaac uggcaggcca ggaagaggag gaagcccugg aggggcugga ggugauggau    60
guuuuccucc gguucucagg gcuccaccuc uuucggggccg uagagccagg gcuggugc     118
```

<210> SEQ ID NO 652
<211> LENGTH: 23
<212> TYPE: RNA
<213> ORGANISM: Homo sapiens

<400> SEQUENCE: 652
cagcccgccc cagccgaggu ucu          23

<210> SEQ ID NO 653
<211> LENGTH: 17
<212> TYPE: RNA
<213> ORGANISM: Homo sapiens

<400> SEQUENCE: 653
agcccgcccc agccgag          17

<210> SEQ ID NO 654
<211> LENGTH: 16
<212> TYPE: RNA
<213> ORGANISM: Homo sapiens

<400> SEQUENCE: 654
cgggcccggc guuccc          16

<210> SEQ ID NO 655
<211> LENGTH: 15
<212> TYPE: RNA
<213> ORGANISM: Homo sapiens

<400> SEQUENCE: 655
ccgggcccgg cguuc          15

<210> SEQ ID NO 656
<211> LENGTH: 25
<212> TYPE: RNA
<213> ORGANISM: Homo sapiens

<400> SEQUENCE: 656
aggaagcccu ggaggggcug gaggu          25

<210> SEQ ID NO 657
<211> LENGTH: 15
<212> TYPE: RNA
<213> ORGANISM: Homo sapiens

<400> SEQUENCE: 657
aggaagagga ggaag          15